(12) United States Patent
Caldwell et al.

(10) Patent No.: US 8,269,043 B2
(45) Date of Patent: Sep. 18, 2012

(54) BICYCLIC ARYL SPHINGOSINE 1-PHOSPHATE ANALOGS

(75) Inventors: Richard D. Caldwell, Somerville, MA (US); Kevin M. Guckian, Marlborough, MA (US); Gnanasambandam Kumaravel, Westford, MA (US); Wen-Cherng Lee, Lexington, MA (US); Edward Yin-Shiang Lin, Chestnut Hill, MA (US); Xiaogao Liu, Dover, MA (US); Bin Ma, Arlington, MA (US); Daniel M. Scott, Weston, MA (US); Zhan Shi, Concord, MA (US); Jermaine Thomas, Chelsea, MA (US); Arthur G. Taveras, Southborough, MA (US); Guo Zhu Zheng, Lexington, MA (US)

(73) Assignee: Biogen Idec MA Inc., Cambridge, MA (US)

( * ) Notice: Subject to any disclaimer, the term of this patent is extended or adjusted under 35 U.S.C. 154(b) by 0 days.

(21) Appl. No.: 12/588,883

(22) Filed: Oct. 30, 2009

(65) Prior Publication Data
US 2010/0160258 A1    Jun. 24, 2010

Related U.S. Application Data

(60) Provisional application No. 61/109,718, filed on Oct. 30, 2008.

(51) Int. Cl.
C07C 211/00 (2006.01)
C09B 11/02 (2006.01)
A61K 31/66 (2006.01)

(52) U.S. Cl. ........................ 564/316; 514/114
(58) Field of Classification Search ............... None
See application file for complete search history.

(56) References Cited

U.S. PATENT DOCUMENTS

| | | | |
|---|---|---|---|
| 5,041,639 A | 8/1991 | Shroot et al. | |
| 7,064,217 B2 | 6/2006 | Lynch et al. | |
| 7,241,790 B2 | 7/2007 | Lynch et al. | |
| 7,560,477 B2 | 7/2009 | Lynch et al. | |
| 7,638,637 B2 | 12/2009 | Lynch et al. | |
| 7,786,173 B2 | 8/2010 | Lynch et al. | |
| 7,915,315 B2 | 3/2011 | Lynch et al. | |
| 2008/0027036 A1 | 1/2008 | Burli et al. | |
| 2009/0042955 A1* | 2/2009 | Lynch et al. | 514/364 |
| 2009/0253759 A1 | 10/2009 | Lynch et al. | |
| 2009/0253760 A1 | 10/2009 | Lynch et al. | |
| 2010/0240617 A1* | 9/2010 | Lynch et al. | 514/143 |

FOREIGN PATENT DOCUMENTS

| | | | |
|---|---|---|---|
| WO | WO2007/092638 | * | 8/2007 |
| WO | WO2009/023854 | * | 2/2009 |
| WO | WO 2011/017561 | | 2/2011 |

OTHER PUBLICATIONS

Silverman (The Organic Chemistry of Drug Design and Drug Action, 1992, Academic Press Inc.).*
International Preliminary Report of Patentability, International Search Report and Written Opinion for PCT/US2009/005897, 2009.

* cited by examiner

*Primary Examiner* — Susanna Moore
*Assistant Examiner* — Jennifer C Sawyer
(74) *Attorney, Agent, or Firm* — Steptoe & Johnson LLP

(57) ABSTRACT

Compounds that have agonist activity at one or more of the S1P receptors are provided. The compounds are sphingosine analogs that, after phosphorylation, can behave as agonists at S1P receptors.

19 Claims, 7 Drawing Sheets

Compounds 21 and 61A S1P1 receptor agonists with potencies similar to both S1P

CoiCompound 21 weak micromolar S1P3 receptor partial agonist activity while no activity was observed with compound 2. S1P was a full S1P3 agonist in this assay.

Compounds 1 & 2 do not antagonize S1P action on the S1P3 receptor when compound is pre-incubated with cells prior to S1P addition

BICYCLIC ARYL SPHINGOSINE 1-PHOSPHATE ANALOGS

CLAIM OF PRIORITY

This application claims priority to U.S. Provisional Patent Application No. 61/109,718, filed on Oct. 30, 2008, which is incorporated by reference in its entirety.

BACKGROUND

Sphingosine 1-phosphate (S1P) is a lysophospholipid mediator that evokes a variety of cellular responses by stimulation of five members of the endothelial cell differentiation gene (EDG) receptor family. The EDG receptors are G-protein coupled receptors (GPCRs) and on stimulation propagate second messenger signals via activation of heterotrimeric G-protein alpha ($G_\alpha$) subunits and beta-gamma ($G_{\beta\gamma}$) dimers. Ultimately, this S1P-driven signaling results in cell survival, increased cell migration and, often, mitogenesis. The recent development of agonists targeting S1P receptors has provided insight regarding the role of this signaling system in physiologic homeostasis. For example, the immunomodulator, FTY720 (2-amino-2-[2-(4-octylphenyl)ethyl] propane 1,3-diol), that following phosphorylation, is an agonist at 4 of 5 S1P receptors, revealed that enhancing S1P tone influences lymphocyte trafficking. Further, S1P type I receptor ($S1P_1$) antagonists cause leakage of the lung capillary endothelium, which suggests that S1P may be involved in maintaining the integrity of the endothelial barrier in some tissue beds.

S1P has been demonstrated to induce many cellular processes, including those that result in platelet aggregation, cell proliferation, cell morphology, tumor-cell invasion, endothelial cell chemotaxis and angiogenesis. For these reasons, S1P receptors are good targets for therapeutic applications such as wound healing and tumor growth inhibition.

Sphingosine-1-phosphate signals cells in part via a set of G protein-coupled receptors named $S1P_1$, $S1P_2$, $S1P_3$, $S1P_4$, and $S1P_5$ (formerly EDG1, EDG5, EDG3, EDG6 and EDG8). The EDG receptors are G-protein coupled receptors (GPCRs) and on stimulation propagate second messenger signals via activation of heterotrimeric G-protein alpha ($G_\alpha$) subunits and beta-gamma ($G_{\beta\gamma}$) dimers. These receptors share 50-55% amino acid sequence identity and cluster with three other receptors ($LPA_1$, $LPA_2$, and $LPA_3$ (formerly EDG2, EDG4 and EDG7) for the structurally related lysophosphatidic acid (LPA).

A conformational shift is induced in the G-Protein Coupled Receptor (GPCR) when the ligand binds to that receptor, causing GDP to be replaced by GTP on the α-subunit of the associated G-proteins and subsequent release of the G-proteins into the cytoplasm. The α-subunit then dissociates from the βγ-subunit and each subunit can then associate with effector proteins, which activate second messengers leading to a cellular response. Eventually the GTP on the G-proteins is hydrolyzed to GDP and the subunits of the G-proteins reassociate with each other and then with the receptor. Amplification plays a major role in the general GPCR pathway. The binding of one ligand to one receptor leads to the activation of many G-proteins, each capable of associating with many effector to proteins leading to an amplified cellular response.

S1P receptors make good drug targets because individual receptors are both tissue and response specific. Tissue specificity of the S1P receptors is desirable because development of an agonist or antagonist selective for one receptor localizes the cellular response to tissues containing that receptor, limiting unwanted side effects. Response specificity of the S1P receptors is also of importance because it allows for the development of agonists or antagonists that initiate or suppress certain cellular responses without affecting other responses. For example, the response specificity of the S1P receptors could allow for an S1P mimetic that initiates platelet aggregation without affecting cell morphology.

Sphingosine-1-phosphate is formed as a metabolite of sphingosine in its reaction with sphingosine kinase and is stored in abundance in the aggregates of platelets where high levels of sphingosine kinase exist and sphingosine lyase is lacking. S1P is released during platelet aggregation, accumulates in serum, and is also found in malignant ascites. Reversible biodegradation of S1P most likely proceeds via hydrolysis by ectophosphohydrolases, specifically the sphingosine 1-phosphate phosphohydrolases. Irreversible degradation of S1P is catalyzed by S1P lyase yielding ethanolamine phosphate and hexadecenal.

A class of S1P agonist compounds are described in provisional U.S. Application No. 60/956,111, filed Aug. 15, 2007, and PCT/US2008/073378, filed Aug. 15, 2008, each of which is incorporated by reference in its entirety.

SUMMARY

Currently, there is a need for novel, potent, and selective agents that are agonists of the S1P receptor having enhanced potency, selectivity, and oral bioavailability. In addition, there is a need in the art for identification of, as well as the synthesis and use of, such compounds. In one aspect, a compound of formula (I):

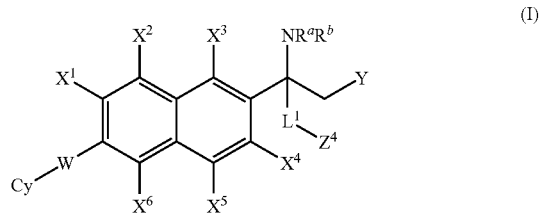

(I)

In formula (I), each of $X^1$, $X^2$, $X^3$, $X^4$, $X^5$, and $X^6$, independently, can be hydrogen, halo, hydroxy, nitro, cyano, alkyl, haloalkyl, cycloalkyl, halocycloalkyl, alkoxy, haloalkoxy, cycloalkoxy, halocycloalkoxy, acyl, aminoacyl, —$NR^fR^g$, —$N(R^f)SO_2R^g$, —$SO_2R^f$, —$SO_2NR^fR^g$, —$CO_2R^f$, trialkylamino, aryl, or heteroaryl.

Y can be —$OR^f$, —$(CR^fR^g)OR^f$, —$(CR^fR^g)_2OR^f$, —O—P(O($OR^f$)$OR^g$, —OC(O)$R^c$, —C(O)$OR^c$, —(CR$^f$R$^g$)—P(O)(O$R^f$)O$R^g$, —(C(OH)$R^f$)—P(O)(O$R^f$)O$R^g$, —S—P(O)(O$R^f$)O$R^g$, tetrazole, —$SO_2NHR^f$, —$SO_3$, —CONH$R^f$, —Si(OH)$_2$, or —B(OH)$_2$.

W can be —C$R^fR^g$—, —N$R^f$—, —O—, —S—, —SO—, or —$SO_2$—.

Cy can be cycloalkyl, cycloalkenyl, heterocyclyl, aryl, or heteroaryl. Cy can be optionally substituted by 1-6 substituents selected from the group consisting of hydrogen, halo, hydroxy, nitro, cyano, —$NR^fR^g$, alkyl, haloalkyl, cycloalkyl, cycloalkenyl, cycloalkylalkyl, cycloalkenylalkyl, heterocyclylalkyl, arylalkyl, heteroarylalkyl, alkoxy, haloalkoxy, cycloalkylalkoxy, cycloalkenylalkoxy, heterocyclylalkoxy, aryloxy, arylalkoxy, heteroaryloxy, heteroarylalkoxy, acyl, cycloalkylacyl, cycloalkenylacyl, heterocyclylacyl, arylacyl, heteroarylacyl, thioalkyl, alkenyl, alkynyl, cycloalkenyl, heterocyclyl, aryl, and heteroaryl.

L¹ can be —CH₂—, —CHF—, or —CF₂—.

Z⁴ can be hydrogen, halo, alkyl, haloalkyl, alkenyl, haloalkenyl, alkynyl, or —OR$^f$.

Z⁴ can be —CH₂— bound to the carbon atom to which Y is bound.

L¹, Z⁴, Y, and the atoms to which they are bound can form a 4-7 membered cycloalkyl group or a 4-7 membered heterocyclyl group having 1 or 2 heteroatoms selected from O and N.

R$^a$ is hydrogen, alkyl, haloalkyl, alkenyl, alkynyl, cycloalkyl, cycloalkenyl, aryl, heteroaryl, or heterocyclyl; wherein each of alkyl, cycloalkyl, cycloalkenyl, aryl, heteroaryl and heterocycle are optionally substituted with 1 to 5 substituents independently selected from the group consisting of halo, oxo, —CN, —CHO, —CF₃, —OH, —NO₂, alkyl, —OCF₃, alkoxy, cycloalkoxy, cycloalkenoxy, amino, alkylamino, dialkylamino, acylamino, aminoacyl, alkylsulfonyl, alkylaminosulfonyl, and dialkylaminosulfonyl.

R$^b$ is hydrogen, alkyl, haloalkyl, alkenyl, alkynyl, cycloalkyl, cycloalkenyl, aryl, heteroaryl, or heterocyclyl; wherein each of alkyl, cycloalkyl, cycloalkenyl, aryl, heteroaryl and heterocycle are optionally substituted with 1 to 5 substituents independently selected from the group consisting of halo, oxo, —CN, —CHO, —CF₃, —OH, —NO₂, alkyl, —OCF₃, alkoxy, cycloalkoxy, cycloalkenoxy, amino, alkylamino, dialkylamino, acylamino, aminoacyl, alkylsulfonyl, alkylaminosulfonyl, and dialkylaminosulfonyl.

R$^b$ and Z⁴ can be taken to together to form —C(O)O— or =C(R$^f$)O—.

R$^c$ is alkyl, aryl, trifluoromethyl, methylsulfonyl, trifluoromethylsulfonyl, p-tolylsulfonyl, or a group selected such that —OCOR$^c$ is a leaving group.

Each R$^f$, independently, is hydrogen, alkyl, haloalkyl, alkenyl, alkynyl, cycloalkyl, cycloalkenyl, aryl, heteroaryl, or heterocyclyl; wherein each of alkyl, cycloalkyl, cycloalkenyl, aryl, heteroaryl and heterocycle are optionally substituted with 1 to 5 substituents independently selected from the group consisting of halo, oxo, —CN, —CHO, —CF₃, —OH, —NO₂, alkyl, —OCF₃, alkoxy, cycloalkoxy, cycloalkenoxy, amino, alkylamino, dialkylamino, acylamino, aminoacyl, alkylsulfonyl, alkylaminosulfonyl, and dialkylaminosulfonyl.

Each R$^g$, independently, is hydrogen, alkyl, haloalkyl, alkenyl, alkynyl, cycloalkyl, cycloalkenyl, aryl, heteroaryl, or heterocyclyl; wherein each of alkyl, cycloalkyl, cycloalkenyl, aryl, heteroaryl and heterocycle are optionally substituted with 1 to 5 substituents independently selected from the group consisting of halo, oxo, —CN, —CHO, —CF₃, —OH, —NO₂, alkyl, —OCF₃, alkoxy, cycloalkoxy, cycloalkenoxy, amino, alkylamino, dialkylamino, acylamino, aminoacyl, alkylsulfonyl, alkylaminosulfonyl, and dialkylaminosulfonyl.

The compound can be in the form of a pharmaceutically acceptable salt or prodrug.

In some embodiments, W is —O—. R$^a$ and R$^b$, independently, can each be H or alkyl. Y can be —OR$^f$. In some circumstances, Y is —OH or —O—P(O)(OR$^f$)OR$^g$. X⁶ can be H, halo, alkyl, cycloalkyl, or haloalkyl.

Cy can have the formula:

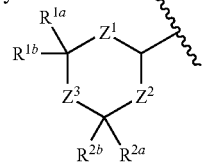

in which Z¹ is a bond, —[C(R$^d$R$^e$)]$_x$—, —CR$^d$=CR$^e$—, —O—, —NR$^f$—; Z² is a bond, —[C(R$^d$R$^e$)]$_y$—, —CR$^d$=CR$^e$—, —O—, —NR$^f$—; Z³ is a bond, —[C(R$^d$R$^e$)]$_z$—, —CR$^d$=CR$^e$—, —O—, —NR$^f$—; and each of x, y, and z, independently, is 1 to 3.

Each R$^d$, independently, can be H, halo, hydroxy, alkyl, haloalkyl, alkenyl, alkoxy, cycloalkyl, —C(O)NR$^f$R$^g$, —NR$^f$R$^g$, —NR$^f$C(O)R$^g$, or —SO₂NR$^f$R$^g$.

Each R$^e$, independently, can be H, halo, hydroxy, alkyl, haloalkyl, alkenyl, alkoxy, cycloalkyl, —C(O)NR$^f$R$^g$, —NR$^f$R$^g$, —NR$^f$C(O)R$^g$, or —SO₂NR$^f$R$^g$.

R$^{1a}$ and R$^{1b}$, independently, can be hydrogen, halo, hydroxy, nitro, cyano, —NR$^f$R$^g$, alkyl, haloalkyl, cycloalkyl, cycloalkenyl, cycloalkylalkyl, cycloalkenylalkyl, heterocyclylalkyl, arylalkyl, heteroarylalkyl, alkoxy, cycloalkylalkoxy, cycloalkenylalkoxy, heterocyclylalkoxy, arylalkoxy, heteroarylalkoxy, acyl, cycloalkylacyl, cycloalkenylacyl, heterocyclylacyl, arylacyl, heteroarylacyl, thioalkyl, alkenyl, alkynyl, cycloalkenyl, heterocyclyl, aryl, or heteroaryl. In some circumstances, R$^{1a}$ and R$^{1b}$, when taken together, are C₂-C₅ alkylene optionally terminated by or inturrepted by 1 or 2 oxygen atoms, or C₂-C₅ alkenylene optionally terminated by or inturrepted by 1 or 2 oxygen atoms, thereby forming a bicyclic ring system.

R$^{2a}$ and R$^{2b}$, independently, can be hydrogen, halo, hydroxy, nitro, cyano, —NR$^f$R$^g$, alkyl, haloalkyl, cycloalkyl, cycloalkenyl, cycloalkylalkyl, cycloalkenylalkyl, heterocyclylalkyl, arylalkyl, heteroarylalkyl, alkoxy, cycloalkylalkoxy, cycloalkenylalkoxy, heterocyclylalkoxy, arylalkoxy, heteroarylalkoxy, acyl, cycloalkylacyl, cycloalkenylacyl, heterocyclylacyl, arylacyl, heteroarylacyl, thioalkyl, alkenyl, alkynyl, cycloalkenyl, heterocyclyl, aryl, or heteroaryl. In some circumstances, R$^{1a}$ and R$^{2a}$, when taken together, are C₁-C₅ alkylene optionally terminated by or inturrepted by 1 or 2 oxygen atoms, or C₂-C₅ alkenylene optionally terminated by or inturrepted by 1 or 2 oxygen atoms, thereby forming a bicyclic ring structure.

R$^{1a}$, R$^{1b}$, R$^{2a}$, and R$^{2b}$ can each, independently, be substituted with 0-5 substituents selected from halo, hydroxy, nitro, cyano, —NR$^f$R$^g$, or —CO₂R$^f$.

In some embodiments, R$^{1a}$ and R$^{2a}$ are both hydrogen. Z¹ can be —CH₂CH₂—. Z² can be —CH₂—. Z³ can be a bond. R$^{1b}$ can be fluoro, chloro, bromo, iodo, methyl, difluoromethyl, trifluoromethyl, ethyl, 1,1-difluoroethyl, propyl, isopropyl, n-butyl, i-butyl, t-butyl, n-pentyl, isopentyl, 1,1-dimethylpropyl, neopentyl, cyclopentyl, n-hexyl, cyclohexyl, methoxy, trifluoromethoxy, ethoxy, n-propoxy, i-propoxy, n-butoxy, i-butoxy, t-butoxy, n-pentyloxy, i-pentyloxy, 1,1-dimethylpropoxy, neopentyloxy, cyclopentyloxy, n-hexyloxy, or cyclohexyloxy.

In another aspect, a compound of formula (II):

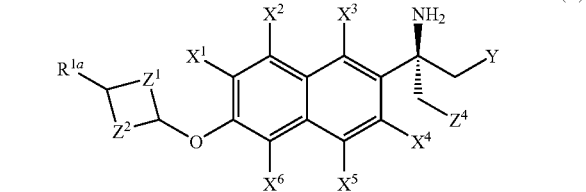

(II)

In formula (II), each of X¹, X², X³, X⁴, X⁵, X⁶, Y and Z⁴ is as defined above for formula (I). R$^{1a}$ can be hydrogen, halo, hydroxy, nitro, cyano, —NR$^f$R$^g$, alkyl, haloalkyl, cycloalkyl, cycloalkenyl, cycloalkylalkyl, cycloalkenylalkyl, heterocyclylalkyl, arylalkyl, heteroarylalkyl, alkoxy, cycloalkylalkoxy, cycloalkenylalkoxy, heterocyclylalkoxy, arylalkoxy, heteroarylalkoxy, acyl, cycloalkylacyl, cycloalkenylacyl, heterocyclylacyl, arylacyl, heteroarylacyl, thioalkyl, alkenyl, alkynyl, cycloalkenyl, heterocyclyl, aryl, or heteroaryl.

In formula (II), $Z^1$ is a bond, —[C($R^dR^e$)]$_x$—, or —$CR^d$=$CR^e$—; $Z^2$ is a bond, —[C($R^dR^e$)]$_y$—, or —$CR^d$=$CR^e$—; and each of x and y independently, is 1 to 3. Each $R^d$, independently, is hydrogen, halo, hydroxy, alkyl, alkenyl, alkoxy, or cycloalkyl. Each $R^e$, independently, is hydrogen, halo, hydroxy, alkyl, alkenyl, alkoxy, or cycloalkyl. The compound of formula (II) can be in the form of a pharmaceutically acceptable salt or prodrug.

In formula (II), Y can be —$OR^f$. In some circumstances, Y can be —OH or —O—P(O)(O$R^f$)O$R^g$. $X^6$ can be H, halo, alkyl, cycloalkyl, or haloalkyl. $Z^1$ can be —$CH_2CH_2$—. $Z^2$ can be —$CH_2CH_2$—. $R^{1a}$ can be hydrogen, halo, hydroxy, alkyl, haloalkyl, cycloalkyl, cycloalkylalkyl, arylalkyl, alkoxy, cycloalkylalkoxy, arylalkoxy, or aryl.

In some embodiments, Y is —OH or —OP(O)(OH)$_2$; $Z^4$ is H or —OH; $X^1$, $X^2$, $X^3$, $X^4$, and $X^5$ are each and $X^6$ is H, halo, alkyl, cycloalkyl, or haloalkyl. $Z^1$ can be —(CH$_2$)$_x$— and $Z^2$ can be —(CH$_2$)$_y$—. $R^{1a}$ can be alkyl, haloalkyl, cycloalkyl, aryl, or arylalkoxy.

In some circumstances, the compound of formula (II) has the formula:

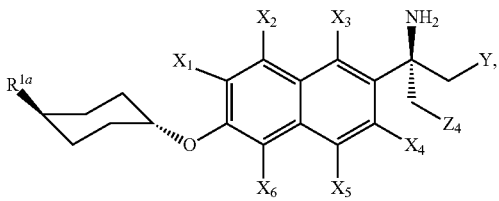

i.e., where $R^{1a}$ and the oxygen atom bound to the cyclohexyl ring are in the trans-orientation with respect to one another.

In another aspect, a compound can be selected from the group consisting of: (R)-2-amino-2-(6-(cis-4-butylcyclohexyloxy)naphthalen-2-yl)propan-1-ol; (R)-2-amino-2-(6-(4-butylcyclohexyloxy)naphthalen-2-yl)propan-1-ol; (R)-2-amino-2-(6-(trans-4-butylcyclohexyloxy)naphthalen-2-yl)propan-1-ol; 2-amino-2-(6-(cis-4-butylcyclohexyloxy)naphthalen-2-yl)propane-1,3-diol; (R)-2-amino-2-(6-(cis-4-butylcyclohexyloxy)-5-(trifluoromethyl)naphthalen-2-yl)propan-1-ol; (R)-2-amino-2-(6-(cis-4-butylcyclohexyloxy)-5-(trifluoromethyl)naphthalen-2-yl)propan-1-phosphoric acid; (R)-2-amino-2-(6-(cis-4-butylcyclohexyloxy)naphthalen-2-yl)propyl dihydrogen phosphate; (R)-2-amino-2-(6-(trans-4-butylcyclohexyloxy)naphthalen-2-yl)propyl dihydrogen phosphate; (R)-2-amino-2-(6-(trans-4-tert-butylcyclohexyloxy)naphthalen-2-yl)propan-1-ol; (R)-2-amino-2-(6-(trans-4-tert-butylcyclohexyloxy)naphthalen-2-yl)propyl dihydrogen phosphate; (R)-2-amino-2-(6-(cis-4-(4-(pentan-3-yloxy)phenyl)cyclohexyloxy)naphthalen-2-yl)propan-1-ol; (R)-2-amino-2-(6-(cis-4-(4-isopropoxyphenyl)cyclohexyloxy)naphthalen-2-yl)propan-1-ol; (R)-2-amino-2-(6-(cis-4-(4-methoxyphenyl)cyclohexyloxy)naphthalen-2-yl)propan-1-ol; (R)-2-amino-2-(6-(cis-4-phenylcyclohexyloxy)naphthalen-2-yl)propan-1-ol; (R)-2-amino-2-(6-(cis-4-phenylcyclohexyloxy)-5-(trifluoromethyl)naphthalen-2-yl)propan-1-ol; (R)-2-amino-2-{6-[trans-4-(1,1-dimethyl-propyl)-cyclohexyloxy]-5-trifluoromethyl-naphthalen-2-yl}-propan-1-ol; (R)-2-amino-2-(6-(4-pentylcyclohexyloxy)naphthalen-2-yl)propan-1-ol; (R)-2-amino-2-(6-(4-propylcyclohexyloxy)naphthalen-2-yl)propan-1-ol; (R)-2-amino-2-(6-(cis-4-methylcyclohexyloxy)naphthalen-2-yl)propan-1-ol; (R)-2-amino-2-(6-(cis-4-ethylcyclohexyloxy)naphthalen-2-yl)propan-1-ol; (R)-2-amino-2-(6-(4-(trifluoromethyl)cyclohexyloxy)naphthalen-2-yl)propan-1-ol; (R)-2-amino-2-(6-(4,4-dimethylcyclohexyloxy)naphthalen-2-yl)propan-1-ol; (R)-2-amino-2-(6-(trans-4-tert-butylcyclohexyloxy)naphthalen-2-yl)propan-1-ol; (R)-2-amino-2-(6-(trans-4-tert-butylcyclohexyloxy)-5-(trifluoromethyl)naphthalen-2-yl)propan-1-ol; 2-amino-2-[6-(cis-4-butylcyclohexyloxy)-5-trifluoromethyl-naphthalen-2-yl]-propane-1,3-diol; 2-amino-2-[6-(cis-4-butylcyclohexyloxy)-5-iodo-naphthalen-2-yl]-propane-1,3-diol; 2-amino-2-[6-(trans-4-tert-butylcyclohexyloxy)-5-trifluoromethyl-naphthalen-2-yl]-propane-1,3-diol; 2-amino-2-[6-(trans-4-tert-butyl-cyclohexyloxy)-naphthalen-2-yl]-propane-1,3-diol; 2-amino-2-[6-(trans-4-tert-butyl-cyclohexyloxy)-5-iodo-naphthalen-2-yl]-propane-1,3-diol; 2-amino-2-(6-trans-[3-(benzyloxymethyl)cyclobutoxy)]naphthalen-2-yl)propane-1,3-diol; 2-amino-2-(6-cis-[3-(benzyloxymethyl)cyclobutoxy)]naphthalen-2-yl)propan-1-ol; 2-amino-2-[6-(3-trans-benzyloxymethylcyclobutoxy)-5-(trifluoromethyl)naphthalen-2-yl)]propane-1,3-diol; 2-amino-2-[6-(3-cis-benzyloxymethylcyclobutoxy)-5-(trifluoromethyl)naphthalen-2-yl)]propane-1,3-diol; (R)-2-amino-2-[6-(3-trans-benzyloxymethylcyclobutoxy)naphthalen-2-yl)]propan-1-ol; (R)-2-amino-2-[6-(3-cis-benzyloxymethylcyclobutoxy)naphthalen-2-yl)]propan-1-ol; (R)-2-amino-2-[6-(4-trans-tert-pentylcyclohexyloxy)naphthalen-2-yl]propan-1-ol; (R)-2-amino-2-[6-(4-cis-tert-pentylcyclohexyloxy)naphthalen-2-yl]propan-1-ol; (R)-2-amino-2-[6-(3-cis-benzyloxymethylcyclobutoxy)-5-trifluoromethyl-naphthalen-2-yl)]propan-1-ol; 2-amino-2-[6-(3-cis-(benzyloxymethylcyclobutoxy)naphthalen-2-yl]-3-hydroxypropyl dihydrogen phosphate; (R)-2-amino-2-{6-[trans-4-(1,1-dimethyl-propyl)-cyclohexyloxy]naphthalen-2-yl}-propan-1-ol; (R)-2-amino-2-(6-(trans-4-tert-butylcyclohexyloxy)-5-methoxynaphthalen-2-yl)propan-1-ol; (R)-2-amino-2-(6-(trans-4-butyl-cyclohexyloxy)-5-trifluoromethylnaphthalen-2-yl)propan-1-ol; (R)-2-amino-2-(6-(trans-4-butyl-cyclohexyloxy)naphthalen-2-yl)propan-1-ol; (R)-2-amino-2-(6-(trans-4-trifluoromethylcyclohexyloxy)-5-fluoronaphthalen-2-yl)propan-1-ol; (R)-2-Amino-2-[6-(decahydro-naphthalen-2-yloxy)-naphthalen-2-yl]-propan-1-ol; (R)-2-Amino-2-[6-(bicyclohexyl-4-yloxy)-naphthalen-2-yl]-propan-1-ol; (R)-2-Amino-2-[6-(4-isopropylcyclohexyloxy)-naphthalen-2-yl]-propan-1-ol; (R)-2-Amino-2-[6-(4-cyclopentyl-cyclohexyloxy)-naphthalen-2-yl]-propan-1-ol; (R)-2-Amino-2-[6-(4-sec-butylcyclohexyloxy)-naphthalen-2-yl]-propan-1-ol; (R)-2-Amino-2-[6-(cis-4-cyclopentylcyclohexyloxy)-5-trifluoromethyl-naphthalen-2-yl]-propan-1-ol; (R)-2-Amino-2-[6-(trans-4-cyclopentyl-cyclohexyloxy)-5-trifluoromethyl-naphthalen-2-yl]-propan-1-ol; Phosphoric acid mono-{(R)-2-amino-2-[6-(4-cyclopentyl-cyclohexyloxy)-5-trifluoromethyl-naphthalen-2-yl]-propyl}ester; 2-Amino-2-[5-trifluoromethyl-6-(4-trifluoromethylcyclohexyloxy)-naphthalen-2-yl]-propane-1,3-diol; (R)-2-[6-(4-tert-butyl-cyclohexyloxy)-naphthalen-2-yl]-2-methylamino-propan-1-ol; phosphoric acid mono-{(R)-2-amino-2-{6-[4-(1,1-dimethylpropyl)-cyclohexyloxy)-5-trifluoromethyl-naphthalen-2-yl]-propyl} Ester; phosphoric acid mono-{(R)-2-amino-2-[6-(4-tert-butyl-cyclohexyloxy)-5-trifluoromethyl-naphthalen-2-yl]-propyl} Ester; (S)-2-amino-2-[6-(4-trans-tert-butyl-cyclohexyloxy)-5-trifluoromethyl-naphthalen-2-yl]-propan-1-ol; (S)-4-[6-(4-cis-tert-butyl-cyclohexyloxy)-naphthalen-2-yl]-4-methyl-oxazol id in-2-one; (S)-4-[6-(4-cis-tert-butyl-cyclohexyloxy)-5-trifluoromethyl-naphthalen-2-yl]-4-methyl-oxazolidin-2-one; (S)-2-amino-2-[6-(4-cis-tertbutyl-cyclohexyloxy)-5-trifluoromethyl-naphthalen-2-yl]-propan-1-ol; (R)-4-(6-hydroxy-5-(trifluoromethyl)naphthalen-2-yl)-4-methyloxazolidin-2-one; (R)-4-(6-(trans-4-tert-butylcyclohexyloxy)-5-(trifluoromethyl)naphthalen-2-yl)-4-methyloxazolidin-2-one; (R)-2-amino-2-(6-((4-tert-butylcyclohexyl)methyl)naphthalen-2-yl)propan-1-ol; 3-(6-(trans-4-tert-Butylcyclohexyloxy)naphthalen-2-yl)oxetan-3-amine; 3-(6-(trans-4-tert-butylcyclohexyloxy)-5-(trifluoromethyl)naphthalen-2-yl)oxetan-3-amine; (R)-2-amino-2-(6-(3-(benzyloxy)phenylthio)naphthalen-2-yl)propan-1-ol; (R)-2-amino-2-(6-(3-(benzyloxy)phenylthio)naphthalen-2-yl)propyl dihydrogen phosphate; (R)-2-Amino-2-(6-(cis-4-cyclohexylcyclohexyloxy)-5-(trifluoromethyl)naphthalen-2-yl)propan-1-ol; (R)-2-Amino-2-(6-(trans-4-cyclohexylcyclohexyloxy)-5-(trifluoromethyl)naphthalen-2-yl)propan-1-ol; (R)-2-amino-2-(6-(trans-4-cyclohexylcyclohexyloxy)-5-(trifluoromethyl)naphthalen-2-yl)propyl dihydrogen phosphate; (R)-2-Amino-2-(6-(cis-4-isopropylcyclohexyloxy)-5-(trifluoromethyl)naphthalen-2-yl)propan-1-ol; (R)-2-Amino-2-(6-(trans-4-isopropylcyclohexyloxy)-5-(trifluoromethyl)naphthalen-2-yl)propan-1-ol; (R)-2-Amino-2-(6-(trans-4-(1,1-difluoroethyl)cyclohexyloxy)-5-(trifluoromethyl)naphthalen-2-yl)propyl dihydrogen phosphate; (R)-2-amino-2-(6-(3-(trifluoromethyl)phenoxy)naphthalen-2-yl)propan-1-ol; (R)-2-Amino-2-(6-(3-chlorophenoxy)naphthalen-2-yl)propan-1-ol; (R)-2-Amino-2-(6-(4-chlorophenoxy)naphthalen-2-yl)propan-1-ol; (R)-2-Amino-2-(6-(3-bromophenoxy)naphthalen-2-yl)propan-1-ol; (R)-2-Amino-2-(6-(3-(trifluoromethoxy)phenoxy)naphthalen-2-yl)propan-1-ol; (R)-2-Amino-2-(6-(4-ethylphenoxy)naphthalen-2-yl)propan-1-ol; (R)-2-Amino-2-(6-(3-isopropylphenoxy)naphthalen-2-yl)propan-1-ol; (R)-2-Amino-2-(6-(4-isobutylphenoxy)naphthalen-2-yl)propan-1-ol; (R)-2-Amino-2-(6-(4-tert-butylphenoxy)naphthalen-2-yl)propan-1-ol; (R)-2-Amino-2-(6-(p-tolyloxy)naphthalen-2-yl)propan-1-ol; (R)-2-Amino-2-(6-(4-(trifluoromethyl)phenoxy)naphthalen-2-yl)propan-1-ol; (R)-2-Amino-2-(6-(2-ethylphenoxy)naphthalen-2-yl)propan-1-ol; (R)-2-Amino-2-(6-(3,4-difluorophenoxy)naphthalen-2-yl)propan-1-ol; (R)-2-Amino-2-(6-(3,4-dimethylphenoxy)naphthalen-2-yl)propan-1-ol; (R)-2-Amino-2-(6-(3-chloro-4-fluorophenoxy)naphthalen-2-yl)propan-1-ol; (R)-2-Amino-2-(6-(3,5-difluorophenoxy)naphthalen-2-yl)propan-1-ol; (R)-2-Amino-2-(6-(3,5-dimethylphenoxy)naphthalen-2-yl)propan-1-ol; (R)-2-Amino-2-[6-(4-isopropoxy-phenoxy)-naphthalen-2-yl]-propan-1-ol; 2-Amino-2-(6-(3-(trifluoromethyl)phenoxy)naphthalen-2-yl)propane-1,3-diol; 2-Amino-2-(6-(3-(benzyloxy)phenylthio)naphthalen-2-yl)propane-1,3-diol; 2-Amino-2-(6-(3-(benzyloxy)phenylthio)naphthalen-2-yl)-3-hydroxypropyl dihydrogen phosphate; 2-Amino-2-(6-(3-(benzyloxy)phenoxy)naphthalen-2-yl)propane-1,3-diol; 2-Amino-2-(6-(3-(benzyloxy)phenoxy)naphthalen-2-yl)-3-hydroxypropyl dihydrogen phosphate; 2-Amino-2-(6-(3-(pentyloxy)phenoxy)naphthalen-2-yl)propane-1,3-diol; 2-Amino-2-(6-(3-phenethoxyphenoxy)naphthalen-2-yl)propane-1,3-diol; 2-Amino-2-(6-(3-(isopentyloxy)phenoxy)naphthalen-2-yl)propane-1,3-diol; 2-Amino-2-(6-(3-(cyclohexylmethoxy)phenoxy)naphthalen-2-yl)propane-1,3-diol; 2-Amino-2-(6-(3-(4,4,4-trifluorobutoxy)phenoxy)naphthalen-2-yl)propane-1,3-diol; 4-amino-4-(6-(trans-4-tert-butylcyclohexyloxy)-5-(trifluoromethyl)naphthalen-2-yl) pentanoic acid; (R)-2-amino-2-(6-(trans-4-tert-butylcyclohexyloxy)-5-cyclopropylnaphthalen-2-yl)propan-1-ol; (R)-2-amino-2-(6-(trans-4-tert-butylcyclohexyloxy)-5-methylnaphthalen-2-yl)propan-1-ol; (R)-2-amino-2-(6-(trans-4-tert-butylcyclohexyloxy)-5-vinylnaphthalen-2-yl)propan-1-ol; (R)-2-amino-2-(6-(trans-4-tert-butylcyclohexyloxy)-5-(4-(trifluoromethoxy)phenyl)naphthalen-2-yl)propan-1-ol; (R)-2-amino-2-(6-(trans-4-tert-butylcyclohexyloxy)-5-(4-(methylsulfonyl)phenyl)naphthalen-2-yl)propan-1-ol; (R)-2-amino-2-(6-(trans-4-tert-butylcyclohexyloxy)-5-(pyrimidin-5-yl)naphthalen-2-yl)propan-1-ol; (R)-2-amino-2-(6-(trans-4-tert-butylcyclohexyloxy)-5-(4-ethoxyphenyl)naphthalen-2-yl)propan-1-ol; (R)-2-amino-2-(6-(trans-4-tert-butylcyclohexyloxy)-5-phenylnaphthalen-2-yl)propan-1-ol; (R)-2-amino-2-(6-(trans-4-tert-butylcyclohexyloxy)-5-(3-chlorophenyl)naphthalen-2-yl)propan-1-ol; (R)-2-amino-2-(6-(trans-4-tert-butylcyclohexyloxy)-5-(4-chlorophenyl)naphthalen-2-yl)propan-1-ol; (R)-2-amino-2-(6-(trans-4-tert-butylcyclohexyloxy)-5-chloronaphthalen-2-yl)propan-1-ol; (R)-2-amino-2-(5-bromo-6-(trans-4-tert-butylcyclohexyloxy)naphthalen-2-yl)propan-1-ol; (R)-2-amino-2-(6-(trans-4-tert-butylcyclohexyloxy)-5,7,8-trichloronaphthalen-2-yl)propan-1-ol; (R)-2-amino-2-(6-(trans-4-tert-butylcyclohexyloxy)-5-fluoronaphthalen-2-yl)propan-1-ol; 2-amino-2-(6-(4-phenoxyphenoxy)naphthalen-2-yl)propane-1,3-diol; 2-amino-2-(6-(4-(benzyloxy)phenoxy)naphthalen-2-yl)propane-1,3-diol; 2-amino-2-(6-(4-(pentyloxy)phenoxy)naphthalen-2-yl)propane-1,3-diol; 2-amino-2-(6-trans-4-tert-butylcyclohexyloxy)-5-(trifluoromethyl)naphthalen-2-yl)-3-hydroxypropyl dihydrogen phosphate Enantiomer 1; 2-amino-2-(6-trans-4-tert-butylcyclohexyloxy)-5-(trifluoromethyl)naphthalen-2-yl)-3-hydroxypropyl dihydrogen phosphate Enantiomer 2; (R)-4-Methyl-4-[6-(4-trifluoromethyl-cyclohexyloxy)-naphthalen-2-yl]-oxazolidin-2-one; (R)-4-Methyl-4-[6-(cis-4-trifluoromethyl-cyclohexyloxy)-naphthalen-2-yl]-oxazolidin-2-one; (R)-4-Methyl-4-[6-(trans-4-trifluoromethyl-cyclohexyloxy)-naphthalen-2-yl]-oxazolidin-2-one; (R)-2-Amino-2-[6-(cis-4-trifluoromethyl-cyclohexyloxy)-naphthalen-2-yl]-propan-1-ol; (R)-2-Amino-2-[6-(trans-4-trifluoromethyl-cyclohexyloxy)-naphthalen-2-yl]-propan-1-ol; Phosphoric acid mono-{(R)-2-amino-2-[6-(trans-4-trifluoromethylcyclohexyloxy)-naphthalen-2-yl]-propyl}Ester; (R)-2-Amino-2-[5-trifluoromethyl-6-(trans-4-trifluoromethyl-cyclohexyloxy)-naphthalen-2-yl]-propan-1-ol; Phosphoric acid mono-{(R)-2-amino-2-[5-trifluoromethyl-6-(trans-4-trifluoromethyl-cyclohexyloxy)-naphthalen-2-yl]-propyl}Ester; (R)-2-Amino-2-[6-(4-pentyl-cyclohexyloxy)-naphthalen-2-yl]-propan-1-ol; (R)-2-Amino-2-[6-(cis-4-pentyl-cyclohexyloxy)-naphthalen-2-yl]-propan-1-ol; (R)-2-Amino-2-[6-(trans-4-pentyl-cyclohexyloxy)-naphthalen-2-yl]-propan-1-ol; 2-[6-(trans-4-tert-Butyl-cyclohexyloxy)-5-trifluoromethyl-naphthalen-2-yl]-propan-1-ol; 2-Amino-2-[6-(trans-4-tert-butyl-cyclohexyloxy)-5-trifluoromethyl-naphthalen-2-yl]-propan-1-ol; 4-Amino-4-[6-(trans-4-trifluoromethyl-cyclohexyloxy)-naphthalen-2-yl]-pentanoic acid; 4-Amino-4-[6-(cis-4-trifluoromethyl-cyclohexyloxy)-naphthalen-2-yl]-pentanoic acid; 4-Amino-4-[5-trifluoromethyl-6-(trans-4-trifluoromethyl-cyclohexyloxy)-naphthalen-2-yl]-pentanoic acid; 4-Amino-4-[5-trifluoromethyl-6-(cis-4-trifluoromethyl-cyclohexyloxy)-naphthalen-2-yl]-pentanoic acid; (R)-2-amino-2-(6-(trans-4-(1,1-difluoroethyl)cyclohexyloxy)naphthalen-2-yl)propan-1-ol; (R)-2-amino-2-(6-(trans-4-(1,1-difluoropropyl)cyclohexyloxy)naphthalen-2-yl)propan-1-ol; (R)-2-amino-2-(6-(trans-4-(1,1-difluorobutyl)cyclohexyloxy)naphthalen-2-yl)propan-1-ol; (R)-2-amino-2-(6-(cis-4-(1,1-difluoroethyl)cyclohexyloxy)naphthalen-2-yl)propan-1-ol; (R)-2-amino-2-(6-(cis-4-(1,1-difluoropropyl)cyclohexyloxy)naphthalen-2-yl)propan-1-ol; (R)-2-amino-2-(6-(cis-4-(1,1- difluorobutyl)cyclohexyloxy)naphthalen-2-yl)propan-1-ol; (R)-2-amino-2-(6-(trans-4-(1,1-difluoroethyl)cyclohexyloxy)-5-(trifluoromethyl)naphthalen-2-yl)propan-1-ol; (R)-2-amino-2-(6-(trans-4-(1,1-difluoropropyl)cyclohexyloxy)-5-(trifluoromethyl)naphthalen-2-yl)propan-1-ol; (R)-2-amino-2-(6-(cis-4-tert-butylcyclohexyloxy)naphthalen-2-yl)propan-1-ol. The compound can be in the form of a pharmaceutically acceptable salt or prodrug.

In another aspect, a pharmaceutical composition includes a pharmaceutically acceptable carrier and a compound of formula (I), as defined above.

In another aspect, a method of making a compound of formula (I) includes contacting a compound of formula III:

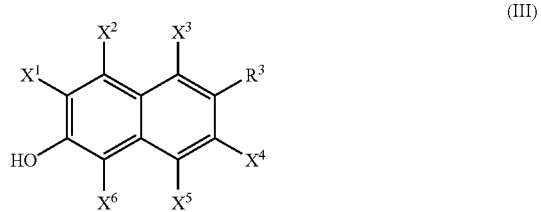

(III)

with a compound having the formula:

Cy-OH.

In formula (III), each of $X^1$, $X^2$, $X^3$, $X^4$, $X^5$, $X^6$, Y and $Z^4$ is as defined above for formula (I), and $R^3$ has the formula:

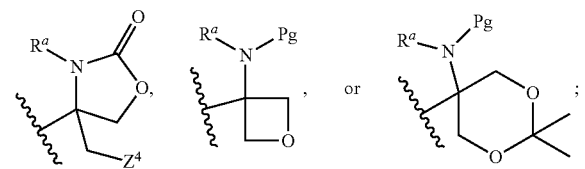

in which $Z^4$ is H or —$OR^f$ (where $R^f$ is as defined in formula (I)), $R^a$ is as defined in formula (I), and Pg is an amino protecting group.

In the compound having the formula Cy-OH, Cy can be cycloalkyl, cycloalkenyl, heterocyclyl, aryl, or heteroaryl; in which Cy is optionally substituted by 1-6 substituents selected from the group consisting of: hydrogen, halo, hydroxy, nitro, cyano, —$NR^fR^g$, alkyl, haloalkyl, cycloalkyl, cycloalkenyl, cycloalkylalkyl, cycloalkenylalkyl, heterocyclylalkyl, arylalkyl, heteroarylalkyl, alkoxy, haloalkoxy, cycloalkylalkoxy, cycloalkenylalkoxy, heterocyclylalkoxy, aryloxy, arylalkoxy, heteroaryloxy, heteroarylalkoxy, acyl, cycloalkylacyl, cycloalkenylacyl, heterocyclylacyl, arylacyl, heteroarylacyl, thioalkyl, alkenyl, alkynyl, cycloalkenyl, heterocyclyl, aryl, and heteroaryl.

In another aspect, a method for prevention or treatment of a pathological condition or symptom in a mammal, wherein the activity of sphingosine 1-phosphate receptors is implicated and agonism of such activity is desired includes administering to said mammal an effective amount of a compound of formula (I).

The pathological condition can be neuropathic pain or an autoimmune disease. The can include administering to said mammal an effective amount of a drug selected from the group consisting of: corticosteroids, bronchodilators, anti-asthmatics, anti inflammatories, antirheumatics, immunosuppressants, antimetabolites, immunomodulators, antipsoriatics, and antidiabetics.

The autoimmune disease can be uveitis, type I diabetes, rheumatoid arthritis, inflammatory bowel diseases, lupus, asthma, psoriasis, or multiple sclerosis. The prevention or treatment of the pathological condition can include altering lymphocyte trafficking. Altering lymphocyte trafficking can provide prolonged allograft survival. The allograft can be for transplantation.

In another aspect, a method for prevention or treatment of a pathological condition or symptom in a mammal, wherein the activity S1P lyase implicated and inhibition of the S1P lyase is desired includes administering to said mammal an effective amount of a compound of formula (I).

In another aspect, an assay includes transfecting HEK293 cells with a plasmid encoding sphingosine kinase 2, obtaining a soluble cell lysate including sphingosine kinase 2, contacting the soluble cell lysate with ATP and a test compound, and determining to whether the test compound is phosphorylated.

The details of one or more embodiments are set forth in the accompanying description below. Other features, objects, and advantages will be apparent from the description and drawings, and from the claims.

DETAILED DESCRIPTION

Figure 1:
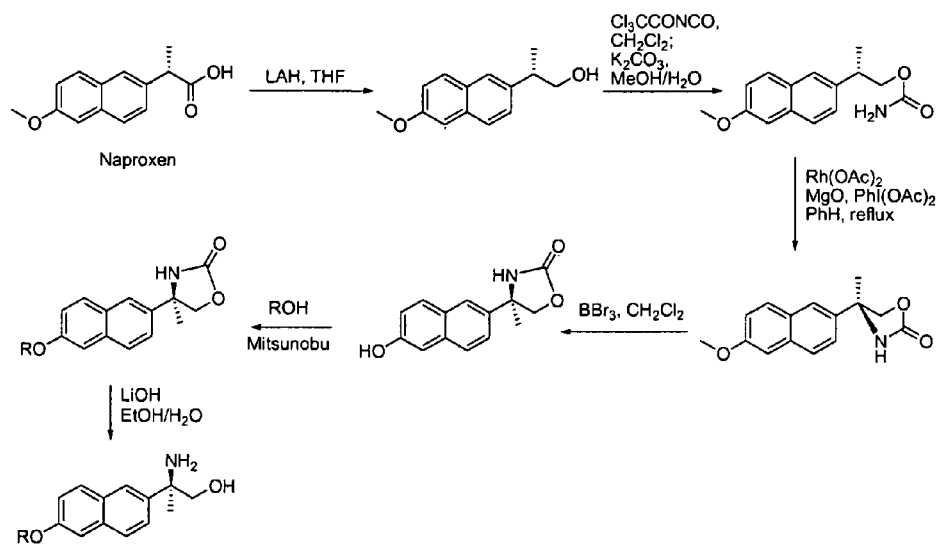
FIGS. 1-6 illustrate schematically synthetic methods for preparing compounds of formula I.

The following abbreviations are used herein: S1P, sphingosine-1-phosphate; $S1P_{1-5}$ S1P receptor types; GPCR, G-protein coupled receptor; SAR, structure-activity relationship; EDG, endothelial cell differentiation gene; EAE, experimental autoimmune encephalomyelitis; NOD non-obese diabetic; TNFα, tumor necrosis factor alpha; HDL, high density lipoprotein; and RT-PCR, reverse transcriptase polymerase chain reaction.

The values listed below for radicals, substituents, and ranges, are for illustration only; they do not exclude other defined values or other values within defined ranges for the radicals and substituents. The disclosed compounds include compounds of formula I having any combination of the values, specific values, more specific values, and preferred values described herein.

The term "halogen" or "halo" includes bromo, chloro, fluoro, and iodo. The term "haloalkyl", refers to an alkyl radical bearing at least one halogen substituent, non-limiting examples include, but are not limited to, chloromethyl, fluoroethyl, trichloromethyl, trifluoromethyl and the like.

The term "$C_1$-$C_{20}$ alkyl" refers to a branched or linear alkyl group having from one to twenty carbons. Non-limiting examples include, but are not limited to, methyl, ethyl, n-propyl, iso-propyl, butyl, iso-butyl, sec-butyl, tert-butyl, pentyl, hexyl, heptyl, octyl and the like.

The term "$C_2$-$C_{20}$ alkenyl", refers to an olefinically unsaturated branched or linear group having from two to twenty carbon atoms and at least one double bond. Typically, $C_2$-$C_{20}$ alkenyl groups include, but are not limited to, 1-propenyl, 2-propenyl, 1,3-butadienyl, 1-butenyl, hexenyl, pentenyl, hexenyl, heptenyl, octenyl and the like.

The term ($C_2$-$C_{20}$)alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl, and the like.

The term "$(C_1-C_{10})$alkoxy" refers to an alkyl group attached through an oxygen atom. Examples of $(C_1-C_{10})$ alkoxy can be methoxy, ethoxy, propoxy, isopropoxy, butoxy, iso-butoxy, sec-butoxy, pentoxy, 3-pentoxy, or hexyloxy and the like.

The term "$C_3-C_{12}$ cycloalkyl" refers to a cyclic alkyl group, such as, for example, cyclopropyl, cyclobutyl, cyclopentyl, cyclohexyl, cycloheptyl, cyclooctyl and the like. Cycloalkyl groups include bicyclic groups such as decalinyl, bridged bicyclic groups such as norbornyl and bicyclo[2.2.2]octyl, tricyclic, bridged tricyclic such as adamantyl, and spiro-linked bicyclic or tricyclic groups.

The term "$(C_6-C_{14})$aryl" refers to a monocyclic, bicyclic, or tricyclic carbocyclic ring system having one or two aromatic rings including, but not limited to, phenyl, benzyl, naphthyl, tetrahydronaphthyl, indanyl, indenyl, anthracyl, and the like.

The term "aryl$(C_1-C_{20})$alkyl" or "arylalkyl" or "aralkyl" refers to an alkyl group substituted with a mono or bicyclic carbocyclic ring system having one or two aromatic rings including, a group such as phenyl, naphthyl, tetrahydronaphthyl, indanyl, indenyl, and the like. Non-limiting examples of arylalkyl include benzyl, phenylethyl, and the like.

The term "$(C_1-C_{14})$heterocyclic group" refers to an optionally substituted mono- or bicyclic carbocyclic ring system containing one, two, three, or four heteroatoms (optionally in each ring) wherein the heteroatoms are oxygen, sulfur, and nitrogen.

The term "$(C_4-C_{14})$heteroaryl" refers to an optionally substituted mono- or bicyclic cyclic ring system containing one, two, or three heteroatoms (optionally in each ring) wherein the heteroatoms are oxygen, sulfur, and nitrogen. Non-limiting examples of heteroaryl groups include furyl, thienyl, pyridyl, and the like.

The term "phosphate analog" and "phosphonate analog" comprise analogs of phosphate and phosphonate wherein the phosphorous atom is in the +5 oxidation state and one or more of the oxygen atoms is replaced with a non-oxygen moiety, including for example, the phosphate analogs phosphorothioate, phosphorodithioate, phosphoroselenoate, phosphorodiselenoate, phosphoroanilothioate, phosphoranilidate, phosphoramidate, boronophosphates, and the like, including associated counterions, e.g., $H^+$, $NH_4^+$, $Na^+$, $K^+$, and the like if such counterions are present.

The term "alpha-substituted phosphonate" includes phosphonate ($—CH_2PO_3H_2$) groups that are substituted on the alpha-carbon such as $—CHFPO_3H_2$, $—CF_2PO_3H_2$, $—CHOHPO_3H_2$, $—C=OPO_3H_2$) and the like.

The term "pharmaceutically acceptable carrier" includes any of the standard pharmaceutical carriers, such as a phosphate buffered saline solution, hydroxypropyl beta-cyclodextrins (HO-propyl beta cyclodextrins), water, emulsions such as an oil/water or water/oil emulsion, and various types of wetting agents. The term also encompasses any of the agents approved by a regulatory agency of the U.S. Federal government or listed in the U.S. Pharmacopeia for use in animals, including humans.

The term "pharmaceutically acceptable salt or prodrug" refers to salts which retain the biological effectiveness and properties of the disclosed compounds and which are not biologically or otherwise undesirable. In many cases, the disclosed compounds are capable of forming acid or base salts by virtue of the presence of amino or carboxyl groups or groups similar thereto. "Prodrug" refers to a compound that can hydrolyze, oxidize, be phosphorylated, or otherwise react under biological conditions (in vitro or in vivo) to provide a compound in pharmacologically active form. In the present context, a compound of Formula (I) can be pharmacologically active (e.g., function as an S1P receptor agonist) when group Y includes, for example, a phosphate group. Suitable prodrugs can therefore include phosphate esters (hydrolyzed to the corresponding phosphate), alcohols (phosphorylated to the corresponding phosphate), esters (hydrolyzed to produce an alcohol, which is phosphorylated to the corresponding phosphate), oxetanes (e.g., where $L^1$, $Z^4$, Y, and the atoms to which they are bound form an oxetane ring; the oxetane can be hydrolyzed to produce an alcohol, which is phosphorylated to the corresponding phosphate) and other compounds that can be converted to a pharmacologically active form.

An "effective amount" means an amount sufficient to produce a selected effect. For example, an effective amount of an S1P receptor agonist is an amount that decreases the cell signaling activity of the S1P receptor.

The disclosed compounds can contain one or more asymmetric centers in the molecule. In accordance with the present disclosure any structure that does not designate the stereochemistry is to be understood as embracing all the various optical isomers, as well as racemic mixtures thereof.

The disclosed compounds may exist in tautomeric forms and the invention includes both mixtures and separate individual tautomers. For example, the following structure:

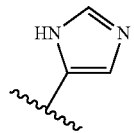

is understood to represent a mixture of the structures:

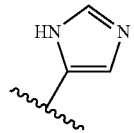

as well as

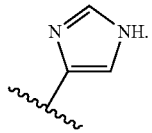

FIG. 1 illustrates schematically a method of making compounds of formula I. Briefly, the carboxylic acid group of naproxen is reduced to an alcohol and treated to afford the carbamoyl derivative, which in turn is subjected to an intramolecular amination that forms the oxazolidone ring. The 6-methoxy substituent on the naphthyl ring is then converted to the corresponding alcohol, and rederivatized under Mitsunobu conditions. Finally, basic hydrolysis of the oxazolidone ring affords the desired product.

Figure 2:
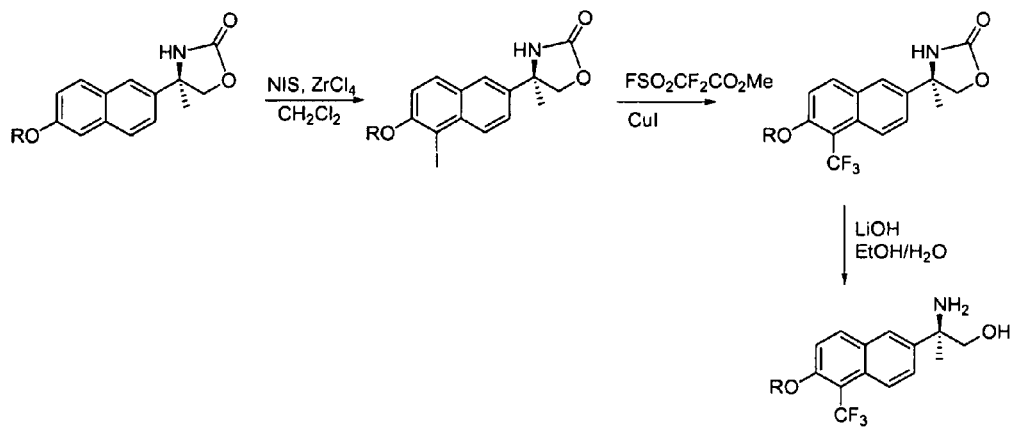

FIG. 2 illustrates schematically functionalization of the naphthyl 5-position with a halo or haloalkyl group.

Figure 3:
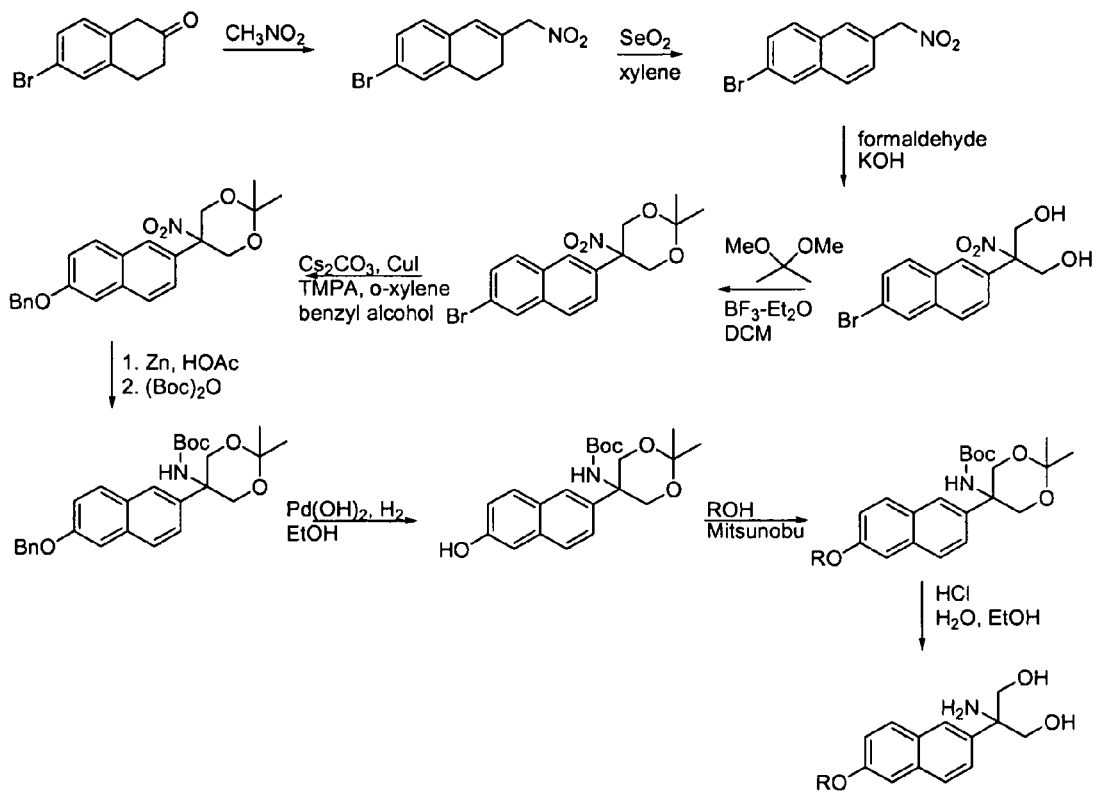

FIG. 3 illustrates schematically a method for making 2-amino-1,3-propanediol compounds according to formula I.

Figure 4:
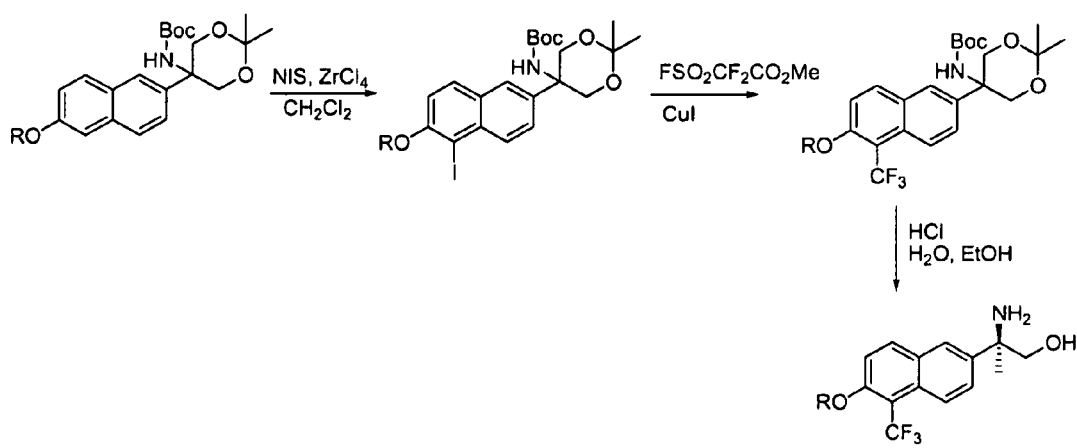

FIG. 4 illustrates schematically a method for making 2-amino-1,3-propanediol compounds according to formula I which are further substituted at the naphthyl 5-position.

Figure 5:
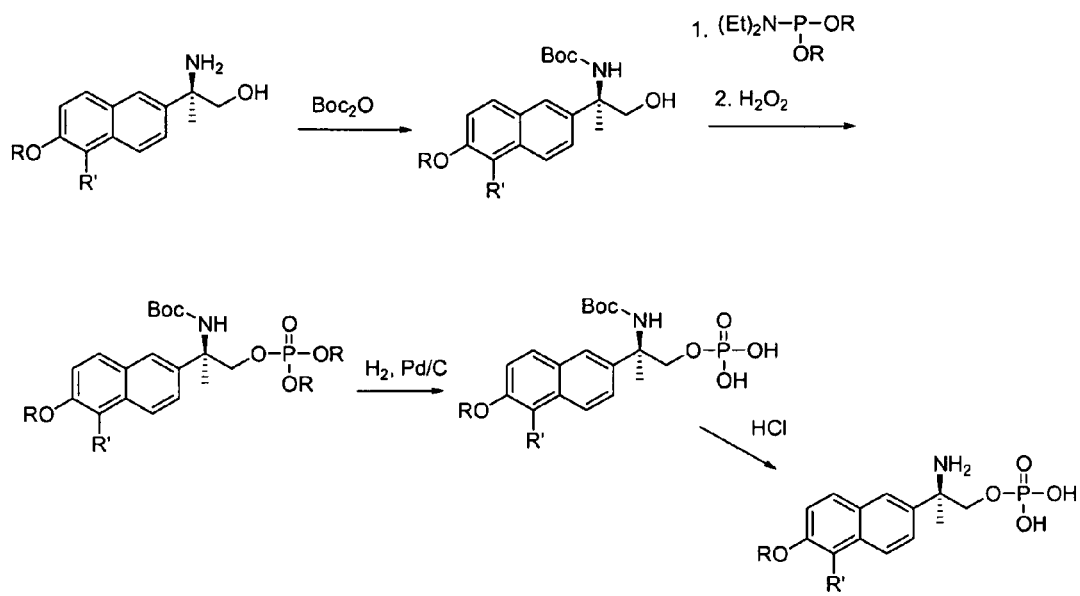
Figure 6:
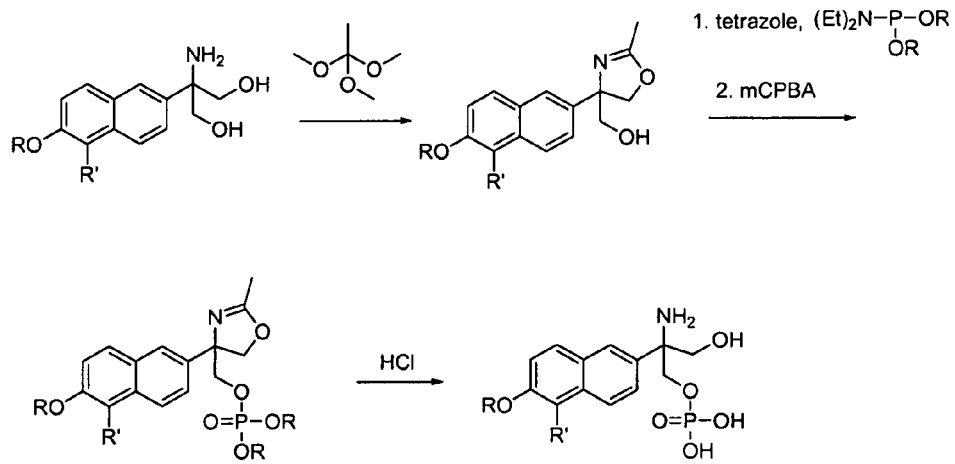

FIGS. 5 and 6 illustrate schematically methods of making compounds of formula that include a phosphate or phosphate ester group.

An "S1P modulating agent" refers a compound or composition that is capable of inducing a detectable change in S1P receptor activity in vivo or in vitro (e.g., at least 10% increase or decrease in S1P activity as measured by a given assay such as the bioassay described in the examples and known in the art. "S1P receptor," refers to all of the S1P receptor subtypes (for example, the S1P receptors $S1P_1$, $S1P_2$, $S1P_3$, $S1P_4$, and $S1P_5$), unless the specific subtype is indicated.

It will be appreciated by those skilled in the art that the disclosed compounds having chiral centers may exist in and be isolated in optically active and racemic forms. It is to be understood that the disclosed compounds encompass any racemic, optically active or stereoisomeric form, or mixtures thereof. It is well known in the art how to prepare such optically active forms (for example, resolution of the racemic form by recrystallization techniques, synthesis from optically-active starting materials, by chiral synthesis, or chromatographic separation using a chiral stationary phase) and how to determine S1P agonist activity using the standard tests described herein, or using other similar tests which are well known in the art. In addition, some compounds may exhibit polymorphism.

In some embodiments, the carbon atom labeled with a * in Formula (I) below can be a stereogenic center.

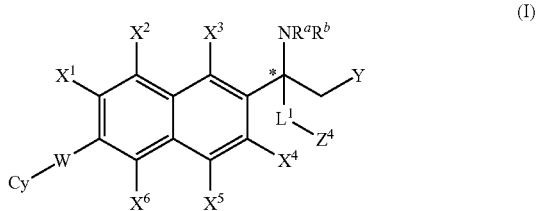

(I)

In such embodiments, there can be a preferred stereochemical configuration. For example, when $L^1$ is —$CH_2$—, $Z^4$ is H, and Y is —OH, the preferred configuration is the R configuration:

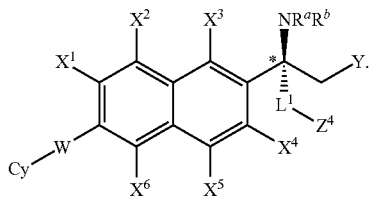

Potential uses of an S1P receptor agonist, and $S1P_1$ receptor type selective agonists particularly, include, but are not limited to, altering lymphocyte trafficking as a method of treatment for neuropathic pain, inflammation-induced pain (e.g., where prostaglandins are involved) or treatment of autoimmune pathologies such as uveitis, type I diabetes, rheumatoid arthritis, inflammatory bowel diseases (e.g., Crohn's disease and ulcerative colitis), multiple sclerosis, lupus, asthma, psoriasis, and in drug-eluting stents. Additional uses can include treatment of brain degenerative diseases, heart diseases, cancers, or hepatitis C. See, for example, WO 2005/085295, WO 2004/010987, WO 03/097028, and WO 2006/072562, each of which is incorporated by reference in its entirety.

"Treatment" of multiple sclerosis includes treating various forms of the disease including relapsing-remitting, chronic progressive, and the S1P receptor agonists can be used alone or in conjunction with other agents to relieve signs and symptoms of the disease as well as prophylactically.

In addition, the disclosed compounds can be used for altering lymphocyte trafficking as a method for prolonging allograft survival, for example solid organ transplants, treatment of graft vs. host disease, bone marrow transplantation, and the like.

In addition, the disclosed compounds can be used to inhibit autotaxin. Autotaxin, a plasma phosphodiesterase, has been demonstrated to undergo end product inhibition. Autotaxin hydrolyzes several substrates to yield lysophosphatidic acid and sphingosine 1-phosphate, and has been implicated in cancer progression and angiogenesis. Therefore, S1P receptor agonist pro-drugs of the disclosed compounds can be used to inhibit autotaxin. This activity may be combined with agonism at S1P receptors or may be independent of such activity.

In addition, disclosed compounds can be useful for inhibition of S1P lyase. S1P lyase is an intracellular enzyme that irreversibly degrades S1P. Inhibition of S1P lyase disrupts lymphocyte trafficking with concomitant lymphopenia. Accordingly, S1P lyase inhibitors can be useful in modulating immune system function. Therefore, the disclosed compounds can be used to inhibit Si P lyase. This inhibition could be in concert with S1P receptor activity, or be independent of activity at any S1P receptor.

In addition, disclosed compounds can be useful as antagonists of the cannabinoid $CB_1$ receptor. $CB_1$ antagonism is associated with a decrease in body weight and an improvement in blood lipid profiles. The $CB_1$ antagonism could be in concert with S1P receptor activity, or be independent of activity at any S1P receptor.

In addition, disclosed compounds can be useful for inhibition of group IVA cytosolic $PLA_2$ ($cPLA_2$). $cPLA_2$ catalyzes the release of eicosanoic acids (e.g., arachidonic acid). The eicosanoic acids are transformed to pro-inflammatory eicosanoids such as prostaglandins and leukotrienes. Thus, disclosed compounds may be useful as anti-inflammatory agents. This inhibition could be in concert with S1P receptor activity, or be independent of activity at any S1P receptor.

In addition, disclosed compounds may be useful for inhibition of the multiple substrate lipid kinase (MuLK). MuLK is highly expressed in many human tumor cells and thus its inhibition might slow the growth or spread of tumors.

Pharmaceutical compositions can include the compounds of formula I. More particularly, such compounds can be formulated as pharmaceutical compositions using standard pharmaceutically acceptable carriers, fillers, solubilizing agents and stabilizers known to those skilled in the art. For example, a pharmaceutical composition including a compound of formula I, or a salt, analog, derivative, or modification thereof, as described herein, is used to administer the appropriate compound to a subject.

The compounds of formula I are useful for treating a disease or disorder including administering to a subject in need thereof of a therapeutically acceptable amount of a compound of formula I, or a pharmaceutical composition comprising a therapeutically effective amount of a compound of formula I, and a pharmaceutically-acceptable carrier.

The disclosed compounds and method are directed to sphingosine 1-phosphate (S1P) analogs that have activity as receptor receptor agonists or antagonists at one or more S1P receptors, specifically the $S1P_1$, $S1P_4$ and $S1P_5$ receptor types. The disclosed compounds and method include both compounds that have a phosphate moiety as well as compounds with hydrolysis-resistant phosphate surrogates such as phosphonates, alpha-substituted phosphonates particularly where the alpha substitution is a halogen and phosphothionates.

The values listed below for radicals, substituents, and ranges, are for illustration only; they do not exclude other defined values or other values within defined ranges for the radicals and substituents.

In cases where compounds of formula I are sufficiently basic or acidic to form stable nontoxic acid or base salts, preparation and administration of the compounds as pharmaceutically acceptable salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Pharmaceutically-acceptable base addition salts can be prepared from inorganic and organic bases. Salts from inorganic bases, include but are not limited to, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are alkyl, substituted alkyl, alkenyl, substituted alkenyl, cycloalkyl, substituted cycloalkyl, cycloalkenyl, substituted cycloalkenyl, aryl, heteroaryl, or heterocyclic and the like. Also included are amines where the two or three substituents, together with the amino nitrogen, form a heterocyclic or heteroaryl group. Non-limiting examples of amines include, isopropylamine, trimethyl amine, diethyl amine, tri(iso-propyl) amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like. It should also be understood that other carboxylic acid derivatives would be useful, for example, carboxylic acid amides, including carboxamides, lower alkyl carboxamides, dialkyl carboxamides, and the like.

The compounds of formula I can be formulated as pharmaceutical compositions and administered to a mammalian host, such as a human patient in a variety of forms adapted to the chosen route of administration, e.g., orally or parenterally, as eyedrops, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least about 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

Exemplary pharmaceutical dosage forms for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, e.g., when they are liquids. However, it will generally be desirable to administer them to the skin as compositions or formulations, in combination with a dermatologically acceptable carrier, which may be a solid or a liquid.

Exemplary solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508), each of which is incorporated by reference in its entirety.

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949, which is incorporated by reference in its entirety.

Generally, the concentration of the compound(s) of formula I in a liquid composition, such as a lotion, will be from about 0.1 to about 25 weight percent, preferably from about 0.5-10 weight percent. The concentration in a semi-solid or solid composition such as a gel or a powder will be about 0.1-5 wt-%, preferably about 0.5-2.5 weight percent based on the total weight of the composition.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician. In general, however, a dose will be in the range of from about 0.1 to about 10 mg/kg of body weight per day.

The compound is conveniently administered in unit dosage form; for example, containing 0.01 to 10 mg, or 0.05 to 1 mg, of active ingredient per unit dosage form. In some embodiments, a dose of 5 mg/kg or less is suitable.

Ideally, the active ingredient should be administered to achieve peak plasma concentrations of the active compound of from about 1 nm to about 50 µM, preferably, about 10 nM to 5 µM, most preferably, about 10 nM to about 1 µM. This may be achieved, for example, by the intravenous injection of a 0.05 to 5% solution of the active ingredient, optionally in saline, or orally administered as a bolus containing about 0.01 to 10 µg of the active ingredient. Desirable blood levels may be maintained by continuous infusion to provide about 0.01-5.0 mg/kg/hr or by intermittent infusions containing about 0.4-15 mg/kg of the active ingredient(s).

The desired dose may conveniently be presented in a single dose or as divided doses administered at appropriate intervals, for example, as two, three, four, or more sub-doses per day, or more infrequently, such as one to five times a week, or one to five times a month. The sub-dose itself may be further divided, e.g., into a number of discrete loosely spaced administrations; such as multiple inhalations from an insufflator or by application of a plurality of drops into the eye.

The disclosed method includes a kit comprising a compound of formula I and instructional material which describes administering the compound or a composition comprising the compound to a cell or a subject. This should be construed to include other embodiments of kits that are known to those skilled in the art, such as a kit comprising a (preferably sterile) solvent for dissolving or suspending the compound or composition prior to administering the compound or composition to a cell or a subject. Preferably, the subject is a human.

In accordance with the disclosed compounds and methods, as described above or as discussed in the Examples below, there can be employed conventional chemical, cellular, histochemical, biochemical, molecular biology, microbiology, and in vivo techniques which are known to those of skill in the art. Such techniques are explained fully in the literature.

The following working examples are provided for the purpose of illustration only, and are not to be construed as limiting in any way the remainder of the disclosure. Therefore, the examples should be construed to encompass any and all variations which become evident as a result of the teaching provided herein.

EXAMPLES

General: Reactions were run under an inert atmosphere. The usual work-up procedure was to add organic solvent, usually ethyl acetate, wash with water or brine, dried, (usually over anhydrous magnesium sulfate) and solvent removed under reduced pressure. If necessary, the mixture was purified by column chromatography.

Example 1

(S)-2-(6-methoxy-naphthalen-2-yl)-propan-ol

To (S)-2-(6-methoxy-naphthalen-2-yl)-propanic acid (naproxen) (23.70 g) in THF (200 mL) at 0° C. was added 125 mL of LAH in THF (2.0 M). The mixture was allowed to warm up to room temperature and refluxed for 2 hr, cooled to 0° C., quenched with Rochelle salt. TLC (EtOAc-hex 1:1)

showed a single spot. The usual manner gave 19.9 g of white precipitate (89%). ¹H NMR (CDCl₃) showed a desired product.

Example 2 carbamic acid (S)-2-(6-methoxy-naphthalen-2-yl)-propyl ester

To (S)-2-(6-methoxy-naphthalen-2-yl)-propan-ol (8.0 g, 37 mmol) in CH₂Cl₂ (200 mL) at 0° C. under N₂ was added trichloroacetyl isocyanate (5.5 mL, 44 mmol). After the mixture was stirred at room temperature for 1 hr, the solvent was concentrated. The residue was treated MeOH (300 mL), water (40 mL) and potassium carbonate (21 g, 0.15 mol) and stirred at RT for 2 hrs to form white precipitate. The precipitate was collected by filtration and dissolved with CH₂Cl₂. The organic phase was washed with water, dried over MgSO₄ and concentrated to give 5.5 g of white precipitate (57%).

Example 3

(R)-4-(6-Methoxy-naphthalen-2-yl)-4-methyl-oxazolidin-2-one

A mixture of carbamic acid (S)-2-(6-methoxy-naphthalen-2-yl)-propyl ester (5.4 g, 0.0208253 mol), iodobenzene diacetate (9.46 g, 0.0294 mol; Acros) and magnesium monoxide (1.93 g, 0.0479 mol; Aldrich), and rhodium(II) acetate dimer (500 mg, 0.001 mol; Janssen) in benzene (250 mL, 2.8 mol; Aldrich) was refluxed overnight under N₂. TLC (EtOAc-hexanes 2:3) showed a slow moving spot. The solution was diluted with EtOAc and filtered through CELITE™ and washed with EtOAc and MeOH. Silica gel was added to the solution, which was then concentrated and purified on a 120 g silica gel column with 10-50% EtOAc/hexanes to give precipitate.

Example 4

(R)-4-(6-hydroxynaphthalen-2-yl)-4-methyloxazolidin-2-one (R)-4-(6-Methoxy-naphthalen-2-yl)-4-methyl-oxazolidin-2-one (215 mg, 0.836 mmol) was dissolved in methylene chloride (5.4 mL) and, at −78° C., 2.5 mL of 1.0 M boron tribromide in methylene chloride was added and was stirred under N₂ to rt. After 5 h, TLC and LCMS showed no starting material (1.34, 213.92, 100%) but only product (1.02, 200.02, 100%). The reaction was quenched with water (10 mL) and extracted with ether (100 mL) and EtOAc (3×10 mL). The organic layer was washed with brine and dried over Na₂SO₄. After concentration, a white solid was obtained (200 mg, 99%).

Example 5

(R)-4-(6-(cis-4-butylcyclohexyl)oxynaphthalen-2-yl)-4-methyloxazolidin-2-one

A mixture of trans-4-butyl-cyclohexanol (441 mg, 2.82 mmol), ((R)-4-(6-hydroxynaphthalen-2-yl)-4-methyloxazolidin-2-one (572.5 mg, 2.353 mmol) and triphenylphosphine (741 mg, 2.82 mmol) in tetrahydrofuran (20 mL, 0.3 mol) was heated to reflux, and diisopropyl azodicarboxylate (0.556 mL, 2.82 mmol) was added dropwise. The reaction was stirred and refluxed for 3 hours. TLC and LCMS monitoring showed the reaction to be incomplete. The mixture was concentrated and taken up into dichloromethane and subjected to chromatography purification with EtOAc/hexane (10:90 to 80:20) to give product (0.793 g, 88% yield). LCMS 2.35 min (382.93, [M+1], 100%).

Example 6

(R)-2-amino-2-(6-(cis-4-butylcyclohexyloxy)naphthalen-2-yl)propan-1-ol

The mixture of (R)-4-(6-(cis-4-butylcyclohexyloxy)naphthalen-2-yl)-4-methyloxazolidin-2-one (294.3 mg, 0.7714 mmol) and lithium hydroxide (203 mg, 8.48 mmol) in Ethanol (4.9 mL, 0.084 mol) and water (1.6 mL, 9.1 mmol) was heated to reflux for overnight. LCMS showed reaction completed. The solvent was removed under vacuum and the residue was partitioned between water and CH₂Cl₂. The aqueous was extensively extracted with CH₂Cl₂. And the combined organic phase was dried over Na₂SO₄. The concentrated residue was taken up into CH₂Cl₂ and subjected to chromatography purification with CH₂Cl₂/MeOH (10:90 to 80:20) to give the product. LCMS 339.53 ([M-NH₂]⁺, 100%). ¹H NMR (400 MHz, CD₃OD) δ ppm 0.92 (t, J=7.0 Hz, 3H), 1.21-1.50 (m, 9H), 1.54 (s, 3H), 1.56-1.71 (m, 4H), 2.05 (brd, J=13.3 Hz, 2 H), 3.71 (AB, J=10.8 Hz, 2H), 4.69 (brs, 1H), 7.14 (dd, J=8.8, 3.3 Hz, 1H), 7.19 (s, 1H), 7.53 (d, J=8.7 Hz, 1H), 7.72 (d, J=8.7 Hz, 1H), 7.76 (d, J=8.7 Hz, 1H), 7.83 (s, 1H).

Example 7

(R)-2-amino-2-(6-(4-butylcyclohexyloxy)naphthalen-2-yl)propan-1-ol

The mixture of 4-n-butylcyclohexanol (49.8 mg, 0.000319 mol), (R)-4-(6-((1R,4S)-4-butylcyclohexyloxy)naphthalen-2-yl)-4-methyloxazolidin-2-one (64.6 mg, 0.000266 mol) and triphenylphosphine (111 mg, 0.000425 mol) in tetrahydrofuran (3 mL, 0.03 mol) was heated to reflux, and diisopropyl azodicarboxylate (0.0836 mL, 0.000425 mol) was added dropwise and was stirred and refluxed for 3 hours. TLC and LCMS monitoring showed the reaction incomplete. The mixture was taken up into DCM and subjected to chromatography purification with EtOAc/hexane (10:90 to 80:20) to give products (36 mg, 36% yield). LCMS 382 ([M+1], 90%).

The mixture of carbamate (36.0 mg, 0.0000944 mol) in ethanol (2 mL, 0.03 mol) and water (0.8 mL, 0.05 mol) with lithium hydroxide (24.8 mg, 0.00104 mol) was heated to reflux overnight. LCMS shows reaction complete. After concentration, the residue was taken up into DCM and was subjected to chromatography purification with DCM/MeOH to give the title compound as a wax (16.1 mg, 48% yield). LCMS 339.53 ([M-NH₂]+, 100%). ¹H NMR (400 MHz, CD₃OD) δ ppm 0.92-2.28 (m, 21H), 3.70-3.90 (m, 2H), 4.35-4.70 (m, 1H), 7.16-7.90 (m, 6H).

Example 8

(R)-2-amino-2-(6-(trans-4-butylcyclohexyloxy)naphthalen-2-yl)propan-1-ol

The mixture of carbamate (Example 7; 360 mg 0.00094 mol, cis and trans mixture) and lithium hydroxide (248 mg, 0.0104 mol) in ethanol (6.0 mL, 0.10 mol) and water (2.0 mL, 0.11 mol) was heated to reflux for overnight. LCMS showed reaction completed. The solvent was removed under vacuum and the residue was partitioned between water/CH₂Cl₂. The aqueous layer was extensively extracted with CH$_2$Cl$_2$. The combined organic phase was dried over Na$_2$SO$_4$. The concentrated residue was taken up into DCM and subjected to chromatographic purification with CH$_2$Cl$_2$/MeOH (10:90 to 80:20) to give the product (220 mg, 66%). Separation on ChiralPak-ADH (5μ, 4.6 mm×250 mm, 2 mL/min, 25% (0.3% DEA in MeOH) in CO$_2$, 100 bar, 36° C.) gave peak 1, R$_f$=8.373 min, 87 mg (87.9% yield, 96.4% ee), and peak 2, R$_f$=12.479 min, 74 mg (74.7% yield, 97.0% ee). Peak 1 was purified on Si gel (0-100% MeOH/DCM) to give 26.2 mg; peak 2 was purified on Si gel (0-100% MeOH/DCM) to give 44.3 mg. LCMS 339.71 ([M-NH$_2$]+, 100%). $^1$H NMR (400 MHz, CD$_3$OD) δ ppm 0.93 (t, J=6.9 Hz, 3H), 1.14 (ddd, J=14.7, 13.4, 3.0 Hz, 2H), 1.24-1.39 (m, 7H), 1.45 (ddd, J=14.7, 12.5, 3.3 Hz, 2H), 1.56 (s, 3H), 1.89 (br d, J=13.0 Hz, 2H), 2.22 (brd, J=12.5 Hz, 2H), 3.70 (d, J=10.9 Hz, 1H), 3.76 (d, J=10.9 Hz, 1H), 4.37 (m, 1H), 7.11 (dd, J=9.0, 2.6 Hz, 1H), 7.21 (d, J=2.5 Hz, 1H), 7.55 (dd, J=8.7, 2.0 Hz, 1H), 7.74 (d, J=6.6 Hz, 1H), 7.76 (d, J=6.9 Hz, 1H), 7.84 (d, J=1.9 Hz, 1H).

Example 9

2-Nitro-2-(6-bromo-naphthalenyl)-1,3-propanediol

Charged 900 g of 6-bromo-2-tetralone, 1.9 L of nitromethane and 37 g of ethylenediamine in 10 L flask. Heated the mixture liquid to 75° C. in a vessel under N$_2$ for 24 hours to complete the reaction. When the reaction was complete, distilled out the excess nitromethane under reduce pressure. Introduced 200 g of silica gel to the residue with cooling. Hexane (10 L×3) was used to extracted, filtered and the hexane layer combined. On cooling, crystals were formed. About 500 g of 7-bromo-1,2-dihydro-3-(nitromethyl)naphthalene was obtained.

26.8 g of 6-bromo-2-nitromethylnaphthalene was dissolved in 500 mL xylene. To the xylene was added 11 g of SeO$_2$. The mixture was heated to reflux, monitored by HPLC until the starting material disappeared. The whole reaction time was around 10 hours. Cooled the reaction liquid to room temperature, filtered to remove the insoluble impurities. The filter liquid was distilled to remove most of the xylene under vacuum. About 40-50 mL of the residue was obtained. Freeze to get the solid. Recrystallized it with toluene to get 8 g of 97% pure 2-bromo-6-(nitromethyl)naphthalene.

8 g of 2-bromo-6-(nitromethyl)naphthalene was dissolved in 200 mL of 37% of formaldehyde, was added 1N KOH (200 mL). The mixture was heated at 40° C. for 8 h, followed by HPLC until the reaction was completed. Cooled the reaction liquid to it Added 100 mL of dichloromethane, stirred, separated the organic layer, distilled out the solvent under reduce pressure at below 40° C. The residue was dissolved in methanol, water was introduced slowly to crystallized the solid. The filtered solid was about 5 g of 2-Nitro-2-(6-bromo-naphthalenyl)-1,3-propanediol, purity greater than 97%.

Example 10

5-(6-bromonaphthalen-2-yl)-2,2-dimethyl-5-nitro-1,3-dioxane 2-(6-Bromo-naphthalen-2-yl)-2-nitro-propane-1,3-diol (32.6 g, 0.100 mol) was dissolved in methylene chloride (150 mL, 2.3 mol; Acros, anhydrous) and 2,2-dimethoxypropane (180 mL, 1.5 mol; Aldrich), cooled with an ice bath. Boron trifluoride is etherate (10.1 mL, 0.0800 mol; Aldrich) was added slowly. The mixture was stirred for 15 min and large amount of solid precipitated. The cooling bath was removed and the mixture was stirred at r.t. for 4 hours. The mixture was quenched with aqueous saturated NaHCO$_3$ (~600 mL) to pH~8, extracted with EtOAc (600 mL, 300 mL, 2×100 mL). The EtOAc layer was washed with water, brine, dried over Na$_2$SO$_4$, filtered. The solvent was evaporated to 100 mL. The resulted solid product was collected by filtration and the mother liquid was concentrated further to afford the second crop of product. R$_f$ of product=0.4 (EtOAc/hexane=1/4). Total product weighed 30.0 g (yield 82%).

Example 11

5-(6-(benzyloxy)naphthalen-2-yl)-2,2-dimethyl-5-nitro-1,3-dioxane

A 40 mL vial was charged with 5-(6-Bromo-naphthalen-2-yl)-2,2-dimethyl-5-nitro-1,3-dioxinane (3.66 g, 0.0100 mol), Copper(I) iodide (0.190 g, 0.00100 mol; Acros), cesium carbonate (4.88 g, 0.0150 mol; Aldrich), 3,4,7,8-Tetramethyl-1,10-phenanthroline (TMPA, 0.472 g, 0.00200 mol; Aldrich), benzyl alcohol (2.07 mL, 0.0200 mol; Aldrich) and 1,2-dimethylbenzene (10.0 mL, 0.0819 mol; Fisher). The suspension was degassed with low vacuum and backfilled with N$_2$ twice. The mixture was heated to 125° C. (heating block) for 16 hours. LCMS showed starting material completely consumed. The mixture was quenched with water and EtOAc was added. The mixture was filtered through CELITE™. The filtrate was extracted with EtOAc, washed with water, brine, dried over Na$_2$SO$_4$, filtered. The filtrate was concentrated in under vacuum and purified by chromatography using EtOAc/hexane (0/100 to 20/80) to afford a solid product (1.43 g, yield 36.3%). R$_f$ (EtOAc/hexane 1/4)=0.4.

Example 12 tert-butyl 5-(6-(benzyloxy)naphthalen-2-yl)-2,2-dimethyl-1,3-dioxan-5-ylcarbamate 5-(6-Benzyloxy-naphthalen-2-yl)-2,2-dimethyl-5-nitro-1,3-dioxane (1.43 g, 0.00363 mol) was dissolved in acetic acid (50.0 mL, 0.879 mol; Fisher). Zinc (2.51 g, 0.0384 mol; Aldrich) was added and the mixture was stirred at room temperature overnight. LCMS showed conversion completed. The mixture was filtered. The filtrate was evaporated and the residue was neutralized with saturated aqueous NaHCO$_3$ to pH~8, and extracted with EtOAc. The EtOAc solution was washed with brine, dried over Na$_2$SO$_4$, filtered, evaporated and dried in high vacuum to give a solid intermediate.

The intermediate was dissolved in methylene chloride (50.0 mL, 0.780 mol). N,N-diisopropylethylamine (2.53 mL, 0.0145 mol) was added, followed by Di-tert-Butyldicarbonate (1.98 g, 0.00909 mol). The mixture was stirred at r.t. overnight. LCMS showed partial conversion. Di-tert-Butyldicarbonate (0.793 g, 0.00363 mol) was added and the mixture was continuously stirred at r.t. for one more day. The mixture was evaporated and purified by chromatograph using EtOAc/hexane (0/100 to 30/70) to give a solid product (1.25 g, yield 74.2%). Rf (EtOAc/hexane 1/4)=0.3.

Example 13 tert-butyl 5-(6-hydroxynaphthalen-2-yl)-2,2-dimethyl-1,3-dioxan-5-ylcarbamate

[5-(6-Benzyloxy-naphthalen-2-yl)-2,2-dimethyl-1,3-dioxinan-5-yl]-carbamic acid tert-butyl ester (1.19 g, 0.00257 mol) and 20% Pd(OH)₂ on carbon (20:80, palladium hydroxide:carbon black, 0.243 g; Aldrich) was suspended in ethanol (200 mL, 3 mol; Fisher), purged with N₂ then stirred under H₂ (balloon) at r.t. overnight. LCMS showed partial conversion. The mixture was transferred to a pressure vessel and continuously stirred under 50 psi of H₂ for one day. The mixture was filtered, evaporated and dried in high vacuum to give a solid product (0.914 g, yield 95.3%).

Example 14

2-amino-2-(6-(cis-4-butylcyclohexyloxy)naphthalen-2-yl)propane-1,3-diol

The mixture of trans-4-butyl-cyclohexanol (100 mg, 0.000643 mol), [5-(6-hydroxynaphthalen-2-yl)-2,2-dimethyl-1,3-dioxinan-5-yl]-carbamic acid tert-butyl ester (200 mg, 0.000536 mol) and triphenylphosphine (168 mg, 0.000643 mol) in tetrahydrofuran (5 mL, 0.06 mol) was heated to reflux, and diisopropyl azodicarboxylate (0.126 mL, 0.000643 mol) was added dropwise and was stirred and refluxed for 3 hours. TLC and LCMS monitoring showed no starting material, complete reaction. After concentration, the mixture was taken up into DCM and subjected to chromatography purification with EtOAc/hexane (10:90 to 80:20) to give product (0.205 g).

The above product (0.205 g, 0.000401 mol) was heated to 50° C. in 6.0 M of HCl in water (3 mL; Fisher) and ethanol (6 mL, 0.1 mol; Fisher) for 3 hours. LCMS indicated conversion completed to desired product R$_f$=1.66 min. The solution was concentrated under vacuum, neutralized with aqueous NH₄OH, and lyophilized to dry. Recrystallized on MeOH/CH₂Cl₂ to give a powder product (81.3 mg, 56% yield). LCMS 372.63 ([M+1], 40%). ¹H NMR (400 MHz, CD₃OD) δ ppm 0.92 (t, J=7.0 Hz, 3H), 1.23-1.76 (m, 14H), 2.05 (dd, J=13.7, 2.3 Hz, 2 H), 3.96 (d, J=11.5 Hz, 2H), 4.06 (d, J=11.5 Hz, 2H), 4.58 (brs, 1H), 7.20 (dd, J=8.7, 2.3 Hz, 1H), 7.24 (d, J=2.3 Hz, 1H), 7.49 (dd, J=8.7, 2.1 Hz, 1H), 7.80-7.85 (m, 3H).

Example 15

(R)-4-(5-iodo-6-(cis-4-butylcyclohexyloxy)naphthalen-2-yl)-4-methyloxazolidin-2-one A mixture of (R)-4-(6-(cis-4-butylcyclohexyloxy)naphthalen-2-yl)-4-methyloxazolidin-2-one (Example 5, 113.2 mg, 0.0002967 mol), N-iodosuccinimide (74.8 mg, 0.000332 mol) and zirconium tetrachloride (10 mg, 0.000044 mol) in methylene chloride (2.43 mL, 0.0380 mol) was heated to reflux under argon in a vial overnight. The precipitate was filtered off and the residue was purified with Isco column eluted with EtOAc in hexane from 0 to 40% to give the product as a solid (128.9 mg, 86% yield). NMR showed identity.

Example 16

(R)-4-(5-trifluoromethyl-6-(cis-4-butylcyclohexyloxy)naphthalen-2-yl)-4-methyloxazolidin-2-one To a solution of (R)-4-(5-iodo-6-(cis-4-butylcyclohexyloxy)naphthalen-2-yl)-4-methyloxazolidin-2-one (128.9 mg, 0.2540 mmol), hexamethylphosphoramide (0.22 mL, 1.3 mmol) and copper(I) iodide (72 mg, 0.38 mmol) in N,N-dimethylformamide (1 mL, 20 mmol) was added methyl fluorosulphonyldifluoroacetate (0.17 mL, 1.3 mmol). The mixture was heated at 80° C. ON. LCMS showed desired product peak 2.45 min 450.28 ([M+1], 80%). The solvent was evaporated and recrystallization with ethyl acetate/hexane gave the product (113.0 mg, 99% yield).

Example 17

(R)-2-amino-2-(6-(cis-4-butylcyclohexyloxy)-5-(trifluoromethyl)naphthalen-2-yl)propan-1-ol The mixture of (R)-4-(5-trifluoromethyl-6-(cis-4-butylcyclohexyloxy)naphthalen-2-yl)-4-methyloxazolidin-2-one (324.6 mg, 0.0007221 mol) and lithium hydroxide (190 mg, 0.0079 mol) in ethanol (10 mL, 0.2 mol) and water (3 mL, 0.1 mol) was heated to reflux for overnight. LCMS showed reaction completed. The solvent was removed under vacuum and the residue was partitioned between water and CH₂Cl₂. The aqueous layer was extensively extracted with CH₂Cl₂. And the combined organic phase was dried over Na₂SO₄. The concentrated residue was taken up into DCM and subjected to chromatographic purification with CH₂Cl₂/MeOH (10:90 to 80:20) to give the product (303.5 mg, 99% yield). LCMS 407.28 ([M-NH₂]+, 100%). ¹H NMR (400 MHz, CD₃OD) δ ppm 0.92 (t, J=6.8 Hz, 3H), 1.20-1.69 (m, 13H), 1.51 (s, 3H), 2.05 (dd, J=13.2, 2.3 Hz, 2 H), 3.66 (d, J=10.9 Hz, 1H), 3.73 (d, J=10.9 Hz, 1H), 4.83 (brs, 1H), 7.43 (d, J=9.4 Hz, 1H), 7.68 (dd, J=9.4, 2.3 Hz, 1H), 7.92 (d, J=2.3 Hz, 1H), 8.03 (d, J=9.4 Hz, 1H), 8.12 (dd, J=9.0, 1.8 Hz, 1H).

Example 18 tert-butyl (R)-2-(6-((cis-4-butylcyclohexyloxy)-5-(trifluoromethyl)naphthalen-2-yl)-1-hydroxypropan-2-ylcarbamate (R)-2-amino-2-(6-(cis-4-butylcyclohexyloxy)-5-(trifluoromethyl)naphthalen-2-yl)propan-1-ol (135.7 mg, 0.0003204 mol) in chloroform (5.9 mL, 0.074 mol) and saturated aqueous sodium bicarbonate solution (3.8 mL, 0.038 mol) and di-tert-butyldicarbonate (83.9 mg, 0.000384 mol) was added and the mixture was stirred at rt for 2 days. TLC showed only a trace of starting material. After separation of organic layer, the aqueous layer was extracted with CHCl₃. The organic layer was washed with brine and dried over anhydrous Na₂SO₄. The concentrated residue was chromatographed with EtOAc/hexane (0-100%) to give the product (164.1 mg, 98% yield).

Example 19

(R)-2-t-butoxycarbonylamino-2-(6-(cis-4-butylcyclohexyloxy)-5-(trifluoromethyl)naphthalen-2-yl)propan-1-phosphoric acid o-xylylene ester To a solution of tert-butyl (R)-2-(6-(cis-4-butylcyclohexyloxy)-5-(trifluoromethyl)naphthalen-2-yl)-1-hydroxypropan-2-ylcarbamate (164.1 mg, 0.0003134 mol) and 1H-tetrazole (65.9 mg, 0.000940 mol) in tetrahydrofuran (3.3 mL, 0.041 mol) was added o-xylylene N,N-diethylphosphoramidite (101 μL, 0.000470 mol) at rt. The resulting mixture was stirred at rt for 3 days, then hydrogen peroxide (700 μL, 0.0069 mol) was added and the mixture was stirred at rt for 1 h. The reaction was quenched with satd. NaS₂O₃, then extracted with EtOAc, then dried over Na₂SO₄. The residue was chromatographed with MeOH—CH₂Cl₂ (0-100%) to give desired product (212 mg, 96%).

Example 20

(R)-2-t-butoxycarbonylamino-2-(6-(cis-4-butylcyclohexyloxy)-5-(trifluoromethyl)naphthalen-2-yl)propan-1-phosphoric acid (R)-2-t-Butoxycarbonylamino-2-(6-(cis-4-butylcyclohexyloxy)-5-(trifluoromethyl)naphthalen-2-yl)propan-1-phosphoric acid o-xylylene ester (212.0 mg, 0.0003004 mol) was dissolved in methanol (2.0 mL, 0.049 mol) and added 10% palladium on Carbon (1:9, palladium:carbon black, 21.2 mg) was added. The mixture was stirred under hydrogen (2 L, 0.07 mol) for 2 h. The resulting solid was filtered through CELITE™ and was washed with MeOH. The concentrated residue was dissolved in $CH_2Cl_2$ and was chromatographed with MeOH/$CH_2Cl_2$ (0-50%) to give the desired product as a white solid (76.8 mg, 42.4%).

Example 21

(R)-2-amino-2-(6-(cis-4-butylcyclohexyloxy)-5-(trifluoromethyl)naphthalen-2-yl)propan-1-phosphoric acid (R)-2-t-Butoxycarbonylamino-2-(6-(cis-4-butylcyclohexyloxy)-5-(trifluoromethyl)naphthalen-2-yl)propan-1-phosphoric acid (76.8 mg, 0.000127 mol) was dissolved in acetic acid (4.0 mL, 0.070 mol) and 10 M HCl in water (1.0 mL) was added and the mixture was stirred for 1 day. LCMS give a single peak $R_f$=1.77 min. Lyophilizing gave a white solid (61.3 mg, 95.7% yield). $^1$H NMR showed pure desired compound. LCMS 504.30 ([M+1]+, 100%). $^1$H NMR (400 MHz, $CD_3OD$) δ ppm 0.92 (t, J=6.8 Hz, 3H), 1.20-1.69 (m, 13H), 1.51 (s, 3H), 2.05 (dd, J=13.2, 2.3 Hz, 2 H), 3.66 (d, J=10.9 Hz, 1H), 3.73 (d, J=10.9 Hz, 1H), 4.83 (brs, 1H), 7.43 (d, J=9.4 Hz, 1H), 7.68 (dd, J=9.4, 2.3 Hz, 1H), 7.92 (d, J=2.3 Hz, 1H), 8.03 (d, J=9.4 Hz, 1H), 8.12 (dd, J=9.0, 1.8 Hz, 1H).

Example 22

(R)-2-amino-2-(6-(cis-4-butylcyclohexyloxy)naphthalen-2-yl)propyl dihydrogen phosphate The title compound was prepared from (R)-2-amino-2-(6-((1R,4S)-4-butylcyclohexyloxy)naphthalen-2-yl)propan-1-ol (Example 6) analogously to the methods of Examples 18-21, affording 7.7 mg, 22% yield. LCMS 453.69, [M+18], 100%. $^1$H NMR (400 MHz, $CD_3OD$) δ ppm 0.93 (t, J=6.9 Hz, 3H), 1.29-1.78 (m, 14H), 1.85 (s, 3H), 2.04 (m, 1H), 4.13 (d, J=10.6, 4.9 Hz, 1H), 4.27 (dd, J=10.6, 4.2 Hz, 1H), 4.81 (brs, 1H), 7.50 (d, J=9.1 Hz, 1H), 7.64 (m, 1H), 7.70 (dd, J=7.6, 2.3 Hz, 1H), 7.89 (d, J=9.5 Hz, 1H), 7.96 (s, 1H), 8.27 (d, J=9.1 Hz, 1H).

Example 23

(R)-2-amino-2-(6-(trans-4-butylcyclohexyloxy)naphthalen-2-yl)propyl dihydrogen phosphate The title compound was prepared from (R)-2-amino-2-(6-((1S,4R)-4-butylcyclohexyloxy)naphthalen-2-yl)propan-1-ol (Example 8) analogously to the methods of Examples 18-21, affording 11.2 mg of solid (39% yield). LCMS (419.76, [M-NH2]+, 100%). $^1$H NMR (400 MHz, $CD_3OD$) δ ppm 0.92 (t, J=7.0 Hz, 3H), 1.05-1.65 (m, 14H), 1.85 (s, 3H), 2.16 (br d, J=12.8 Hz, 1H), 4.21 (dd, J=11.2, 4.8 Hz, 1H), 4.35 (dd, J=11.2, 6.0 Hz, 1H), 4.42 (m, 1H), 7.50 (d, J=9.1 Hz, 1H), 7.64 (m, 1H), 7.69 (m, 1H), 7.88 (d, J=9.2 Hz), 7.96 (s, 1H), 8.26 (d, J=9.0 Hz, 1H).

Example 24

(R)-4-[6-(trans-4-tert-Butyl-cyclohexyloxy)-naphthalen-2-yl]-4-methyl-oxazolidin-2-one (R)-4-(6-hydroxynaphthalen-2-yl)-4-methyloxazolidin-2-one (Example 4, 0.0509 g, 0.000209 mol) was dissolved in tetrahydrofuran (3.00 mL, 0.0370 mol) in a capped 40 mL EPA vial equipped with a magnetic stir bar. Cis-4-tert-butyl-cyclohexanol (0.0392 g, 0.000251 mol) was added, followed by triphenylphosphine (0.0878 g, 0.000335 mol) and the reaction was heated to reflux. Diisopropyl azodicarboxylate (0.0659 mL, 0.000335 mol) was added and the reaction was heated at reflux overnight with stirring. TLC analysis showed that the reaction was complete. The mixture was concentrated under vacuum. The resulting product was purified by flash chromatography (0-30% EtOAc in methylene chloride) to give 0.3141 g of the title compound (66% yield).

Example 25

(R)-2-amino-2-(6-(trans-4-tert-butylcyclohexyloxy)naphthalen-2-yl)propan-1-ol (R)-4-[6-trans-(4-tert-Butyl-cyclohexyloxy)-naphthalen-2-yl]-4-methyl-oxazolidin-2-one (Example 24, 0.03878 g, 0.0001016 mol) was dissolved in Ethanol (1.00 mL, 0.0171 mol) in a capped 40 mL vial equipped with a magnetic stir bar. 4.2 M of lithium hydroxide monohydrate in water (1.00 mL) was added and the reaction was refluxed overnight. TLC analysis showed that the reaction was complete. The solvent was removed under vacuum. The product was diluted in methylene chloride (5 mL) and water was added (5 mL). The layers were separated and the organic phase was then concentrated to dryness under vacuum, and purified by HPLC to give 48 mg of the title compound (13% yield). MS: m/z=339.47 [M-NH2]+. $^1$H NMR (400 MHz, MeOD) δ 0.92-0.97 (m, 9 H), 1.10-1.20 (m, 1 H), 1.23-1.35 (m, 2 H), 1.39-1.51 (m, 2 H), 1.79 (s, 3 H), 1.90-1.98 (m, 2 H), 2.29 (dd, J=12.55, 2.01 Hz, 2 H), 3.81-3.86 (m, 1 H), 3.91-3.96 (m, 1 H), 4.32-4.43 (m, 1 H), 7.19 (dd, J=8.78, 2.51 Hz, 1 H), 7.28 (d, J=2.26 Hz, 1 H), 7.53 (dd, J=8.66, 2.13 Hz, 1 H), 7.80-7.89 (m, 3 H)

Example 26

(R)-2-amino-2-(6-(trans-4-tert-butylcyclohexyloxy)naphthalen-2-yl)propyl dihydrogen phosphate (R)-2-amino-2-(6-(trans-4-tert-butylcyclohexyloxy)naphthalen-2-yl)propan-1-ol (Example 25, 30.0 mg, 0.0000844 mol) in chloroform (4 mL, 0.05 mol) and saturated aqueous sodium bicarbonate solution (2 mL, 0.02 mol) and di tert-butyldicarbonate (27.6 mg, 0.000126 mol) was added and the mixture was stirred at rt for 24 h. TLC showed complete reaction. After separation of organic layer, the aqueous layer was extracted with $CHCl_3$. The organic layer was washed with brine and dried over anhydrous $Na_2SO_4$. The concentrated residue was chromatographed with MeOH/$CH_2Cl_2$ (0-55%) to give the product (25.2 mg, 66% yield).

To a solution of the above product (25.2 mg, 0.0000553 mol) and 1H-tetrazole (17.7 mg, 0.000253 mol) in tetrahydrofuran (0.9 mL, 0.01 mol) was added di tert-butyl N,N- diethylphosphoramidite (35.1 µL, 0.000126 mol) at rt. The resulting mixture was stirred at rt overnight, then hydrogen peroxide (100 µL, 0.001 mol) was added and the mixture was is stirred at rt for 1 h. The reaction was quenched with satd. $NaS_2O_3$, then extracted with EtOAc, then dried over $Na_2SO_4$. The residue was chromatographed with MeOH—$CH_2Cl_2$ (0-20%) to give desired product.

The above product (42.6 mg, 0.0000658 mol) was dissolved in acetic acid (2.0 mL, 0.035 mol) and 10 M hydrogen chloride in water (0.5 mL) was added and the mixture was stirred for 1 day. LCMS give a single peak $R_f$=1.61. Removal of solvent and lyophilizing gave an oil, chromatography with HPLC $H_2O$/acetonitrile (0.1% TFA) gave product (7.5 mg, 26% yield). LCMS 419.28, [M-NH2]+, 100%), 871.49 ([M+ M+1]+, 30%). $^1$H NMR (400 MHz, $CD_3OD$) δ ppm 0.92 (s, 9H), 1.08-1.93 (m, 8H), 1.86 (s, 3H), 2.27 (br d, J=13.3 Hz, 1 H), 4.24 (dd, J=10.9, 4.4 Hz, 1H), 4.35 (dd, J=10.9, 4.1 Hz, 1H), 4.40 (m, 1H), 7.18 (dd, J=10.8, 1.6 Hz, 1H), 7.28 (s, 1H), 7.55 (d, J=8.5 Hz, 1H), 7.83 (d, J=8.9 Hz, 1H), 7.88 (d, J=8.9 Hz, 1H), 7.89 (s, 1H).

Example 27

(R)-2-amino-2-(6-(cis-4-(4-(pentan-3-yloxy)phenyl) cyclohexyloxy)naphthalen-2-yl)propan-1-ol (R)-4-(6-(4-(4-(pentan-3-yloxy)phenyl)cyclohexyloxy) naphthalen-2-yl)-4-methyloxazolidin-2-one was prepared from (R)-4-(6-hydroxynaphthalen-2-yl)-4-methyloxazolidin-2-one and trans-4-(4-(pentan-3-yloxy)phenyl)cyclohexanol analogously to Example 5. Then a mixture of (R)-4-(6-(4-(4-(pentan-3-yloxy)phenyl)cyclohexyloxy)naphthalen-2-yl)-4-methyloxazolidin-2-one (47.8 mg, 0.0000980 mol) and lithium hydroxide (26 mg, 0.0011 mol) in ethanol (2 mL, 0.04 mol) and water (0.5 mL, 0.03 mol) was heated to reflux for overnight. LCMS showed reaction completed. The solvent was removed under vacuum and the residue was partitioned between water and $CH_2Cl_2$. The aqueous layer was extensively extracted with $CH_2Cl_2$. The combined organic phase was dried over $Na_2SO_4$. The concentrated residue was taken up into DCM and subjected to chromatography purification with $CH_2Cl_2$/MeOH (10:90 to 80:20) to give the product (29.0 mg, 64% yield). LCMS 445.33 ([M-NH$_2$]+, 100%). $^1$H NMR (400 MHz, $CD_3OD$) δ ppm 0.95 (t, J=7.2 Hz, 6 H), 1.53 (s, 3 H), 1.60-1.73 (m, 6 H), 1.73-1.81 (m, 2H), 1.89-1.99 (m, 2 H), 2.22 (d, J=13.2 Hz, 2 H), 2.59 (br. d, J=12.0, 10.9 Hz, 1H), 3.68 (d, J=10.9 Hz, 1H), 3.72 (d, J=10.9 Hz, 1H), 4.12 (m, 1H), 4.80 (brs, 1 H), 6.83 (d, J=8.6 Hz, 2H), 7.15 (d, J=8.6 Hz, 2H), 7.21 (dd, J=8.9, 2.4 Hz, 1H), 7.25 (br s, 7.55 (dd, J=8.9, 1.8 Hz, 1H), 7.73 (d, J=8.7 Hz, 1H), 7.79 (d, J=8.7 Hz, 1H), 7.85 (br s, 1H).

Example 28

(R)-2-amino-2-(6-(cis-4-(4-isopropoxyphenyl)cyclohexyloxy)naphthalen-2-yl)propan-1-ol The mixture of 4-trans-(4-isopropoxyphenyl)cyclohexanol (116 mg, 0.000493 mol), (R)-4-(6-hydroxynaphthalen-2-yl)-4-methyloxazolidin-2-one (Example 4, 100.0 mg, 0.0004111 mol) and triphenylphosphine (129 mg, 0.000493 mol) in tetrahydrofuran (4 mL, 0.05 mol) was heated to reflux, and diisopropyl azodicarboxylate (0.0971 mL, 0.000493 mol) was added dropwise and was stirred and refluxed for overnight. TLC monitoring showed the reaction to be incomplete. The mixture was taken up into DCM and subjected to chromatographic purification with EtOAc/hex- ane (10:90 to 80:20) to give (R)-4-(6-(4-trans-(4-isopropoxyphenyl)cyclohexyloxy)naphthalen-2-yl)-4-methyloxazolidin-2-one (80.7 mg, 42% yield). LCMS 460.44 ([M+ 1]+, 100%).

The mixture of (R)-4-(6-(4-cis-(4-isopropoxyphenyl)cyclohexyloxy)naphthalen-2-yl)-4-methyloxazolidin-2-one (80.7 mg, 0.000176 mol) and lithium hydroxide (46 mg, 0.0019 mol) in ethanol (4 mL, 0.08 mol) and water (0.9 mL, 0.05 mol) was heated to reflux overnight. LCMS showed reaction complete. The solvent was removed under vacuum and the residue was partitioned between water and $CH_2Cl_2$. The aqueous layer was extensively extracted with $CH_2Cl_2$. The combined organic phase was dried over $Na_2SO_4$. The concentrated residue was taken up into DCM and subjected to chromatographic purification with $CH_2Cl_2$/MeOH (10:90 to 80:20) to give the product as a white solid (44.8 mg, 59% yield). LCMS 417.30 ([M-NH$_2$]+, 100%). $^1$H NMR (400 MHz, $CD_3OD$) δ ppm 1.29 (d, J=6.0 Hz, 6 H), 1.52 (s, 3 H), 1.67 (dd, J=12.3, 2.6 Hz, 2 H), 1.77 (dd, J=13.5, 13.5 Hz, 2 H), 1.93 (ddd, J=12.9, 12.6, 3.1 Hz, 2 H), 2.22 (d, J=14.8 Hz, 2 H), 2.59 (tt, J=11.9, 3.4 Hz, 1H), 3.68 (d, J=10.9 Hz, 1H), 3.72 (d, J=10.9 Hz, 1H), 4.54 (m, 1 H), 4.79 (brs, 1H), 6.83 (d, J=8.6 Hz, 2H), 7.15 (d, J=8.6 Hz, 2H), 7.21 (dd, J=8.8, 2.4 Hz, 1H), 7.25 (br s, 1H), 7.55 (dd, J=8.8, 2.0 Hz, 1H), 7.73 (d, J=8.7 Hz, 1H), 7.79 (d, J=8.7 Hz, 1H), 7.85 (br s, 1H).

Example 29

(R)-2-amino-2-(6-(cis-4-(4-methoxyphenyl)cyclohexyloxy)naphthalen-2-yl)propan-1-ol The mixture of 4-trans-(4-methoxyphenyl)cyclohexanol (102 mg, 0.000493 mol), (R)-4-(6-hydroxynaphthalen-2-yl)-4-methyloxazolidin-2-one (Example 4, 100.0 mg, 0.0004111 mol) and triphenylphosphine (129 mg, 0.000493 mol) in tetrahydrofuran (4 mL, 0.05 mol) was heated to reflux, and diisopropyl azodicarboxylate (0.0971 mL, 0.000493 mol) was added dropwise and was stirred and refluxed for overnight. TLC monitoring showed the reaction to be incomplete. The mixture was taken up into DCM and subjected to chromatographic purification with EtOAc/hexane (10:90 to 80:20) to give (R)-4-(6-(4-trans-(4-methoxyphenyl)cyclohexyloxy)naphthalen-2-yl)-4-methyloxazolidin-2-one (85.5 mg, 48% yield). LCMS 432.42 ([M+1]+, 100%).

The mixture of (R)-4-(6-(4-cis-(4-methoxyphenyl)cyclohexyloxy)naphthalen-2-yl)-4-methyloxazolidin-2-one (85.5 mg 0.000198 mol) and lithium hydroxide (52 mg, 0.0022 mol) in ethanol (4 mL, 0.08 mol) and water (0.9 mL, 0.05 mol) was heated to reflux overnight. LCMS showed reaction complete. The solvent was removed under vacuum and the residue was partitioned between water and $CH_2Cl_2$. The aqueous layer was extensively extracted with $CH_2Cl_2$. The combined organic phase was dried over $Na_2SO_4$. The concentrated residue was taken up into DCM and subjected to chromatographic purification with $CH_2Cl_2$/MeOH (10:90 to 80:20) to give the product as a white solid (60.3 mg, 75% yield). LCMS 389.26 ([M-NH$_2$]+, 100%). $^1$H NMR (400 MHz, $CD_3OD$) δ ppm 1.52 (s, 3 H), 1.67 (dd, J=12.2 Hz, 2 H), 1.77 (dd, J=13.9, 13.9 Hz, 2 H), 1.93 (ddd, J=12.9, 12.7, 2.3 Hz, 2 H), 2.22 (d, J=13.3 Hz, 2 H), 2.60 (dd, J=12.3, 11.6 Hz, 1H), 3.68 (d, J=10.8 Hz, 1H), 3.72 (d, J=10.8 Hz, 1H), 3.76 (s, 3H), 4.79 (brs, 1H), 6.85 (d, J=8.5 Hz, 2H), 7.17 (d, J=8.5 Hz, 2H), 7.21 (dd, J=9.0, 2.4 Hz, 1H), 7.25 (br s, 1H), 7.55 (dd, J=8.7, 1.8 Hz, 1H), 7.73 (d, J=8.7 Hz, 1H), 7.79 (d, J=8.9 Hz, 1H), 7.85 (br s, 1H).

Example 30

(R)-2-amino-2-(6-(cis-4-phenylcyclohexyloxy)naphthalen-2-yl)propan-1-ol

The mixture of trans-4-phenyl-cyclohexanol (86.9 mg, 0.000493 mol), (R)-4-(6-hydroxynaphthalen-2-yl)-4-methyloxazolidin-2-one (Example 4, 100.0 mg, 0.0004111 mol) and triphenylphosphine (129 mg, 0.000493 mol) in tetrahydrofuran (4 mL, 0.05 mol) was heated to reflux, and diisopropyl azodicarboxylate (0.0971 mL, 0.000493 mol) was added dropwise and was stirred and refluxed for 3 hours. TLC monitoring showed the reaction to be complete. The mixture was taken up into DCM and subjected to chromatographic purification with EtOAc/hexane (10:90 to 80:20) to give (R)-4-(6-(trans-4-phenylcyclohexyloxy)naphthalen-2-yl)-4-methyloxazolidin-2-one (160 mg, 97% yield). LCMS 402.28 ([M+1]+, 100%).

The mixture of (R)-4-(6-(cis-4-phenyl-cyclohexyloxy)naphthalen-2-yl)-4-methyloxazolidin-2-one (160 mg, 0.00040 mol) and lithium hydroxide (100 mg, 0.0044 mol) in ethanol (4 mL, 0.08 mol) and water (0.9 mL, 0.05 mol) was heated to reflux overnight. LCMS showed reaction complete. The solvent was removed under vacuum and the residue was partitioned between water and $CH_2Cl_2$. The aqueous layer was extensively extracted with $CH_2Cl_2$. The combined organic phase was dried over $Na_2SO_4$. The concentrated residue was taken up into DCM and subjected to chromatographic purification with $CH_2Cl_2$/MeOH (10:90 to 80:20) to give the product. A final purification on Gilson HPLC 0.1% TFA-ACN/$H_2O$ to gave the product as a white solid (62.0 mg, 41% yield). LCMS 359.33 ([M-$NH_2$]+, 100%). $^1$H NMR (400 MHz, $CD_3OD$) δ ppm 1.71 (brd, J=13.1 Hz, 2 H), 1.78 (s, 3 H), 1.83 (brd, J=14.7 Hz, 2 H), 1.98 (dd, J=13.7, 11.1 Hz, 2 H), 2.24 (d, J=12.6 Hz, 2 H), 2.67 (dd, J=11.6, 11.5 Hz, 1H), 3.82 (d, J=11.7 Hz, 1H), 3.92 (d, J=11.7 Hz, 1H), 4.84 (brs, 1H), 7.16 (m, 1H), 7.27-7.32 (m, 6H), 7.52 (d, J=8.7 Hz, 1H), 7.85 (m, 3H).

Example 31

(R)-2-amino-2-(6-(cis-4-phenylcyclohexyloxy)-5-(trifluoromethyl)naphthalen-2-yl)propan-1-ol A mixture of (R)-4-(6-(cis-4-phenyl-cyclohexyloxy)naphthalen-2-yl)-4-methyloxazolidin-2-one (Example 30, 71.4 mg 0.000178 mol), N-iodosuccinimide (44.8 mg, 0.000199 mol) and zirconium tetrachloride (6.2 mg, 0.000027 mol) in methylene chloride (1.46 mL, 0.0228 mol) was heated to reflux under Ar in a vial for 6 h. LCMS showed the reaction to be completed. The precipitate was filtered off and the residue was purified with Isco column eluted with EtOAc in hexane from 0 to 40% to give (R)-4-(6-(trans-4-phenyl-cyclohexyloxy)-5-iodonaphthalen-2-yl)-4-methyloxazolidin-2-one as a solid (81.0 mg, 86% yield). LCMS 528.27 ([M+1], 80%).

To a solution of (R)-4-(6-(cis-4-phenyl-cyclohexyloxy)-5-iodonaphthalen-2-yl)-4-methyloxazolidin-2-one (81.0 mg, 0.154 mmol), hexamethylphosphoramide (0.13 mL, 0.77 mmol) and copper(I) iodide (44 mg, 0.23 mmol) in N,N-dimethylformamide (0.8 mL, 10 mmol) was added methyl fluorosulphonyldifluoroacetate (0.10 mL, 0.77 mmol). The mixture was heated at 80° C. overnight. The mixture was diluted with EtOAc and filtered through CELITE™. After washing with water, the solvent was evaporated and chromatographically separated with EtOAc and hexane, giving (R)-4-(6-(trans-4-phenylcyclohexyloxy)-5-trifluoromethyl-naphthalen-2-yl)-4-methyloxazolidin-2-one (46.7 mg, 65% yield). LCMS 470.28 ([M+1], 80%).

The mixture of (R)-4-(6-(cis-4-phenyl-cyclohexyloxy)-5-trifluoromethylnaphthalen-2-yl)-4-methyloxazolidin-2-one (46.7 mg, 0.0000995 mol) and lithium hydroxide (26 mg, 0.0011 mol) in ethanol (2 mL, 0.04 mol) and water (0.4 mL, 0.02 mol) was heated to reflux overnight. LCMS showed reaction complete. The solvent was removed under vacuum and the residue was partitioned between water and $CH_2Cl_2$. The aqueous layer was extensively extracted with $CH_2Cl_2$. The combined organic phase was dried over $Na_2SO_4$. The concentrated residue was taken up into DCM and subjected to chromatographic purification with $CH_2Cl_2$/MeOH (10:90 to 80:20) to give the product as a white solid (22.1 mg, 50% yield). LCMS 427.26 ([M-$NH_2$]+, 100%). $^1$H NMR (400 MHz, $CD_3OD$) δ ppm 1.52 (s, 3 H), 1.67 (brd, J=11.8 Hz, 2 H), 1.82 (dd, J=13.4, 13.1 Hz, 2 H), 2.02 (ddd, J=13.1, 12.8, 3.0 Hz, 2 H), 2.20 (d, J=14.8 Hz, 2 H), 2.65 (ddd, J=12.2, 12.2, 3.8 Hz, 1H), 3.68 (d, J=10.9 Hz, 1H), 3.73 (d, J=10.9 Hz, 1H), 5.01 (brs, 1H), 7.14-7.30 (m, 5H), 7.50 (d, J=9.3 Hz, 1H), 7.71 (dd, J=9.3, 2.2 Hz, 1H), 7.95 (d, J=2.1 Hz, 1H), 8.08 (d, J=9.3 Hz, 1H), 8.16 (d, J=9.3 Hz, 1 H).

Example 32

(R)-4-{6-[4-(1,1-dimethylpropyl)-cyclohexyloxy]-naphthalen-2-yl}-4-methyloxazolidin-2-one To a mixture of (R)-4-(6-hydroxy-naphthalen-2-yl)-4-methyl-oxazolidin-2-one (Example 4, 300.0 mg, 1.233 mmol) and 4-(1,1-dimethyl-propyl)-cyclohexanol (252 mg, 1.48 mmol) in tetrahydrofuran (5 mL, 60 mmol) was added triphenylphosphine polymer-bound (1.07 g, 1.97 mmol). After the mixture was stirred at room temperate for 10 min, diisopropyl azodicarboxylate (0.388 mL, 1.97 mmol) was added dropwise. The mixture was stirred at room temperate for 48 hrs. The insoluble material was passed over a CELITE™ bed and washed with ethyl acetate. After the solvent was concentrated, the residue was purified with silica gel column eluted with ethyl acetate in hexanes from 0 to 40% to give 410 mg of white precipitate (R)-4-{6-[4-(1,1-dimethylpropyl)-cyclohexyloxy]-naphthalen-2-yl}-4-methyloxazolidin-2-one (84% yield). MS: m/z=396.30 M+H.

Example 33

(R)-4-{6-[trans-4-(1,1-dimethyl-propyl)-cyclohexyloxy]-5-iodonaphthalen-2-yl}-4-methyl-oxazolidin-2-one A mixture of N-iodosuccinimide (204.77 mg, 0.91016 mmol), (R)-4-{6-[trans-4-(1,1-dimethyl-propyl)-cyclohexyloxy]-naphthalen-2-yl}-4-methyl-oxazolidin-2-one (300.00 mg, 0.75847 mmol) and zirconium tetrachloride (35.3 mg, 0.152 mmol) in methylene chloride (10.00 mL) was stirred RT for 2.5 hrs. LCMS showed the reaction was completed. The solution was purified with 4 g of silica gel column eluted with ethyl acetate in hexanes from 10 to 50% to give 100 mg of white precipitate, (R)-4-{6-[trans-4-(1,1-dimethylpropyl)-cyclohexyloxy]-5-iodo-naphthalen-2-yl}-4-methyl-oxazolidin-2-one. (20% yield). MS: m/z=522.20 M+H.

Example 34

(R)-4-{6-[trans-4-(1,1-dimethyl-propyl)-cyclohexyloxy]-5-trifluoromethyl-naphthalen-2-yl}-4-methyl-oxazolidin-2-one To a solution of (R)-4-{6-[trans-4-(1,1-dimethyl-propyl)-cyclohexyloxy]-5-iodonaphthalen-2-yl}-4-methyl-oxazolidin-2-one (100.00 mg, 0.19178 mmol), hexamethylphosphoramide (0.1685 mL, 0.9589 mmol) and copper(I) iodide (54.79 mg, 0.2877 mmol) in N,N-dimethylformamide (1.0 mL) was added methyl fluorosulphonyldifluoroacetate (0.1258 mL, 0.9589 mmol). The mixture was heated at 80° C. overnight. The solution was diluted with EtOAc and washed with water 3×. After the solvent was concentrated and residue was purified with column (4 g silica gel) and eluted with EtOAc in hexanes from 0 to 50% to give 35 mg of white precipitate, (R)-4-{6-[trans-4-(1,1-dimethyl-propyl)-cyclohexyloxy]-5-trifluoromethyl-naphthalen-2-yl}-4-methyloxazolidin-2-one (39% yield). MS: m/z=464.30 M+H.

Example 35

(R)-2-amino-2-{6-[trans-4-(1,1-dimethyl-propyl)-cyclohexyloxy]-5-trifluoromethyl-naphthalen-2-yl}-propan-1-ol A mixture of (R)-4-{6-[trans-4-(1,1-dimethyl-propyl)-cyclohexyloxy]-5-trifluoromethyl-naphthalen-2-yl}-4-methyl-oxazolidin-2-one (33.00 mg, 0.07119 mmol) in 4.2 M lithium hydroxide in a mixture solvent of water (0.9 mL) and ethanol (0.9 mL) was heated at 80° C. overnight. The solution was concentrated and the residue was partitioned between methylene chloride (4 mL) and water (2 mL). The organic phase was washed with water, dried over MgSO$_4$, filtered and concentrated to give 28 mg of white precipitate, (R)-2-amino-2-{6-[trans-4-(1,1-dimethyl-propyl)-cyclohexyloxy]-5-trifluoromethyl-naphthalen-2-yl}-propan-1-ol (90% yield). MS: m/z=421.30 M-16. $^1$H NMR (400 MHz, CDCl$_3$) δ ppm 0.74-0.89 (m, 10 H), 1.04-1.22 (m, 2H), 1.22-1.35 (m, 2 H), 1.43-1.61 (m, 5H), 1.82 (d, J=11.29 Hz, 2H), 2.18 (d, J=12.80 Hz, 2H), 2.35 (s, 3H), 3.63-3.82 (m, 2H), 4.23-4.36 (m, 1H), 7.28 (d, 1H), 7.61 (dd, J=9.16, 1.88 Hz, 1H), 7.82-7.95 (m, 2H), 8.19 (d, J=7.78 Hz, 1H).

Example 36

(R)-4-methyl-4-(6-(4-pentylcyclohexyloxy)naphthalen-2-yl)oxazolidin-2-one (R)-4-(6-Hydroxnaphthalen-2-yl)-4-methyl-oxazolidin-2-one (Example 4, 0.3303 g, 0.001358 mol) was added to a capped 40 mL vial equipped with a magnetic stir bar. 4-Pentyl-cyclohexanol (0.277 g, 0.00163 mol) was added, followed by tetrahydrofuran (6.00 mL, 0.0740 mol). Triphenylphosphine polymer-bound (1.17 g, 0.00217 mol) was then added and the mixture was stirred for 5 minutes. Diisopropyl azodicarboxylate (0.428 mL, 0.00217 mol) was then added and the mixture was stirred for 48 hours at room temperature. The mixture was diluted in ethyl acetate, filtered through CELITE™, concentrated under vacuum and purified by flash chromatography (0-5% MeOH in dichloromethane) to give 0.3672 g of the title compound (68% yield).

Example 37

(R)-2-amino-2-(6-(4-pentylcyclohexyloxy)naphthalen-2-yl)propan-1-ol (R)-4-methyl-4-(6-(4-pentylcyclohexyloxy)naphthalen-2-yl)oxazolidin-2-one (0.3672 g, 0.0009284 mol) was dissolved in ethanol (5.00 mL, 0.0856 mol) in a capped 40 mL EPA vial equipped with a stir bar. 4.2 M Lithium hydroxide, monohydrate in water (2.00 mL) was added and the mixture was heated at 80° C. overnight. TLC analysis showed that the reaction was complete. The mixture was concentrated to dryness under vacuum. The product was dissolved in methylene chloride (5 mL) and washed with water (2×5 mL). The layers were separated (phase separator cartridge) and the organic layer was concentrated to dryness and purified by HPLC to give 0.467 g of the title compound (14% yield). MS: m/z=353.36 [M-NH$_2$]+. $^1$H NMR (400 MHz, MeOD) δ 0.90-0.98 (m, 3 H), 1.10-1.24 (m, 1 H), 1.26-1.54 (m, 8 H), 1.58-1.74 (m, 2 H), 1.80 (s, 3 H), 1.86-1.95 (m, 2 H), 2.03-2.13 (m, 2 H), 2.20-2.29 (m, 2 H), 3.80-3.87 (m, 1 H), 3.91-3.97 (m, 1 H), 4.36-4.79 (m, 1 H, 1:1 ratio), 7.17-7.26 (m, 1 H, 1:1 ratio), 7.28 (d, J=2.51 Hz, 1 H), 7.53 (dd, J=8.78, 2.01 Hz, 1 H), 7.80-7.90 (m, 3 H)

Example 38

(R)-4-methyl-4-(6-(4-propylcyclohexyloxy)naphthalen-2-yl)oxazolidin-2-one (R)-4-(6-Hydroxynaphthalen-2-yl)-4-methyl-oxazolidin-2-one (Example 4, 0.301 g, 0.00124 mol) was dissolved in tetrahydrofuran (5.00 mL, 0.0616 mol). 4-Propylcyclohexanol (0.211 g, 0.00148 mol) and triphenylphosphine polymer-bound (1.07 g, 0.00198 mol) were added and the mixture was stirred at room temperature. Diisopropyl azodicarboxylate (0.390 mL, 0.00198 mol) was then added and the mixture was stirred for 2 days at room temperature. The mixture was filtered through CELITE™, concentrated and purified by flash chromatography (0-30% EtOAc in methylene chloride) to give 0.4942 g of to the title product (109% yield).

Example 39

(R)-2-amino-2-(6-(4-propylcyclohexyloxy)naphthalen-2-yl)propan-1-ol (R)-4-methyl-4-(6-(4-propylcyclohexyloxy)naphthalen-2-yl)oxazolidin-2-one (0.4786 g, 0.001302 mol) was dissolved in ethanol (5.00 mL, 0.0856 mol) in a capped 40 mL vial equipped with a magnetic stir bar. 4.2 M Lithium hydroxide, monohydrate in water (2.8 mL) was added and the mixture was heated overnight at 80° C. TLC analysis showed that the reaction was complete. The reaction mixture was concentrated under vacuum. The product was dissolved in methylene chloride (5 mL) and washed with water (2×5 mL). The layers were separated (phase separator cartridge) and the organic layer was concentrated under vacuum and purified by HPLC to give 0.418 g of the title compound (9% yield). MS: m/z=325.35 [M-NH$_2$]+. $^1$H NMR (400 MHz, MeOD) δ 0.95 (t, J=7.28 Hz, 3 H), 1.10-1.23 (m, 1 H), 1.25-1.33 (m, 2 H), 1.35-1.51 (m, 5 H), 1.57-1.74 (m, 3 H), 1.80 (s, 3 H), 1.87-1.95 (m, 1 H), 2.04-2.13 (m, 2 H), 2.21-2.28 (m, 1 H), 3.80-3.86 (m, 1 H), 3.91-3.97 (m, 1 H), 4.36-4.46 (m, 0.3 H), 4.73-4.78 (m, 0.7 H), 7.19 (dd, J=8.91, 2.38 Hz, 0.3 H), 7.24 (dd, J=8.91, 2.38 Hz, 0.7 H), 7.28 (d, J=2.26 Hz, 1 H), 7.53 (dd, J=8.78, 2.01 Hz, 1 H), 7.80-7.90 (m, 3 H)

Example 40

(R)-4-methyl-4-(6-(cis-4-methylcyclohexyloxy)naphthalen-2-yl)oxazolidin-2-one (R)-4-(6-Hydroxynaphthalen-2-yl)-4-methyl-oxazolidin-2-one (Example 4, 0.3144 g, 0.001292 mol) was dissolved in tetrahydrofuran (5.00 mL, 0.0616 mol) in a capped 40 mL vial. trans-4-Methyl-cyclohexanol (0.177 g, 0.00155 mol) and triphenylphosphine polymer-bound (1.12 g, 0.00207 mol) were added and the mixture was stirred at room temperature. Diisopropyl azodicarboxylate (0.407 mL, 0.00207 mol) was added and the mixture was stirred for 2 days at room temperature. The mixture was filtered through CELITE™, concentrated and purified by flash column chromatography (0-30% EtOAc in methylene chloride) to give 0.3059 g of the title compound (69% yield).

Example 41

(R)-2-amino-2-(6-(cis-4-methylcyclohexyloxy)naphthalen-2-yl)propan-1-ol

To a solution of (R)-4-Methyl-4-[6-(cis4-methyl-cyclohexyloxy)-naphthalen-2-yl]-oxazolidin-2-one (0.4420 g, 0.001302 mol) in ethanol (5.00 mL, 0.0856 mol) in a capped 40 mL vial was added 4.2 M Lithium hydroxide, monohydrate in water (2.8 mL). The mixture was heated overnight at 80° C. TLC analysis showed the reaction was complete. The mixture was concentrated to dryness under vacuum. Methylene chloride (5 mL) and water (5 mL) were added and the layers were separated (2×). The organic layer was concentrated under vacuum and purified by HPLC to give 0.0233 g of the title compound (6% yield). MS: m/z=297.29 [M-NH$_2$]+. $^1$H NMR (400 MHz, MeOD) δ 0.98 (d, J=6.02 Hz, 3 H), 1.40-1.51 (m, 2 H), 1.51-1.60 (m, 3 H), 1.64-1.74 (m, 2 H), 1.79 (s, 3 H), 2.03-2.14 (m, 2 H), 3.83 (d, J=11.55 Hz, 1 H), 3.93 (d, J=11.55 Hz, 1 H), 4.69-4.77 (m, 1 H), 7.23 (dd, J=8.91, 2.38 Hz, 1 H), 7.27 (d, J=2.51 Hz, 1 H), 7.53 (dd, J=8.78, 2.01 Hz, 1 H), 7.79-7.89 (m, 3 H)

Example 42

(R)-4-[6-(cis4-Ethyl-cyclohexyloxy)-naphthalen-2-yl]-4-methyloxazolidin-2-one (R)-4-(6-Hydroxynaphthalen-2-yl)-4-methyl-oxazolidin-2-one (0.3594 g, 0.001477 mol) was added to a capped 40 mL vial. trans-4-Ethylcyclohexanol (0.227 g, 0.00177 mol) was added, followed by tetrahydrofuran (6.00 mL, 0.0740 mol). Triphenylphosphine polymer-bound (1.28 g, 0.00236 mol) was added and the mixture was stirred for 5 minutes. Diisopropyl azodicarboxylate (0.465 mL, 0.00236 mol) was added and the mixture was stirred for 48 hours at room temperature. The mixture was diluted in ethyl acetate, filtered through CELITE™, concentrated under vacuum and purified by flash chromatography (0-20% EtOAc in methylene chloride) to give 0.4603 g of the title compound (88% yield).

Example 43

(R)-2-amino-2-(6-(cis-4-ethylcyclohexyloxy)naphthalen-2-yl)propan-1-ol (R)-4-[6-(cis-4-Ethyl-cyclohexyloxy)-naphthalen-2-yl]-4-methyl-oxazolidin-2-one (0.4603 g, 0.001302 mol) was dissolved in ethanol (5.00 mL, 0.0856 mol) in a capped 40 mL vial equipped with a magnetic stir bar. 4.2 M Lithium hydroxide, monohydrate in water (2.8 mL) was added and the mixture was heated overnight at 80° C. TLC analysis showed the reaction was complete. The mixture was concentrated to dryness under vacuum. Methylene chloride (5 mL) and water (5 mL) were added and the layers were separated by phase separator cartridge. The organic layer was dried with MgSO$_4$, filtered, concentrated and purified by HPLC to give 0.038 g of the title compound (9% yield). MS: m/z=311.26 [M-NH2]+. $^1$H NMR (400 MHz, MeOD) δ 0.95 (t, J=7.15 Hz, 3 H), 1.28-1.38 (m, 3 H), 1.39-1.50 (m, 2 H), 1.58-1.74 (m, 4 H), 1.80 (s, 3 H), 2.04-2.14 (m, 2 H), 3.83 (d, J=11.55 Hz, 1 H), 3.94 (d, J=11.55 Hz, 1 H), 4.76 (br. s., 1 H), 7.21-7.30 (m, 2 H), 7.53 (dd, J=8.91, 1.88 Hz, 1 H), 7.82-7.88 (m, 3 H)

Example 44

(R)-4-methyl-4-(6-(4-(trifluoromethyl)cyclohexyloxy)naphthalen-2-yl)oxazolidin-2-one (R)-4-(6-Hydroxynaphthalen-2-yl)-4-methyl-oxazolidin-2-one (0.1042 g, 0.0004284 mol) was dissolved in tetrahydrofuran (5.00 mL, 0.0616 mol) in a capped 40 mL vial. 4-Trifluoromethylcyclohexanol (0.101 g, 0.000600 mol) was added, followed by triphenylphosphine (0.180 g, 0.000685 mol) and the mixture was refluxed for 5 minutes. Diisopropyl azodicarboxylate (0.135 mL, 0.000685 mol) was then added and the mixture was heated at reflux overnight. TLC analysis showed that the reaction was complete. The mixture was concentrated to dryness under vacuum and purified by flash chromatography (0-20% EtOAc in methylene chloride).

Example 45

(R)-2-amino-2-(6-(4-(trifluoromethyl)cyclohexyloxy)naphthalen-2-yl)propan-1-ol (R)-4-methyl-4-(6-(4-(trifluoromethyl)cyclohexyloxy)naphthalen-2-yl)oxazolidin-2-one (0.1442 g, 0.0003665 mol) was dissolved in ethanol (1.00 mL, 0.0171 mol) in a capped vial equipped with a magnetic stir bar. 4.2 M Lithium hydroxide, monohydrate in water (1.00 mL) was added and the mixture was heated overnight at 80° C. with stirring. TLC analysis showed that the reaction was complete. The mixture was concentrated to dryness under vacuum. Water (3 mL) and methylene chloride (3 mL) were added and the layers were separated (2×). The combined organic layers were concentrated under vacuum and purified by HPLC to give the title compound as a TFA salt in 0.0388 g (29% yield). MS: m/z=351.41 [M-NH$_2$]+. $^1$H NMR (400 MHz, MeOD) δ 1.48-1.65 (m, 2 H), 1.75-1.80 (m, 4 H), 2.04-2.11 (m, 2 H), 2.17-2.25 (m, 2 H), 2.33 (d, J=11.04 Hz, 2 H), 3.79-3.85 (m, 1 H), 3.90-3.95 (m, 1 H), 4.41-4.83 (m, 1 H, 2:1 ratio), 7.16-7.27 (m, 1 H, 2:1 ratio) 7.29-7.32 (m, 1 H), 7.52 (dd, J=8.66, 2.13 Hz, 1 H), 7.79-7.88 (m, 3 H)

Example 46

(R)-4-(6-(4,4-dimethylcyclohexyloxy)naphthalen-2-yl)-4-methyloxazolidin-2-one

To a mixture of 4,4-Dimethylcyclohexanol (63.2 mg, 0.000493 mol), (R)-4-(6-hydroxynaphthalen-2-yl)-4-methyl-oxazolidin-2-one (100 mg, 0.0004 mol), triphenylphosphine (129 mg, 0.000493 mol), and tetrahydrofuran (4 mL, 0.05 mol), diisopropyl azodicarboxylate (0.0971 mL, 0.000493 mol) was added dropwise and was stirred at room temperature overnight. The mixture was diluted with EA and washed with 5% citric acid and brine then dried with magnesium sulfate and concentrated. The crude was taken up into DCM and subjected to ISCO combiflash purification with EtOAc/hexane (0-70) to give product.

Example 47

(R)-2-amino-2-(6-(4,4-dimethylcyclohexyloxy)naphthalen-2-yl)propan-1-ol

The mixture of (R)-4-(6-(4,4-dimethylcyclohexyloxy)naphthalen-2-yl)-4-methyloxazolidin-2-one and lithium hydroxide (45 mg, 0.0019 mol) in ethanol (1.1 mL, 0.019 mol) and water (0.37 mL, 0.021 mol) was heated to reflux for overnight. The crude product was partitioned between ethyl acetate and water and the ethyl acetate layer was concentrated and the crude was brought up in methanol and purified by HPLC. MS: m/z=311.2 [M-NH$_2$]+

Example 48

(R)-4-(6-(trans-4-tert-butylcyclohexyloxy)naphthalen-2-yl)-4-methyloxazolidin-2-one (R)-4-(6-Hydroxynaphthalen-2-yl)-4-methyl-oxazolidin-2-one (0.0509 g, 0.000209 mol) was dissolved in tetrahydrofuran (3.00 mL, 0.0370 mol) in a capped 40 mL EPA vial equipped with a magnetic stir bar. Cis-4-tert-butylcyclohexanol (0.0392 g, 0.000251 mol) was added, followed by triphenylphosphine (0.0878 g, 0.000335 mol) and the reaction was heated to reflux. Diisopropyl azodicarboxylate (0.0659 mL, 0.000335 mol) was added and the reaction was heated at reflux overnight with stirring. TLC analysis showed that the reaction was complete. The mixture was concentrated under vacuum. The resulting product was purified by flash chromatography (0-30% EtOAc in methylene chloride) to give 0.3141 g of the title compound (66% yield).

Example 49

(R)-2-amino-2-(6-(trans-4-tert-butylcyclohexyloxy)naphthalen-2-yl)propan-1-ol (R)-4-[6-(4-tert-Butylcyclohexyloxy)naphthalen-2-yl]-4-methyl-oxazolidin-2-one (0.03878 g, 0.0001016 mol) was dissolved in ethanol (1.00 mL, 0.0171 mol) in a capped 40 mL vial equipped with a magnetic stir bar. 4.2 M Lithium hydroxide, monohydrate in water (1.00 mL) was added and the reaction was refluxed overnight. TLC analysis showed that the reaction was complete. The solvent was removed under vacuum. The product was diluted in methylene chloride (5 mL) and water was added (5 mL). The layers were separated and the organic phase was then concentrated to dryness under vacuum, and purified by HPLC to give 0.0048 g of the title compound (13% yield). MS: m/z=339.47 [M-NH$_2$]+

Example 50

(R)-4-(6-(trans-4-tert-butylcyclohexyloxy)-5-iodonaphthalen-2-yl)-4-methyloxazolidin-2-one (R)-4-[6-(trans-4-tert-Butylcyclohexyloxy)naphthalen-2-yl]-4-methyl-oxazolidin-2-one (0.4719 g, 0.001237 mol) was dissolved in methylene chloride (5.00 mL, 0.0780 mol) in a 40 mL vial. N-Iodosuccinimide (0.312 g, 0.00138 mol) and zirconium tetrachloride (0.043 g, 0.00018 mol) were added and the mixture was stirred at room temperature. After 3 hours the reaction was complete. The mixture was adsorbed onto silica and purified by flash chromatography (0-60% EtOAc in hexanes) to give 0.112 g of the title compound (42% yield).

Example 51

(R)-4-(6-(trans-4-tert-butylcyclohexyloxy)-5-(trifluoromethyl)naphthalen-2-yl)-4-methyloxazolidin-2-one (R)-4-(6-(trans-4-tert-butylcyclohexyloxy)-5-iodonaphthalen-2-yl)-4-methyloxazolidin-2-one (0.2123 g, 0.0004184 mol) was dissolved in N,N-dimethylformamide (2 mL, 0.03 mol) in a capped 40 mL vial equipped with a magnetic stir bar. The solution was flushed with nitrogen for several minutes and degassed via vacuum. Hexamethylphosphoramide (0.364 mL, 0.00209 mol) was then added, followed by copper(I) iodide (0.120 g, 0.000628 mol) and the mixture was stirred for 5 minutes. Again, the mixture was degassed and flushed with nitrogen, then methyl fluorosulphonyldifluoroacetate (0.266 mL, 0.00209 mol) was added and the mixture was heated at 80° C. under nitrogen. After 2.5 hours, HPLC and LCMS analysis showed that all of the starting material had been consumed. The solvent was removed under vacuum. The product was dissolved in DCM and purified by flash chromatography (0-60% EtOAc in hexanes) to give 0.1771 g of the title compound (47% yield).

Example 52

(R)-2-amino-2-(6-(trans-4-tert-butylcyclohexyloxy)-5-(trifluoromethyl)naphthalen-2-yl)propan-1-ol (R)-4-[6-(trans4-tert-Butylcyclohexyloxy)-5-trifluoromethylnaphthalen-2-yl]-4-methyl-oxazolidin-2-one (0.3341 g, 0.0007433 mol) was dissolved in ethanol (3.00 mL, 0.0514 mol) in a 40 mL capped vial equipped with a magnetic stir bar. 4.2 M Lithium hydroxide, monohydrate in water (3.00 mL) was added and the mixture was heated at 80° C. overnight. HPLC and LCMS analysis showed that the reaction was complete. The solvent was removed under vacuum. Methylene chloride (5 mL) and water (5 mL) were added and the layers were separated. The combined organic layers were concentrated under vacuum and purified by HPLC to give the title compound as a TFA salt in 0.105 g (33% yield). MS: m/z=407.38 [M-NH$_2$]+. $^1$H NMR (400 MHz, MeOD) δ 0.93 (s, 9 H), 1.10-1.31 (m, 3 H), 1.58 (d, J=12.55 Hz, 2 H), 1.81 (s, 3 H), 1.89-1.98 (m, 2 H), 2.20-2.29 (m, 2 H), 3.82-3.88 (m, 1 H), 3.92-4.00 (m, 1 H), 4.38-4.48 (m, 1 H), 7.40 (d, J=8.78 Hz, 1 H), 7.64 (dd, J=9.04, 2.01 Hz, 1 H), 7.89 (d, J=2.01 Hz, 1 H), 7.93 (d, J=9.04 Hz, 1 H), 8.21 (d, J=9.04 Hz, 1 H)

Example 53

{5-[6-(cis-4-Butylcyclohexyloxy)-naphthalen-2-yl]-2,2-dimethyl-1,3-dioxinan-5-yl}-carbamic acid tert-butyl ester

[5-(6-Hydroxynaphthalen-2-yl)-2,2-dimethyl-1,3-dioxinan-5-yl]-carbamic acid tert-butyl ester (Example 13, 498 mg, 0.00133 mol, Apex), PS-triphenylphosphine (3.00 mmol/g loading, 689 mg, 0.00207 mol, Aldrich) were slurried in Tetrahydrofuran (10 mL, Acros), then trans-4-butylcyclohexanol (0.255 g, 0.00163 mol, Synthon) and diisopropyl azodicarboxylate (0.315 mL, 0.00160 mol, Acros) was added. The reaction was stirred at room temperature. After 4 d, the mixture was diluted with ethyl acetate, filtered and concentrated and the crude product was taken up into methylene chloride and subjected to silica gel chromatography purification to give the title compound in 353 mg yield (52%).

Example 54

{5-[6-(cis-4-Butylcyclohexyloxy)-5-iodo-naphthalen-2-yl]-2,2-dimethyl-1,3-dioxinan-5-yl}-carbamic acid tert-butyl ester A solution of {5-[6-(cis-4-butylcyclohexyloxy)-naphthalen-2-yl]-2,2-dimethyl-1,3-dioxinan-5-yl}-carbamic acid tert-butyl ester (0.101 g, 0.000197 mol) and N-iodosuccinimide (56 mg, 0.00025 mol, Acros) in methylene chloride (3.0 mL, 0.047 mol, Acros) was stirred at room temperature under an atmosphere of Argon. To this was added zirconium tetrachloride (14 mg, 0.000060 mol, Strem). After 5 min, the reaction mixture was evaporated then diluted with methylene chloride, silica gel was added and the solvent was evaporated. The material was purified by silica gel chromatography to give the product in 111 mg yield (88%).

Example 55

{5-[6-(cis-4-butylcyclohexyloxy)-5-trifluoromethyl-naphthalen-2-yl]-2,2-dimethyl-1,3-dioxinan-5-yl}-carbamic acid tert-butyl ester To a mixture of {5-[6-(cis-4-Butyl-cyclohexyloxy)-5-iodo-naphthalen-2-yl]-2,2-dimethyl-1,3-dioxinan-5-yl}-carbamic acid tert-butyl ester (149 mg, 0.234 mmol), hexamethylphosphoramide (0.206 mL, 1.17 mmol, Aldrich) and copper(I) iodide (78 mg, 0.41 mmol, Aldrich) in N,N-dimethylformamide (1.00 mL, Acros) was added methyl fluorosulphonyldifluoroacetate (0.154 mL, 1.17 mmol, Aldrich). The mixture was heated at 80° C. under an atmosphere of Argon overnight. The reaction was evaporated under reduced pressure (some solvent remained), then diluted with methylene chloride. Silica gel was added and the solvent removed. The material was purified by silica gel chromatography to give the product in 92 mg yield (68%).

Example 56

2-Amino-2-[6-(cis-4-butylcyclohexyloxy)-5-trifluoromethylnaphthalen-2-yl]-propane-1,3-diol hydrogen chloride salt {5-[6-(cis-4-Butyl-cyclohexyloxy)-5-trifluoromethyl-naphthalen-2-yl]-2,2-dimethyl-1,3-dioxinan-5-yl}-carbamic acid tert-butyl ester (92 mg, 0.00016 mol) was dissolved in methanol (4.0 mL, Acros), followed by the addition of 1 M of hydrogen chloride in water (4.0 mL, Fisher). The reaction mixture was then heated at 80° C. for 2 hours. The mixture was partially concentrated under reduced pressure and the resulting water suspension was freeze-dried to give the product as HCl salt (64 mg, 100%). MS: m/z=462.30 M+Na+. $^1$H NMR (400 MHz, CDCl$_3$-CD$_3$OD) δ ppm 8.24 (d, J=9.0 Hz, 1H) 7.98 (d, J=9.0 Hz, 1H) 7.90 (s, 1H) 7.54 (d, J=9.3 Hz, 1H) 7.31 (d, J=9.0 Hz, 1H) 4.79-4.74 (m, 1H) 4.10 (d, J=12.3 Hz, 2H) 4.02 (d, J=12.3 Hz, 2H) 2.06-1.97 (m, 2H) 1.64-1.48 (m, 4H) 1.48-1.35 (m, 2H) 1.35-1.16 (m, 7H) 0.87 (t, J=6.01 Hz, 3H). $^{19}$F NMR (400 MHz, CDCl$_3$—CD$_3$OD) δ ppm −52.53

Example 57

2-Amino-2-[6-(cis-4-butylcyclohexyloxy)-5-iodo-naphthalen-2-yl]-propane-1,3-diol, hydrogen chloride salt The title compound was prepared from {5-[6-(cis-4-butyl-cyclohexyloxy)-5-iodonaphthalen-2-yl]-2,2-dimethyl-1,3-dioxinan-5-yl}-carbamic acid tert-butyl ester (Example 54) following the method of Example 56. MS: m/z=520.20 M+Na+. $^1$H NMR (400 MHz, CDCl$_3$—CD$_3$OD) δ ppm 8.16 (d, J=9.0 Hz, 1H) 7.83-7.77 (m, 2H) 7.51 (d, J=9.0 Hz, 1H) 7.20 (d, J=8.8 Hz, 1H) 4.32-4.19 (m, 1H) 4.08 (dd, J=4.3, 12.6 Hz, 2H) 4.01 (dd, J=4.3, 12.0 Hz, 2H) 2.22-2.13 (m, 2H) 1.90-1.73 (m, 2H) 1.62-1.45 (m, 2H) 1.25-1.03 (m, 3H) 0.87-0.78 (m, 9H).

Example 58

{5-[6-(trans-4-tert-butylcyclohexyloxy)-naphthalen-2-yl]-2,2-dimethyl-1,3-dioxinan-5-yl}-carbamic acid tert-butyl ester The title compound was prepared from cis-4-tertbutylcyclohexanol and [5-(6-hydroxynaphthalen-2-yl)-2,2-dimethyl-1,3-dioxinan-5-yl]-carbamic acid tert-butyl ester in 42% yield according to the method of Example 53.

Example 59

{5-[6-(trans-4-tert-butyl-cyclohexyloxy)-5-iodonaphthalen-2-yl]-2,2-dimethyl-1,3-dioxinan-5-yl}-carbamic acid tert-butyl ester The title compound was prepared from {5-[6-(trans-4-tert-butylcyclohexyloxy)-naphthalen-2-yl]-2,2-dimethyl-1,3-dioxinan-5-yl}-carbamic acid tert-butyl ester in 79% to yield according to the method of Example 54.

Example 60

{5-[6-(trans-4-tert-butyl-cyclohexyloxy)-5-trifluoromethylnaphthalen-2-yl]-2,2-dimethyl-1,3-dioxinan-5-yl}-carbamic acid tert-butyl ester The title compound was prepared from {5-[6-(trans-4-tert-butyl-cyclohexyloxy)-5-iodonaphthalen-2-yl]-2,2-dimethyl-1,3-dioxinan-5-yl}-carbamic acid tert-butyl ester in 67% is yield according to the method of Example 55.

Example 61

2-amino-2-[6-(trans-4-tert-butylcyclohexyloxy)-5-trifluoromethylnaphthalen-2-yl]-propane-1,3-diol, hydrogen chloride salt The title compound was prepared from {5-[6-(trans-4-tert-butyl-cyclohexyloxy)-5-trifluoromethylnaphthalen-2-yl]-2,2-dimethyl-1,3-dioxinan-5-yl}-carbamic acid tert-butyl ester in 88% yield according to the method of Example 56. MS: m/z=462.30 M+Na+. $^1$H NMR (400 MHz, CDCl$_3$—CD$_3$OD) δ ppm 8.21 (d, J=7.5 Hz, 1H) 7.96 (d, J=9.3 Hz, 1H) 7.89 (d, J=2.3 Hz, 1H) 7.53 (dd, J=2.3, 9.3 Hz, 1H) 7.32 (d, J=9.3 Hz, 1H) 4.34-4.23 (m, 1H) 4.07 (d, J=12.0 Hz, 2H) 4.01 (d, J=12.0 Hz, 2H) 2.18-2.09 (m, 2H) 1.88-1.74 (m, 2H) 1.56-1.42 (m, 2H) 1.25-0.98 (m, 3H) 0.87-0.75 (m, 9H). $^{19}$F NMR (400 MHz, CDCl$_3$—CD$_3$OD) δ ppm −52.56

Example 61A 2-amino-2-[6-(trans-4-tert-butylcyclohexyloxy)-5-trifluoromethyl-naphthalen-2-yl]-propane-1,3-diphosphoric acid The title compound was prepared from 2-Amino-2-[6-(trans-4-tert-butylcyclohexyloxy)-5-trifluoromethyl-naphthalen-2-yl]-propane-1,3-diol (Example 61) analogously to the methods of Examples 18-21.

Example 62

2-amino-2-[6-(trans-4-tert-butyl-cyclohexyloxy)-naphthalen-2-yl]-propane-1,3-diol, hydrogen chloride salt The title compound was prepared from {5-[6-(trans-4-tert-butylcyclohexyloxy)-naphthalen-2-yl]-2,2-dimethyl-1,3-dioxinan-5-yl}-carbamic acid tert-butyl ester in 82% yield according to the method of Example 56. MS: m/z=394.30 M+Na+. $^1$H NMR (400 MHz, CDCl$_3$—CD$_3$OD) δ ppm 7.77 (s, 1H) 7.75-7.70 (m, 2H) 7.42 (d, J=8.8 Hz, 1H) 7.12 (dd, J=2.1, 9.2 Hz, 1H) 7.10 (s, 1H) 4.29-4.19 (m, 1H) 4.07 (d, J=12.3 Hz, 2H) 4.00 (d, J=12.3 Hz, 2H) 2.26-2.17 (m, 2H) 1.90-1.81 (m, 2H) 1.46-1.30 (m, 2H) 1.24-0.99 (m, 3H) 0.87-0.76 (m, 9H).

Example 63

2-amino-2-[6-(trans-4-tert-butyl-cyclohexyloxy)-5-iodonaphthalen-2-yl]-propane-1,3-diol, hydrogen chloride salt The title compound was prepared from {5-[6-(trans-4-tert-butylcyclohexyloxy)-5-iodonaphthalen-2-yl]-2,2-dimethyl-1,3-dioxinan-5-yl}-carbamic acid tert-butyl ester in 92% yield according to the method of Example 56. MS: m/z=520.20 M+Na+. $^1$H NMR (400 MHz, CDCl$_3$—CD$_3$OD) δ ppm 8.16 (d, J=9.0 Hz, 1H) 7.83-7.77 (m, 2H) 7.51 (d, J=9.0 Hz, 1H) 7.20 (d, J=8.8 Hz, 1H) 4.32-4.19 (m, 1H) 4.08 (dd, J=4.3, 12.6 Hz, 2H) 4.01 (dd, is J=4.3, 12.0 Hz, 2H) 2.22-2.13 (m, 2H) 1.90-1.73 (m, 2H) 1.62-1.45 (m, 2H) 1.25-1.03 (m, 3H) 0.87-0.78 (m, 9H).

Example 64

{5-[6-(trans-3-Benzyloxymethylcyclobutoxy)-naphthalen-2-yl]-2,2-dimethyl-1,3-dioxinan-5-yl}-carbamic acid tert-butyl ester To a solution of [5-(6-Hydroxynaphthalen-2-yl)-2,2-dimethyl-1,3-dioxinan-5-yl]-carbamic acid tert-butyl ester (Example 13, 30.0 mg, 0.0000723 mol), cis-3-benzyloxymethyl-cyclobutanol (13.9 mg, 0.0000723 mol), and triphenylphosphine (22.8 mg, 0.0000868 mol) in THF (2 mL), a solution of diisopropyl azodicarboxylate (18.7 mg, 0.0000868 mol) in THF (1 mL), was added dropwise at 23° C. The reaction mixture was then allowed to stir at 23° C. for 2 days. Solvent was removed, and the crude mixture was purified via chromatography (SiO$_2$, 4 g, ethyl acetate 0-35%) to give a pure product (18 mg, 45%). MS (ES, M-113): 434.30.

Example 65

2-amino-2-(6-trans-[3-(benzyloxymethyl)cyclobutoxy)]naphthalen-2-yl)propane-1,3-diol hydrochloride {5-[6-(3-Benzyloxymethylcyclobutoxy)-naphthalen-2-yl]-2,2-dimethyl-1,3-dioxinan-5-yl}-carbamic acid tort-butyl ester (18.0 mg, 0.0000329 mol) was dissolved in methanol (1.0 mL, 0.025 mol), followed by 6 M of hydrogen chloride in water (1.0 mL). The reaction mixture was then heated at 60° C. for 30 minutes to give a clean product (15.0 mg, 100%). MS (ES, M+Na+): 430.30. $^1$H NMR (400 MHz, MeOD) δ 7.78-7.86 (m, 3H), 7.50 (dd, J=8.5, 2.0 Hz, 1H), 7.27-7.43 (m, 5H), 7.15 (dt, J=9.0, 2.3 Hz, 1H), 7.03 (d, J=2.3 Hz, 1H), 4.89-4.95 (m, 1H), 4.59 (s, 2H), 4.07 (d, J=11.8 Hz, 2H), 3.98 (d, J=11.5 Hz, 2H), 3.65 (d, J=6.5 Hz, 2H), 3.33-3.39 (m, 1H), 2.41-2.50 (m, 2H), 2.27-2.38 (m, 2H).

Example 66

2-amino-2-(6-cis-[3-(benzyloxymethyl)cyclobutoxy)]naphthalen-2-yl)propane-1,3-diol hydrochloride The title compound was prepared from [5-(6-Hydroxynaphthalen-2-yl)-2,2-dimethyl-1,3-dioxinan-5-yl]-carbamic acid tert-butyl ester and trans-3-benzyloxymethyl-cyclobutanol according to the methods of Examples 64 and 65. MS (ES, M+Na+): 430.30. $^1$H NMR (400 MHz, MeOD) δ ppm 7.78-7.88 (m, 3H), 7.50 (dd, J=8.8, 2.0 Hz, 1H), 7.32-7.37 (m, 4H), 7.25-7.32 (m, 1H), 7.10-7.19 (m, 2H), 4.71-4.80 (m, 1H), 4.53 (s, 2H), 4.08 (d, J=11.5 Hz, 2H), 3.95-4.01 (m, J=11.3 Hz, 2H), 3.54 (d, J=6.3 Hz, 2H), 2.63-2.74 (m, 2H), 2.33-2.43 (m, OH), 1.89-2.02 (m, 2H).

Example 67

5-(6-Benzyloxy-5-iodo-naphthalen-2-yl)-2,2-dimethyl-5-nitro-1,3-dioxinane

To a solution of 5-(6-Benzyloxynaphthalen-2-yl)-2,2-dimethyl-5-nitro-1,3-dioxinane (Example 13, 2.25 g, 0.00572 mol) in methylene chloride (250 mL, 3.9 mol), N-iodosuccinimide (1.42 g, 0.00629 mol) was added, followed by zirconium tetrachloride (0.20 g, 0.00086 mol) at 23° C. The reaction mixture was then heated to reflux at 55° C. for 4 hours. The reaction mixture was then cooled down to 23° C., and majority of solvent was removed under vacuum. Solid was removed via filtration through a CELITE™ pad. The mixture was then loaded onto a column (SiO$_2$, 120 g, 0-50% ethyl acetate/hexanes) to give a pure product (2.53 g, 85%). MS (ES, M+Na+): 542.30.

Example 68

5-(6-(Benzyloxy)-5-(trifluoromethyl)naphthalen-2-yl)-2,2-dimethyl-5-nitro-1,3-dioxinane 5-(6-Benzyloxy-5-iodo-naphthalen-2-yl)-2,2-dimethyl-5-nitro-1,3-dioxinane (100 mg, 0.0002 mol), copper(I) iodide (55.0 mg, 0.000289 mol) was placed in a vial, and purged with N$_2$. N,N-Dimethylformamide (0.8 mL, 0.01 mol) was added followed by hexamethylphosphoramide (172 mg, 0.000963 mol). Methyl fluorosulphonyldifluoroacetate (185 mg, 0.000963 mol) was added dropwise at 23° C. The reaction mixture was then heated to at 80° C. for 10 hours. The desired product was formed. A pure product was obtained after chromatography (SiO$_2$, ethyl acetate/hexanes) (53 mg, 60%). MS (ES, M+Na+): 484.30.

Example 69

5-(6-Benzyloxy-5-trifluoromethyl-naphthalen-2-yl)-2,2-dimethyl-1,3-dioxinan-5-ylamine 5-(6-(benzyloxy)-5-(trifluoromethyl)naphthalen-2-yl)-2,2-dimethyl-5-nitro-1,3-dioxinane (2.00 g, 0.00433 mol) was dissolved in acetic acid (20 mL, 0.4 mol), followed by zinc (2.834 g, 0.04334 mol) in small portions at 23° C. The reaction mixture was then allowed to stir at 23° C. for 4 hours. Excess of acetic acid was removed, and the residue was

Example 70 tert-Butyl 5-(6-hydroxy-5-(trifluoromethyl)naphthalen-2-yl)-2,2-dimethyl-1,3-dioxan-5-ylcarbamate 5-(6-Benzyloxy-5-trifluoromethyl-naphthalen-2-yl)-2,2-dimethyl-1,3-dioxinan-5-ylamine (1.50 g, 0.00348 mol) was dissolved in methylene chloride (120 mL, 1.9 mol), followed by di-tert-butyldicarbonate (1.14 g, 0.00522 mol). The reaction mixture was then cooled to −10° C., and N,N-diisopropylethylamine (0.908 mL, 0.00522 mol) was added. The reaction mixture was then warmed up to at 23° C. and allowed to stir for 10 hours, additional di-tert-butyldicarbonate was added (same amounts), and the reaction mixture was then allowed to stir for additional for 20 hours. The reaction mixture was then quenched with $K_2CO_3$ (saturated), and washed with water (100 mL) and brine, and then dried over $MgSO_4$. The product was then purified via chromatography ($SiO_2$, 40 g, 0-50% ethyl acetate/hexanes) to give 1.25 g pure product (68%). MS (ES, M-113): 418.20.

Example 71

(5-(6-hydroxy-5-trifluoromethylnaphthalen-2-yl)-2,2-dimethyl-1,3-dioxan-5-yl)-carbamic acid tert-butyl ester tert-Butyl 5-(6-hydroxy-5-(trifluoromethyl)naphthalen-2-yl)-2,2-dimethyl-1,3-dioxan-5-ylcarbamate (1.25 g, 0.00235 mol) was dissolved in methanol (190 mL, 4.7 mol), followed by palladium hydroxide (1.07 g, 0.00762 mol). The reaction mixture was then purged with $N_2$, and then $H_2$ was introduced at 23° C. The reaction mixture was then allowed to stir at 23° C. for 12 hours. The reaction mixture was then filtrated through a CELITE™ pad, and the filtrate was cooled down to −78° C. and treated with 2 mL HCl (4.0 N) in dioxane dropwise. The excess of solvents were removed. The residue solid was then treated with DCM (50 mL), and filtered. After removing of solvent, a pure product was obtained (1.05 g, 100%). MS (ES, M+Na+): 464.20.

Example 72

[5-(6-(3-trans-benzyloxymethylcyclobutoxy)-5-(trifluoromethyl)naphthalen-2-yl)-2,2-dimethyl-1,3-dioxan-5-yl]carbamic acid tert-butyl ester

[5-(6-Hydroxy-5-trifluoromethyl-naphthalen-2-yl)-2,2-dimethyl-1,3-dioxan-5-yl]carbamic acid tert-butyl ester (50.0 mg, 0.000113 mol), cis-3-benzyloxymethylcyclobutanol (21.8 mg, 0.000113 mol) and triphenylphosphine (35.6 mg, 0.000136 mol) were please in a vial purged with $N_2$. Tetrahydrofuran (3 mL, 0.04 mol) was added, followed by a solution of diisopropyl azodicarboxylate (29.2 mg, 0.000136 mol) in THF (1 mL) dropwise at 23° C. The reaction mixture was then stirred at 23° C. for 2 days. Solvent was removed, and the residue was purified vial chromatography ($SiO_2$, 4 g, 0-35% ethyl acetate/hexanes) to give a pure product (33 mg, 47%). MS (ES, M-113): 502.30.

Example 73

2-amino-2-[6-(3-trans-benzyloxymethylcyclobutoxy)-5-(trifluoromethyl)naphthalen-2-yl)]propane-1,3-diol 2-amino-2-[6-(3-trans-benzyloxymethylcyclobutoxy)-5-(trifluoromethyl)naphthalen-2-yl)]propane-1,3-diol (33.0 mg, 0.0000536 mol) was dissolved in methanol (2 mL, 0.05 mol), followed by 1 M of Hydrogen chloride in water (2 mL). The reaction mixture was then heated at 80° C. for 2 hours. Excess of solvents were removed to give a pure product (33 mg, 100%). MS (ES, M+Na+): 498.30.

Example 74

2-Amino-2-[6-(3-cis-benzyloxymethylcyclobutoxy)-5-(trifluoromethyl)naphthalen-2-yl)]propane-1,3-diol The title compound was prepared from (5-(6-hydroxy-5-trifluoromethylnaphthalen-2-yl)-2,2-dimethyl-1,3-dioxan-5-yl)-carbamic acid tert-butyl ester and 3-trans-benzyloxymethylcyclobutanol according to the methods of Examples 72 and 73. MS (ES, M+Na+): 498.30. $^1$H NMR (400 MHz, MeOD) δ ppm 8.19-8.26 (m, 1H), 8.09 (d, J=9.3 Hz, 1H), 7.93 (d, J=2.3 Hz, 1H), 7.66 (dd, J=9.3, 2.3 Hz, 1H), 7.32-7.41 (m, 4H), 7.24-7.32 (m, 2H), 4.99-5.07 (m, 1H), 4.57 (s, 2H), 4.06 (d, J=11.5 Hz, 2H), 3.97 (d, J=11.5 Hz, 2H), 3.59 (d, J=6.3 Hz, 2H), 2.60-2.71 (m, 1H), 2.39 (m, 4H).

Example 75

(R)-4-[6-(3-trans-Benzyloxymethylcyclobutoxy)naphthalen-2-yl]-4-methyloxazolidin-2-one (R)-4-(6-hydroxynaphthalen-2-yl)-4-methyloxazolidin-2-one (Example 4, 300 mg, 0.001 mol), cis-3-benzyloxymethylcyclobutanol (237 mg, 0.00123 mol) and triphenylphosphine polymer bound (3 mmol/g loading; 800 mg, 0.0025 mol) were placed in a 40 mL vial, followed by tetrahydrofuran (10 mL, 0.1 mol). A solution of diisopropyl azodicarboxylate (318 mg, 0.00148 mol) in THF (5 mL) was then added dropwise to the reaction mixture at 23° C. The reaction mixture was allowed to stir for 12 hours. The reaction mixture was then filtered through a CELITE™ pad, and concentrated. The crude mixture was purified via chromatography ($SiO_2$, 20 g, 0-35% ethyl acetate/hexanes) to give the desired product (372 mg, 70%). MS (ES, M+1): 418.30.

Example 76

(R)-2-Amino-2-[6-(3-trans-benzyloxymethylcyclobutoxy)naphthalen-2-yl)]propan-1-ol (R)-4-[6-(3-trans-benzyloxymethylcyclobutoxy)naphthalen-2-yl]-4-methyl-oxazolidin-2-one (30.0 mg, 0.0000718 mol) was dissolved in ethanol (2 mL, 0.03 mol), followed by 4 M of Lithium hydroxide in water (1 mL). The reaction mixture was then heated at 80° C. for 5 hours. All solvent was removed. The solid was extracted with DCM, and was purified via HPLC to give the desired product (12 mg, 42%). MS (ES, M-NH2): 375.30. $^1$H NMR (400 MHz, MeOD) δ ppm 7.84 (s, 1H), 7.70 (d, J=8.8 Hz, 1H), 7.75 (d, J=8.8 Hz, 1H), 7.55 (d, J=8.5 Hz, 1H), 7.25-7.43 (m, 5H), 7.07 (dd, J=8.9, 2.4 Hz, 1H), 6.97 (d, J=1.8 Hz, 1H), 5.49 (s, 1H), 4.87-4.94 (m,

--- treated with DCM, and filtered. The organic layer was then treated with NaOH (2N, 2 mL), and separated. The organic layer washed with water (30 mL) and brine (30 mL), and then dried over $Na_2SO_4$. Removal of the solvent gave a pure product (1.88 g, 100%). MS (ES, M+1): 432.30.

1H), 4.58 (s, 2H), 3.63-3.74 (m, 2H), 3.61 (d, J=6.3 Hz, 2H), 2.56-2.71 (m, 1H), 2.37-2.48 (m, 2H), 2.25-2.37 (m, 2H), 1.50 (s, 3H).

Example 77

(R)-2-Amino-2-[6-(3-cis-benzyloxymethylcyclobutoxy)naphthalen-2-yl)]propan-1-ol

The title compound was prepared from (R)-4-(6-hydroxynaphthalen-2-yl)-4-methyloxazolidin-2-one and trans-3-benzyloxymethylcyclobutanol according to the methods of Examples 75 and 76. MS (ES, M-NH2): 375.20. $^1$H NMR (MeOD) δ ppm 7.84 (d, J=1.8 Hz, 1H), 7.68-7.78 (m, 2H), 7.55 (dd, J=8.8, 2.0 Hz, 1H), 7.23-7.37 (m, 5H), 7.04-7.09 (m, 2H), 5.49 (s, 1H), 4.67-4.77 (m, 1H), 4.52 (s, 2H), 3.64-3.74 (m, 2H), 3.52 (d, J=6.0 Hz, 2H), 2.60-2.73 (m, 2H), 2.27-2.41 (m, 1H), 1.88-2.00 (m, 2H), 1.50 (s, 3H).

Example 78

(R)-2-Amino-2-[6-(4-trans-tert-pentylcyclohexyloxy)naphthalen-2-yl]propan-1-ol

The title compound was prepared from (R)-4-(6-hydroxynaphthalen-2-yl)-4-methyloxazolidin-2-one and 4-cis-tert-pentylcyclohexanol according to the methods of Examples 75 and 76. MS (ES, M-NH2): 353.20. $^1$H NMR (400 MHz, MeOD) δ ppm 7.62 (d, J=1.8 Hz, 1H), 7.48-7.56 (m, 2H), 7.33 (dd, J=8.5, 2.0 Hz, 1H), 6.98 (d, J=2.3 Hz, 1H), 6.87 (dd, J=8.8, 2.5 Hz, 1H), 4.07-4.14 (m, 1H), 3.44-3.51 (m, 2H), 2.02-2.09 (m, 2H), 1.60-1.67 (m, 2H), 1.29 (s, 3H), 1.00-1.25 (m, 7H), 0.59-0.67 (m, 9H).

Example 79

(R)-2-Amino-2-[6-(4-cis-tert-pentylcyclohexyloxy)naphthalen-2-yl]propan-1-ol

The title compound was prepared from (R)-4-(6-hydroxynaphthalen-2-yl)-4-methyloxazolidin-2-one and 4-trans-tert-pentylcyclohexanol according to the methods of Examples 75 and 76. MS (ES, M-NH2): 353.20. $^1$H NMR (400 MHz, MeOD) δ ppm 7.85 (d, J=1.3 Hz, 1H), 7.77 (d, J=8.8 Hz, 1H), 7.71 (d, J=8.8 Hz, 1H), 7.55 (dd, J=8.7, 1.9 Hz, 1H), 7.19 (d, J=2.3 Hz, 1H), 7.14 (dd, J=8.9, 2.4 Hz, 1H), 4.72 (br. s., 1H), 3.64-3.75 (m, 2H), 2.12-2.23 (m, 2H), 1.48-1.65 (m, 9H), 1.31-1.38 (m, 2H), 1.22-1.31 (m, 1H), 0.81-0.93 (m, 9H).

Example 80

(R)-4-[6-(3-trans-Benzyloxymethylcyclobutoxy)-5-iodonaphthalen-2-yl]-4-methyloxazolidin-2-one (R)-4-[6-(3-trans-Benzyloxymethylcyclobutoxy)naphthalen-2-yl]-4-methyloxazolidin-2-one (Example 75, 0.150 g, 0.000359 mol) was dissolved in methylene chloride (6.0 mL, 0.094 mol), cooled with ice bath. N-Iodosuccinimide (93.0 mg, 0.000413 mol) was added, followed by zirconium tetrachloride (11.7 mg, 0.0000502 mol). The mixture was stirred with cooling for 2 hours then brought to 23° C. for 2 hours. The red-brown solution was concentrated under vacuum and the residue was purified by chromatograph using EtOAc/hexane (0/100 to 50/50) to give a solid product (190.0 mg, 92%). MS (ES, M+MeCN+H+). 585.30.

Example 81

(R)-4-[6-(3-trans-Benzyloxymethylcyclobutoxy)-5-trifluoromethylnaphthalen-2-yl]-4-methyloxazolidin-2-one A mixture of (R)-4-[6-(3-trans-Benzyloxymethylcyclobutoxy)-5-iodonaphthalen-2-yl]-4-methyl-oxazolidin-2-one (0.0901 g, 0.000152 mol), copper(I) iodide (53.7 mg, 0.000282 mol) and hexamethylphosphoramide (0.144 mL, 0.000829 mol) in N,N-dimethylformamide (5.0 mL, 0.064 mol) was purged with N$_2$ 5 times. Methyl fluorosulphonyldifluoroacetate (0.100 mL, 0.000786 mol) was added and the mixture was heated to 80° C. for 20 hours. The mixture was cooled to 23° C., concentrated under vacuum, quenched with saturated NH$_4$Cl, extracted with EtOAc (3×), washed with brine, dried over Na$_2$SO$_4$, filtered, evaporated to give a crude product. Chromatograph using EtOAC/hexane (0/100 to 50/50) gave a product (47.0 mg, 64%). MS (ES, M+H+): 486.0.

Example 82

(R)-2-Amino-2-[6-(3-trans-benzyloxymethylcyclobutoxy)-5-trifluoromethylnaphthalen-2-yl)]propan-1-ol The title compound was prepared from (R)-4-[6-(3-trans-benzyloxymethylcyclobutoxy)-5-trifluoromethylnaphthalen-2-yl]-4-methyloxazolidin-2-one according to the method of Example 76 (20 mg, 84%). $^1$H NMR (MeOD) δ ppm 8.14 (dd, J=9.3, 1.8 Hz, 1H), 8.01 (d, J=9.3 Hz, 1H), 7.84 (d, J=2.3 Hz, 1H), 7.57 (dd, J=9.3, 2.3 Hz, 1H), 7.22-7.32 (m, 4H), 7.14-7.22 (m, 2H), 4.89-4.99 (m, 1H), 4.48 (s, 2H), 3.83 (d, J=11.5 Hz, 1H), 3.73 (d, J=11.8 Hz, 1H), 3.50 (d, J=6.0 Hz, 2H), 2.50-2.67 (m, 1H), 2.19-2.40 (m, 4H), 1.68 (s, 3H).

Example 83

{4-[6-(3-cis-(benzyloxymethylcyclobutoxy)naphthalen-2-yl)]-2-methyl-4,5-dihydrooxazol-4-yl}methanol 2-Amino-2-(6-cis-[3-(benzyloxymethyl)cyclobutoxy)]naphthalen-2-yl)propane-1,3-diol (Example 66) was treated with triethyl orthoacetate (12.4 mg, 0.0000767 mol) and acetic acid (0.006 mg, 0.0000001 mol) in 1,2-dichloroethane (3 mL, 0.04 mol), and heated at 80° C. for 12 hours. The reaction mixture was treated with Na$_2$CO$_3$ (sat), and the crude intermediate was purified via chromatography (SiO$_2$, 4 g, 0-90% ethyl acetate/hexanes) to give the desired product. MS (ES, M+1): 432.30.

Example 84

{4-[6-(3-cis-benzyloxymethylcyclobutoxy)naphthalen-2-yl]-2-methyl-4,5-dihydrooxazol-4-yl}methyl di-tert-butyl phosphate {4-[6-(3-cis-(benzyloxymethylcyclobutoxy)naphthalen-2-yl)]-2-methyl-4,5-dihydrooxazol-4-yl}methanol was the treated with di-tert-butyl N,N-diethylphosphoramidite (54.6 mg, 0.000219 mol), 1H-tetrazole (19.2 mg, 0.000274 mol) in tetrahydrofuran (1 mL, 0.02 mol) for 5 hours, and then m-chloroperbenzoic acid (63.0 mg, 0.000219 mol) was added at 23° C. for 1 hour, followed by sodium thiosulfate (200 mg, 0.001 mol). The reaction mixture was treated with water and filtrated. White solid was washed with H₂O twice to give the product. MS (ES, M+1): 624.50.

Example 85

2-Amino-2-[6-(3-cis-(benzyloxymethylcyclobutoxy) naphthalen-2-yl]-3-hydroxypropyl dihydrogen phosphate {4-[6-(3-cis-benzyloxymethylcyclobutoxy)naphthalen-2-yl]-2-methyl-4,5-dihydrooxazol-4-yl}methyl di-tert-butyl phosphate was treated with 6 M of hydrogen chloride in water (1 mL) and MeOH, and heated at 80° C. for 3 hours. The final product was purified via HPLC to give the title compound. MS (ES, M+1): 488.30. ¹H NMR (MeOD) δ ppm 7.56-7.72 (m, 3H), 7.29-7.40 (m, 1H), 7.03-7.18 (m, 5H), 6.88-6.99 (m, 2H), 4.48-4.62 (m, 3H), 4.33 (s, 2H), 4.18-4.27 (m, 1H), 4.09-4.18 (m, 1H), 3.85-3.95 (m, 1H), 3.74-3.85 (m, 1H), 2.39-2.55 (m, 2H), 2.09-2.23 (m, 1H), 1.69-1.82 (m, 2H).

Example 86

(R)-4-[6-(Decahydro-naphthalen-2-yloxy)-naphthalen-2-yl]-4-methyl-oxazolidin-2-one (R)-4-(6-hydroxynapthalen-2-yl)-4-(2.2 g, 0.0090 mol, 2-naphthalenol, decahydro-(1.5 g, 0.0097 mol), and triphenylphosphine (2.8 g, 0.011 mol) were combined in tetrahydrofuran (40 mL, 0.5 mol). The solution cooled to 0° C. on an ice bath and diisopropyl azodicarboxylate (2.2 g, 0.011 mol) was added. Once all diisopropyl azodicarboxylate was added the mixture was stirred on an ice bath for 30 minutes. The ice bath was then removed and the mixture was allowed to warm to room temperature while stirring over night at RT. The reaction was then quenched with water and diluted with 100 mL EtOAc. The mixture was then washed with 1.0 N HCl, Sat. Na₂CO₃, and Brine. The organic layer was dried over MgSO₄, filtered, and concentrated to dryness under reduced pressure. The crude reaction was then dissolved in DCM, absorbed onto 5 g silica and purified (dry load) via column chromatography (0-50% EtoAC/Hexanes) to give 1.3 g the desired compound as a white solid (38%). ESI-MS: 381 (M+H)⁺. ¹H NMR (400 MHz, CDCl₃) δ=7.43-7.19 (m, 3 H), 7.15 (s, 1 H), 6.97-6.90 (m, 1 H), 6.88 (s, 1 H), 5.04-4.97 (m, 1 H), 4.31-4.03 (m, 2 H), 3.64-3.48 (m, 2 H), 2.85-0.91 (m, 20 H)

Example 87

(R)-2-Amino-2-[6-(decahydro-naphthalen-2-yloxy)-naphthalen-2-yl]-propan-1-ol (R)-4-[6-(Decahydro-naphthalen-2-yloxy)-naphthalen-2-yl]-4-methyl-oxazolidin-2-one (200 mg, 0.0005 mol) was dissolved in ethanol (2.2 g, 0.049 mol) and treated with 4.2 M lithium hydroxide, monohydrate in water (2.1 mL, 0.0090 mol). The mixture was then heated to 80° C. overnight. The reaction was then cooled to room temperature and quenched with 1 N HCl. The reaction was then diluted with water and white solid formed. Solid was removed via filtration and dried overnight on filter to give 4 mg the desired product as a white solid (2%). ESI-MS: 337 (M-16)⁺. ¹H NMR (400 MHz, DMSO-d6) δ=7.11-6.92 (m, 3 H), 6.75-6.64 (m, 1 H), 6.48-6.29 (m, 2 H), 3.74-3.58 (m, 1 H), 3.20-2.95 (m, 2 H), 1.21-0.96 (s, 22 H).

Example 88

(R)-4-[6-(Bicyclohexyl-4-yloxy)-naphthalen-2-yl]-4-methyl-oxazolidin-2-one

The compound was prepared in a manner similar as to that described above using bicyclohexyl-4-ol (1.6 g, 0.0090 mol), triphenylphosphine (2.6 g, 0.0099 mol), tetrahydrofuran (45 mL, 0.55 mol), and diisopropyl azodicarboxylate (2.0 g, 0.0099 mol) to give 3.2 g of the desired product (48%). ESI-MS: 408 (M+H)⁺. ¹H NMR (400 MHz, CDCl₃) δ=7.81-7.63 (m, 3 H), 7.48-7.37 (m, 1 H), 7.15 (s, 2 H), 4.41 (s, 2 H), 4.33-4.18 (m, 1 H), 2.39-2.16 (m, 2 H), 1.95-0.84 (m, 22 H).

Example 89

(R)-2-Amino-2-[6-(bicyclohexyl-4-yloxy)-naphthalen-2-yl]-propan-1-ol

The compound was prepared in a manner similar as to that described above using (R)-4-[6-(Bicyclohexyl-4-yloxy)-naphthalen-2-yl]-4-methyl-oxazolidin-2-one (200 mg, 0.0005 mol), ethanol (2.2 g, 0.049 mol), and 4.2 M lithium hydroxide, monohydrate in water (2.1 mL, 0.0090 mol) to give 46 mg of the desired product as a white solid (46%). ESI-MS: 365 (M-16)⁺. ¹H NMR (400 MHz, CDCl₃) δ=7.99-7.55 (m, 3 H), 7.29-7.12 (m, 1 H), 7.08 (s, 2 H), 4.70 (s, 1 H), 4.32-4.17 (m, 1 H), 3.27-2.99 (m, 2 H), 2.32-0.81 (m, 25 H).

Example 90

(R)-4-[6-(4-Isopropyl-cyclohexyloxy)-naphthalen-2-yl]-4-methyl-oxazolidin-2-one

The compound was prepared in a manner similar as to that described above using (R)-4-(6-hydroxynaphthalen-2-yl)-4-methyloxazolidin-2-one (2.0 g, 0.0082 mol), cyclohexanol, 4-(1-methylethyl)-(1.3 g, 0.0090 mol), triphenylphosphine (2.6 g, 0.0099 mol), tetrahydrofuran (45 mL, 0.55 mol), and diisopropyl azodicarboxylate (2.0 g, 0.0099 mol) to give 1.6 g of the desired product as a yellow solid (52%). ESI-MS: 368 (M+H)⁺. ¹H NMR (400 MHz, CDCl₃) δ=7.81-7.59 (m, 2 H), 7.49-7.30 (m, 1 H), 7.22-7.04 (m, 2 H), 6.88-6.64 (m, 1 H), 4.66 (br. s., 1 H), 4.40 (s, 2 H), 4.34-4.18 (m, 1 H), 2.29-2.07 (m, 2 H), 1.91-1.69 (m, 6 H), 1.64-1.09 (m, 5 H), 0.96-0.69 (m, 6 H).

Example 91

(R)-2-Amino-2-[6-(4-isopropyl-cyclohexyloxy)-naphthalen-2-yl]-propan-1-ol

The compound was prepared in a manner similar as to that described above using (R)-4-[6-(4-Isopropyl-cyclohexyloxy)-naphthalen-2-yl]-4-methyl-oxazolidin-2-one (200 mg, 0.0005 mol), ethanol (2.2 g, 0.049 mol), 4.2 M lithium hydroxide, monohydrate in water (2.1 mL, 0.0090 mol) to give 56 mg of the desired compound as a yellow brown solid (30%). ESI-MS: 325 (M-16)⁺. ¹H NMR (400 MHz, CDCl₃) δ=7.94-7.61 (m, 3 H), 7.50 (d, J=8.5 Hz, 1 H), 7.23-7.05 (m, 2 H), 4.67 (br. s., 1 H), 4.33-4.17 (m, 1 H), 3.84-3.51 (m, 2 H), 2.35-1.75 (m, 4 H), 1.68-1.08 (m, 10 H), 1.01-0.68 (m, 6 H).

Example 92

4-Cyclopentyl-cyclohexanol

Phenol, 4-cyclopentyl-(1 g, 0.007 mol) was dissolved in acetic acid (50 mL, 0.8 mol) and treated with platinum dioxide (0.3 g, 0.001 mol). The system was evacuated under reduced pressure, purged with nitrogen, evacuated, and the flask was charged with hydrogen (2 g, 1 mol). The reaction was allowed to stir at ambient temperature for 17 hours. The reaction was then filtered through a bed of Celite to remove solids and the solvent was removed under reduced pressure to give 991 mg of a 1 to 1 diasteromeric mixture of 4-cyclopentyl-cyclohexanol as a colorless oil (80%). $^1$H NMR (400 MHz, CDCl$_3$) δ=3.95 (br. s., 0.48 H)cis, 3.69-3.28 (tt, J=4.2, 6.5 Hz, 0.47 H)trans, 2.21-0.65 (m, 18 H).

Example 93

(R)-4-[6-(4-Cyclopentyl-cyclohexyloxy)-naphthalen-2-yl]-4-methyl-oxazolidin-2-one The compound was prepared in a manner similar as to that described above using (R)-4-(6-hydroxynaphthalen-2-yl)-4-methyloxazolidin-2-one, 4-cyclopentyl-cyclohexanol (1.5 g, 0.0090 mol), triphenylphosphine (2.6 g, 0.0099 mol), tetrahydrofuran (45 mL, 0.55 mol) and diisopropyl azodicarboxylate (2.0 g, 0.0099 mol) to give 895 mg of a 1.6 to 1 diasteromeric ratio of the desired compound as a yellow solid (27%). ESI-MS: 368 (M+H)$^+$. $^1$H NMR (400 MHz, CDCl$_3$) δ=7.80-7.63 (m, 3 H), 7.39 (dd, J=1.9, 8.7 Hz, 1 H), 7.22-7.08 (m, 2 H), 4.70-4.58 (br. s., 0.63 H), 4.43-4.36 (s, 2 H), 4.34-4.21 (tt, J=4.2, 6.5 Hz, 0.39 H), 2.04 (s, 2 H), 1.87-1.70 (m, 2 H), 1.65-0.77 (m, 17 H)

Example 94

(R)-2-Amino-2-[6-(4-cyclopentyl-cyclohexyloxy)-naphthalen-2-yl]-propan-1-ol

The compound was prepared in a manner similar as to that described above using (R)-4-[6-(4-Cyclopentyl-cyclohexyloxy)-naphthalen-2-yl]-4-methyl-oxazolidin-2-one (200 mg, 0.0005 mol), ethanol (2.2 g, 0.049 mol), 4.2 M lithium hydroxide, monohydrate in water (2.1 mL, 0.0090 mol) to give 114 mg the desired product as a white solid (90%). ESI-MS: 351 (M+H)$^+$. $^1$H NMR (400 MHz, DMSO-d$_6$) δ=7.87 (s, 1 H), 7.81-7.55 (m, 3 H), 7.31-7.21 (m, 1 H), 7.18-7.00 (m, 1 H), 4.98-4.59 (m, 3 H), 4.43-4.27 (m, 0.63 H), 3.57-3.14 (m, 4 H), 2.19-0.84 (m, 17 H)

Example 95

4-sec-butyl-cyclohexanol

Phenol, 4-(1-methylpropyl)-(1 g, 0.007 mol) was dissolved in acetic acid (50 mL, 0.8 mol) and treated with platinum dioxide (0.3 g, 0.001 mol). The system was evacuated under reduced pressure, purged with nitrogen, evacuated, and the flask was charged with hydrogen (2 g, 1 mol). Reaction was allowed to stir at ambient temperature for 48 hours. The reaction was then filtered through a bed of Celite to remove solids and the solvent was removed under reduced pressure to give 980 mg of the 4-sec-butyl-cyclohexanol as a colorless oil (80%). $^1$H NMR (400 MHz, CDCl$_3$) δ=4.01 (br. s., 0.31 H), 3.65-3.40 (m, 0.55 H), 2.67-0.59 (m, 18 H)

Example 96

(R)-4-[6-(4-sec-Butyl-cyclohexyloxy)-naphthalen-2-yl]-4-methyl-oxazolidin-2-one

The compound was prepared in a manner similar as to that described above using (R)-4-(6-hydroxynaphthalen-2-yl)-4-methyloxazolidin-2-one, cyclohexanol, 4-sec-butyl-(1.4 g, 0.0090 mol), triphenylphosphine (2.6 g, 0.0099 mol), tetrahydrofuran (45 mL, 0.55 mol), and diisopropyl azodicarboxylate (2.0 g, 0.0099 mol) to give 1.4 g of the desired compound as a brown amorphous solid (41%). ESI-MS: 381 (M+H)$^+$. $^1$H NMR (400 MHz, DMSO-d$_6$) δ=8.45 (s, 1 H), 7.99-7.69 (m, 2 H), 7.47 (d, J=8.5 Hz, 1 H), 7.41-7.25 (m, 1 H), 7.19 (dd, J=2.3, 9.0 Hz, 1 H), 4.73 (br. s., 1 H), 4.53-4.08 (m, 2 H), 2.23-1.93 (m, 2 H), 1.79-1.04 (m, 17 H), 0.94-0.68 (m, 3 H)

Example 97

(R)-2-Amino-2-[6-(4-sec-butyl-cyclohexyloxy)-naphthalen-2-yl]-propan-1-ol

The compound was prepared in a manner similar as to that described above using (R)-4-[6-(4-sec-Butyl-cyclohexyloxy)-naphthalen-2-yl]-4-methyl-oxazolidin-2-one (200 mg, 0.0005 mol), ethanol (2.2 g, 0.049 mol) and 4.2 M lithium hydroxide, monohydrate in water (2.1 mL, 0.0090 mol) to give 152 mg of the desired product as a white solid (50%). ESI-MS: 339 (M-16)$^+$. $^1$H NMR (400 MHz, DMSO-d$_6$) δ=8.30 (s, 1 H), 7.88 (s, 1 H), 7.75 (d, J=8.8 Hz, 1 H), 7.71-7.56 (m, 1 H), 7.24 (d, J=2.0 Hz, 1 H), 7.12 (dd, J=2.3, 8.8 Hz, 1 H), 4.70 (d, J=5.8 Hz, 1 H), 4.40-4.28 (m, 1 H), 3.55-3.41 (m, 2 H), 2.26-1.07 (m, 12 H), 0.94-0.79 (m, 3 H)

Example 98

(R)-4-(6-cis-4-cyclopentylcyclohexyloxy)-5-iodonaphthalen-2-yl)-4-methyloxazolidin-2-one (R)-4-[6-(cis-4-Cyclopentyl-cyclohexyloxy)-naphthalen-2-yl]-4-methyl-oxazolidin-2-one (124 mg, 0.000315 mol) was combined with N-iodosuccinimide (160 mg, 0.00069 mol) and zirconium chloride (0.01 g, 0.00006 mol) in methylene chloride (3 mL, 0.05 mol) in a sealed microwave tube. The mixture was sonicated then stirred at ambient temperature for 5 minutes. Added methanol and white solid formed which was removed via filtration and dried on filter to give 98 mg the desired product as a white solid (59%). ESI-MS: 519 (M+H)$^+$. $^1$H NMR (400 MHz, CDCl$_3$) δ=8.18 (d, J=8.8 Hz, 1 H), 7.94 (m, 1 H), 7.82-7.68 (m, 2 H), 7.58-7.44 (m, 1 H), 7.22 (d, J=9.0 Hz, 1 H), 4.90-4.79 (br. s., 0.63 H), 4.43-4.36 (s, 2 H), 2.04 (s, 2 H), 1.87-1.70 (m, 2 H), 1.65-0.77 (m, 17 H)

Example 99

(R)-4-(6-(cis-4-cyclopentylcyclohexyloxy)-5-(trifluoromethyl)naphthalen-2-yl)-4-methyloxazolidin-2-one (R)-4-(6-((1s,4s)-4-cyclopentylcyclohexyloxy)-5-iodonaphthalen-2-yl)-4-methyloxazolidin-2-one (211 mg, 0.406 mmol) and copper(I) iodide (54 mg, 0.28 mmol) were combined in a 40 mL vial and purged with nitrogen. N,N-Dimethylformamide (2.40 mL, 30.9 mmol) was then added followed by hexamethylphosphoramide (0.2 mL, 0.9 mmol). Methyl fluorosulphonyldifluoroacetate (0.1 mL, 0.9 mmol) was then added dropwise at ambient temperature. The reaction mixture was then heated to 80° C. on a heating block for 3 hours. Reaction was then filtered and most of the DMF was removed under reduced pressure. The residue was then dissolved in ethyl ether/EtOAc (4:1) and washed with water three times. Organics were dried over MgSO$_4$, filtered, and concentrated to dryness. Material was purified via column chromatography (0-40% EtOAc/Hexanes) to give 188 mg the desired product as a yellow solid (88%). ESI-MS: 462 (M+H)+. 1H NMR (400 MHz, CDCl3) δ=8.01 (d, J=8.8 Hz, 1 H), 7.93 (m, 1 H), 7.82-7.68 (m, 2 H), 7.58-7.44 (m, 1 H), 7.22 (d, J=9.0 Hz, 1 H), 5.10-4.91 (br. s., 0.63 H), 4.43-4.36 (s, 2 H), 2.04 (s, 2 H), 1.87-1.70 (m, 2 H), 1.64-0.79 (m, 17H)

Example 100

(R)-2-Amino-2-[6-(cis-4-cyclopentyl-cyclohexyloxy)-5-trifluoromethyl-naphthalen-2-yl]-propan-1-ol (R)-4-[6-(cis-4-Cyclopentyl-cyclohexyloxy)-5-trifluoromethyl-naphthalen-2-yl]-4-methyl-oxazolidin-2-one (200 mg, 0.0005 mol) was dissolved in ethanol (2.2 g, 0.049 mol) and treated with 4.2 M lithium hydroxide, monohydrate in water (2.1 mL, 0.0090 mol). The mixture was then heated to 80° C. overnight. The reaction was then cooled to room temperature and diluted with water. Solid formed. Solid was removed via filtration and dried on the filter for 4 hours to give 158 mg the desired product as a white solid (58%). ESI-MS: 419 (M-16)+. 1H NMR (400 MHz, MeOD) δ=8.64-8.50 (m, 1 H), 8.17-7.98 (m, 2 H), 7.98-7.87 (m, 1 H), 7.73-7.62 (m, 1 H), 7.50-7.40 (m, 1 H), 4.21-4.09 (m, 2 H), 3.80-3.58 (m, 2 H), 2.12-1.96 (m, 2 H), 1.85-1.42 (m, 18 H), 1.21-1.05 (m, 2 H).

Example 101

(R)-4-(6-(trans-4-cyclopentylcyclohexyloxy)-5-iodonaphthalen-2-yl)-4-methyloxazolidin-2-one The compound was prepared in a manner similar as to that described above using (R)-4-[6-(trans-4-Cyclopentyl-cyclohexyloxy)-naphthalen-2-yl]-4-methyl-oxazolidin-2-one (89 mg, 0.00023 mol), N-iodosuccinimide (110 mg, 0.00050 mol), zirconium chloride (0.007 g, 0.00004 mol), and methylene chloride (3 mL, 0.04 mol). ESI-MS: 519 (M+H). 1H NMR (400 MHz, CDCl3) δ=8.17 (d, J=9.0 Hz, 1 H), 7.72-7.59 (m, 2 H), 7.45 (dd, J=1.9, 8.9 Hz, 1 H), 7.24 (d, J=9.0 Hz, 1 H), 5.90 (s, 1 H), 4.44-4.28 (m, 2 H), 4.20 (t, J=4.1 Hz, 1 H), 2.09 (d, J=10.5 Hz, 2 H), 1.91-1.30 (m, 16 H), 1.15-0.87 (m, 5 H)

Example 102

(R)-4-[6-(trans-4-Cyclopentyl-cyclohexyloxy)-5-trifluoromethylnaphthalen-2-yl]-4-methyl-oxazolidin-2-one The compound was prepared in a manner similar as to that described above using (S)-4-(6-((1s,4s)-4-cyclopentylcyclohexyloxy)naphthalen-2-yl)-4-methyloxazolidin-2-one (39 mg, 0.000075 mol), copper(I) iodide (21 mg, 0.00011 mol), N,N-dimethylformamide (0.953 mL, 0.0123 mol), hexamethylphosphoramide (0.06 mL, 0.0004 mol) and methyl fluorosulphonyldifluoroacetate (0.05 mL, 0.0004 mol) to give 19 mg the desired product as a yellow solid (53%). ESI-MS: 462 (M+H)+. 1H NMR (400 MHz, CDCl3) δ=8.01 (d, J=8.8 Hz, 1 H), 7.93 (m, 1 H), 7.81-7.67 (m, 2 H), 7.58-7.44 (m, 1 H), 7.22 (d, J=9.0 Hz, 1 H), 4.76-4.55 (m, 1 H), 4.43-4.36 (m, 2 H), 2.04 (s, 2 H), 1.87-1.70 (m, 2 H), 1.62-0.78 (m, 17 H)

Example 103

(R)-2-Amino-2-[6-(trans-4-cyclopentyl-cyclohexyloxy)-5-trifluoromethyl-naphthalen-2-yl]-propan-1-ol The compound was prepared in a manner similar as to that described above (R)-4-[6-(4-Cyclopentyl-cyclohexyloxy)-5-trifluoromethyl-naphthalen-2-yl]-4-methyl-oxazolidin-2-one (15 mg, 0.000032 mol), (0.14 g, 0.0030 mol), 4.2 M lithium hydroxide, monohydrate in water (0.13 mL, 0.00055 mol) to give 12 mg of the desired product as a white solid (81%). ESI-MS: 419 (M-16)+. 1H NMR (400 MHz, MeOD) δ=8.64-8.50 (m, 1 H), 8.17-7.98 (m, 2 H), 7.98-7.87 (m, 1 H), 7.73-7.62 (m, 1 H), 7.50-7.40 (m, 1 H), 4.84-4.76 (m, 2 H), 3.80-3.58 (m, 2 H), 2.12-1.96 (m, 2 H), 1.85-1.42 (m, 18 H), 1.21-1.05 (m, 2 H).

Example 104

(R)-4-[6-((1S,4R)-Bicyclo[2.2.1]hept-2-yloxy)-naphthalen-2-yl]-4-methyl-oxazolidin-2-one The compound was prepared in a manner similar as to that described above (R)-4-(6-hydroxynaphthalen-2-yl)-4-methyloxazolidin-2-one, (1S,4R)-Bicyclo[2.2.1]heptan-2-ol (1.0 g, 0.0090 mol), triphenylphosphine (2.6 g, 0.0099 mol), h (45 mL, 0.55 mol), and diisopropyl azodicarboxylate (2.0 g, 0.0099 mol) to give 502 mg of the desired product as a white solid (40%). 1H NMR (400 MHz, CDCl3) δ=7.94-7.61 (m, 3 H), 7.50 (d, J=8.5 Hz, 1 H), 7.23-7.05 (m, 2 H), 4.67 (br. s., 2 H), 4.33-4.17 (m, 1 H), 3.84-3.51 (m, 2 H), 2.49-0.78 (m, 11H).

Example 105

(R)-2-amino-2-(6-((1R,2R,4S)-bicyclo[2.2.1]heptan-2-yloxy)naphthalen-2-yl)propan-1-ol The compound was prepared in a manner similar as to that described (R)-4-(6-((1R,2R,4S)-bicyclo[2.2.1]heptan-2-yloxy)naphthalen-2-yl)-4-methyloxazolidin-2-one (100 mg, 0.0003 mol), ethanol (2.2 g, 0.049 mol), 4.2 M lithium hydroxide, monohydrate in water (2.1 mL, 0.0090 mol) to give 32 mg of the desired product as a white solid (32%). ESI-MS: 339 (M-16)+. 1H NMR (400 MHz, CDCl3) δ=7.94-7.61 (m, 3 H), 7.50 (d, J=8.5 Hz, 1 H), 7.23-7.05 (m, 2 H), 4.33-4.17 (m, 1 H), 3.84-3.51 (m, 2 H), 2.49-0.78 (m, 13 H).

Example 106

{(R)-1-[6-(4-Cyclopentyl-cyclohexyloxy)-5-trifluoromethylnaphthalen-2-yl]-2-hydroxy-1-methylethyl}-carbamic acid tert-butyl ester (R)-2-Amino-2-[6-(4-cyclopentyl-cyclohexyloxy)-5-trifluoromethyl-naphthalen-2-yl]-propan-1-ol (18 mg, 0.041 mmol) was combined with di-tert-butyldicarbonate (13.5 mg, 0.0620 mmol) in chloroform (2 mL, 20 mmol) and the mixture was treated with 2 M of sodium bicarbonate in water (1 mL, 2 mmol) and the biphasic mixture was stirred vigorously for 18 hours. The organic layer was removed and added directly to a column and the reaction was purified via column chromatography (0-50% EtoAC/Hex on a 4 g column) to give 11 mg of the desired product as a tan oil (49%). ESI-MS: 536 (M+H)+.

$^1$H NMR (400 MHz, CDCl$_3$) δ=8.20-8.05 (m, 1 H), 7.82 (d, J=9.0 Hz, 1 H), 7.65-7.43 (m, 2 H), 7.22 (dd, J=5.0, 9.0 Hz, 1 H), 5.22 (br. s., 2H), 4.32-4.11 (m, 1 H), 3.72 (d, J=11.3 Hz, 2 H), 2.18-1.98 (m, 2 H), 1.92-0.71 (m, 26 H)

Example 107

[(R)-1-[6-(4-Cyclopentyl-cyclohexyloxy)-5-trifluoromethylnaphthalen-2-yl]-2-(di-tert-butoxy-phosphoryloxy)-1-methyl-ethyl]-carbamic acid tert-butyl ester To a solution of {(R)-1-[6-(4-Cyclopentyl-cyclohexyloxy)-5-trifluoromethylnaphthalen-2-yl]-2-hydroxy-1-methyl-ethyl}-carbamic acid tert-butyl ester (11 mg, 0.000020 mol) and 1H-tetrazole (14 mg, 0.00020 mol) in tetrahydrofuran (3 mL, 0.04 mol) was added di-tert-butyl N,N-Diethylphosphoramidite (28 μL, 0.00010 mol) at RT. The reaction was then quenched with 10% NaS$_2$O$_3$ in saturated sodium bicarbonate, extracted with EtOAc, washed with saturated sodium chloride and then dried with Na$_2$SO$_4$. The drying agent was filtered and the organic layer was concentrated under vacuum, yielding the crude product. The crude was taken up in DCM and purified using silica gel chromatography (24 g column), 0-100% ethyl acetate in hexanes) to give 12 mg of the desired compound as a white solid (77%). ESI-MS: 728 (M+H)+. $^1$H NMR (400 MHz, DMSO-d6) δ=8.18-8.08 (m, 1 H), 7.92 (d, J=9.0 Hz, 1 H), 7.63-7.42 (m, 2 H), 7.22 (dd, J=5.0, 9.0 Hz, 1 H), 4.32-4.11 (m, 1 H), 3.98-3.80 (m, 2 H), 2.18-1.98 (m, 2 H), 1.92-0.71 (m, 46 H)

Example 108

Phosphoric acid mono-{(R)-2-amino-2-[6-(4-cyclopentylcyclohexyloxy)-5-trifluoromethyl-naphthalen-2-yl]-propyl}ester

[(R)-1-[6-(4-Cyclopentyl-cyclohexyloxy)-5-trifluoromethyl-naphthalen-2-yl]-2-(di-tert-butoxy-phosphoryloxy)-1-methyl-ethyl]-carbamic acid tert-butyl ester (11 mg, 0.000015 mol) was added 12 M of hydrogen chloride in water (1 mL, 0.01 mol; Supplier=Aldrich) and acetic acid (1 mL, 0.02 mol) and the solution was stirred for 1.5 h at RT. All solvent was then removed inder reduced pressure and the residue was dried on high-vac over night to give the desired product 8 mg was a white HCl salt (98%). ESI-MS: 499 (M-16)+. $^1$H NMR (400 MHz, DMSO-d6) δ=8.19-8.07 (m, 1 H), 7.84 (d, J=9.0 Hz, 1 H), 7.63-7.42 (m, 2 H), 7.22 (dd, J=5.0, 9.0 Hz, 1 H), 5.10 (br. s., 1 H), 4.32-4.11 (m, 1 H), 3.72 (m, 2 H), 2.18-1.98 (m, 2 H), 1.92-0.71 (m, 21 H)

Example 109 tert-butyl 2,2-dimethyl-5-(5-(trifluoromethyl)-6-(4-(trifluoromethyl)cyclohexyloxy)naphthalen-2-yl)-1,3-dioxan-5-ylcarbamate

[5-(6-Hydroxy-5-trifluoromethyl-naphthalen-2-yl)-2,2-dimethyl-1,3-dioxinan-5-yl]-carbamic acid tert-butyl ester (1 g, 0.003 mol), 4-Trifluoromethyl-cyclohexanol (0.50 g, 0.0029 mol), and triphenylphosphine (0.84 g, 0.0032 mol) were combined in dry toluene (15 mL, 0.14 mol) and stirred under nitrogen. The solution cooled to 0° C. on an ice bath and diisopropyl azodicarboxylate (0.65 g, 0.0032 mol) was added slowly (dropwise) over 30 min. Once all DIAD was added the mixture was stirred on an icebath for 30 minutes. The ice bath was then removed and the mixture was allowed to warm to room temperature while stirring under nitrogen for 16 hours. The mixture was then washed with 1.0 N HCl, and washed with Sat. Na$_2$CO$_3$, and brine. The organic layer was dried over MgSO$_4$, filtered, and concentrated to dryness under reduced pressure. The crude reaction was then dissolved in methylene chloride, absorbed onto 10 g silica and purified (dry load) via column chromatography 0-50% EtoAC/Hexanes using a 125 g column to give 1.1 g the desired product as a white solid. Material was carried forward without additional purification. ESI-MS: 592 (M+H)+

Example 110

2-Amino-2-[5-trifluoromethyl-6-(4-trifluoromethyl-cyclohexyloxy)-naphthalen-2-yl]-propane-1,3-diol Tert-butyl 2,2-dimethyl-5-(5-(trifluoromethyl)-6-(4-(trifluoromethyl)cyclohexyloxy)naphthalen-2-yl)-1,3-dioxan-5-ylcarbamate (1000.1 mg, 0.0016906 mol) (impure, assume 100% purity) was dissolved in methanol (30 mL, 0.73 mol), followed by 1 M of hydrogen chloride in water (30 mL, 0.030 mol). The reaction mixture was then heated at 80° C. for 2.5 hours. The solvent was removed under reduced pressure and the crude residue was treated with 4 N HCl in 1,4-dioxane. The solution was stirred for 1 hour and the solvent was then removed under reduced pressure. Ethyl ether was then added and the resulting solid was removed via filtration to give 815 mg of the desired product a white solid (64%). ESI-MS: 417 (M-16)+ $^1$H NMR (400 MHz, DMSO-d$_6$) δ=8.21-7.97 (m, 3 H), 7.82-7.61 (m, 2 H), 5.57-5.41 (m, 4 H), 5.10 (br. s., 0.61 H), 4.98-4.88 (m, 0.32 H), 3.97-3.72 (m, 1 H), 2.15-1.91 (m, 2 H), 1.82-1.08 (m, 6 H)

Example 111

(R)-4-[6-(4-tert-butyl-cyclohexyloxy)-naphthalen-2-yl]-3,4-dimethyl-oxazolidin-2-one To a solution of (R)-4-[6-(4-tert-butyl-cyclohexyloxy)-naphthalen-2-yl]-4-methyl-oxazolidin-2-one (73 mg, 0.19 mmol) in THF (1 mL) and DMF (1 mL) was added sodium hydride (60% in mineral oil, 12 mg, 0.29 mmol). After the mixture was stirred at room temperature for 2 hrs, methyl iodide (60 μL, 0.96 mmol) was added. The mixture was stirred at room temperature for 3 hrs. LCMS showed about 30% of conversion. Additional sodium hydride (60% in mineral oil, 50 mg) was added. After the mixture was stirred at room temperature overnight, the mixture was partitioned between NH$_4$Cl aq and EtOAc. The organic phase was washed with water, dried over anhydrous MgSO$_4$, filtered, and concentrated to give 80 mg of crude product, 106%. ESI-MS (M+H)+: 396.20, room temperature 2.53 min.

Example 112

(R)-2-[6-(4-tert-butyl-cyclohexyloxy)-naphthalen-2-yl]-2-methylamino-propan-1-ol A mixture of (R)-4-[6-(4-tert-butyl-cyclohexyloxy)-naphthalen-2-yl]-3,4-dimethyl-oxazolidin-2-one (80 mg, 0.2 mmol) in 4.2 M of LiOH aqueous (1.5 mL, 6 mmol) and ethanol (1.5 mL) was heated at 120° C. for 5 hrs. The solvent was concentrated and the residue was washed with water to give white precipitate. The crude was purified with silica gel column eluted with 2 M NH$_3$ in MeOH and DCM from 0 to 8% to give 7 mg of product, 10%. ESI-MS (M-30)$^+$: 339.30, room temperature 1.57 min. $^1$H NMR (400 MHz, CDCl$_3$) δ: 7.76~7.70 (m, 3H), 7.51 (d, 1H), 7.17~7.12 (m, 2H), 4.27 (m, 1H), 3.88 (d, 1H), 3.71 (d, 1H), 2.32~2.23 (m, 5H), 1.89 (d, 2H), 1.62 (s, 3H), 1.44 (m, 2H), 1.25~1.05 (m, 3H), 0.90 (s, 9H)

Example 113

((R)-1-{6-[4-(1,1-dimethyl-propyl)-cyclohexyloxy]-5-trifluoromethyl-naphthalen-2-yl}-2-hydroxy-1-methyl-ethyl)-carbamic acid tert-butyl ester (R)-2-amino-2-{6-[4-(1,1-dimethyl-propyl)-cyclohexyloxy]-5-trifluoromethyl-naphthalen-2-yl}-propan-1-ol (Example 35, 110 mg, 0.25 mmol) was dissolved in chloroform (8 mL) and saturated aqueous sodium bicarbonate solution (4 mL). To the solution was added di-tert-butyldicarbonate (158 mg, 0.7 mmol) and stirred at room temperature overnight. After the organic phase was separated, the aqueous layer was extracted with DCM. The combined organic phases were washed with water, dried over anhydrous MgSO$_4$, filtered and concentrated. The residue was purified with a silica gel column (EtOAc/hexanes from 0 to 50%) to give 84 mg of sticky waxy product, 62%. ESI-MS (M-(CH$_3$)$_3$COH)$^+$: 464.30, room temperature 2.53 min.

Example 114

[(R)-1-{6-[4-(1,1-dimethyl-propyl)-cyclohexyloxy]-5-trifluoromethyl-naphthalen-2-yl}-1-methyl-2-(3-oxo-1,5-dihydro-3l(5)-2,4,3-benzodioxaphosphepin-3-yloxy)-ethyl]-carbamic acid tert-butyl ester To a solution of ((R)-1-{6-[4-(1,1-dimethyl-propyl)-cyclohexyloxy]-5-trifluoromethyl-naphthalen-2-yl}-2-hydroxy-1-methyl-ethyl)-carbamic acid tert-butyl ester (83 mg, 0.15 mmol) and 1H-tetrazole (33 mg, 0.46 mmol) in THF (3 mL) was added o-xylylene N,N-diethylphosphoramidite (58 µL, 0.27 mmol) at room temperature The mixture was stirred at room temperature for 16 hrs. HPLC showed 2 peaks. Hydrogen peroxide (30% in water, 0.35 mL) was added and the mixture was stirred at room temperature for 2 h. LCMS showed a single peak with M-100 at m/z 620.40, room temperature 2.55 min. The reaction was quenched with Na$_2$S$_2$O$_3$ (0.1 N aq), extracted with EtOAc, then dried over MgSO$_4$. After the dry agent was filtered off, the residue was purified with a silica gel column eluted with EtOAc in hexanes from 0-40% to give 56 mg of product, 50%. ESI-MS (M-100)$^+$: 620.40, room temperature 2.56 min.

Example 115

((R)-1-{6-[4-(1,1-dimethyl-propyl)-cyclohexyloxy]-5-trifluoromethyl-naphthalen-2-yl}-1-methyl-2-phosphonooxy-ethyl)-carbamic acid tert-butyl ester A mixture of [(R)-1-{6-[4-(1,1-dimethyl-propyl)-cyclohexyloxy]-5-trifluoromethyl-naphthalen-2-yl}-1-methyl-2-(3-oxo-1,5-dihydro-3l(5)-2,4,3-benzodioxaphosphepin-3-yloxy)-ethyl]-carbamic acid tert-butyl ester (56 mg, 0.078 mmol) and 10% Pd/C (8 mg) in methanol (5 mL) was stirred under hydrogen atmosphere for 3 h. HPLC showed a major single peak at room temperature 2.29 min. The Pd/C catalyst was filtered off through a Celite bed. The solvent was concentrated to afford 45 mg of product, 93%. ESI-MS: 481.30, room temperature 2.29 min.

Example 116 phosphoric acid mono-{(R)-2-amino-2-{6-[4-(1,1-dimethylpropyl)-cyclohexyloxy)-5-trifluoromethyl-naphthalen-2-yl]propyl}ester A solution of ((R)-1-{6-[4-(1,1-dimethyl-propyl)-cyclohexyloxy]-5-trifluoromethyl-naphthalen-2-yl}-1-methyl-2-phosphonooxy-ethyl)-carbamic acid tert-butyl ester (45 mg, 0.07 mmol) in 4 M of HCl in dioxane (3 mL, 10 mmol) was stirred at room temperature for 3 hrs. After the solution was concentrated, the crude product was treated with acetonitrile to form precipitate. The precipitate was purified with a silica gel column eluted with 10% TFA in MeOH and DCM from 0 to 30% to give 24 mg of product, 63%. ESI-MS (M+H)$^+$: 518.30, room temperature 1.70 min. $^1$H NMR (400 MHz, CD$_3$OD) δ: 8.24 (d, 1H), 8.11 (d, 1H), 7.99 (s, 1H), 7.69 (s, 1H), 7.58 (s, 1H), 4.48 (m, 1H), 4.35 (m, 1H), 4.22 (m, 1H), 2.20 (d, 2H), 1.85 (s, 5H), 1.49 (m, 2H), 1.38-1.16 (m, 6H), 0.85 (m, 9H).

Example 117

{(R)-1-[6-(4-tert-butyl-cyclohexyloxy)-5-trifluoromethyl-naphthalen-2-yl]-2-hydroxy-1-methyl-ethyl}-carbamic acid tert-butyl ester The reaction procedure used was same as that of Example 113. Yield 0.27 g, 83%. $^1$H NMR (400 MHz, CDCl$_3$) δ: 8.19 (d, 1H), 7.89 (d, 1H), 7.77 (d, 1H), 7.57 (dd, 1H), 7.30 (d, 1H), 4.28 (m, 1H), 4.03 (d, 1H), 3.79 (d, 1H), 2.18 (d, 2H), 1.87 (d, 2H), 1.68 (s, 3H), 1.55 (m, 2H), 1.44 (s, 9H), 1.18-1.02 (m, 3H), 0.87 (s, 9H).

Example 118

[(R)-1-[6-(4-tert-butyl-cyclohexyloxy)-5-trifluoromethyl-naphthalen-2-yl]-1-methyl-2-(3-oxo-1,5-dihydro-2,4,3-benzodioxaphosphepin-3-yloxy)-ethyl]-carbamic acid tert-butyl ester The reaction procedure was same as that of Example 114. White foam, 0.27 g, 83%). ESI-MS (M-100): 606.40, room temperature 2.47 min.

Example 119

{(R)-1-[6-(4-tert-butyl-cyclohexyloxy)-5-trifluoromethyl-naphthalen-2-yl]-1-methyl-2-phosphonooxy-ethyl}-carbamic acid tert-butyl ester The reaction procedure used was the same as that of Example 115 (white precipitate, 0.23 g, 91%). ESI-MS (M-136): 467.20, room temperature 2.21 min.

Example 120 phosphoric acid mono-{(R)-2-amino-2-[6-(4-tert-butyl-cyclohexyloxy)-5-trifluoromethyl-naphthalen-2-yl]-propyl}ester The reaction procedure used was the same as that of Example 116 (white solid, HCl salt, 0.18 g, 94%). ESI-MS (M+H): 504.30, room temperature 1.65 min. $^1$H NMR (400 MHz, DMSO-$d_6$) δ: 8.12 (d, 1H), 8.10 (s, 1H), 8.04 (d, 1H), 7.79 (dd, 1H), 7.66 (d, 1H), 4.54 (m, 1H), 4.23~4.05 (m, 2H), 2.12 (d, 2H), 1.79 (d, 2H), 1.69 (s, 3H), 1.38 (m, 2H), 1.16 (m, 2H), 1.06 (m, 1H), 0.86 (s, 9H).

Example 121

(S)-4-[6-(4-cis-tert-butyl-cyclohexyloxy)-naphthalen-2-yl]-4-methyl-oxazolidin-2-one The reaction procedure used was the same as that of Example 32. (940 mg, 35%). $^1$H NMR (400 MHz, DMSO-$d_6$) δ: 8.45 (s, 1H), 7.85-7.77 (m, 3H), 7.48 (dd, 1H), 7.36 (d, 1H), 7.15 (dd, 1H), 4.41 (d, 1H), 4.38 (m, 1H), 4.27 (d, 1H), 2.20 (d, 2H), 1.81 (d, 2H), 1.65 (s, 3H), 1.35 (q, 2H), 1.21 (q, 2H), 1.07 (m, 1H), 0.88 (s, 9H).

Example 122

(S)-4-[6-(4-trans-tert-butyl-cyclohexyloxy)-5-iodo-naphthalen-2-yl]-4-methyl-oxazolidin-2-one The reaction procedure used was the same as that of Example 33. (870 mg, 83%). ESI-MS (M+H): 508.30, room temperature 2.32 min.

Example 123

(S)-4-[6-(4-trans-tert-butyl-cyclohexyloxy)-5-trifluoromethyl-naphthalen-2-yl]-4-methyl-oxazolidin-2-one The reaction procedure used was the same as that of Example 34 (330 mg, 43%). ESI-MS (M+23): 446.30, room temperature 1.67 min.

Example 124

(S)-2-amino-2-[6-(4-trans-tert-butyl-cyclohexyloxy)-5-trifluoromethyl-naphthalen-2-yl]-propan-1-ol The reaction procedure used was the same as that of Example 36 (93 mg, 33%). ESI-MS (M+23)$^+$: 446.30, room temperature 1.67 min. $^1$H NMR (400 MHz, DMSO-$d_6$) δ: 8.11 (d, 1H), 8.03 (d, 1H), 7.96 (dd, 1H), 7.78 (dd, 1H), 7.57 (d, 1H), 4.76 (t, 1H), 4.51 (m, 1H), 3.49 (m, 2H), 2.12 (d, 2H), 1.92 (s, 2H), 1.79 (d, 2H), 1.44-1.30 (m, 5H), 1.22-1.01 (m, 3H), 0.85 (s, 9H).

Example 125

(S)-4-[6-(4-cis-tert-butyl-cyclohexyloxy)-naphthalen-2-yl]-4-methyl-oxazolidin-2-one The reaction procedure used was the same as that of Example 32 (200 mg, 16%). $^1$H NMR (400 MHz, DMSO-$d_6$) δ: 8.45 (s, 1H), 7.85~7.77 (m, 3H), 7.48 (dd, 1H), 7.36 (d, 1H), 7.15 (dd, 1H), 4.41 (d, 1H), 4.38 (m, 1H), 4.27 (d, 1H), 2.20 (d, 2H), 1.81 (d, 2H), 1.65 (s, 3H), 1.35 (q, 2H), 1.21 (q, 2H), 1.07 (m, 1H), 0.88 (s, 9H).

Example 126

(S)-4-[6-(4-cis-tert-butyl-cyclohexyloxy)-5-iodo-naphthalen-2-yl]-4-methyl-oxazolidin-2-one The reaction procedure used was the same as that of Example 33 (226 mg, 100%). $^1$H NMR (400 MHz, CDCl$_3$) δ: 8.18 (d, 1H), 7.76 (d, 1H), 7.72 (d, 1H), 7.48 (dd, 1H), 7.19 (d, 1H), 4.84 (s, 1H), 4.42 (q, 2H), 2.16 (d, 2H), 1.85 (s, 3H), 1.71 (m, 2H), 1.63-1.47 (m, 4H), 1.13 (m, 1H), 0.92 (s, 9H).

Example 127

(S)-4-[6-(4-cis-tert-butyl-cyclohexyloxy)-5-trifluoromethyl-naphthalen-2-yl]-4-methyl-oxazolidin-2-one The reaction procedure used was the same as that of Example 34 (45 mg, 46%). ESI-MS (M+H): 450.20, room temperature 2.52 min.

Example 128

(S)-2-amino-2-[6-(4-cis-tert-butyl-cyclohexyloxy)-5-trifluoromethyl-naphthalen-2-yl]-propan-1-ol The reaction procedure used was the same as that of Example 35 (31 mg, 75%). ESI-MS (M-16): 407.20, room temperature 1.78 min. $^1$H NMR (400 MHz, DMSO-$d_6$) δ: c3.64 (q, 2H), 2.14 (m, 2H), 1.74-1.46 (m, 9H), 1.09 (m, 1H), 0.86 (s, 9H).

Example 129

(R)-4-(6-hydroxy-5-iodonaphthalen-2-yl)-4-methyloxazolidin-2-one

The mixture of (R)-4-(6-Hydroxy-naphthalen-2-yl)-4-methyl-oxazolidin-2-one (221.7 mg, 0.0009114 mol), N-iodosuccinimide (226 mg, 0.00100 mol) and zirconium tetrachloride (33 mg, 0.00014 mol) in methylene chloride (16 mL, 0.25 mol) was stirred at room temperature for 3 h. After filtrating through Celite and washing with methylene chloride, the concentrated residue was chromatographed to give (R)-4-(6-hydroxy-5-iodonaphthalen-2-yl)-4-methyloxazolidin-2-one as a light yellow solid (290 mg, 86%). LCMS: Rf=1.33 min (370.07, M+1, 100%), $^1$H NMR (400 MHz, MeOD) δ=8.10 (d, J=8.9 Hz, 1 H), 7.79 (s, 1 H), 7.77 (d, J=8.8 Hz, 1 H), 7.56 (dd, J=2.1, 8.9 Hz, 1 H), 7.18 (d, J=8.8 Hz, 1 H), 4.52 (d, J=8.5 Hz, 1 H), 4.43 (d, J=8.5 Hz, 1 H), 1.80 (s, 3 H).

Example 130

(R)-4-(6-hydroxy-5-(trifluoromethyl)naphthalen-2-yl)-4-methyloxazolidin-2-one

To a solution of (R)-4-(6-hydroxy-5-iodonaphthalen-2-yl)-4-methyloxazolidin-2-one (290 mg, 0.78 mmol), hexamethylphosphoramide (0.69 mL, 3.9 mmol) and Copper(I) iodide (220 mg, 1.2 mmol) in N,N-dimethylformamide (4.0 mL, 51 mmol) was added methyl fluorosulphonyldifluoroacetate (0.52 mL, 3.9 mmol). The mixture was bubbled through N$_2$ for 10 min, and was heated at 80° C. overnight. The mixture was diluted with EtOAc, filtrated through Celite, washed with water and dried over Na$_2$SO$_4$. The solvent was evaporated and chromatographed to give the product (R)-4-(6-hydroxy-5-s (trifluoromethyl)naphthalen-2-yl)-4-methyloxazolidin-2-one (240 mg, 99%). LC showed desired product peak Rf=1.13 min. $^1$H NMR (400 MHz, CDCl$_3$) δ 8.15 (d, J=7.5 Hz, 1H), 7.96 (d, J=9.0 Hz, 1H), 7.86 (d, J=1.8 Hz, 1H), 7.60 (dd, J=9.0, 1.8 Hz, 1H), 7.21 (d, J=9.0 Hz, 1H), 4.53 (d, J=8.5 Hz, 1H), 4.44 (d, J=8.5 Hz, 1H), 1.81 (s, 3H).

Example 131

(R)-4-(6-(trans-4-tert-butylcyclohexyloxy)-5-(trifluoromethyl)naphthalen-2-yl)-4-methyloxazolidin-2-one The mixture of cis-4-tert-butylcyclohexanol (30.4 mg, 0.000195 mol), (R)-4-(6-hydroxy-5-(trifluoromethyl)naphthalen-2-yl)-4-methyloxazolidin-2-one (50.5 mg, 0.000162 mol) and triphenylphosphine (51.1 mg, 0.000195 mol) in tetrahydrofuran (2 mL, 0.02 mol) was heated to reflux, and diisopropyl azodicarboxylate (0.0383 mL, 0.000195 mol) was added dropwise and was stirred and refluxed for 3 hours. The mixture was taken up into methylene chloride and subjected to chromatography purification with EtOAc/hexane (10:90 to 80:20) to give product (R)-4-(6-(trans-4-tert-butylcyclohexyloxy)-5-(trifluoromethyl)naphthalen-2-yl)-4-methyloxazolidin-2-one (22.2 mg, 30%). LCMS: Rf=2.41 min (450.46, M+1, 70%; 491.47, M+ACN, 100%). $^1$H NMR (400 MHz, CHLOROFORM-d) δ=8.25 (dd, J=8.7, 1.4 Hz, 1 H), 7.91 (d, J=9.0 Hz, 1 H), 7.79 (d, J=2.0 Hz, 1 H), 7.52 (dd, J=9.3, 2.3 Hz, 1 H), 7.34 (d, J=9.3 Hz, 1 H), 5.98 (br. s., 1 H), 4.45 (d, J=8.6 Hz, 1 H), 4.41 (d, J=8.6 Hz, 1 H), 4.38-4.26 (m, 1 H), 2.19 (d, J=13.1 Hz, 2 H), 1.89 (d, J=10.0 Hz, 2 H), 1.87 (s, 3 H), 1.59-1.48 (m, 2 H), 1.21-1.05 (m, 3 H), 0.89 (s, 9 H).

Example 132

(4R)-4-methyl-4-(6-(spiro[5.5]undecan-3-yloxy)naphthalen-2-yl)oxazolidin-2-one

The mixture of spiro[5.5]undecan-3-ol (166.0 mg, 0.0009866 mol), (R)-4-(6-hydroxynaphthalen-2-yl)-4-methyloxazolidin-2-one (200.0 mg, 0.0008222 mol), and triphenylphosphine (259 mg, 0.000987 mol) in tetrahydrofuran (7 mL, 0.08 mol) was heated to reflux, and diisopropyl azodicarboxylate (0.194 mL, 0.000987 mol) was added dropwise and was stirred and refluxed for overnight. The mixture was taken up into methylene chloride and subjected to chromatography purification with EtOAc/hexane (10:90 to 80:20) to give product (4R)-4-methyl-4-(6-(spiro[5.5]undecan-3-yloxy)naphthalen-2-yl)oxazolidin-2-one as a white solid (324 mg, 100%). LCMS Rf=2.34 min 394.45 ([M+1]+, 100%).

Example 133

(2R)-2-amino-2-(6-(spiro[5.5]undecan-3-yloxy)naphthalen-2-yl)propan-1-ol

The mixture of (4R)-4-methyl-4-(6-(spiro[5.5]undecan-3-yloxy)naphthalen-2-yl)oxazolidin-2-one (324 mg, 0.000823 mol) and lithium hydroxide (294 mg, 0.0123 mol) in ethanol (7.1 mL, 0.12 mol) and water (2.4 mL, 0.13 mol) was heated to reflux for overnight. The solvent was removed under vacuum and the residue was partitioned between water/$CH_2Cl_2$. The aqueous was extensively extracted with $CH_2Cl_2$ and the combined organic phase was dried over $Na_2SO_4$. The concentrated residue was taken up into methylene chloride and subjected to chromatography purification with MeOH/$CH_2Cl_2$ (10:90 to 80:20) to give the product (2R)-2-amino-2-(6-(spiro[5.5]undecan-3-yloxy)naphthalen-2-yl)propan-1-ol as a white powder (94.5 mg, 31.2%). LCMS Rf=1.70 min 351.34 ([M-NH$_2$]+, 100%). $^1$H NMR (400 MHz, MeOD) δ=7.86 (d, J=1.6 Hz, 1 H), 7.78 (d, J=9.0 Hz, 1 H), 7.74 (d, J=8.8 Hz, 1 H), 7.57 (dd, J=2.0, 8.7 Hz, 1 H), 7.22 (d, J=2.1 Hz, 1 H), 7.14 (dd, J=2.4, 8.9 Hz, 1 H), 4.53-4.44 (m, 1 H), 3.75 (d, J=11.0 Hz, 1 H), 3.70 (d, J=11.0 Hz, 1 H), 2.01-1.88 (m, 2 H), 1.80-1.65 (m, 4 H), 1.55 (s, 3 H), 1.50 (m, 8 H), 1.42-1.30 (m, 4 H).

Example 134 tert-butyl (2R)-1-hydroxy-2-(6-(spiro[5.5]undecan-3-yloxy)naphthalen-2-yl)propan-2-ylcarbamate (2R)-2-amino-2-(6-(spiro[5.5]undecan-3-yloxy)naphthalen-2-yl)propan-1-ol (30.0 mg, 0.0000816 mol) in chloroform (2 mL, 0.03 mol) and saturated aqueous sodium bicarbonate solution (1 mL, 0.01 mol) was added and ditert-butyldicarbonate (26.7 mg, 0.000122 mol) and the mixture was stirred at room temperature for 24 h. TLC showed complete reaction. After separation of organic layer, the aqueous layer was extracted with $CHCl_3$. The organic layer was washed with brine and dried over anhydrous $Na_2SO_4$. The concentrated residue was chromatographed with MeOH/$CH_2Cl_2$ (0-55%) to give tert-butyl (2R)-1-hydroxy-2-(6-(spiro[5.5]undecan-3-yloxy)naphthalen-2-yl)propan-2-ylcarbamate (36.3 mg, 95%).

Example 135 tert-Butyl (2R)-1-(phosphonooxy-o-xylylene)-2-(6-(spiro[5.5]undecan-3-yloxy)naphthalen-2-yl)propan-2-ylcarbamate To a solution of tert-butyl (2R)-1-hydroxy-2-(6-(spiro[5.5]undecan-3-yloxy)naphthalen-2-yl)propan-2-ylcarbamate (36.5 mg, 0.0000780 mol) and 1H-tetrazole (16.4 mg, 0.000234 mol) in tetrahydrofuran (0.82 mL, 0.010 mol) was added o-xylylene N,N-diethylphosphoramidite (25.2 μL, 0.000117 mol) at rt. The resulting mixture was stirred at room temperature for 3 d, then hydrogen peroxide (180 μL, 0.0017 mol) was added and the mixture was stirred at room temperature for 1 h. The reaction was quenched with satd. $NaS_2O_3$, then extracted with EtOAc, then dried over $Na_2SO_4$. The residue was chromatographed with MeOH/$CH_2Cl_2$ (0-100%) to give the phosphate (36.7 mg, 72%).

Example 136 tert-Butyl (2R)-1-(phosphonooxy)-2-(6-(spiro[5.5]undecan-3-yloxy)naphthalen-2-yl)propan-2-ylcarbamate To the compound of Example 135 (37.4 mg, 0.0000575 mol) in methanol (1.6 mL, 0.039 mol) was added 10% palladium on carbon (1:9, palladium:carbon black, 6.1 mg). The mixture was stirred under hydrogen (0.3 L, 0.01 mol) for 2 h. After the crude was filtered through Celite and washed with MeOH. The concentrated residue was dissolved in $CH_2Cl_2$ and was chromatographed with MeOH/$CH_2Cl_2$ (0-50%) to give the desired product tert-butyl (2R)-1-(phosphonooxy)-2-(6-(spiro[5.5]undecan-3-yloxy)naphthalen-2-yl)propan-2-ylcarbamate as a white solid (13.6 mg, 43%).

Example 137

(2R)-2-amino-2-(6-(spiro[5.5]undecan-3-yloxy)naphthalen-2-yl)propyl dihydrogen phosphate tert-Butyl (2R)-1-(phosphonooxy)-2-(6-(spiro[5.5]undecan-3-yloxy)naphthalen-2-yl)propan-2-ylcarbamate (13.6 mg, 0.0000248 mol) was dissolved in acetic acid (0.78 mL, 0.014 mol) and 10 M of hydrogen chloride in water (0.2 mL) was added and the mixture was stirred for 1d. Lypholyzing gave (2R)-2-amino-2-(6-(spiro[5.5]undecan-3-yloxy)naphthalen-2-yl)propyl dihydrogen phosphate as a white solid (4.0 mg, 36%). LCMS give a single peak Rf=1.64 min (431.41, [M−16]+, 100%, 895.73, [M+M+1], 20%). $^1$H NMR (400 MHz, MeOD) δ=7.82-7.89 (m, 3 H), 7.56 (d, J=5.5 Hz, 1 H), 7.27 (s, 1 H), 7.21 (d, J=8.6 Hz, 1 H), 4.54-4.47 (m, 1 H), 4.14-4.17 (m, 2H), 1.99-1.90 (m, 2 H), 1.86 (s, 3 H), 1.78-1.66 (m, 4 H), 1.50 (m, 8 H), 1.42-1.30 (m, 4 H).

Example 138

(4R)-4-methyl-4-(6-(spiro[5.5]undecan-3-yloxy)-5-(trifluoromethyl)naphthalen-2-yl)oxazolidin-2-one The mixture of spiro[5.5]undecan-3-ol (39.3 mg, 0.000234 mol) and (R)-4-(6-hydroxy-5-(trifluoromethyl)naphthalen-2-yl)-4-methyloxazolidin-2-one (60.6 mg, 0.000195 mol), and triphenylphosphine (61.2 mg, 0.000234 mol) in tetrahydrofuran (2 mL, 0.02 mol) was heated to reflux, and diisopropyl azodicarboxylate (0.0460 mL, 0.000234 mol) was added dropwise and was stirred and refluxed for overnight. The mixture was taken up into methylene chloride and subjected to chromatography purification with EtOAc/hexane (10:90 to 80:20) to give (4R)-4-methyl-4-(6-(spiro[5.5]undecan-3-yloxy)-5-(trifluoromethyl)naphthalen-2-yl)oxazolidin-2-one as a white solid (62.5 mg, 70%). LCMS Rf=2.45 min 462.40 ([M+1]+, 70%), 503.43 [M+42], 100%).

Example 139

(2R)-2-amino-2-(6-(spiro[5.5]undecan-3-yloxy)-5-(trifluoromethyl)naphthalen-2-yl)propan-1-ol The mixture of (4R)-4-methyl-4-(6-(spiro[5.5]undecan-3-yloxy)-5-(trifluoromethyl)naphthalen-2-yl)oxazolidin-2-one (62.5 mg, 0.000135 mol) and lithium hydroxide (36 mg, 0.0015 mol) in ethanol (2 mL, 0.04 mol) and water (0.7 mL, 0.04 mol) was heated to reflux for overnight. The solvent was removed under vacuum and the residue was partitioned between water/CH$_2$Cl$_2$. The aqueous was extensively extracted with CH$_2$Cl$_2$. And the combined organic phase was dried over Na$_2$SO$_4$. The concentrated residue was taken up into methylene chloride and subjected to chromatography purification with MeOH/CH$_2$Cl$_2$ (10:90 to 80:20) to give (2R)-2-amino-2-(6-(spiro[5.5]undecan-3-yloxy)-5-(trifluoromethyl)naphthalen-2-yl)propan-1-ol as a white gel (39.0 mg, 66%). LCMS: Rf=1.86 min 419.30 ([M−16], 100%). $^1$H NMR (400 MHz, MeOD) δ=8.15 (dd, J=1.9, 9.2 Hz, 1 H), 8.07 (d, J=9.2 Hz, 1 H), 7.96 (d, J=2.1 Hz, 1 H), 7.71 (dd, J=2.2, 9.3 Hz, 1 H), 7.47 (d, J=9.3 Hz, 1 H), 4.68-4.59 (m, 1 H), 3.76 (d, J=10.8 Hz, 1 H), 3.70 (d, J=10.8 Hz, 1 H), 1.95-1.83 (m, 2 H), 1.82-1.67 (m, 4 H), 1.54 (s, 3 H), 1.53-1.42 (m, 8 H), 1.42-1.28 (m, 4 H).

Example 140 tert-butyl (2R)-1-hydroxy-2-(6-(spiro[5.5]undecan-3-yloxy)-5-(trifluoromethyl)naphthalen-2-yl)propan-2-ylcarbamate (2R)-2-amino-2-(6-(spiro[5.5]undecan-3-yloxy)-5-(trifluoromethyl)naphthalen-2-yl)propan-1-ol (17.2 mg, 0.0000395 mol) was dissolved in chloroform (2.0 mL, 0.026 mol) and saturated aqueous sodium bicarbonate solution (1.0 mL, 0.010 mol) and di-tert-butyldicarbonate (12.9 mg, 0.0000592 mol) was added and was stirred at room temperature for 24 h. TLC showed complete reaction. After separation of organic layer, the aqueous layer was extracted with CHCl$_3$. The organic layer was washed with brine and dried over anhydrous Na$_2$SO$_4$. The concentrated residue was chromatographed with MeOH/CH$_2$Cl$_2$ (0-55%) to give product as a gel (15.3 mg, 72%).

Example 141 tert-butyl (2R)-1-(phosphonooxy-o-xylylene)-2-(6-(spiro[5.5]undecan-3-yloxy)-5-(trifluoromethyl)naphthalen-2-yl)propan-2-yl carbamate To a solution of tert-butyl (2R)-1-hydroxy-2-(6-(spiro[5.5]undecan-3-yloxy)-5-(trifluoromethyl)naphthalen-2-yl)propan-2-ylcarbamate (15.3 mg, 0.0000286 mol) and 1H-tetrazole (6.00 mg, 0.0000857 mol) in tetrahydrofuran (0.30 mL, 0.0037 mol) was added o-xylylene N,N-diethylphosphoramidite (9.24 μL, 0.0000428 mol) at rt. The resulting mixture was stirred at room temperature for 3 d, then hydrogen peroxide (64 μL, 0.00063 mol) was added and the mixture was stirred at room temperature for 1 h. The reaction was quenched with satd. NaS$_2$O$_3$, then extracted with EtOAc, then dried over Na$_2$SO$_4$. The residue was chromatographed with MeOH/CH$_2$Cl$_2$ (0-100%) to give the phosphate (20.5 mg, 99%).

Example 142 tert-butyl (2R)-1-(phosphonooxy)-2-(6-(spiro[5.5]undecan-3-yloxy)-5-(trifluoromethyl)naphthalen-2-yl)propan-2-yl carbamate The above intermediate (20.5 mg, 0.0000286 mol) in methanol (0.79 mL, 0.020 mol) was added 10% palladium on carbon (1:9, palladium:carbon black, 3.0 mg, 0.0000028 mol). The mixture was stirred under hydrogen (0.1 L, 0.006 mol) for 2 h. Filtrate through Celite and was washed with MeOH. The concentrated residue was dissolved in CH$_2$Cl$_2$ and was chromatographed with MeOH/CH$_2$Cl$_2$ (0-50%) to give tert-butyl (2R)-1-(phosphonooxy)-2-(6-(spiro[5.5]undecan-3-yloxy)-5-(trifluoromethyl)naphthalen-2-yl)propan-2-yl carbamate as a white solid (7.0 mg, 40%).

Example 143

(2R)-2-amino-2-(6-(spiro[5.5]undecan-3-yloxy)-5-(trifluoromethyl)naphthalen-2-yl)propyl dihydrogen phosphate tert-Butyl (2R)-1-(phosphonooxy)-2-(6-(spiro[5.5]undecan-3-yloxy)-5-(trifluoromethyl)naphthalen-2-yl)propan-2-yl carbamate (7.0 mg, 0.000011 mol) was dissolved in methylene chloride (0.40 mL, 0.0063 mol) and trifluoroacetic acid (0.07 mL, 0.0009 mol) was added and the mixture was stirred for 1 h. Lypholyzing gave (2R)-2-amino-2-(6-(spiro[5.5]undecan-3-yloxy)-5-(trifluoromethyl)naphthalen-2-yl)propyl dihydrogen phosphate as a white solid (6.0 mg, 100%). LCMS: Rf=1.74 min (516.35, [M+1]+, 100%). $^1$H NMR (400 MHz, MeOD) δ=8.22 (d, J=9.4 Hz, 1 H), 8.09 (d, J=9.2 Hz, 1 H), 7.96 (s, 1 H), 7.66 (d, J=9.3 Hz, 1 H), 7.53 (d, J=9.2 Hz, 1 H), 4.69-4.61 (m, 1 H), 4.31 (dd, J=1.9, 9.0 Hz, 1 H), 4.20-4.12 (m, 1 H), 1.90-1.83 (m, 2 H), 1.82 (s, 3 H), 1.79-1.60 (m, 4 H), 1.50-1.30 (m, 12 H).

Example 144

(R)-6-(4-methyl-2-oxooxazolidin-4-yl)naphthalen-2-yl trifluoromethanesulfonate

Trifluoromethanesulfonic anhydride (0.144 mL, 0.000859 mol) was slowly added to a solution containing (R)-4-(6-hydroxynaphthalen-2-yl)-4-methyloxazolidin-2-one (190 mg, 0.00078 mol), pyridine (2 mL, 0.02 mol), and methylene chloride (2 mL, 0.03 mol) at 0° C. After stirring overnight TLC showed complete reaction. After concentration, the crude was purified by chromatography using a 0-100% EtOAc/hexane gradient to give (R)-6-(4-methyl-2-oxooxazolidin-4-yl)naphthalen-2-yl trifluoromethanesulfonate as a yellow gel (259 mg, 88%). $^1$H NMR (400 MHz, CDCl$_3$-d) δ=7.95 (s, 1 H), 7.94-7.89 (m, 2 H), 7.77 (d, J=1.9 Hz, 1 H), 7.59 (dd, J=1.6, 8.6 Hz, 1 H), 7.42 (d, J=9.0 Hz, 1 H), 4.48 (d, J=8.4 Hz, 1 H), 4.43 (d, J=8.4 Hz, 1 H), 1.88 (s, 3 H).

Example 145

(R)-4-(6-((4-tert-butylcyclohexyl)methyl)naphthalen-2-yl)-4-methyloxazolidin-2-one A solution of potassium 4-tert-butylcyclohexylmethyltrifluoroborate (100 mg, 0.0004 mol), [1,1'-Bis(diphenylphosphino)ferrocene]dichloropalladium(II), complex with dichloromethane (1:1) (31.4 mg, 0.0000384 mol), (R)-6-(4-methyl-2-oxooxazolidin-4-yl)naphthalen-2-yl trifluoromethanesulfonate (144 mg, 0.000384 mol) and cesium carbonate (0.376 g, 0.00115 mol) in 1,4-dioxane (4.6 mL, 0.059 mol) and water (0.5 mL, 0.03 mol) was heated at reflux under a nitrogen atmosphere. The reaction mixture was stirred at 100° C. overnight, then cooled to room temperature, and diluted with EtOAc, filtrate, followed by extraction of ether. The organic layers were combined and dried over MgSO$_4$, and filtered. The concentrated residue was chromatographed with silica gel under 0-100% EtOAc/hexane to give (R)-4-(6-((4-tert-butylcyclohexyl)methyl)naphthalen-2-yl)-4-methyloxazolidin-2-one as a solid (18.6 mg, 12.8%). $^1$H NMR (400 MHz, CHLOROFORM-d) δ=7.84 (d, J=8.7 Hz, 1 H), 7.79 (br. s., 1 H), 7.77 (d, J=8.5 Hz, 1 H), 7.60 (s, 1 H), 7.45 (dd, J=1.9, 8.6 Hz, 1 H), 7.38 (d, J=8.4 Hz, 1 H), 5.83 (br. s., 1 H), 4.46-4.39 (m, 2 H), 2.82 (d, J=7.9 Hz, 2 H), 2.09 (m., 1 H), 1.87 (s, 3 H), 1.68-1.40 (m, 5 H), 1.39-1.24 (m, 2 H), 1.08-0.96 (m, 1 H), 0.91 (s, 9 H).

Example 146

(R)-2-amino-2-(6-((4-tert-butylcyclohexyl)methyl)naphthalen-2-yl)propan-1-ol

The mixture of (R)-4-(6-((4-tert-butylcyclohexyl)methyl)naphthalen-2-yl)-4-methyloxazolidin-2-one (18.6 mg, 0.0000490 mol) and lithium hydroxide (12.9 mg, 0.000539 mol) in ethanol (1 mL, 0.02 mol) and water (0.50 mL, 0.028 mol) was heated to reflux overnight. The solvent was removed under vacuum and the residue was partitioned between water/CH$_2$Cl$_2$. The aqueous was extensively extracted with CH$_2$Cl$_2$ and the combined organic phase was dried over Na$_2$SO$_4$. The concentrated residue was taken up into methylene chloride and subjected to chromatography with MeOH/CH$_2$Cl$_2$ (10:90 to 80:20) to give (R)-2-amino-2-(6-((4-tert-butylcyclohexyl)methyl)naphthalen-2-yl)propan-1-ol as a white solid (4.6 mg, 26%). LCMS: Rf=1.76 min 337.36 [M-NH2]+. $^1$H NMR (400 MHz, CHLOROFORM-d) δ=7.88 (s, 1 H), 7.77 (d, J=8.0 Hz, 1 H), 7.74 (d, J=7.0 Hz, 1 H), 7.56 (s, 1 H), 7.52 (dd, J=1.8, 8.7 Hz, 1 H), 7.32 (d, J=8.3 Hz, 1 H), 3.82-3.75 (m, 1 H), 3.72-3.67 (m, 1 H), 2.80 (d, J=8.0 Hz, 2 H), 2.69 (br. s., 1 H), 2.08 (br. s., 1 H), 1.64 (d, J=12.9 Hz, 2 H), 1.56 (br. s., 5 H), 1.46 (tt, J=4.0, 13.0 Hz, 2 H), 1.38-1.24 (m, 2 H), 1.03 (tt, J=3.1, 11.9 Hz, 1 H), 0.91 (s, 9 H).

Example 147

2-Bromo-6-(trans-4-tert-butyl-cyclohexyloxy)-naphthalene

2-Naphthalenol, 6-bromo-(7 g, 0.03 mol), 4-tert-Butyl-cyclohexanol (5.4 g, 0.034 mol), and triphenylphosphine (9.9 g, 0.038 mol) were combined in dry toluene (100 mL, 1 mol) and stirred under nitrogen. Diisopropyl azodicarboxylate (7.6 g, 0.038 mol) was added dropwise and the mixture was stirred for 2.5 hours. The reaction was then quinched with 100 mL water and diluted with 100 mL ethyl ether. The mixture was then washed with 1.0 N HCl, sat. Na$_2$CO$_3$, and brine. The organic layer was dried over MgSO$_4$, filtered, and concentrated to dryness under reduced pressure. The crude reaction was then dissolved in DCM, absorbed onto 25 g silica and purified in two equal portions (dry load) via column chromatography (0-10% EtoAC/Hexanes, 220 g column, peak is broad until about 2-3% EtOAC portion of the gradient) to give 5.5 g of the desired compound as a white solid (50%). ESI-MS: 362 (M+H)$^+$.

Example 148

6-bromo-2-(trans-4-tert-butylcyclohexyloxy)-1-iodonaphthalene

To a solution of 2-Bromo-6-(trans-4-tert-butyl-cyclohexyloxy)-naphthalene (500 mg, 0.001 mol) in Methylene chloride (2 mL, 0.03 mol), N-iodosuccinimide (600 mg, 0.003 mol) was added, followed by zirconium tetrachloride (60 mg, 0.0003 mol) at 23° C. The reaction mixture was then sonicated and stirred for 5 minutes at 23° C. Reaction was then diluted with DCM and the solids were removed via filtration through a 4 micron filter. 1 g of SiO$_2$ was added directly to the solution and the solvent was then removed under reduced pressure. The SiO$_2$ was then loaded onto a column (SiO$_2$, 24 g, 0-10% ethyl acetate/hexanes (ran neat hexanes for first 9 minutes of a 30 min gradient)) to give the DP as a tan amorphous solid with 20% impurity (SM) by HNMR. Material was then triturated with methanol, filtered, and dried on filter to give 386 mg of the desired product as a white solid in (60%). ESI-MS: 488 (M+H)$^+$.

Example 149

6-bromo-2-(trans-4-tert-butylcyclohexyloxy)-1-(trifluoromethyl)naphthalene 6-bromo-2-(trans-4-tert-butylcyclohexyloxy)-1-iodonaphthalene (1.09 g, 2.24 mmol) and Copper(I) iodide (298 mg, 1.57 mmol) were combined in a 40 mL vial and purged with nitrogen. N,N-Dimethylformamide (13.2 mL, 1.70E2 mmol) was then added followed by hexamethylphosphoramide (0.778 mL, 4.47 mmol). Methyl fluorosulphonyldifluoroacetate (0.569 mL, 4.47 mmol) was then added dropwise at to ambient temperature. The reaction mixture was then heated to 80° C. on a heating block for 3 hours. Reaction was then filtered and most of the DMF was removed under reduced pressure. The residue was then dissolved in ethyl ether/hexanes (4:1) and washed with water three times. Organics were dried over MgSO₄, filtered, and concentrated to dryness. Material was purified via column chromatography (0-40% EtOAc/Hexanes) to give 634 mg is the desired product as a yellow solid (58%). ESI-MS: 430 (M+H)⁺.

Example 150

2-Methyl-propane-2-sulfinic acid {3-[6-(4-tert-butyl-cyclohexyloxy)-naphthalen-2-yl]-oxetan-3-yl}-amide A solution of 2-bromo-6-(trans-4-tert-butylcyclohexyloxy)naphthalene (0.500 g, 0.00138 mol) in ether (2.4 mL, 0.023 mol) at −78° C. was added 2.0 M of n-butyllithium in cyclohexane (0.755 mL, 0.00151 mol) and stirred for 30 min and allowed to warm to 0° C. for 5 min. To the solution of 2-methyl-propane-2-sulfinic acid (S)-oxetan-3-ylideneamide (0.220 g, 0.00126 mol) in toluene (12 mL, 0.12 mol) at −78° C. was added 2.0 M of trimethylaluminum in toluene (0.692 mL, 0.00138 mol). The organolithium solution was transferred to the above mixture by syringe. And the mixture was stirred at −41° C. for 3 h. The reaction was quenched with a Na₂SO₄ aqueous saturated solution, diluted with EtOAc, filtered through Celite. washed with brine and dried. The mixture was concentrated and subjected to chromatography on silica gel with 0-100% EtOAc/hexane to give (R)—N-(3-(6-(trans-4-tert-butylcyclohexyloxy)naphthalen-2-yl)oxetan-3-yl)-2-methylpropane-2-sulfinamide as a white sticky solid (0.35 g, 61%). LCMS: Rf=2.24 min 458.30 [M+1], 100%. ¹H NMR (400 MHz, CHLOROFORM-d) δ=7.80-7.72 (m, 3 H), 7.34 (dd, J=1.8, 8.6 Hz, 1 H), 7.21-7.15 (m, 2 H), 5.35 (d, J=6.9 Hz, 1 H), 5.14 (d, J=6.9 Hz, 1 H), 5.11 (d, J=7.0 Hz, 1 H), 5.08 (d, J=7.0 Hz, 1 H), 4.29 (tt, J=4.3, 10.8 Hz, 1 H), 4.16 (br. s., 1 H), 2.29 (d, J=10.6 Hz, 2 H), 1.91 (d, J=11.6 Hz, 2 H), 1.78 (br. s., 1 H), 1.46 (q, J=12.0 Hz, 2 H), 1.21 (s, 9 H), 1.20-1.06 (m, 3 H), 0.91 (s, 9 H).

Example 151

3-(6-(trans-4-tert-Butylcyclohexyloxy)naphthalen-2-yl)oxetan-3-amine

To a solution of 2-methyl-propane-2-sulfinic acid {3-[6-(4-tert-butyl-cyclohexyloxy)-naphthalen-2-yl]-oxetan-3-yl}-amide (86 mg, 0.19 mmol) in methylene chloride (2 mL, 30 mmol) was added 2.0 M of hydrogen chloride in ether (0.188 mL, 0.376 mmol) and was stirred 10 min. A precipitate formed and cyclohexane was added to dilute the mixture. After removal of solvent, the residue was dissolved in methylene chloride, 1 M aq. NH₄OH was added and the extracted organic layer was dried and chromatographed with MeOH/CH₂Cl₂ (20-40%) to give 3-(6-(trans-4-tert-butylcyclohexyloxy)naphthalen-2-yl)oxetan-3-amine as a solid (44.8 mg, 67%). LCMS: Rf=1.55 min 337.20 ([M-16]). ¹H NMR (400 MHz, CHLOROFORM-d) δ=7.84 (d, J=1.4 Hz, 1 H), 7.81-7.70 (m, 2 H), 7.66 (d, J=1.9 Hz, 1 H), 7.22-7.12 (m, 2 H), 5.09 (d, J=6.7 Hz, 2 H), 4.81 (d, J=6.7 Hz, 2 H), 4.29 (tt, J=4.2, 10.8 Hz, 1 H), 2.29 (d, J=13.2 Hz, 2 H), 1.91 (d, J=12.5 Hz, 2 H), 1.56-1.39 (m, 2 H), 1.29-1.02 (m, 3 H), 0.91 (s, 9 H).

Example 152

2-Methyl-propane-2-sulfinic acid {3-[6-(trans-4-tert-butyl-cyclohexyloxy)-5-trifluoromethyl-naphthalen-2-yl]-oxetan-3-yl}-amide To a solution of 6-bromo-2-(trans-4-tert-butylcyclohexyloxy)-1-(trifluoromethyl)naphthalene (0.594 g, 0.00138 mol) in ether (2.4 mL, 0.023 mol) at −78° C. was added 2.0 M of n-butyllithium in cyclohexane (0.755 mL, 0.00151 mol) and stirred for 30 min and then warmed to 0° C. for 5 min. To a solution of 2-methyl-propane-2-sulfinic acid (S)-oxetan-3-ylideneamide (0.220 g, 0.00126 mol) in toluene (12 mL, 0.12 mol) at −78° C. was added 2.0 M of trimethylaluminum in toluene (0.692 mL, 0.00138 mol). The organolithium solution was transferred to the above mixture by syringe. And the mixture was stirred at −41° C. for 3 h. The reaction was quenched with a saturated Na₂SO₄ solution, diluted with EtOAc, filtered through Celite. washed with brine, and dried. The mixture was concentrated and subjected to silica gel chromatography with 0-100% EtOAc/hexane to give (R)—N-(3-(6-(trans-4-tert-butylcyclohexyloxy)-5-(trifluoromethyl)naphthalen-2-yl)oxetan-3-yl)-2-methylpropane-2-sulfinamide as a white sticky solid. LCMS: Rf=2.37 min 526.20 [M+1], 100%. ¹H NMR (400 MHz, CHLOROFORM-d) δ=8.25 (d, J=8.2 Hz, 1 H), 7.96 (d, J=9.2 Hz, 1 H), 7.86 (d, J=2.0 Hz, 1 H), 7.47 (dd, J=2.1, 9.2 Hz, 1 H), 7.36 (d, J=9.1 Hz, 1 H), 5.34 (d, J=7.0 Hz, 1 H), 5.15 (d, J=7.0 Hz, 1 H), 5.10 (d, J=6.9 Hz, 1 H), 5.04 (d, J=6.9 Hz, 1 H), 4.39-4.28 (m, 1 H), 4.15 (s, 1 H), 2.21 (d, J=9.9 Hz, 2 H), 1.89 (d, J=10.2 Hz, 2 H), 1.65-1.47 (m, 3 H), 1.23 (s, 9 H), 1.21-1.01 (m, 4 H), 0.89 (s, 9 H). M.p. 86.8-90° C.

Example 153

3-(6-(trans-4-tert-butylcyclohexyloxy)-5-(trifluoromethyl)naphthalen-2-yl)oxetan-3-amine To a solution of 2-methyl-propane-2-sulfinic acid {3-[6-(trans-4-tert-butyl-cyclohexyloxy)-5-trifluoromethyl-naphthalen-2-yl]-oxetan-3-yl}-amide (332 mg, 0.632 mmol) in methylene chloride (7 mL, 100 mmol) was added 2.0 M of hydrogen chloride in ether (0.632 mL, 1.26 mmol) and stirred for 10 min. A precipitate formed and cyclohexane was added to dilute the mixture. After removal of solvent, the residue was dissolved in methylene chloride, 1M aq. NH₄OH was added, the extracted organic layer was dried and subjected to silica gel chromatography with MeOH/CH₂Cl₂ (20-40%) to give 3-(6-(trans-4-tert-butylcyclohexyloxy)-5-(trifluoromethyl)naphthalen-2-yl)oxetan-3-amine as a solid (213.7 mg, 80%). LCMS: Rf=1.67 min 405.20 ([M-16]). ¹H NMR (400 MHz, CHLOROFORM-d) δ=8.27 (d, J=9.3 Hz, 1 H), 7.93 (d, J=9.2 Hz, 1 H), 7.91 (d, J=1.9 Hz, 1 H), 7.81 (dd, J=2.1, 9.3 Hz, 1 H), 7.33 (d, J=9.2 Hz, 1 H), 5.06 (d, J=6.5 Hz, 2 H), 4.82 (d, J=6.5 Hz, 2 H), 4.38-4.24 (m, 1 H), 2.20 (d, J=12.4 Hz, 2 H), 1.93-1.82 (m, 2 H), 1.55 (br. s., 2 H), 1.41-1.09 (m, 5 H), 0.89 (s, 9 H).

Example 154

(R)-4-(6-(3-(benzyloxy)phenylthio)naphthalen-2-yl)-4-methyloxazolidin-2-one (R)-6-(4-methyl-2-oxooxazolidin-4-yl)naphthalen-2-yl-trifluoromethanesulfonate (30.0 mg, 0.0000799 mol), 3-benzyloxy-benzenethiol (20.7 mg, 0.0000959 mol), tris(dibenzylideneacetone)dipalladium(0) (8.78 mg, 9.59E-6 mol) and xantphos (11.1 mg, 0.0000192 mol) were dissolved in 1,4-dioxane (3 mL, 0.04 mol, anhydrous), degassed in low vacuum and backfilled with N₂ five times. N,N-diisopropylethylamine (0.0418 mL, 0.000240 mol) pre-degassed in the same way was added under N₂ atmosphere. The mixture was heated to reflux for 20 hours. The mixture was cooled to room temperature, filtered, evaporated, and the residue was chromatographed with EtOAc/hexane (0:100 to 10:90) to give (R)-4-(6-(3-(benzyloxy)phenylthio)naphthalen-2-yl)-4-methyloxazolidin-2-one as a solid product (30.0 mg, 85%). Rf (EtOAc:hexane=1:9)=0.3.

Example 155

(R)-2-amino-2-(6-(3-(benzyloxy)phenylthio)naphthalen-2-yl)propan-1-ol (R)-4-(6-(3-(benzyloxy)phenylthio)naphthalen-2-yl)-4-methyloxazolidin-2-one (30.0 mg, 0.0000679 mol) was dissolved in ethanol (2 mL, 0.03 mol) and water (0.8 mL, 0.05 mol) then lithium hydroxide (17 mg, 0.00072 mol) was added and was heated to reflux overnight. LCMS shows no SM and a new peak at 1.51 399.17 ([M-NH2]+, 100). After concentration, the residue was taken up into methylene chloride and water. The aqueous layer was extracted with methylene chloride and concentrated. Column chromatography with MeOH/methylene chloride gave (R)-2-amino-2-(6-(3-(benzyloxy)phenylthio)naphthalen-2-yl)propan-1-ol as a white solid (26.0 mg, 92%). LCMS 1.51 399.17 ([M-NH$_2$]+, 100%). $^1$H NMR (400 MHz, MeOD) δ=7.95 (br. s., 1 H), 7.89-7.76 (m, 3 H), 7.64 (d, J=8.6 Hz, 1 H), 7.43-7.20 (m, 7 H), 6.98-6.87 (m, 3 H), 5.00 (br. s., 2 H), 3.84-3.77 (m, 1 H), 3.77-3.69 (m, 1 H), 1.60 (s., 3 H).

Example 155

(R)-tert-butyl 2-(6-(3-(benzyloxy)phenylthio)naphthalen-2-yl)-1-hydroxypropan-2-ylcarbamate To a solution of (R)-2-amino-2-(6-(3-(benzyloxy)phenylthio)naphthalen-2-yl)propan-1-ol (26.0 mg, 0.0000626 mol) in chloroform (3 mL, 0.04 mol) and saturated aqueous sodium bicarbonate (2 mL, 0.02 mol) was added di-tert-butyldicarbonate (25.4 mg, 0.000116 mol). The mixture was stirred at room temperature for 24 h. TLC showed complete reaction. After separation of organic layer, the aqueous layer was extracted with CHCl$_3$. The organic layer was washed with brine and dried over anhydrous Na$_2$SO$_4$. The concentrated residue was chromatographed with MeOH/CH$_2$Cl$_2$ (0-55%) to give the product. $^1$HNMR confirmed the structure.

Example 156

(R)-tert-butyl 2-(6-(3-(benzyloxy)phenylthio)naphthalen-2-yl)-1-(di-tert-butoxyphosphoryloxy)propan-2-ylcarbamate To a solution of (R)-tert-butyl 2-(6-(3-(benzyloxy)phenylthio)naphthalen-2-yl)-1-hydroxypropan-2-ylcarbamate (20.0 mg, 0.0000388 mol) and 1H-tetrazole (30.4 mg, 0.000434 mol) in tetrahydrofuran (2 mL, 0.02 mol) was added di-tert-butyl N,N-diethylphosphoramidite (60.1 µL, 0.000216 mol) at room temperature. The resulting mixture was stirred at room temperature overnight, then hydrogen peroxide (180 µL, 0.0017 mol) was added and the mixture was stirred at room temperature for 1 h. The reaction was quenched with saturated. Na$_2$S$_2$O$_3$, then extracted with EtOAc, and dried over Na$_2$SO$_4$. The residue was chromatographed with MeOH—CH$_2$Cl$_2$ (0-20%) to give (R)-tert-butyl 2-(6-(3-(benzyloxy)phenylthio)naphthalen-2-yl)-1-(di-tert-butoxyphosphoryloxy)propan-2-ylcarbamate as a gel (28 mg, 100%).

Example 157

(R)-2-amino-2-(6-(3-(benzyloxy)phenylthio)naphthalen-2-yl)propyl dihydrogen phosphate (R)-tert-butyl 2-(6-(3-(benzyloxy)phenylthio)naphthalen-2-yl)-1-(di-tert-butoxyphosphoryloxy)propan-2-ylcarbamate was dissolved in acetic acid (2.0 mL, 0.035 mol) and 10 M hydrogen chloride in water (0.5 mL) and stirred for 1 d. Removal solvent and concentration gave an oil, which was added to water and ether. The aqueous layer was concentrated and purified by preparative HPLC 0.1% TFA water/ACN to give (R)-2-amino-2-(6-(3-(benzyloxy)phenylthio)naphthalen-2-yl)propyl dihydrogen phosphate as a solid (1.1 mg, 4%). LCMS 1.56 496.25 (M+1, 40%), 991.66. $^1$HNMR shows quite pure. $^1$H NMR (400 MHz, MeOD) δ=7.98 (s, 1 H), 7.89 (d, J=8.5 Hz, 2 H), 7.82 (s, 1 H), 7.65 (d, J=6.7 Hz, 1 H), 7.43 (d, J=10.4 Hz, 1 H), 7.39-7.25 (m, 6 H), 7.05-6.95 (m, 3 H), 5.06 (s, 2 H), 4.29 (dd, J=5.0, 11.0 Hz, 1 H), 4.16 (dd, J=5.4, 11.0 Hz, 1 H), 1.86 (s, 3 H).

Example 158

(R)-4-(6-(cis-4-cyclohexylcyclohexyloxy)-5-iodonaphthalen-2-yl)-4-methyloxazolidin-2-one To a solution of (R)-4-(6-(cis-4-cyclohexylcyclohexyloxy)naphthalen-2-yl)-4-methyloxazolidin-2-one (35.0 mg, 0.0000859 mol) in methylene chloride (2 mL, 0.03 mol), N-iodosuccinimide (38.6 mg, 0.000172 mol) was added, followed by zirconium tetrachloride (4.00 mg, 0.0000172 mol) at 23° C. The reaction mixture was then sonicated and stirred for 5 minutes at 23° C. TLC and LC/MS indicated a clean reaction. The majority of solvent was removed. Solid was removed via filtration through a Celite pad. The mixture was then loaded onto a column (SiO$_2$, 4 g, 0-50% ethyl acetate/hexanes) to give a pure product (42.3 g, 92%).

$^1$H NMR (CHLOROFORM-d) δ: 8.17 (d, J=9.0 Hz, 1H), 7.75 (d, J=9.0 Hz, 1H), 7.71 (d, J=1.3 Hz, 1H), 7.47 (dd, J=9.0, 1.8 Hz, 1H), 7.18 (d, J=9.3 Hz, 1H), 6.22 (s, 1H), 4.82 (br. s., 1H), 4.37-4.46 (m, 2H), 4.12 (q, J=7.0 Hz, 1H), 2.05-2.13 (m, 2H), 1.84 (s, 3H), 1.62-1.79 (m, 9H), 1.46-1.60 (m, 4H), 1.10-1.30 (m, 4H), 0.95-1.08 (m, 1H); MS: (M+1): 534.30.

Example 159

(R)-(6-(cis-4-cyclohexylcyclohexyloxy)-5-trifluoromethyl-naphthalen-2-yl)-4-methyloxazolidin-2-one (R)-(6-(cis-4-cyclohexylcyclohexyloxy)-5-iodonaphthalen-2-yl)-4-methyloxazolidin-2-one (42.0 mg, 0.0000787 mol), copper(I) iodide (22.5 mg, 0.000118 mol) was placed in a vial, and purged with N$_2$. N,N-Dimethylformamide (1.00 mL, 0.0129 mol) was added followed by hexamethylphosphoramide (68.5 µL, 0.000394 mol). Methyl fluorosulphonyldifluoroacetate (50.1 µL, 0.000394 mol) was added dropwise at 23° C. The reaction mixture was then heated to at 80° C. for 3 hours. The reaction was completed and the desired product was formed. The reaction mixture was then cooled to 23° C., and filtrated. Majority of the solvent was removed under vacuum, and water was added to the residue solution. Solid was collected, and washed with water (50×5 mL) and then hexanes (20×3 mL) to give a pure product (35 mg g, 93%). $^1$H NMR (CHLOROFORM-d) δ: 8.26 (d, J=9.0 Hz, 1H), 7.91 (d, J=9.0 Hz, 1H), 7.78 (d, J=1.8 Hz, 1H), 7.51 (dd, J=9.2, 1.9 Hz, 1H), 7.31 (d, J=9.3 Hz, 1H), 6.07 (s, 1H), 4.80 (br. s., 1H), 4.38-4.48 (m, 2H), 2.04-2.15 (m, 2H), 1.85 (s, 3H), 1.74 (d, J=8.5 Hz, 4H), 1.49-1.66 (m, 81-1), 1.08-1.32 (m, 5H), 0.94-1.06 (m, 1H). MS (M+1): 476.30.

Example 160

(R)-2-Amino-2-(6-(cis-4-cyclohexylcyclohexyloxy)-5-(trifluoromethyl)naphthalen-2-yl)propan-1-ol (R)-(6-(cis-4-cyclohexylcyclohexyloxy)-5-trifluoromethylnaphthalen-2-yl)-4-methyloxazolidin-2-one (55.4 mg, 0.000116 mol) was dissolved in ethanol (2 mL, 0.03 mol), followed by 4 M lithium hydroxide in water (1 mL, 0.004 mol). The reaction mixture was then heated at 80° C. for 5 hours. All solvent was removed. The solid was extracted with DCM, and dried over $Na_2SO_4$. removal of solvent gave the desired product (25 mg, 48%). $^1$H NMR (MeOD) δ: 7.99-8.06 (m, 1H), 7.93 (d, J=9.3 Hz, 1H), 7.83 (d, J=2.0 Hz, 1H), 7.58 (dd, J=9.3, 2.3 Hz, 1H), 7.32 (d, J=9.3 Hz, 1H), 4.74 (s, 1H), 3.54-3.65 (m, 2H), 1.89-2.04 (m, 2H), 1.65 (d, J=9.3 Hz, 2H), 1.43-1.59 (m, 8H), 1.41 (s, 3H), 1.00-1.22 (m, 7H), 0.87-0.99 (m, 1H). MS (M+Na+): 472.30.

Example 161

(R)-(6-(trans-4-cyclohexylcyclohexyloxy)-5-iodonaphthalen-2-yl)-4-methyloxazolidin-2-one The same procedures as described above in Examples 158 gave product in 98% yield. $^1$H NMR (CHLOROFORM-d) δ: 8.14 (d, J=8.8 Hz, 1H), 7.66-7.74 (m, 2H), 7.46 (dd, J=8.9, 1.9 Hz, 1H), 7.16 (d, J=9.0 Hz, 1H), 6.87 (s, 1H), 4.37-4.46 (m, 2H), 4.22-4.34 (m, 1H), 2.18 (d, J=10.3 Hz, 2H), 1.78-1.90 (m, 7H), 1.54-1.76 (m, 9H), 1.05-1.30 (m, 6H), 0.91-1.03 (m, 1H). MS (M+1): 534.30

Example 162

(R)-(6-(trans-4-cyclohexylcyclohexyloxy)-5-trifluoromethyl-naphthalen-2-yl)-4-methyloxazolidin-2-one The same procedures as described above in Examples 159 gave product in 91% yield. $^1$H NMR (CHLOROFORM-d) δ: 8.23 (d, J=8.8 Hz, 1H), 7.89 (d, J=9.3 Hz, 1H), 7.78 (d, J=2.0 Hz, 1H), 7.51 (dd, J=9.2, 2.1 Hz, 1H), 7.32 (d, J=9.3 Hz, 1H), 6.15 (s, 1H), 4.38-4.48 (m, 2H), 4.25-4.36 (m, 1H), 2.15 (d, J=11.3 Hz, 2H), 1.84 (s, 5H), 1.46-1.77 (m, 8H), 1.04-1.23 (m, 7H), 0.92-1.02 (m, 1H). MS (M+1): 476.30.

Example 163

(R)-2-Amino-2-(6-(trans-4-cyclohexylcyclohexyloxy)-5-(trifluoromethyl)naphthalen-2-yl)propan-1-ol The same procedures as described above in Examples 160 gave product in 79% yield. $^1$H NMR (MeOD) δ: 8.09-8.16 (m, 1H), 8.03 (d, J=9.0 Hz, 1H), 7.94 (d, J=1.8 Hz, 1H), 7.69 (dd, J=9.3, 2.0 Hz, 1H), 7.44 (d, J=9.3 Hz, 1H), 4.35-4.47 (m, 1H), 3.64-3.77 (m, 2H), 2.16 (d, J=11.3 Hz, 2H), 1.84 (d, J=10.3 Hz, 2H), 1.74 (d, J=8.8 Hz, 4H), 1.66 (d, J=11.0 Hz, 1H), 1.40-1.55 (m, 5H), 1.07-1.31 (m, 7H), 0.95-1.07 (m, 2H). MS (M+Na+): 472.30.

Example 164 tert-butyl (R)-2-(6-(trans-4-cyclohexylcyclohexyloxy)-5-(trifluoromethyl)naphthalen-2-yl)-1-hydroxypropan-2-ylcarbamate (R)-2-Amino-2-(6-(trans-4-cyclohexylcyclohexyloxy)-5-(trifluoromethyl)naphthalen-2-yl)propan-1-ol (30.0 mg, 0.0000667 mol) was dissolved in methylene chloride (6 mL, 0.09 mol), followed by di-tert-butyldicarbonate (30.6 mg, 0.000140 mol), potassium carbonate (18.4 mg, 0.000133 mol) and water (4 mL, 0.2 mol) at 23° C. The reaction mixture was then allowed to stir for 5 h till all the SM was converted to the desired intermediate. Standard work up, and purified via chromatography ($SiO_2$, 4 g, 0-100% ethyl acetate/exanes) to give the desired intermediate, tert-butyl (R)-2-(6-(trans-4-cyclohexylcyclohexyloxy)-5-(trifluoromethyl)naphthalen-2-yl)-1-hydroxypropan-2-ylcarbamate (28.2 mg, 77%). $^1$H NMR (MeOD) δ: 7.99 (d, J=7.8 Hz, 1H), 7.90 (d, J=9.3 Hz, 1H), 7.72 (d, J=1.8 Hz, 1H), 7.51 (dd, J=9.3, 1.8 Hz, 1H), 7.34 (d, J=9.3 Hz, 1H), 4.26-4.38 (m, 1H), 3.64-3.75 (m, 1H), 3.54-3.62 (m, 1H), 2.07 (d, J=11.3 Hz, 2H), 1.74 (d, J=10.3 Hz, 2H), 1.62 (s, 3H), 1.23-1.47 (m, 11H), 0.99-1.16 (m, 5H), 0.81 (d, J=6.8 Hz, 9H)

Example 165 tert-butyl (R)-2-(6-(trans-4-cyclohexylcyclohexyloxy)-5-(trifluoromethyl)naphthalen-2-yl)-1-(di-tert-butoxyphosphoryloxy)propan-2-ylcarbamate tert-Butyl (R)-2-(6-(trans-4-cyclohexylcyclohexyloxy)-5-(trifluoromethyl)naphthalen-2-yl)-1-hydroxypropan-2-ylcarbamate was then treated with di-tert-butyl N,N-diethylphosphoramidite (66.6 mg, 0.000267 mol) and 1H-tetrazole (23.4 mg, 0.000334 mol) in tetrahydrofuran (2 mL, 0.03 mol) at 23° C. for 8 hours. 9 M of hydrogen peroxide in water (0.0296 mL, 0.000267 mol) was added to the reaction mixture at −20° C., and the reaction mixture was then stirred for 1 hour at 23° C., followed by sodium thiosulfate (52.8 mg, 0.000334 mol) at −30° C. All the excess of solvents were removed, and the residue was purified via chromatography ($SiO_2$, 4 g, 0-35% ethyl acetate/hexanes) to give a pure intermediate (30.3 mg, 80%). $^1$H NMR (MeOD) δ: 8.11 (d, J=9.3 Hz, 1H), 8.02 (d, J=9.0 Hz, 1H), 7.84 (d, J=1.8 Hz, 1H), 7.62 (dd, J=9.2, 1.9 Hz, 1H), 7.46 (d, J=9.3 Hz, 1H), 4.38-4.49 (m, 1H), 4.34 (br. s., 1H), 4.25-4.31 (m, 1H), 2.17 (d, J=11.3 Hz, 2H), 1.85 (d, J=10.5 Hz, 2H), 1.70-1.79 (m, 6H), 1.60-1.69 (m, 1H), 1.51 (m, 13H), 1.41-1.47 (m, 23H), 0.97-1.32 (m, 2H)

Example 166

(R)-2-amino-2-(6-(trans-4-cyclohexylcyclohexyloxy)-5-(trifluoromethyl)naphthalen-2-yl)propyl dihydrogen phosphate tert-Butyl (R)-2-(6-(trans-4-cyclohexylcyclohexyloxy)-5-(trifluoromethyl)naphthalen-2-yl)-1-(di-tert-butoxyphosphoryloxy)propan-2-ylcarbamate was then dissolved in methanol (2 mL, 0.06 mol) followed by 6 M of hydrogen chloride in water (1 mL, 0.007 mol). The reaction mixture was then heated at 80° C. for 3 hours. All solvents were removed, the crude product was then purified via reverse chromatography (4.3 g, 10-90% acetonitrile with 0.1% TFA/water with 0.1% TFA 7.2 mg, 17%). $^1$H NMR (MeOD) δ: 8.24 (d, J=8.8 Hz, 1H), 8.11 (d, J=9.3 Hz, 1H), 7.98 (s, 1H), 7.69 (d, J=8.0 Hz, 1H), 7.57 (d, J=9.3 Hz, 1H), 4.43-4.56 (m, 1H), 4.33 (d, J=8.3 Hz, 1H), 4.19 (d, J=7.0 Hz, 1H), 2.18 (d, J=10.5 Hz, 2H), 1.81-1.91 (m, 5H), 1.71-1.79 (m, 4H), 1.67 (d, J=11.5 Hz, 1H), 1.40-1.57 (m, 2H), 1.10-1.32 (m, 7H), 0.97-1.08 (m, 2H). MS (M+1): 530.0

Example 167

(R)-2-Amino-2-(6-(cis-4-isopropylcyclohexyloxy)-5-(trifluoromethyl)naphthalen-2-yl)propan-1-ol (R)-2-Amino-2-(6-(cis-4-isopropylcyclohexyloxy)-5-(trifluoromethyl)naphthalen-2-yl)propan-1-ol was prepared from (R)-4-(6-(cis-4-isopropylcyclohexyloxy)naphthalen-2-yl)-4-methyloxazolidin-2-one by the same 3-step procedure as described above in Examples 158-160. (62% yield). $^1$H NMR (MeOD) δ: 8.03 (dd, J=9.4, 1.9 Hz, 1H), 7.94 (d, J=9.1 Hz, 1H), 7.83 (d, J=2.3 Hz, 1H), 7.58 (dd, J=9.4, 2.3 Hz, 1H), 7.33 (d, J=9.1 Hz, 1H), 4.78 (br. s., 1H), 3.53-3.67 (m, 2H), 1.90-2.05 (m, 2H), 1.31-1.61 (m, 9H), 1.18 (m, 1H), 1.10 (m, 1H), 0.81 (d, J=6.8 Hz, 6H).
MS (M+Na+): 432.30.

Example 168

(R)-2-Amino-2-(6-(trans-4-isopropylcyclohexyloxy)-5-(trifluoromethyl)naphthalen-2-yl)propan-1-ol (R)-2-Amino-2-(6-(trans-4-isopropylcyclohexyloxy)-5-(trifluoromethyl)naphthalen-2-yl)propan-1-ol was prepared from was prepared from (R)-4-(6-(trans-4-isopropylcyclohexyloxy)naphthalen-2-yl)-4-methyloxazolidin-2-one by the same 3-step procedure as described above in Examples 158-160 (81% yield). $^1$H NMR (CHLOROFORM-d) δ: 8.07-8.16 (m, 1H), 8.02 (d, J=9.1 Hz, 1H), 7.93 (d, J=1.9 Hz, 1H), 7.68 (dd, J=9.3, 2.1 Hz, 1H), 7.42 (d, J=9.1 Hz, 1H), 4.32-4.48 (m, 1H), 3.62-3.76 (m, 2H), 2.15 (d, J=10.2 Hz, 2H), 1.81 (d, J=9.8 Hz, 2H), 1.38-1.57 (m, 7H), 1.23-1.36 (m, 1H), 1.07-1.21 (m, 1H), 0.89 (d, J=6.8 Hz, 6H). MS (M+Na+): 432.30.

Example 169

(R)-2-Amino-2-(6-(trans-4-(1,1-difluoroethyl)cyclohexyloxy)-5-(trifluoromethyl)naphthalen-2-yl)propyl dihydrogen phosphate (R)-2-Amino-2-(6-(trans-4-(1,1-difluoroethyl)cyclohexyloxy)-5-(trifluoromethyl)naphthalen-2-yl)propyl dihydrogen phosphate was prepared from (R)-2-amino-2-(6-(trans-4-(1,1-difluoroethyl)cyclohexyloxy)-5-(trifluoromethyl)naphthalen-2-yl)propan-1-ol by the same procedures as described above in Examples 164-166 (29% yield). $^1$H NMR (MeOD) δ: 8.25 (d, J=8.8 Hz, 1H), 8.14 (d, J=9.3 Hz, 1H), 8.00 (s, 1H), 7.70 (d, J=9.3 Hz, 1H), 7.61 (d, J=9.3 Hz, 1H), 4.56 (m, 4.35 (dd, J=11.0, 4.5 Hz, 1H), 4.21 (dd, J=11.2, 4.9 Hz, 1H), 2.25 (d, J=11.5 Hz, 2H), 2.00 (d, J=12.8 Hz, 2H), 1.85 (s, 3H), 1.50-1.75 (m, 6H), 1.45 (m, 2H). MS (M+1): 512.20.

Example 170

(R)-4-Methyl-4-(6-(3-(trifluoromethyl)phenoxy)naphthalen-2-yl)oxazolidin-2-one (R)-4-(6-hydroxynaphthalen-2-yl)-4-methyloxazolidin-2-one (Example 4, 65 mg, 0.27 mmol), 3-(trifluoromethyl)phenylboronic acid (101 mg, 0.54 mmol) and cupric acetate (48.5 mg, 0.000267 mol) were placed in a vial, purged with N$_2$, following by methylene chloride (2 mL, 0.03 mol) and triethylamine (0.186 mL, 0.00134 mol) at 23° C. The reaction was allowed to stir for about for 10 hours, and filtrated. The crude material was then purified via chromatography (SiO$_2$, 4 g, 0-35%) to give a pure product (22 mg, 31%). $^1$H NMR (CHLOROFORM-d) δ: 7.87 (d, J=9.0 Hz, 1H), 7.83 (s, 1H), 7.78 (d, J=8.8 Hz, 1H), 7.45-7.52 (m, 2H), 7.37-7.43 (m, 1H), 7.35 (d, J=2.0 Hz, 1H), 7.27-7.31 (m, 2H), 7.22 (d, J=8.3 Hz, 1H), 6.01 (s, 1H), 4.39-4.49 (m, 2H), 1.87 (s, 3H). MS (M+1): 388.20.

Example 171

(R)-2-amino-2-(6-(3-(trifluoromethyl)phenoxy)naphthalen-2-yl)propan-1-ol (R)-4-Methyl-4-(6-(3-(trifluoromethyl)phenoxy)naphthalen-2-yl)oxazolidin-2-one (20.0 mg, 0.000052 mol) was dissolved in ethanol (2 mL, 0.03 mol), followed by 4 M of lithium hydroxide in water (1 mL, 0.004 mol). The reaction mixture was then heated at 80° C. for 5 hours. All solvent was removed. The solid was extracted with DCM, and was purified via HPLC to give the desired product (10 mg, 52%). $^1$H NMR (MeOD) δ: 7.91-8.00 (m, 2H), 7.77 (d, J=8.8 Hz, 1H), 7.64 (dd, J=8.8, 1.8 Hz, 1H), 7.51-7.58 (m, 1H), 7.35-7.44 (m, 2H), 7.22-7.30 (m, 3H), 3.64-3.78 (m, 2H), 1.52 (s, 3H).
MS (M+1): 362.0

Example 172

(R)-2-Amino-2-(6-(3-chlorophenoxy)naphthalen-2-yl)propan-1-ol

The compound was prepared in a two step procedure analagous to that described in Examples 170-171. $^1$H NMR (MeOD) δ: 7.79-7.89 (m, 2H), 7.66 (d, J=8.8 Hz, 1H), 7.53 (dd, J=8.7, 1.6 Hz, 1H), 7.19-7.29 (m, 2H), 7.13 (dd, J=8.8, 2.5 Hz, 1H), 7.03 (dd, J=8.0, 1.3 Hz, 1H), 6.91 (t, J=2.1 Hz, 1H), 6.85 (dd, J=8.3, 1.8 Hz, 1H), 3.54-3.67 (m, 2H), 1.42 (s, 3H). MS (M+Na+): 350.10.

Example 173

(R)-2-Amino-2-(6-(4-chlorophenoxy)naphthalen-2-yl)propan-1-ol

The compound was prepared in a two step procedure analagous to that described in Examples 170-171. $^1$H NMR (MeOD) δ: 7.79-7.89 (m, 2H), 7.66 (d, J=8.8 Hz, 1H), 7.50-7.56 (m, 1H), 7.25 (s, 1H), 7.17 (d, J=5.0 Hz, 2H), 7.12 (dd, J=8.9, 2.1 Hz, 1H), 7.06 (s, 1H), 6.90 (td, J=4.5, 2.3 Hz, 1H), 3.55-3.67 (m, 2H), 1.42 (s, 3H).
MS (M+Na+): 350.10.

Example 174

(R)-2-Amino-2-(6-(3-bromophenoxy)naphthalen-2-yl)propan-1-ol

The compound was prepared in a two step procedure analagous to that described in Examples 170-171. $^1$H NMR (MeOD) δ: 7.79-7.88 (m, 2H), 7.66 (d, J=8.8 Hz, 1H), 7.49-7.56 (m, 1H), 7.25 (s, 1H), 7.17 (d, J=5.0 Hz, 2H), 7.12 (dd, J=8.9, 2.1 Hz, 1H), 7.06 (s, 1H), 6.90 (td, J=4.5, 2.3 Hz, 1H), 3.55-3.67 (m, 2H), 1.42 (s, 3H).
MS (M-16): 355.10, 357.10.

Example 175

(R)-2-Amino-2-(6-(3-(trifluoromethoxy)phenoxy)naphthalen-2-yl)propan-1-ol

The compound was prepared in a two step procedure analagous to that described in Examples 170-171. $^1$H NMR (MeOD) δ: 7.81-7.90 (m, 2H), 7.67 (d, J=8.8 Hz, 1H), 7.54 (dd, J=8.5, 1.8 Hz, 1H), 7.27-7.38 (m, 2H), 7.15 (dd, J=8.8, 2.3 Hz, 1H), 6.87-6.97 (m, 2H), 6.81 (s, 1H), 3.55-3.68 (m, 2H), 1.42 (s, 3H). MS (M-16): 361.20.

Example 176

(R)-2-Amino-2-(6-(4-ethylphenoxy)naphthalen-2-yl)propan-1-ol

The compound was prepared in a two step procedure analagous to that described in Examples 170-171. $^1$H NMR (MeOD) δ: 7.81 (s, 1H), 7.76 (d, J=9.5 Hz, 1H), 7.53-7.61 (m, 1H), 7.48 (dd, J=8.7, 1.9 Hz, 1H), 7.06-7.16 (m, 4H), 6.82-6.90 (m, 2H), 3.53-3.65 (m, 2H), 2.55 (q, J=7.6 Hz, 2H), 1.40 (s, 3H), 1.15 (t, J=7.7 Hz, 4H)
MS (M+Na+): 344.20.

Example 177

(R)-2-Amino-2-(6-(3-isopropylphenoxy)naphthalen-2-yl)propan-1-ol

The compound was prepared in a two step procedure analagous to that described in Examples 170-171. $^1$H NMR (MeOD) δ: 7.93 (s, 1H), 7.87 (d, J=8.8 Hz, 1H), 7.66-7.74 (m, 114), 7.59 (dd, J=8.7, 1.6 Hz, 1H), 7.27-7.33 (m, 1H), 7.24 (s, 1H), 7.21 (dd, J=8.8, 2.0 Hz, 1H), 7.03 (d, J=7.5 Hz, 1H), 6.92 (s, 1H), 6.78-6.86 (m, 1H), 3.64-3.76 (m, 2H), 2.88 (quin, J=6.9 Hz, 1H), 1.51 (s, 3H), 1.23 (d, J=6.8 Hz, 6H).
MS (M+Na+): 358.20.

Example 178

(R)-2-Amino-2-(6-(4-isobutylphenoxy)naphthalen-2-yl)propan-1-ol

The compound was prepared in a two step procedure analagous to that described in Examples 170-171. $^1$H NMR (MeOD) δ: 7.92 (s, 1H), 7.86 (d, J=9.5 Hz, 1H), 7.65-7.71 (m, 1H), 7.58 (dd, J=8.8, 1.8 Hz, 1H), 7.19-7.25 (m, 2H), 7.17 (d, J=8.5 Hz, 2H), 6.96 (d, J=8.5 Hz, 2H), 3.63-3.75 (m, 2H), 2.48 (d, J=7.3 Hz, 2H), 1.87 (dt, J=13.6, 6.8 Hz, 1H), 1.51 (s, 3H), 0.93 (d, J=6.5 Hz, 6H). MS (M+Na+): 372.30.

Example 179

(R)-2-Amino-2-(6-(4-tert-butylphenoxy)naphthalen-2-yl)propan-1-ol

The compound was prepared in a two step procedure analagous to that described in Examples 170-171. $^1$H NMR (MeOD) δ: 7.92 (s, 1H), 7.86 (d, J=9.5 Hz, 1H), 7.69 (d, J=8.8 Hz, 1H), 7.58 (dd, J=8.8, 1.8 Hz, 1H), 7.42 (d, J=8.8 Hz, 2H), 7.17-7.25 (m, 2H), 6.98 (d, J=8.8 Hz, 2H), 3.64-3.75 (m, 2H), 1.51 (s, 3H), 1.34 (s, 9H).
MS (M+Na+): 372.30.

Example 180

(R)-2-Amino-2-(6-(p-tolyloxy)naphthalen-2-yl)propan-1-ol

The compound was prepared in a two step procedure analagous to that described in Examples 170-171. $^1$H NMR (MeOD) δ: 7.91 (s, 1H), 7.85 (d, J=8.5 Hz, 1H), 7.63-7.71 (m, 1H), 7.57 (d, J=8.8 Hz, 1H), 7.14-7.24 (m, 4H), 6.94 (d, J=8.3 Hz, 2H), 3.63-3.75 (m, 2H), 2.34 (s, 3H), 1.50 (s, 3H).
MS (M+Na+): 330.20.

Example 181

(R)-2-Amino-2-(6-(4-(trifluoromethyl)phenoxy)naphthalen-2-yl)propan-1-ol

The compound was prepared in a two step procedure analagous to that described in Examples 170-171. $^1$H NMR (MeOD) δ: 7.88-7.97 (m, 2H), 7.75 (d, J=8.5 Hz, 1H), 7.62 (dd, J=8.8, 1.8 Hz, 1H), 7.34 (d, J=2.0 Hz, 1H), 7.29 (d, J=8.5 Hz, 2H), 7.24 (dd, J=8.9, 2.4 Hz, 1H), 7.06-7.14 (m, 2H), 3.65-3.76 (m, 2H), 1.51 (s, 3H). MS (M+1): 362.20.

Example 182

(R)-2-Amino-2-(6-(2-ethylphenoxy)naphthalen-2-yl)propan-1-ol

The compound was prepared in a two step procedure analagous to that described in Examples 170-171. $^1$H NMR (MeOD) δ: 7.81 (s, 1H), 7.76 (d, J=9.0 Hz, 1H), 7.50-7.57 (m, 1H), 7.43-7.50 (m, 1H), 7.23 (dd, J=7.4, 1.1 Hz, 1H), 7.08-7.15 (m, 2H), 6.99-7.07 (m, 1H), 6.96 (d, J=2.3 Hz, 1H), 6.83 (d, J=7.8 Hz, 1H), 3.52-3.65 (m, 2H), 2.54 (q, J=7.4 Hz, 2H), 1.40 (s, 3H), 1.08 (t, J=7.5 Hz, 3H). MS (M+Na+): 344.20.

Example 183

(R)-2-Amino-2-(6-(3,4-difluorophenoxy)naphthalen-2-yl)propan-1-ol

The compound was prepared in a two step procedure analagous to that described in Examples 170-171. $^1$H NMR (MeOD) δ: 7.88-7.99 (m, 2H), 7.75 (d, J=8.5 Hz, 1H), 7.63 (dd, J=8.7, 1.6 Hz, 1H), 7.33 (d, J=2.3 Hz, 1H), 7.19-7.29 (m, 2H), 6.98 (ddd, J=11.5, 6.8, 3.0 Hz, 1H), 6.79-6.88 (m, 1H), 3.64-3.77 (m, 2H), 1.52 (s, 3H).
MS (M+Na+): 352.20.

Example 184

(R)-2-Amino-2-(6-(3,4-dimethylphenoxy)naphthalen-2-yl)propan-1-ol

The compound was prepared in a two step procedure analagous to that described in Examples 170-171. $^1$H NMR (MeOD) δ: 7.91 (s, 1H), 7.84 (d, J=8.5 Hz, 1H), 7.62-7.70 (m, 1H), 7.57 (dd, J=8.9, 1.6 Hz, 1H), 7.15-7.23 (m, 2H), 7.12 (d, J=8.0 Hz, 1H), 6.84 (d, J=2.3 Hz, 1H), 6.76 (dd, J=8.2, 2.4 Hz, 1H), 3.62-3.75 (m, 2H), 2.25 (s, 3H), 2.24 (s, 3H), 1.50 (s, 3H).

MS (M+Na+): 344.20.

Example 185

(R)-2-Amino-2-(6-(3-chloro-4-fluorophenoxy)naphthalen-2-yl)propan-1-ol

The compound was prepared in a two step procedure analagous to that described in Examples 170-171. $^1$H NMR (MeOD) δ: 7.88-7.98 (m, 2H), 7.75 (d, J=8.8 Hz, 1H), 7.62 (dd, J=8.8, 1.8 Hz, 1H), 7.31 (d, J=2.0 Hz, 1H), 7.19-7.29 (m, 2H), 7.15 (dd, J=6.1, 2.9 Hz, 1H), 7.00 (dt, J=9.0, 3.4 Hz, 1H), 3.66-3.76 (m, 2H), 1.52 (s, 3H).

MS (M+Na+): 368.10.

Example 186

(R)-2-Amino-2-(6-(3,5-difluorophenoxy)naphthalen-2-yl)propan-1-ol

The compound was prepared in a two step procedure analagous to that described in Examples 170-171. $^1$H NMR (MeOD) δ: 7.92-8.02 (m, 2H), 7.80 (d, J=8.8 Hz, 1H), 7.66 (dd, J=8.8, 1.8 Hz, 1H), 7.47 (d, J=2.0 Hz, 1H), 7.25 (dd, J=8.9, 2.4 Hz, 1H), 6.63-6.73 (m, 1H), 6.58 (dd, J=8.7, 2.1 Hz, 2H), 3.65-3.78 (m, 2H), 1.52 (s, 3H).

MS (M-16): 313.20.

Example 187

(R)-2-Amino-2-(6-(3,5-dimethylphenoxy)naphthalen-2-yl)propan-1-ol

The compound was prepared in a two step procedure analagous to that described in Examples 170-171. $^1$H NMR (MeOD) δ: 7.92 (s, 1H), 7.86 (d, J=8.8 Hz, 1H), 7.69 (d, J=8.8 Hz, 1H), 7.58 (dd, J=8.8, 1.8 Hz, 1H), 7.15-7.25 (m, 2H), 6.80 (s, 1H), 6.64 (s, 2H), 3.63-3.75 (m, 2H), 2.27 (s, 6H), 1.51 (s, 31-1). MS (M+Na+): 344.20.

Example 188

(R)-4-(6-(4-isopropoxyphenoxy)naphthalen-2-yl)-4-methyloxazolidin-2-one (R)-4-(6-hydroxynaphthalen-2-yl)-4-methyloxazolidin-2-one (3 g, 0.01 mol), 4-isopropoxyphenylboronic acid (5 g, 0.03 mol), and cupric acetate (2.55 g, 0.0140 mol) were placed in a vial followed by methylene chloride (100 mL, 2 mol) and finally triethylamine (9.78 mL, 0.0702 mol) at 23° C. The flask was then purged with nitrogen, sealed and stirred at room temperature overnight. The reaction was allowed to stir for 16 hours. Reaction was then heated to 50° C. for two hours. The reaction mixture was then cooled to RT and filtrated and the crude material was then purified via chromatography (SiO$_2$, 40 g, 0-75% EtOAC/Hexane) to give 2.4 g of the desired product as a colorless solid. Material was used without additional purification. ESI-MS: 378 (M+H)$^+$

Example 189

(R)-2-Amino-2-[6-(4-isopropoxy-phenoxy)-naphthalen-2-yl]-propan-1-ol (R)-4-[6-(4-Isopropoxy-phenoxy)-naphthalen-2-yl]-4-methyl-oxazolidin-2-one (1.092 g, 0.002894 mol) was dissolved in ethanol (60 mL, 1 mol), followed by 4 M lithium hydroxide in water (30 mL, 0.1 mol). The reaction mixture was then heated at 80° C. for 5 hours. LCMS indicates no SM remains with mostly DP RT=1.26 min, M+1=352. All solvent was removed under reduced pressure. The solid was triturated with DCM, and the solvent was then washed with water. Organic was dried over MgSO$_4$, filtered and concentrated to dryness. Residue was then placed on the high vac for 5 hours. 1H NMR and LCMS were consistent with structure. ESI-MS: 360 (M-16)$^+$ $^1$H NMR (400 MHz, CHLOROFORM-d) δ=7.88-7.67 (m, 3 H), 7.50-7.21 (m, 5 H), 7.00 (m, 2 H), 6.45-6.13 (m, 1 H), 4.82-4.67 (m, 1 H), 4.43 (s, 2 H), 2.17 (s, 3 H), 1.46-1.28 (d, J=9.0 Hz, 6 H)

Example 190 tert-Butyl 2,2-dimethyl-5-(6-(3-(trifluoromethyl) phenoxy)naphthalen-2-yl)-1,3-dioxan-5-ylcarbamate

[5-(6-Hydroxy-naphthalen-2-yl)-2,2-dimethyl-1,3-dioxinan-5-yl]-carbamic acid tert-butyl ester (Example 13, 50.0 mg, 0.000134 mol), 3-(trifluoromethyl)phenylboronic acid (50.8 mg, 0.000268 mol), cupric acetate (24.3 mg, 0.000134 mol) were placed in a vial, purged with N$_2$, following by methylene chloride (2 mL, 0.03 mol) and triethylamine to (0.0933 mL, 0.000669 mol) at 23° C. The reaction was allowed to stir for about for 10 hours, and filtrated. The crude material was then purified via chromatography (SiO$_2$, 4 g, 0-35%) to give a pure product (43 mg, 62%). $^1$H NMR (CHLOROFORM-d) δ: 7.84 (d, J=8.8 Hz, 1H), 7.79 (s, 1H), 7.73 (d, J=8.5 Hz, 1H), 7.55 (dd, J=8.7, 1.6 Hz, 1H), 7.41-7.49 (m, 1H), 7.31-7.40 (m, 2H), 7.16-7.30 (m, 3H), 5.57 (br. s., 1H), 4.22-4.29 (m, 2H), 4.14 (d, J=11.3 Hz, 2H), 1.49-1.58 (m, 6H), 1.36 (br. s., 9H). MS (M-113): 404.20.

Example 191

2-Amino-2-(6-(3-(trifluoromethyl)phenoxy)naphthalen-2-yl)propane-1,3-diol tert-Butyl 2,2-Dimethyl-5-(6-(3-(trifluoromethyl)phenoxy)naphthalen-2-yl)-1,3-dioxan-5-ylcarbamate (35.0 mg, 0.0000676 mol) was dissolved in methanol (2 mL, 0.06 mol), followed by 2 M hydrogen chloride in water (2 mL, 0.004 mol). The reaction mixture was then heated at 50° C. for 3 hours. All solvents were removed to give a pure product (23 mg, 100%). $^1$H NMR (MeOD) δ: 8.00 (d, J=9.0 Hz, 1H), 7.96 (s, 1H), 7.90 (d, J=8.8 Hz, 1H), 7.54-7.64 (m, 2H), 7.42-7.48 (m, 2H), 7.24-7.37 (m, 3H), 4.05-4.13 (m, 2H), 3.94-4.03 (m, 2H). MS (M+1): 378.20.

Example 192

2-Amino-2-(6-(3-(benzyloxy)phenylthio)naphthalen-2-yl)propane-1,3-diol

The compound was prepared from tert-butyl 2,2-dimethyl-5-(6-(trifluoromethylsulfonyloxy)naphthalen2-yl)-1,3-dioxan-5-ylcarbamate and 3-benzyloxy-benzenethiol in reactions analogous to those described in Examples 154 and 191. $^1$H NMR (MeOD) δ: 7.82 (s, 1H), 7.76 (d, J=8.6 Hz, 2H), 7.71 (s, 1H), 7.48 (dd, J=8.6, 2.0 Hz, 1H), 7.31 (dd, J=8.6, 1.5 Hz, 1H), 7.11-7.26 (m, 6H), 6.80-6.89 (m, 3H), 4.93 (s, 2H), 3.95-4.03 (m, 2H), 3.86-3.94 (m, 2H). MS (M+1): 432.0.

Example 193

2-Amino-2-(6-(3-(benzyloxy)phenylthio)naphthalen-2-yl)-3-hydroxypropyl dihydrogen phosphate The compound was prepared from 2-amino-2-(6-(3-(benzyloxy)phenylthio)naphthalen-2-yl)propane-1,3-diol in a 3-step process analogous to that described in Examples 83-85. $^1$H NMR (MeOD) δ: 7.86 (s, 1H), 7.76 (d, J=8.6 Hz, 2H), 7.70 (s, 1H), 7.51 (d, J=8.6 Hz, 1H), 7.30 (d, J=7.1 Hz, 1H), 7.10-7.26 (m, 6H), 6.80-6.91 (m, 3H), 4.93 (s, 2H), 4.27-4.35 (m, 1H), 4.17-4.25 (m, 1H), 3.97-4.05 (m, 1H), 3.88-3.96 (m, 1H). MS (M+1): 512.0.

Example 194

2-Amino-2-(6-(3-(benzyloxy)phenoxy)naphthalen-2-yl)propane-1,3-diol

The compound was prepared analogously to Examples 190-191. $^1$H NMR (MeOD) δ: 7.79-7.86 (m, 2H), 7.73 (d, J=8.8 Hz, 1H), 7.44 (dd, J=8.8, 2.0 Hz, 1H), 7.14-7.32 (m, 9H), 6.73 (dd, J=8.3, 2.0 Hz, 1H), 6.58 (t, J=2.3 Hz, 1H), 6.53 (dd, J=8.0, 1.8 Hz, 1H), 4.96 (s, 2H), 3.95-4.04 (m, 2H), 3.85-3.94 (m, 2H). MS (M+1): 416.0.

Example 195

2-Amino-2-(6-(3-(benzyloxy)phenoxy)naphthalen-2-yl)-3-hydroxypropyl dihydrogen phosphate The compound was prepared from 2-amino-2-(6-(3-(benzyloxy)phenoxy)naphthalen-2-yl)propane-1,3-diol analogously to Example 193. $^1$H NMR (MeOD) δ: 7.95 (m, 2H), 7.83 (m, 1H), 7.57 (m, 1H), 7.34 (m, 2H), 7.30 (m, 6H), 6.83 (m, 1H), 6.69 (m, 1H), 6.60 (m, 1H), 5.07 (s, 2H), 4.52 (m, 2H), 4.10 (m, 1H), 4.05 (m, 1H). MS (M+1): 496.0.

Example 196

2-Amino-2-(6-(3-(pentyloxy)phenoxy)naphthalen-2-yl)propane-1,3-diol

The compound was prepared analogously to Examples 190-191. $^1$H NMR (MeOD) δ: 7.90-7.97 (m, 2H), 7.83 (d, J=8.8 Hz, 1H), 7.54 (dd, J=8.8, 1.8 Hz, 1H), 7.23-7.35 (m, 3H), 6.73 (dd, J=8.9, 1.6 Hz, 1H), 6.55-6.64 (m, 2H), 4.05-4.13 (m, 2H), 3.96-4.03 (m, 2H), 3.94 (t, J=6.4 Hz, 2H), 1.69-1.82 (m, 2H), 1.32-1.49 (m, 4H), 0.85-0.99 (m, 3H). MS (M+1): 396.0

Example 197

2-Amino-2-(6-(3-phenethoxyphenoxy)naphthalen-2-yl)propane-1,3-diol

The compound was prepared analogously to Examples 190-191. $^1$H NMR (MeOD) δ: 7.80-7.87 (m, 2H), 7.68-7.78 (m, 1H), 7.43 (dd, J=8.8, 2.0 Hz, 1H), 7.03-7.26 (m, 8H), 6.64 (dd, J=8.3, 1.8 Hz, 1H), 6.44-6.55 (m, 1H), 4.02-4.12 (m, 2H), 3.95-4.02 (m, 2H), 3.83-3.93 (m, 2H), 2.90-2.98 (m, 2H). MS (M+1): 430.0

Example 198

2-Amino-2-(6-(3-(isopentyloxy)phenoxy)naphthalen-2-yl)propane-1,3-diol

The compound was prepared analogously to Examples 190-191. $^1$H NMR (MeOD) δ: 7.90-7.98 (m, 2H), 7.84 (d, J=8.8 Hz, 1H), 7.54 (dd, J=8.7, 1.6 Hz, 1H), 7.24-7.37 (m, 3H), 6.70-6.79 (m, 1H), 6.56-6.65 (m, 2H), 4.05-4.13 (m, 2H), 3.92-4.03 (m, 4H), 1.81 (dt, J=13.4, 6.7 Hz, 1H), 1.64 (q, J=6.8 Hz, 2H), 0.85-1.05 (m, 6H). MS (M+1): 396.0.

Example 199

2-Amino-2-(6-(3-(cyclohexylmethoxy)phenoxy)naphthalen-2-yl)propane-1,3-diol

The compound was prepared analogously to Examples 190-191. $^1$H NMR (MeOD) δ: 7.89-7.98 (m, 2H), 7.84 (d, J=8.8 Hz, 1H), 7.54 (dd, J=8.8, 1.8 Hz, 1H), 7.22-7.37 (m, 3H), 6.73 (dd, J=8.3, 1.5 Hz, 1H), 6.54-6.64 (m, 2H), 4.05-4.15 (m, 2H), 3.94-4.03 (m, 2H), 3.74 (d, J=6.5 Hz, 2H), 1.64-1.91 (m, 5H), 1.17-1.45 (m, 4H), 1.00-1.14 (m, 2H). MS (M+1): 422.0.

Example 200

2-Amino-2-(6-(3-(4,4,4-trifluorobutoxy)phenoxy)naphthalen-2-yl)propane-1,3-diol

The compound was prepared analogously to Examples 190-191. $^1$H NMR (MeOD) δ: 7.80-7.89 (m, 2H), 7.74 (d, J=8.8 Hz, 1H), 7.44 (dd, J=8.8, 2.0 Hz, 1H), 7.15-7.27 (m, 3H), 6.67 (dd, J=8.3, 1.5 Hz, 1H), 6.50-6.58 (m, 2H), 3.96-4.04 (m, 2H), 3.84-3.95 (m, 4H), 2.14-2.34 (m, 2H), 1.83-1.98 (m, 2H). MS (M+1): 436.0.

Example 201 methyl 4-(6-(trans-4-tert-butylcyclohexyloxy)-5-(trifluoromethyl)naphthalen-2-yl)-4-nitrobutanoate A 200 mL round-bottom flask containing a stir bar was charged with 6-bromo-2-(trans-4-tert-butylcyclohexyloxy)-1-(trifluoromethyl)naphthalene (5.00 g, 11.6 mmol), tris(dibenzylideneacetone)dipalladium(0) (0.400 g, 0.437 mmol; Strem), 2-(di-t-butylphosphino)-2'-methylbiphenyl (0.546 g, 1.75 mmol; Strem), and cesium carbonate (4.55 g, 14.0 mmol; Alfa Aesar). The reaction vessel was capped with a rubber septum, evacuated, backfilled with argon three times and 1,2-dimethoxyethane (100 mL, 1000 mmol) and 4-nitrobutyric acid methyl ester (3.02 mL, 24.4 mmol) were added via syringe under argon. After the mixture was stirred vigorously for 2 min at room temperature, the flask was equipped with a condenser and heated at 50° C. overnight. The reaction was allowed to cool to ambient temperature and quenched with a solution of sat. aqueous ammonium chloride. The layers were separated and the aqueous phase was extracted with ethyl acetate. The combined organic phase was washed with water then dried with magnesium sulfate, filtered and concentrated under reduced pressure. The crude product was dissolved in methylene chloride and absorbed onto silica gel, then purified by flash column chromatography (0-20% hexanes in ethylacetate) to give 2.34 g of the title compound in 41% yield.

Example 202

4-(6-(trans-4-tert-butylcyclohexyloxy)-5-(trifluoromethyl)naphthalen-2-yl)-4-nitrobutanoic acid A 2 M solution of lithium hydroxide, monohydrate in water (1.00 mL, 2.00 mmol) was added to a solution of 4-[6-(trans-4-tert-butyl-cyclohexyloxy)-5-trifluoromethyl-naphthalen- 2-yl]-4-nitro-butyric acid methyl ester (0.114 g, 0.230 mmol) in methanol (1.00 mL, 24.7 mmol) and tetrahydrofuran (1.00 mL, 12.3 mmol). The mixture was stirred at room temperate. After 2 h, HPLC analysis showed that the reaction was complete. The mixture was concentrated to dryness under reduced pressure then dissolved in methylene chloride and partitioned between 1N HCl aqueous solution. The organic phase was then dried over MgSO$_4$, filtered, concentrated and purified by flash chromatography (0-5% MeOH in methylene chloride) to give 81.2 mg of the title compound (73% yield).

Example 203

4-amino-4-(6-(trans-4-tert-butylcyclohexyloxy)-5-(trifluoromethyl)naphthalen-2-yl) butanoic acid Zinc (0.194 g, 2.96 mmol) was added to a solution of 4-[6-(trans-4-tert-butyl-cyclohexyloxy)-5-trifluoromethyl-naphthalen-2-yl]-4-nitro-butyric acid (0.102 g, 0.212 mmol) in acetic acid (3.00 mL, 52.8 mmol). The mixture was stirred for 2 hours at room temperature. HPLC analysis showed that the reaction was complete. The mixture was filtered and the filtrate was concentrated to dryness under reduced pressure. The resulting crude product was dissolved in DMSO (4 mL) and purified by HPLC. The product was dried for 2 days under vacuum to give 28 mg of the title compound as a white solid (26% yield). MS: m/z=435.66 [M-16]+. $^1$H NMR (MeOD, 400 MHz): δ=8.24-8.30 (m, 1 H), 8.09-8.14 (m, 1 H), 7.92-7.96 (m, 1 H), 7.56-7.65 (m, 2 H), 4.45-4.57 (m, 2 H), 2.65-2.69 (m, 2 H), 2.26-2.46 (m, 4 H), 2.18-2.26 (m, 2 H), 1.87-1.97 (m, 2 H), 1.45-1.58 (m, 2 H), 1.18-1.31 (m, 2 H), 1.06-1.17 (m, 1 H), 0.92 (s, 9 H)

Example 204

2-(trans-4-tert-butylcyclohexyloxy)-6-(1-nitroethyl) naphthalene

A 40 mL vial equipped with a magnetic stir bar was charged with 2-bromo-6-(trans-4-tert-butylcyclohexyloxy) naphthalene (0.6695 g, 1.853 mmol), tris(dibenzylideneacetone)dipalladium(0) (0.06363 g, 0.06948 mmol), 2-(di-t-butylphosphino)-2'-methylbiphenyl (0.08684 g, 0.2779 mmol), and cesium carbonate (0.7245 g, 2.224 mmol). The reaction vessel was capped, evacuated, and backfilled with argon three times then 1,2-dimethoxyethane (20.00 mL, 192.4 mmol) was added via syringe under argon. After the mixture was stirred vigorously for 2 min at room temperature, nitroethane (0.2795 mL, 3.891 mmol) was added and the reaction was heated overnight at 50° C. The reaction was allowed to cool to ambient temperature. The mixture was quenched with a solution of sat. aqueous ammonium chloride. The layers were separated and the aqueous phase was extracted with ethyl acetate. The combined organic phase was washed with water then dried with magnesium sulfate, filtered and concentrated under reduced pressure. The residue was taken up in methylene chloride and silica gel was added. The solvent was removed and the residue was purified by flash column chromatography using 0-20% ethylacetate in hexanes to give the title compound in 58% yield.

Example 205 methyl 4-(6-(trans-4-tert-butylcyclohexyloxy)naphthalen-2-yl)-4-nitropentanoate

To a mixture of potassium carbonate (0.1783 g, 1.290 mmol), tetrabutylammonium hydrogen sulfate (0.005110 g, 0.01505 mmol) and N,N-dimethylformamide (3.00 mL, 38.7 mmol) was added 2-(4-tert-butyl-cyclohexyloxy)-6-(1-nitroethyl)-naphthalene (0.3821 g, 1.075 mmol). The mixture was stirred for 15 minutes, then methyl acrylate (0.1162 mL, 1.290 mmol) was added while maintaining the temperature at 20° C. (cool water bath). The mixture was stirred and allowed to reach room temperature. Stirring was continued (in slightly below room temperature water bath) for 2 hours and the reaction was monitored by HPLC. Ethylacetate and saturated aq. ammonium chloride were added and the layers were separated. The combined organic layer was dried over MgSO$_4$, filtered, concentrated and purified by flash chromatography (0-20% EtOAc in hexanes) to give the title compound in 72% yield.

Example 206

4-(6-(trans-4-tert-butylcyclohexyloxy)naphthalen-2-yl)-4-nitropentanoic acid 4-(6-(trans-4-tert-butylcyclohexyloxy)naphthalen-2-yl)-4-nitropentanoic acid was synthesized as per 4-(6-(trans-4-tert-butylcyclohexyloxy)-5-(trifluoromethyl)naphthalen-2-yl)-4-nitrobutanoic acid (Example 202) in 96% yield using methyl 4-(6-(trans-4-tert-butylcyclohexyloxy) naphthalen-2-yl)-4-nitropentanoate as starting material.

Example 207

4-amino-4-(6-(trans-4-tert-butylcyclohexyloxy) naphthalen-2-yl)pentanoic acid 4-amino-4-(6-(trans-4-tert-butylcyclohexyloxy)naphthalen-2-yl) pentanoic acid was synthesized as per 4-amino-4-(6-(trans-4-tert-butylcyclohexyloxy)-5-(trifluoromethyl) naphthalen-2-yl) butanoic acid (Example 203) in 3% yield using 4-(6-(trans-4-tert-butylcyclohexyloxy) naphthalen-2-yl)-4-nitropentanoic acid as starting material. MS: m/z=381.53 [M-NH$_2$]+. $^1$H NMR (MeOD) δ: 7.91 (d, J=8.7 Hz, 1H), 7.83-7.88 (m, 2H), to 7.55 (dd, J=8.7, 1.9 Hz, 1H), 7.31 (d, J=2.3 Hz, 1H), 7.21 (dd, J=9.1, 2.3 Hz, 1H), 4.34-4.47 (m, 1H), 2.69 (s, 3H), 2.40-2.57 (m, 2H), 2.23-2.39 (m, 3H), 2.06-2.19 (m, 1H), 1.91-2.01 (m, 2H), 1.88 (s, 2H), 1.39-1.55 (m, 2H), 1.11-1.39 (m, 3H), 0.96 (s, 9H)

Example 208

2-(trans-4-tert-butylcyclohexyloxy)-6-(1-nitroethyl)-1-(trifluoromethyl)naphthalene 2-(trans-4-tert-butylcyclohexyloxy)-6-(1-nitroethyl)-1-(trifluoromethyl)naphthalene was synthesized as per 2-(trans-4-tert-butylcyclohexyloxy)-6-(1-nitroethyl)naphthalene (Example 204) in 35% yield using 6-bromo-2-(trans-4-tert-butylcyclohexyloxy)-1-(trifluoromethyl)naphthalene as starting material.

Example 209 methyl 4-(6-(trans-4-tert-butylcyclohexyloxy)-5-(trifluoromethyl)naphthalen-2-yl)-4-nitropentanoate Methyl 4-(6-(trans-4-tert-butylcyclohexyloxy)-5-(trifluoromethyl)naphthalen-2-yl)-4-nitropentanoate was synthesized as per methyl 4-(6-(trans-4-tert-butylcyclohexyloxy) naphthalen-2-yl)-4-nitropentanoate (Example 205) in 62% yield using 2-(trans-4-tert-butylcyclohexyloxy)-6-(1-nitroethyl)-1-(trifluoromethyl)naphthalene as starting material.

Example 210

4-(6-(trans-4-tert-butylcyclohexyloxy)-5-(trifluoromethyl)naphthalen-2-yl)-4-nitropentanoic acid 4-(6-(trans-4-tert-butylcyclohexyloxy)-5-(trifluoromethyl)naphthalen-2-yl)-4-nitropentanoic acid was synthesized as per 4-(6-(trans-4-tert-butylcyclohexyloxy)naphthalen-2-yl)-4-nitropentanoic acid (Example 206) in 10% yield using methyl 4-(6-(trans-4-tert-butylcyclohexyloxy)-5-(trifluoromethyl)naphthalen-2-yl)-4-nitropentanoate as starting material.

Example 211

4-amino-4-(6-(trans-4-tert-butylcyclohexyloxy)-5-(trifluoromethyl)naphthalen-2-yl) pentanoic acid 4-amino-4-(6-(trans-4-tert-butylcyclohexyloxy)-5-(trifluoromethyl)naphthalen-2-yl) pentanoic acid was synthesized as per 4-amino-4-(6-(trans-4-tert-butylcyclohexyloxy) naphthalen-2-yl) pentanoic acid (Example 207) in 26% yield using 4-(6-(trans-4-tert-butylcyclohexyloxy)-5-(trifluoromethyl)naphthalen-2-yl)-4-nitropentanoic acid as starting material. MS: m/z=449.71 [M-NH$_2$]+. $^1$H NMR (MeOD) δ: 8.25-8.31 (m, 1H), 8.14 (d, J=9.3 Hz, 7.96 (d, J=2.3 Hz, 1H), 7.69 (dd, J=9.3, 2.5 Hz, 7.60 (d, J=9.3 Hz, 1H), 4.46-4.56 (m, 1H), 2.65-2.70 (m, 3H), 2.37-2.54 (m, 2H), 2.18-2.35 (m, 2H), 2.07-2.18 (m, 2H), 1.95 (br. s., 2H), 1.87 (s, 2H), 1.50 (br. s., 2H), 1.19-1.34 (m, 2H), 1.07-1.18 (m, 1H), 0.88-0.95 (m, 9H)

Example 212

(R)-4-(5-bromo-6-hydroxynaphthalen-2-yl)-4-methyloxazolidin-2-one (R)-4-(6-Hydroxynaphthalen-2-yl)-4-methyloxazolidin-2-one (Example 4, 5.05 g, 20.8 mmol) was suspended in acetonitrile (50 mL, 1000 mmol) in a capped 200 mL round-bottom flask equipped with a magnetic stir bar. The mixture was cooled to 0° C. and N-bromosuccinimide (3.88 g, 21.8 mmol) was added. The reaction mixture was stirred for 1 hour. HPLC analysis indicated that the reaction was complete. The mixture was filtered. The residue was rinsed with acetonitrile, air dried under vacuum and collected (5.54 g). The crude product required no purification (82% yield).

Example 213

(R)-4-(5-bromo-6-(trans-4-tert-butylcyclohexyloxy) naphthalen-2-yl)-4-methyloxazolidin-2-one (R)-4-(5-Bromo-6-hydroxy-naphthalen-2-yl)-4-methyloxazolidin-2-one (2.16 g, 6.70 mmol) was dissolved in tetrahydrofuran (22.50 mL, 277.4 mmol) in a capped 250 mL round-bottom flask equipped with a magnetic stir bar. trans-4-tert-Butyl-cyclohexanol (2.095 g, 13.41 mmol) and triphenylphosphine (3.517 g, 13.41 mmol) were added and the mixture was stirred for 5 minutes. Diisopropyl azodicarboxylate (2.640 mL, 13.41 mmol) was then slowly added and the reaction mixture was stirred at room temperature overnight. The mixture was concentrated in vacuo, diluted in methylene chloride and adsorbed onto silica gel under reduced pressure, then purified by flash chromatography (0-55% EtOAC in hexanes) to give 1.37 g of the title compound (45% yield).

Example 214

(R)-4-(6-(trans-4-tert-butylcyclohexyloxy)-5-cyclopropylnaphthalen-2-yl)-4-methyloxazolidin-2-one (R)-4-[5-Bromo-6-(4-tert-butyl-cyclohexyloxy)-naphthalen-2-yl]-4-methyl-oxazolidin-2-one (0.2047 g, 0.0004446 mol), cyclopropyl trifluoroborate potassium salt (0.0658 g, 0.000445 mol), [1,1' Bis(diphenylphosphino)ferrocene] dichloropalladium(II), complex with dichloromethane (1:1) (0.03 g, 0.00004 mol) and cesium carbonate (0.434 g, 0.00133 mol) were added to a capped 40 mL vial equipped with a magnetic stir bar. The vial was degassed and purged with nitrogen. tetrahydrofuran (5.00 mL, 0.0616 mol) and water (0.50 mL, 0.028 mol) were added and the reaction mixture was stirred at reflux for 24 h under a nitrogen atmosphere. HPLC analysis showed that the reaction was complete. The reaction mixture was cooled to room temperature, diluted with water (10 mL) and extracted with ethylacetate. The combined organic extracts were washed with 1N HCl (20 mL) and brine (20 mL) and then dried over magnesium sulfate. The solvent was removed under vacuum and the crude product was purified by silica gel chromatography (0-50% EtOAc in hexanes) to give 109.3 mg of the title compound (58% yield).

Example 215

(R)-2-amino-2-(6-(trans-4-tert-butylcyclohexyloxy)-5-cyclopropylnaphthalen-2-yl)propan-1-ol (R)-4-[6-(4-tert-Butyl-cyclohexyloxy)-5-cyclopropyl-naphthalen-2-yl]-4-methyl-oxazolidin-2-one (0.1093 g, 0.0002593 mol) was dissolved in ethanol (2.00 mL, 0.0342 mol) in a capped 40 mL vial equipped with a magnetic stir bar. 4.2 M lithium hydroxide, monohydrate in water (1.00 mL, 0.00420 mol) was added and the reaction was stirred overnight at 80° C. HPLC analysis showed that the reaction was complete. The solvent was removed under reduced pressure. Methylene chloride and water were added and the layers were separated. The combined organic layer was concentrated to dryness and purified by HPLC to give 41.0 mg of the title compound (40% yield). MS; m/z=379.33 [M-16]+. $^1$H NMR (MeOD) δ: 8.52 (d, J=9.0 Hz, 1H), 7.84 (d, J=2.0 Hz, 1H), 7.77 (d, J=9.0 Hz, 1H), 7.57 (dd, J=9.2, 2.1 Hz, 1H), 7.34 (d, J=9.3 Hz, 1H), 4.26-4.36 (m, 1H), 3.95 (d, J=11.5 Hz, 1H), 3.84 (d, J=11.5 Hz, 1H), 2.18-2.27 (m, 2H), 1.85-1.95 (m, 3H), 1.80 (s, 3H), 1.43-1.57 (m, 2H), 1.08-1.28 (m, 5H), 0.92 (s, 9H), 0.68-0.75 (m, 2H)

Example 216

(R)-4-(6-(trans-4-tert-butylcyclohexyloxy)-5-methyl-naphthalen-2-yl)-4-methyloxazolidin-2-one (R)-4-(6-(trans-4-tert-butylcyclohexyloxy)-5-methyl-naphthalen-2-yl)-4-methyloxazolidin-2-one was synthesized as per (R)-4-(6-(trans-4-tert-butylcyclohexyloxy)-5-cyclopropylnaphthalen-2-yl)-4-methyloxazolidin-2-one (Example 214) in 72% yield using methyl trifluoroborate potassium salt (0.0670 g, 0.000550 mol) as reagent.

Example 217

(R)-2-amino-2-(6-(trans-4-tert-butylcyclohexyloxy)-5-methylnaphthalen-2-yl)propan-1-ol (R)-2-amino-2-(6-(trans-4-tert-butylcyclohexyloxy)-5-methylnaphthalen-2-yl)propan-1-ol was synthesized as per (R)-2-amino-2-(6-(trans-4-tert-butylcyclohexyloxy)-5-cyclopropylnaphthalen-2-yl)propan-1-ol (Example 215) in 64% yield using (R)-4-(6-(trans-4-tert-butylcyclohexyloxy)-5-methylnaphthalen-2-yl)-4-methyloxazolidin-2-one as starting material. MS: m/z=353.44 [M-16]+. $^1$H NMR (MeOD) δ: 8.06 (d, J=9.0 Hz, 1H), 7.86 (d, J=2.0 Hz, 1H), 7.77 (d, J=9.0 Hz, 1H), 7.58 (dd, J=9.0, 2.3 Hz, 1H), 7.40 (d, J=9.0 Hz, 1H), 4.21-4.31 (m, 1H), 3.95 (d, J=11.5 Hz, 1H), 3.84 (d, J=11.5 Hz, 1H), 2.53 (s, 3H), 2.17-2.26 (m, 2H), 1.87-1.95 (m, 2H), 1.80 (s, 3H), 1.42-1.56 (m, 2H), 1.10-1.28 (m, 3H), 0.93 (s, 9H)

Example 218

(R)-4-(6-(trans-4-tert-butylcyclohexyloxy)-5-vinylnaphthalen-2-yl)-4-methyloxazolidin-2-one (R)-4-(6-(trans-4-tert-butylcyclohexyloxy)-5-vinylnaphthalen-2-yl)-4-methyloxazolidin-2-one was synthesized as per (R)-4-(6-(trans-4-tert-butylcyclohexyloxy)-5-cyclopropylnaphthalen-2-yl)-4-methyloxazolidin-2-one (Example 214) in 48% yield using potassium vinyltrifluoroborate (0.0675 g, 0.000504 mol) as reagent.

Example 219

(R)-2-amino-2-(6-(trans-4-tert-butylcyclohexyloxy)-5-vinylnaphthalen-2-yl)propan-1-ol (R)-2-amino-2-(6-(trans-4-tert-butylcyclohexyloxy)-5-vinylnaphthalen-2-yl)propan-1-ol was synthesized as per (R)-2-amino-2-(6-(trans-4-tert-butylcyclohexyloxy)-5-cyclopropylnaphthalen-2-yl)propan-1-ol (Example 215) in 76% yield using (R)-4-(6-(trans-4-tert-butylcyclohexyloxy)-5-vinylnaphthalen-2-yl)-4-methyloxazolidin-2-one as starting material. MS: m/z=365.48 [M-16]+. $^1$H NMR (MeOD) δ: 8.29 (d, J=9.0 Hz, 1H), 7.87 (d, J=2.0 Hz, 1H), 7.84 (d, J=9.3 Hz, 1H), 7.55 (dd, J=9.0, 2.3 Hz, 1H), 7.45 (d, J=9.0 Hz, 1H), 7.11 (dd, J=17.9, 11.7 Hz, 1H), 5.66-5.79 (m, 2H), 4.28-4.41 (m, 1H), 3.95 (d, J=11.5 Hz, 1H), 3.84 (d, J=11.5 Hz, 1H), 2.18-2.27 (m, 2H), 1.87-1.95 (m, 2H), 1.80 (s, 3H), 1.41-1.55 (m, 2H), 1.09-1.29 (m, 3H), 0.92 (s, 9H)

Example 220

(R)-4-(6-(trans-4-tert-butylcyclohexyloxy)-5-(4-(trifluoromethoxy)phenyl)naphthalen-2-yl)-4-methyloxazolidin-2-one (R)-4-[5-Bromo-6-(4-tert-butyl-cyclohexyloxy)-naphthalen-2-yl]-4-methyl-oxazolidin-2-one (0.2079 g, 0.0004516 mol), 4-trifluoromethoxy phenylboronic acid (0.130 g, 0.000632 mol), tetrakis(triphenylphosphine)palladium(0) (0.03 g, 0.00002 mol) and sodium carbonate (0.191 g, 0.00181 mol) were added to a capped 40 mL EPA vial equipped with a magnetic stir bar. The vial was degassed and purged with nitrogen. 1,2-Dimethoxyethane (5.00 mL, 0.0481 mol) was added and the mixture was stirred for 5 minutes. Water (3.00 mL, 0.166 mol) was then added and the mixture was heated at 95° C. After 3 h, HPLC analysis showed that the reaction was complete. Ethylacetate (5 mL) and water (5 mL) were added and the layers were separated. The combined organic phase was then dried over MgSO$_4$, filtered, concentrated and purified by flash chromatography (0-55% EtOAc in hexane) to give 204.1 mg of the title compound (83% yield).

Example 221

(R)-2-amino-2-(6-(trans-4-tert-butylcyclohexyloxy)-5-(4-(trifluoromethoxy)phenyl)naphthalen-2-yl)propan-1-ol (R)-4-[6-(4-tert-Butyl-cyclohexyloxy)-5-(4-trifluoromethoxy-phenyl)-naphthalen-2-yl]-4-methyl-oxazolidin-2-one (0.2041 g, 0.0003768 mol) was dissolved in ethanol (4.00 mL, 0.0685 mol) in a capped 40 mL EPA vial equipped with a magnetic stir bar. 4.2 M lithium hydroxide, monohydrate in water (2.00 mL, 0.00840 mol) was added and the mixture was stirred overnight at 80° C. HPLC analysis showed that the reaction was complete. The reaction mixture was concentrated to dryness under reduced pressure. The product was partitioned between water and methylene chloride. The combined organic phase was dried over MgSO$_4$, filtered, concentrated and purified by flash chromatography [0-50% of 2M NH$_3$ solution in MeOH (10% in methylene chloride) and methylene chloride to give the title compound in 69% yield. MS: m/z=499.23 [M-NH$_2$]+. $^1$H NMR (MeOD) δ: 7.93-7.96 (m, 1H), 7.91 (d, J=9.3 Hz, 1H), 7.47-7.52 (m, 1H), 7.38-7.45 (m, 6H), 4.06-4.16 (m, 1H), 3.72 (d, J=10.8 Hz, 1H), 3.67 (d, J=10.8 Hz, 1H), 1.99-2.07 (m, 2H), 1.76-1.84 (m, 2H), 1.51 (s, 3H), 0.91-1.24 (m, 5H), 0.86 (s, 9H)

Example 222

(R)-4-(6-(trans-4-tert-butylcyclohexyloxy)-5-(4-(methylsulfonyl)phenyl)naphthalen-2-yl)-4-methyloxazolidin-2-one (R)-4-(6-(trans-4-tert-butylcyclohexyloxy)-5-(4-(methylsulfonyl)phenyl)naphthalen-2-yl)-4-methyloxazolidin-2-one was synthesized as per (R)-4-(6-(trans-4-tert-butylcyclohexyloxy)-5-(4-(trifluoromethoxy)phenyl)naphthalen-2-yl)-4-methyloxazolidin-2-one (Example 220) in 86% yield using 4-methanesulfonyl phenylboronic acid as the reagent (0.0997 g, 0.000498 mol).

Example 223

(R)-2-amino-2-(6-(trans-4-tert-butylcyclohexyloxy)-5-(4-(methylsulfonyl)phenyl)naphthalen-2-yl)propan-1-ol (R)-2-amino-2-(6-(trans-4-tert-butylcyclohexyloxy)-5-(4-(methylsulfonyl)phenyl)naphthalen-2-yl)propan-1-ol was synthesized as per (R)-2-amino-2-(6-(trans-4-tert-butylcyclohexyloxy)-5-(4-(trifluoromethoxy)phenyl)naphthalen-2-yl)propan-1-ol (Example 221) in 36% yield using (R)-4-(6-(trans-4-tert-butylcyclohexyloxy)-5-(4-(methylsulfonyl)phenyl)naphthalen-2-yl)-4-methyloxazolidin-2-one as starting material.
MS: m/z 493.26 [M-16]+. $^1$H NMR (MeOD) δ: 8.03-8.12 (m, 2H), 7.91-7.99 (m, 2H), 7.55-7.63 (m, 2H), 7.42-7.53 (m, 2H), 7.32-7.40 (m, 1H), 4.21 (br. s., 1H), 3.58-3.76 (m, 2H), 3.25 (br. s., 3H), 2.05 (br. s., 2H), 1.80 (br. s., 2H), 1.52 (br. s., 3H), 1.05-1.25 (m, 4H), 0.90-1.04 (m, 1H), 0.87 (br. s., 9H)

Example 224

(R)-4-(6-(trans-4-tert-butylcyclohexyloxy)-5-(pyrimidin-5-yl)naphthalen-2-yl)-4-methyloxazolidin-2-one (R)-4-(6-(trans-4-tert-butylcyclohexyloxy)-5-(pyrimidin-5-yl)naphthalen-2-yl)-4-methyloxazolidin-2-one was synthesized as per (R)-4-(6-(trans-4-tert-butylcyclohexyloxy)-5-(4-(trifluoromethoxy)phenyl)naphthalen-2-yl)-4-methyloxazolidin-2-one (Example 220) in 85% yield using pyrimidin-5-ylboronic acid (0.0885 g, 0.000714 mol) as the reagent.

Example 225

(R)-2-amino-2-(6-(trans-4-tert-butylcyclohexyloxy)-5-(pyrimidin-5-yl)naphthalen-2-yl)propan-1-ol (R)-2-amino-2-(6-(trans-4-tert-butylcyclohexyloxy)-5-(pyrimidin-5-yl)naphthalen-2-yl)propan-1-ol was synthesized as per (R)-2-amino-2-(6-(trans-4-tert-butylcyclohexyloxy)-5-(4-(trifluoromethoxy)phenyl)naphthalen-2-yl)propan-1-ol (Example 221) in 48% yield using (R)-4-(6-(trans-4-tert-butylcyclohexyloxy)-5-(pyrimidin-5-yl)naphthalen-2-yl)-4-methyloxazolidin-2-one as starting material.
MS: m/z 417.28 [M-16]+. $^1$H NMR (MeOD) δ: 9.21 (s, 1H), 8.79 (s, 2H), 7.99-8.05 (m, 2H), 7.59 (dd, J=9.0, 2.0 Hz, 1H), 7.52 (d, J=9.3 Hz, 1H), 7.42 (d, J=9.0 Hz, 1H), 4.26-4.35 (m, 1H), 3.73 (d, J=10.8 Hz, 1H), 3.69 (d, J=10.8 Hz, 1H), 2.08-2.15 (m, 2H), 1.80-1.87 (m, 2H), 1.52 (s, 3H), 1.14-1.23 (m, 4H), 0.96-1.06 (m, 1H), 0.88 (s, 9H)

Example 226

(R)-4-(6-(trans-4-tert-butylcyclohexyloxy)-5-(4-ethoxyphenyl)naphthalen-2-yl)-4-methyloxazolidin-2-one (R)-4-(6-(trans-4-tert-butylcyclohexyloxy)-5-(4-ethoxyphenyl)naphthalen-2-yl)-4-methyloxazolidin-2-one was synthesized as per (R)-4-(6-(trans-4-tert-butylcyclohexyloxy)-5-(4-(trifluoromethoxy)phenyl)naphthalen-2-yl)-4-methyloxazolidin-2-one (Example 220) in 70% yield using 4-(ethoxy)phenylboronic acid as the reagent.

Example 227

(R)-2-amino-2-(6-(trans-4-tert-butylcyclohexyloxy)-5-(4-ethoxyphenyl)naphthalen-2-yl)propan-1-ol (R)-2-amino-2-(6-(trans-4-tert-butylcyclohexyloxy)-5-(4-ethoxyphenyl)naphthalen-2-yl)propan-1-ol was synthesized as per (R)-2-amino-2-(6-(trans-4-tert-butylcyclohexyloxy)-5-(4-(trifluoromethoxy)phenyl)naphthalen-2-yl)propan-1-ol (Example 221) in 35% yield using (R)-4-(6-(trans-4-tert-butylcyclohexyloxy)-5-(4-ethoxyphenyl)naphthalen-2-yl)-4-methyloxazolidin-2-one as starting material. MS; m/z=459.45 [M-16]+. $^1$H NMR (MeOD) δ: 7.91-7.95 (m, 1H), 7.83-7.88 (m, 1H), 7.53 (d, J=9.0 Hz, 1H), 7.44-7.49 (m, 1H), 7.37 (s, 1H), 7.19-7.26 (m, 2H), 7.01-7.07 (m, 2H), 4.10-4.19 (m, 2H), 3.98-4.07 (m, 1H), 3.73 (d, J=10.8 Hz, 1H), 3.69 (d, J=11.0 Hz, 1H), 1.97-2.04 (m, 2H), 1.75-1.82 (m, 2H), 1.52 (s, 3H), 1.48 (t, J=6.9 Hz, 3H), 1.14-1.23 (m, 2H), 0.96-1.12 (m, 3H), 0.87 (s, 9H)

Example 228

(R)-4-(6-(trans-4-tert-butylcyclohexyloxy)-5-phenylnaphthalen-2-yl)-4-methyloxazolidin-2-one (R)-4-(6-(trans-4-tert-butylcyclohexyloxy)-5-phenylnaphthalen-2-yl)-4-methyloxazolidin-2-one was synthesized as per (R)-4-(6-(trans-4-tert-butylcyclohexyloxy)-5-(4-(trifluoromethoxy)phenyl)naphthalen-2-yl)-4-methyloxazolidin-2-one (Example 220) in 79% yield using phenylboronic acid as the reagent.

Example 229

(R)-2-amino-2-(6-(trans-4-tert-butylcyclohexyloxy)-5-phenylnaphthalen-2-yl)propan-1-ol (R)-2-amino-2-(6-(trans-4-tert-butylcyclohexyloxy)-5-phenylnaphthalen-2-yl)propan-1-ol was synthesized as per (R)-2-amino-2-(6-(trans-4-tert-butylcyclohexyloxy)-5-(4-(trifluoromethoxy)phenyl)naphthalen-2-yl)propan-1-ol (Example 221) in 88% yield using (R)-4-(6-(trans-4-tert-butylcyclohexyloxy)-5-phenylnaphthalen-2-yl)-4-methyloxazolidin-2-one as starting material. MS: m/z=415.44 [M-NH$_2$]+. $^1$H NMR (MeOD) δ: 7.93 (s, 1H), 7.88 (d, J=9.0 Hz, 1H), 7.44-7.52 (m, 4H), 7.38-7.44 (m, 2H), 7.29-7.34 (m, 2H), 4.00-4.09 (m, 1H), 3.66-3.75 (m, 2H), 1.97-2.04 (m, 2H), 1.75-1.82 (m, 2H), 1.52 (s, 3H), 0.92-1.23 (m, 5H), 0.86 (s, 9H)

Example 230

(R)-4-(6-(trans-4-tert-butylcyclohexyloxy)-5-(3-chlorophenyl)naphthalen-2-yl)-4-methyloxazolidin-2-one (R)-4-(6-(trans-4-tert-butylcyclohexyloxy)-5-(3-chlorophenyl)naphthalen-2-yl)-4-methyloxazolidin-2-one was synthesized as per (R)-4-(6-(trans-4-tert-butylcyclohexyloxy)-5-(4-(trifluoromethoxy)phenyl)naphthalen-2-yl)-4-methyloxazolidin-2-one (Example 220) in 69% yield using 3-chlorophenylboronic acid as the reagent.

Example 231

(R)-2-amino-2-(6-(trans-4-tert-butylcyclohexyloxy)-5-(3-chlorophenyl)naphthalen-2-yl)propan-1-ol (R)-2-amino-2-(6-(trans-4-tert-butylcyclohexyloxy)-5-(3-chlorophenyl)naphthalen-2-yl)propan-1-ol was synthesized as per (R)-2-amino-2-(6-(trans-4-tert-butylcyclohexyloxy)-5-(4-(trifluoromethoxy)phenyl)naphthalen-2-yl)propan-1-ol (Example 221) in 82% yield using (R)-4-(6-(trans-4-tert-butylcyclohexyloxy)-5-(3-chlorophenyl)naphthalen-2-yl)-4-methyloxazolidin-2-one as starting material. MS: m/z=449.40 [M-16]+. $^1$H NMR (MeOD) δ: 7.93 (d, J=2.0 Hz, 1H), 7.90 (d, J=9.0 Hz, 1H), 7.47-7.52 (m, 1H), 7.45 (d, J=7.3 Hz, 1H), 7.38-7.44 (m, 3H), 7.30 (d, J=1.5 Hz, 1H), 7.23 (dd, J=7.2, 1.4 Hz, 1H), 4.08-4.17 (m, 1H), 3.72 (d, J=10.8 Hz, 1H), 3.67 (d, J=10.8 Hz, 1H), 1.98-2.09 (m, 1.75-1.84 (m, 2H), 1.51 (s, 3H), 1.03-1.23 (m, 4H), 0.90-1.02 (m, 1H), 0.85 (s, 9H)

Example 232

(R)-4-(6-(trans-4-tert-butylcyclohexyloxy)-5-(4-chlorophenyl)naphthalen-2-yl)-4-methyloxazolidin-2-one (R)-4-(6-(trans-4-tert-butylcyclohexyloxy)-5-(4-chlorophenyl)naphthalen-2-yl)-4-methyloxazolidin-2-one was synthesized as per (R)-4-(6-(trans-4-tert-butylcyclohexyloxy)-5-(4-(trifluoromethoxy)phenyl)naphthalen-2-yl)-4-methyloxazolidin-2-one (Example 220) in 76% yield using 4-chlorophenylboronic acid as the reagent.

Example 233

(R)-2-amino-2-(6-(trans-4-tert-butylcyclohexyloxy)-5-(4-chlorophenyl)naphthalen-2-yl)propan-1-ol (R)-2-amino-2-(6-(trans-4-tert-butylcyclohexyloxy)-5-(4-chlorophenyl)naphthalen-2-yl)propan-1-ol was synthesized as per (R)-2-amino-2-(6-(trans-4-tert-butylcyclohexyloxy)-5-(4-(trifluoromethoxy)phenyl)naphthalen-2-yl)propan-1-ol (Example 221) in 81% yield using (R)-4-(6-(trans-4-tert-butylcyclohexyloxy)-5-(4-chlorophenyl)naphthalen-2-yl)-4-methyloxazolidin-2-one as starting material. MS: m/z=449.41 [M-16]+. $^1$H NMR (MeOD) δ: 7.94 (d, J=1.8 Hz, 1H), 7.90 (d, J=8.8 Hz, 1H), 7.46-7.52 (m, 3H), 7.42 (d, J=9.3 Hz, 2H), 7.29 (d, J=8.0 Hz, 2H), 4.07-4.17 (m, 1H), 3.66-3.75 (m, 2H), 2.00-2.08 (m, 2H), 1.77-1.84 (m, 2H), 1.52 (s, 3H), 0.92-1.25 (m, 5H), 0.84-0.89 (m, 9H)

Example 234

(R)-4-(5-chloro-6-hydroxynaphthalen-2-yl)-4-methyloxazolidin-2-one (R)-4-(6-hydroxynaphthalen-2-yl)-4-methyloxazolidin-2-one (0.5895 g, 0.002423 mol) was suspended in acetonitrile (3.37 mL, 0.0646 mol) in a 40 mL vial equipped with a magnetic stir bar. N-Chlorosuccinimide (0.356 g, 0.00266 mol) was added and the mixture was heated at 80° C. After 2 hours, HPLC analysis showed that the reaction was complete. The mixture was cooled to room temperature and filtered. The residue was washed with acetonitrile, azeotroped with toluene then dried under vacuum and collected to give 590 mg of the title compound (62% yield).

Example 235

(R)-4-(6-(trans-4-tert-butylcyclohexyloxy)-5-chloronaphthalen-2-yl)-4-methyloxazolidin-2-one (R)-4-(6-(trans-4-tert-butylcyclohexyloxy)-5-chloronaphthalen-2-yl)-4-methyloxazolidin-2-one was synthesized as per (R)-4-(5-bromo-6-(trans-4-tert-butylcyclohexyloxy) naphthalen-2-yl)-4-methyloxazolidin-2-one (Example 213) in 57% yield using (R)-4-(5-chloro-6-hydroxynaphthalen-2-yl)-4-methyloxazolidin-2-one as the to starting material.

Example 236

(R)-2-amino-2-(6-(trans-4-tert-butylcyclohexyloxy)-5-chloronaphthalen-2-yl)propan-1-ol (R)-2-amino-2-(6-(trans-4-tert-butylcyclohexyloxy)-5-chloronaphthalen-2-yl)propan-1-ol was synthesized as per (R)-2-amino-2-(6-(trans-4-tert-butylcyclohexyloxy)-5-(4-(trifluoromethoxy)phenyl)naphthalen-2-yl)propan-1-ol (Example 221) in 39% yield using (R)-4-(6-(trans-4-tert-butylcyclohexyloxy)-5-chloronaphthalen-2-yl)-4-methyloxazolidin-2-one as starting material. MS: m/z: 373.28 [M-NH$_2$]+. $^1$H NMR (MeOD) δ: 8.14 (d, J=9.0 Hz, 1H), 7.93 (d, J=1.8 Hz, 1H), 7.81 (d, J=8.8 Hz, 1H), 7.71 (dd, J=9.0, 2.0 Hz, 1H), 7.39 (d, J=9.0 Hz, 1H), 4.26-4.37 (m, 1H), 3.73 (d, J=11.0 Hz, 1H), 3.69 (d, J=11.0 Hz, 1H), 2.18-2.26 (m, 2H), 1.85-1.93 (m, 2H), 1.46-1.58 (m, 5H), 1.05-1.26 (m, 3H), 0.85-0.94 (m, 9H)

Example 237

(R)-2-amino-2-(5-bromo-6-(trans-4-tert-butylcyclohexyloxy)naphthalen-2-yl)propan-1-ol (R)-2-amino-2-(5-bromo-6-(trans-4-tert-butylcyclohexyloxy)naphthalen-2-yl)propan-1-ol was synthesized as per (R)-2-amino-2-(6-(trans-4-tert-butylcyclohexyloxy)-5-(4-(trifluoromethoxy)phenyl)naphthalen-2-yl)propan-1-ol (Example 221) in 31% yield using (R)-4-(5-bromo-6-(trans-4-tert-butylcyclohexyloxy)naphthalen-2-yl)-4-methyloxazolidin-2-one as starting material. MS: m/z=419.29 [M-NH$_2$]+. $^1$H NMR (MeOD) δ: 8.29 (d, J=9.0 Hz, 1H), 7.92-7.96 (m, 2H), 7.69 (dd, J=9.0, 2.0 Hz, 1H), 7.50 (d, J=9.3 Hz, 1H), 4.37-4.47 (m, 1H), 3.96 (d, J=11.5 Hz, 1H), 3.85 (d, J=11.5 Hz, 1H), 2.20-2.29 (m, 2H), 1.90-1.97 (m, 2H), 1.78-1.83 (m, 3H), 1.50-1.63 (m, 2H), 1.10-1.30 (m, 3H), 0.94 (s, 9H)

Example 238

(R)-4-(6-(trans-4-tert-butylcyclohexyloxy)naphthalen-2-yl)-4-methyloxazolidin-2-one (R)-4-(6-hydroxynaphthalen-2-yl)-4-methyloxazolidin-2-one (2.0460 g, 0.0084108 mol) was dissolved in tetrahydrofuran (20 mL, 0.2 mol) in a 100 mL RBF equipped with a magnetic stir bar. 4-tert-Butyl-cyclohexanol (1.58 g, 0.0101 mol) was added, followed by triphenylphosphine (3.53 g, 0.0134 mol) and the mixture was stirred for a few minutes. Diisopropyl azodicarboxylate (2.65 mL, 0.0134 mol) was then slowly added and the mixture was stirred overnight at room temperature. The mixture was concentrated under reduced pressure. The resulting product was adsorbed to silica gel and purified by flash chromatography (0-55% EtOAc in hexanes) to give 2.07 g of the title compound (64% yield). MS: m/z=382.23 [M+1] $^1$H NMR (MeOD) δ: 7.77-7.85 (m, 3H), 7.48 (dd, J=8.5, 2.0 Hz, 1H), 7.27 (d, J=2.5 Hz, 1H), 7.16 (dd, J=8.8, 2.5 Hz, 1H), 4.49-4.54 (m, 1H), 4.41-4.46 (m, 1H), 4.32-4.41 (m, 1H), 2.25-2.35 (m, 2H), 1.94 (d, J=13.3 Hz, 2H), 1.81 (s, 3H), 1.38-1.52 (m, 2H), 1.16 (d, J=11.8 Hz, 2H), 0.92-0.98 (m, 9H)

Example 239

(R)-4-(6-(trans-4-tert-butylcyclohexyloxy)-5,7,8-trichloronaphthalen-2-yl)-4-methyloxazolidin-2-one (R)-4-[6-(4-tert-Butyl-cyclohexyloxy)-naphthalen-2-yl]-4-methyl-oxazolidin-2-one (0.4090 g, 0.001072 mol) was dissolved in methylene chloride (5.00 mL, 0.0780 mol) in a capped 40 mL vial equipped with a magnetic stir bar. N-Chlorosuccinimide (0.429 g, 0.00322 mol) was added, followed by zirconium tetrachloride (0.050 g, 0.00021 mol) and the mixture was stirred at room temperature. After 3 hours, HPLC analysis showed that the reaction was complete. The mixture was concentrated to dryness under reduced pressure and purified by flash chromatography (0-55% EtOAc in hexanes) to give 176.4 mg of the title compound (34% yield).

Example 240

(R)-2-amino-2-(6-(trans-4-tert-butylcyclohexyloxy)-5,7,8-trichloronaphthalen-2-yl)propan-1-ol (R)-2-amino-2-(6-(trans-4-tert-butylcyclohexyloxy)-5,7,8-trichloronaphthalen-2-yl)propan-1-ol was synthesized as per (R)-2-amino-2-(6-(trans-4-tert-butylcyclohexyloxy)-5-(4-(trifluoromethoxy)phenyl)naphthalen-2-yl)propan-1-ol (Example 221) in 37% yield using (R)-4-(6-(trans-4-tert-butylcyclohexyloxy)-5,7,8-trichloronaphthalen-2-yl)-4-methyloxazolidin-2-one as starting material. MS: m/z=441.25 [M-NH$_2$]+. $^1$H NMR (MeOD) δ: 8.42 (d, J=1.5 Hz, 1H), 8.28 (d, J=9.5 Hz, 1H), 7.89 (dd, J=9.0, 2.0 Hz, 1H), 4.31-4.42 (m, 1H), 3.78 (d, J=11.0 Hz, 1H), 3.72 (d, J=11.0 Hz, 1H), 2.14-2.22 (m, 2H), 1.85-1.93 (m, 2H), 1.63-1.76 (m, 2H), 1.56 (s, 3H), 1.04-1.15 (m, 3H), 0.90 (s, 9H)

Example 241

(R)-4-(6-(trans-4-tert-butylcyclohexyloxy)-5-fluoronaphthalen-2-yl)-4-methyloxazolidin-2-one (R)-4-[6-(4-tert-Butyl-cyclohexyloxy)-naphthalen-2-yl]-4-methyl-oxazolidin-2-one (0.3012 g, 0.0007895 mol) was dissolved in methylene chloride (5.00 mL, 0.0780 mol) in a capped 40 mL vial equipped with a magnetic stir bar. N-fluoro-N-(phenylsulfonyl)benzenesulfonamide (0.249 g, 0.000789 mol) was added followed by zirconium tetrachloride (0.184 g, 0.000789 mol) and the mixture was heated overnight at 40° C. The reaction mixture was cooled to room temperature then concentrated to dryness under reduced pressure, adsorbed onto silica gel and purified by flash chromatography (0-55% EtOAc in hexanes) to give 131.3 mg of the title compound (42% yield).

Example 242

(R)-2-amino-2-(6-(trans-4-tert-butylcyclohexyloxy)-5-fluoronaphthalen-2-yl)propan-1-ol (R)-2-amino-2-(6-(trans-4-tert-butylcyclohexyloxy)-5-fluoronaphthalen-2-yl)propan-1-ol was synthesized as per (R)-2-amino-2-(6-(trans-4-tert-butylcyclohexyloxy)-5-(4-(trifluoromethoxy)phenyl)naphthalen-2-yl)propan-1-ol (Example 221) in 34% yield using (R)-4-(6-(trans-4-tert-butylcyclohexyloxy)-5-fluoronaphthalen-2-yl)-4-methyloxazolidin-2-one as starting material. MS: m/z=357.34 [M-16]+. $^1$H NMR (MeOD) δ: 8.25 (d, J=9.0 Hz, 1H), 7.92 (d, J=2.0 Hz, 1H), 7.88 (d, J=9.0 Hz, 1H), 7.68 (dd, J=9.3, 2.3 Hz, 1H), 7.49 (d, J=9.3 Hz, 1H), 4.33-4.42 (m, 1H), 3.94 (d, J=11.5 Hz, 1H), 3.84 (d, J=11.5 Hz, 1H), 2.17-2.26 (m, 2H), 1.86-1.95 (m, 2H), 1.79 (s, 3H), 1.46-1.58 (m, 2H), 1.08-1.27 (m, 3H), 0.90 (s, 9H)

Example 243

2,2-dimethyl-5-nitro-5-(6-(4-phenoxyphenoxy)naphthalen-2-yl)-1,3-dioxane 5-(6-Bromo-naphthalen-2-yl)-2,2-dimethyl-5-nitro-1,3-dioxinane (0.2719 g, 0.0007425 mol) (Example 10), 4-phenoxyphenol (0.2074 g, 0.001114 mol), copper(I) iodide (0.0141 g, 0.0000742 mol) cesium carbonate (0.4838 g, 0.001485 mol) and N,N-dimethylglycine HCl (0.0311 g, 0.000223 mol) were placed in a 40 mL reaction vial equipped with a magnetic stir bar. The vial was capped and flushed with nitrogen. The gas was then removed under vacuum. The flask was again flushed with nitrogen, evacuated and filled with nitrogen. 1,4-Dioxane (4 mL, 0.05 mol) was then added via syringe and the mixture was flushed with nitrogen and evacuated several times. The mixture was then heated to 90° C. and stirred overnight. TLC analysis showed that the reaction was complete. The cooled mixture was partitioned between EtOAc and water. The organic layer was separated and the aqueous layer was extracted with EtOAc. The combined organic layers were washed with brine, dried over Na$_2$SO$_4$ and concentrated to dryness under reduced pressure. The residual oil was loaded on a silica gel column and eluted with ethylacetate:hexane (20:80) to afford 286 mg of the title compound (82% yield).

Example 244

2,2-dimethyl-5-(6-(4-phenoxyphenoxy)naphthalen-2-yl)-1,3-dioxan-5-amine 2,2-Dimethyl-5-nitro-5-[6-(4-phenoxy-phenoxy)-naphthalen-2-yl]-1,3-dioxinane to (0.1618 g, 0.0003432 mol) was dissolved in acetic acid (10 mL, 0.2 mol) in a 40 mL reaction vial equipped with a magnetic stir bar. Zinc dust (0.2244 g, 0.003432 mol) was added and the mixture was stirred overnight at room temperature. TLC analysis showed that the reaction was complete. The mixture was filtered and the residue was rinsed with methanol. The filtrate was collected and concentrated to dryness under reduced pressure to give 112 is mg of the title compound (76% yield).

Example 245

2-amino-2-(6-(4-phenoxyphenoxy)naphthalen-2-yl)propane-1,3-diol 2,2-Dimethyl-5-[6-(4-phenoxy-phenoxy)-naphthalen-2-yl]-1,3-dioxinan-5-ylamine (0.1241 g, 0.0002811 mol) was dissolved in methanol (3 mL, 0.07 mol) and a solution of 1 M of hydrogen chloride in water (5 mL, 0.005 mol) in a 40 mL reaction vial equipped with a magnetic stir bar. The vial was capped and heated at 90° C. overnight. TLC analysis showed that the reaction was complete. The reaction mixture was concentrated to dryness under reduced pressure. The resulting solid was dissolved in methylene chloride (5 mL) and washed with water then aqueous sodium carbonate. The combined organic layer was dried over magnesium sulfate, then concentrated under vacuum and purified by HPLC to give 88.3 mg of the title compound (78% yield). MS: m/z=424.45 [M+Na$^+$]. $^1$H NMR (DMSO-d$_6$) δ: 8.00 (s, 1H), 7.93 (d, J=8.7 Hz, 1H), 7.80 (d, J=8.7 Hz, 1H), 7.62-7.68 (m, 1H), 7.39-7.44 (m, 2H), 7.35-7.39 (m, 2H), 7.30 (dd, J=8.9, 2.5 Hz, 1H), 7.00-7.17 (m, 6H), 3.73 (d, J=3.8 Hz, 4H)

Example 246

5-(6-(4-(benzyloxy)phenoxy)naphthalen-2-yl)-2,2-dimethyl-5-nitro-1,3-dioxane 5-(6-(4-(benzyloxy)phenoxy)naphthalen-2-yl)-2,2-dimethyl-5-nitro-1,3-dioxane was synthesized as per 2,2-dimethyl-5-nitro-5-(6-(4-phenoxyphenoxy)naphthalen-2-yl)-1,3-dioxane (Example 243) in 41% yield using 4-(benzyloxy)phenol as the reagent.

Example 247

5-(6-(4-(benzyloxy)phenoxy)naphthalen-2-yl)-2,2-dimethyl-1,3-dioxan-5-amine 5-(6-(4-(benzyloxy)phenoxy)naphthalen-2-yl)-2,2-dimethyl-1,3-dioxan-5-amine was synthesized as per 2,2-dimethyl-5-(6-(4-phenoxyphenoxy)naphthalen-2-yl)-1,3-dioxan-5-amine (Example 344) in 81% yield using 5-(6-(4-(benzyloxy)phenoxy)naphthalen-2-yl)-2,2-dimethyl-5-nitro-1,3-dioxane as starting material.

Example 248

2-amino-2-(6-(4-(benzyloxy)phenoxy)naphthalen-2-yl)propane-1,3-diol 2-amino-2-(6-(4-(benzyloxy)phenoxy)naphthalen-2-yl)propane-1,3-diol was synthesized as per 2-amino-2-(6-(4-phenoxyphenoxy)naphthalen-2-yl)propane-1,3-diol (Example 245) in 81% yield using 5-(6-(4-(benzyloxy)phenoxy)naphthalen-2-yl)-2,2-dimethyl-1,3-dioxan-5-amine as starting material. MS: m/z=438.24 [M+Na$^+$]. $^1$H NMR (MeOD) δ: 7.95 (s, 1H), 7.87 (d, J=9.0 Hz, 1H), 7.66-7.70 (m, 1H), 7.59-7.63 (m, 1H), 7.47 (d, J=7.5 Hz, 2H), 7.37-7.43 (m, 2H), 7.34 (d, J=7.0 Hz, 1H), 7.22 (dd, J=8.8, 2.5 Hz, 1H), 7.15 (d, J=2.3 Hz, 1H), 7.00-7.08 (m, 4H), 5.11 (s, 2H), 3.87-3.93 (m, 2H), 3.80-3.86 (m, 2H)

Example 249

2,2-dimethyl-5-nitro-5-(6-(4-(pentyloxy)phenoxy)naphthalen-2-yl)-1,3-dioxane 2,2-dimethyl-5-nitro-5-(6-(4-(pentyloxy)phenoxy)naphthalen-2-yl)-1,3-dioxane was synthesized as per 2,2-dimethyl-5-nitro-5-(6-(4-phenoxyphenoxy)naphthalen-2-yl)-1,3-dioxane (Example 243) in 58% yield using 4-pentyloxyphenol as the reagent.

Example 250

2,2-dimethyl-5-(6-(4-(pentyloxy)phenoxy)naphthalen-2-yl)-1,3-dioxan-5-amine 2,2-dimethyl-5-(6-(4-(pentyloxy)phenoxy)naphthalen-2-yl)-1,3-dioxan-5-amine was synthesized as per 2,2-dimethyl-5-(6-(4-phenoxyphenoxy)naphthalen-2-yl)-1,3-dioxan-5-amine (Example 244) in 87% yield using 2,2-dimethyl-5-nitro-5-(6-(4-(pentyloxy)phenoxy)naphthalen-2-yl)-1,3-dioxane as starting material.

Example 251

2-amino-2-(6-(4-(pentyloxy)phenoxy)naphthalen-2-yl)propane-1,3-diol 2-amino-2-(6-(4-(pentyloxy)phenoxy)naphthalen-2-yl)propane-1,3-diol was synthesized as per 2-amino-2-(6-(4-phenoxyphenoxy)naphthalen-2-yl)propane-1,3-diol (Example 245) in 55% yield using 2,2-dimethyl-5-(6-(4-(pentyloxy)phenoxy)naphthalen-2-yl)-1,3-dioxan-5-amine as starting material. MS: m/z=418.45 [M+Na$^+$]. $^1$H NMR (MeOD) δ: 7.88-7.94 (m, 2H), 7.78 (d, J=8.8 Hz, 1H), 7.51 (dd, J=8.8, 2.0 Hz, 1H), 7.30 (dd, J=9.0, 2.5 Hz, 1H), 7.17 (d, J=2.3 Hz, 1H), 7.01-7.07 (m, 2H), 6.94-7.01 (m, 2H), 4.05-4.12 (m, 2H), 3.96-4.02 (m, 4H), 1.70-1.85 (m, 2H), 1.37-1.54 (m, 4H), 0.92-1.01 (m, 3H)

Example 252

{4-[6-(trans-4-tert-Butyl-cyclohexyloxy)-5-trifluoromethyl-naphthalen-2-yl]-2-methyl-4,5-dihydro-oxazol-4-yl}-methanol 2-Amino-2-[6-(trans-4-tert-butyl-cyclohexyloxy)-5-trifluoromethyl-naphthalen-2-yl]-propane-1,3-diol, hydrogen chloride salt (271 mg, 0.000569 mol) was dissolved in 1,2-dichloroethane (15 mL, Aldrich) in a capped 40 mL reaction vial equipped with a magnetic stir bar. Triethyl orthoacetate (146 μL, 0.000797 mol, Aldrich) was added, followed by acetic acid (8.1 μL, 0.00014 mol, Fisher) and the mixture was heated at 80° C. After 2 h, the mixture was concentrated and then purified by flash chromatography (0-10% MeOH in DCM). Product was isolated in 137 mg yield (52%).

Example 253 di-tert-butyl (4-(6-(trans-4-tert-butylcyclohexyloxy)-5-(trifluoromethyl)naphthalen-2-yl)-2-methyl-4,5-dihydrooxazol-4-yl)methyl phosphate {4-[6-(trans-4-tert-Butyl-cyclohexyloxy)-5-trifluoromethyl-naphthalen-2-yl]-2-methyl-4,5-dihydro-oxazol-4-yl}-methanol (227 mg, 0.000490 mol) was treated with di-tert-butyl N,N-diethylphosphoramidite (545 pt, 0.00196 mol, Aldrich), 1H-tetrazole (177 mg, 0.00253 mol, ChemPacific) in tetrahydrofuran (10.0 mL, Aldrich) overnight. m-Chloroperbenzoic acid (570 mg, 0.00198 mol) was added to a cooled solution (ice bath) and the reaction was stirred at room temperature for 1 hour. Sodium thiosulfate was added as a 10% solution in saturated sodium bicarbonate (10 mL) and the reaction stirred for 2 h. The reaction was evaporated. The mixture was partitioned between methylene chloride and water/saturated sodium bicarbonate. The organic layer was further washed once with water and then dried with magnesium sulfate, filtered and evaporated. The residue was purified by silica gel chromatography on a column pre-treated with 1% triethylamine/methylene chloride, then eluted with 0-10% methanol in methylene chloride. Concentrating appropriate fractions gave the product in 234 mg yield (73%).

Example 254

(+)-Di-tert-butyl (4-(6-(trans-4-tert-butylcyclohexyloxy)-5-(trifluoromethyl)naphthalen-2-yl)-2-methyl-4,5-dihydrooxazol-4-yl)methyl phosphate and (−)-Di-tert-butyl (4-(6-(trans-4-tert-butylcyclohexyloxy)-5-(trifluoromethyl)naphthalen-2-yl)-2-methyl-4,5-dihydrooxazol-4-yl)methyl phosphate Racemic di-tert-butyl (4-(6-(trans-4-tert-butylcyclohexyloxy)-5-(trifluoromethyl)naphthalen-2-yl)-2-methyl-4,5-dihydrooxazol-4-yl)methyl phosphate (234 mg) was separated into the two enantiomers. Preparative method: Chiralpak AD-H (2×15 cm), 15% ethanol (0.1% DEA)/CO2, 100 bar, 50 mL/min, 220 nm, 3 mL inj vol, 12 mg/mL methanol. Analytical method: Chiralpak AD-H (25×0.46 cm), 15% ethanol (0.1% DEA)/CO2, 100 bar, 3 mL/min, 220 nm).

Enantiomer 1: 115 mg (36%), >99% pure, >99% ee, RT=2.20 min. Specific rotation [alpha]D=+8.0 deg.
Enantiomer 2: 98 mg (30%), >99% pure, >99% ee, RT=2.67 min. Specific rotation [alpha]D=−7.0 deg.

Example 255

2-amino-2-(6-trans-4-tert-butylcyclohexyloxy)-5-(trifluoromethyl)naphthalen-2-yl)-3-hydroxypropyl dihydrogen phosphate Enantiomer 1

(+)-di-tert-Butyl (4-(6-(trans-4-tert-butylcyclohexyloxy)-5-(trifluoromethyl)naphthalen-2-yl)-2-methyl-4,5-dihydrooxazol-4-yl)methyl phosphate (57.5 mg, 0.0877 mmol) was dissolved in methanol (2.0 mL, Acros) and 2.00 M of hydrogen chloride in water (2.0 mL, 4.0 mmol). The reaction was heated at 80° C. After 6 h, the reaction was dried to give the product in 28.8 mg yield as HCl salt (59%). MS: m/z=520.30 [M+H]+. $^1$H NMR (400 MHz, METHANOL-d4) δ ppm: 8.26 (dd, J=9.3, 1.8 Hz, 1H), 8.13 (d, J=9.3 Hz, 1H), 8.01 (d, J=2.3 Hz, 1H), 7.69 (dd, J=9.4, 2.4 Hz, 1H), 7.60 (d, J=9.0 Hz, 1H), 4.42-4.56 (m, 3H), 4.13 (d, J=11.8 Hz, 1H), 4.04 (d, J=12.0 Hz, 1H), 2.18-2.27 (m, 2H), 1.89-1.98 (m, 2H), 1.46-1.59 (m, 2H), 1.20-1.34 (m, 2H), 1.12-1.19 (m, 1H), 0.94 (s, 9H).

Example 256

2-amino-2-(6-trans-4-tert-butylcyclohexyloxy)-5-(trifluoromethyl)naphthalen-2-yl)-3-hydroxypropyl dihydrogen phosphate Enantiomer 2

2-Amino-2-(6-trans-4-tert-butylcyclohexyloxy)-5-(trifluoromethyl)naphthalen-2-yl)-3-hydroxypropyl dihydrogen phosphate Enantiomer 2 was synthesized in 65% yield as per 2-amino-2-(6-trans-4-tert-butylcyclohexyloxy)-5-(trifluoromethyl)naphthalen-2-yl)-3-hydroxypropyl dihydrogen phosphate Enantiomer 1 (Example 255), using (−)-di-tert-butyl (4-(6-(trans-4-tert-butylcyclohexyloxy)-5-(trifluoromethyl)naphthalen-2-yl)-2-methyl-4,5-dihydrooxazol-4-yl) methyl phosphate as the starting material. MS: m/z=520.30 [M+H]+. 1H NMR (400 MHz, METHANOL-d4) δ ppm: 8.27 (dd, J=9.3, 1.8 Hz, 1H), 8.13 (d, J=9.5 Hz, 1H), 8.01 (d, J=2.3 Hz, 1H), 7.69 (dd, J=9.3, 2.5 Hz, 1H), 7.61 (d, J=9.3 Hz, 1H), 4.47-4.56 (m, 3H), 4.12 (d, J=11.8 Hz, 1H), 4.03 (d, J=11.8 Hz, 1H), 2.20-2.27 (m, 2H), 1.89-1.99 (m, 2H), 1.46-1.59 (m, 2H), 1.19-1.33 (m, 2H), 1.08-1.19 (m, 1H), 0.94 (s, 9H).

Example 257

(R)-4-Methyl-4-[6-(4-trifluoromethyl-cyclohexyloxy)-naphthalen-2-yl]-oxazolidin-2-one In a 40 mL vial, 4-trifluoromethyl-cyclohexanol (713.2 mg, 0.004241 mol) was diluted with tetrahydrofuran (19.0 mL), then (R)-4-(6-hydroxy-naphthalen-2-yl)-4-methyloxazolidin-2-one (0.9462 g, 0.003890 mol) and triphenylphosphine (1.3031 g, 0.0049682 mol) were added. The mixture was stirred and then diisopropyl azodicarboxylate (0.91 mL, 0.0046 mol) was added. The reaction was stirred at room temperature for 38 h. The reaction mixture was concentrated in vacuo, taken up in DCM, adsorbed onto silica gel and chromatographed (0-100% EtOAc/Hexanes). Isolated was 223.5 mg (15%) of product as cis/trans mixture.

Example 258

(R)-4-Methyl-4-[6-(cis-4-trifluoromethyl-cyclohexyloxy)-naphthalen-2-yl]-oxazolidin-2-one and (R)-4-Methyl-4-[6-(trans-4-trifluoromethylcyclohexyloxy)-naphthalen-2-yl]-oxazolidin-2-one Separation of (R)-4-Methyl-4-[6-(4-trifluoromethyl-cyclohexyloxy)-naphthalen-2-yl]-oxazolidin-2-one (361 mg) was by ChiralPak IA (3×15 cm) 15% methanol/CO2, 100 bar 75 mL/min, 220 nm, inj. vol. 0.5 mL, 20 mg/mL ethanol. Analytical method: ChiralPak IA (15×0.46 cm) 20% methanol (0.1% DEA)/CO2, 100 bar, 3 mL/min, 220 nm.
Isomer 1 cis: 22.3 mg (6%) characterized by chiral HPLC (RT=4.89 min, 99.89%).
Isomer 2 trans: 247.2 mg (68%) characterized by chiral HPLC (RT=5.36 min, 99.81%).

Example 259

(R)-2-Amino-2-[6-(cis-4-trifluoromethyl-cyclohexyloxy)-naphthalen-2-yl]-propan-1-ol The mixture of (R)-4-Methyl-4-[6-(cis-4-trifluoromethyl-cyclohexyloxy)-naphthalen-2-yl]-oxazolidin-2-one (30.6 mg, 0.0000778 mol) and 4.20 M aqueous lithium hydroxide (0.300 mL, 0.00126 mol) and ethanol (0.900 mL, 0.0154 mol) was heated to reflux for 4.5 h. The reaction was evaporated to remove organics. The aqueous phase was extracted with methylene chloride, and the organics were evaporated. The residue was purified by silica gel chromatography using 0-100% methanol in methylene chloride to yield the product in 13.4 mg yield (47%). MS: m/z=351.20 [M-NH2]+. 1H NMR (400 MHz, METHANOL-d4) δ ppm: 7.87 (d, J=2.0 Hz, 1H), 7.80 (d, J=9.0 Hz, 1H), 7.75 (d, J=9.0 Hz, 1H), 7.57 (dd, J=8.5, 2.0 Hz, 1H), 7.25 (d, J=2.3 Hz, 1H), 7.18 (dd, J=8.8, 2.5 Hz, 1H), 4.77-4.82 (m, 1H), 3.74 (d, J=10.8 Hz, 1H), 3.70 (d, J=10.8 Hz, 1H), 2.25-2.34 (m, 1H), 2.18-2.25 (m, 2H), 1.65-1.88 (m, 6H), 1.54 (s, 3H).

Example 260

(R)-2-Amino-2-[6-(trans-4-trifluoromethyl-cyclohexyloxy)-naphthalen-2-yl]-propan-1-ol (R)-2-Amino-2-[6-(trans-4-trifluoromethyl-cyclohexyloxy)-naphthalen-2-yl]-propan-1-ol was synthesized as per (R)-2-amino-2-[6-(cis-4-trifluoromethyl-cyclohexyloxy)-naphthalen-2-yl]-propan-1-ol (Example 259) in 83% yield using (R)-4-Methyl-4-[6-(trans-4-trifluoromethyl-cyclohexyloxy)-naphthalen-2-yl]-oxazolidin-2-one as the starting material. MS: m/z=351.20 [M-NH2]+. 1H NMR (400 MHz, METHANOL-d4) δ ppm: 7.86 (d, J=2.0 Hz, 1H), 7.73-7.80 (m, 2H), 7.57 (dd, J=8.8, 2.0 Hz, 1H), 7.26 (d, J=2.5 Hz, 1H), 7.12 (dd, J=8.9, 2.4 Hz, 1H), 4.39-4.49 (m, 1H), 3.74 (d, J=11.0 Hz, 1H), 3.67-3.72 (m, 1H), 2.29-2.38 (m, 2H), 2.19-2.30 (m, 1H), 2.03-2.11 (m, 2H), 1.46-1.66 (m, 7H).

Example 261

{(R)-2-Hydroxy-1-methyl-1-[6-(trans-4-trifluoromethyl-cyclohexyloxy)-naphthalen-2-yl]-ethyl}-carbamic acid tert-butyl ester (R)-2-Amino-2-[6-(trans-4-trifluoromethyl-cyclohexyloxy)-naphthalen-2-yl]-propan-1-ol (166 mg, 0.000452 mol, crude without silica gel purification) was dissolved in chloroform (4.0 mL, 0.050 mol, Aldrich) along with di-tert-butyldicarbonate (0.222 g, 0.00102 mol, Aldrich). Saturated aqueous sodium bicarbonate solution (2.0 mL, 0.020 mol) was added and the reaction was stirred vigorously for 16 h. The reaction was diluted with methylene chloride and the aqueous layer removed. Evaporation of solvent and purification by silica gel chromatography using 0-50% ethyl acetate in hexanes gave the product in 172 mg (81%) yield (Rf=0.56 in 1:1 hexanes/ethyl acetate). Note that $^1$H NMR suggested that there was 1.5 equiv of DIAD-H2 in the product.

Example 262

{(R)-2-(Di-tert-butoxy-phosphoryloxy)-1-methyl-1-[6-(trans-4-trifluoromethyl-cyclohexyloxy)-naphthalen-2-yl]-ethyl}-carbamic acid tert-butyl ester To a solution of {(R)-2-Hydroxy-1-methyl-1-[6-(trans-4-trifluoromethyl-cyclohexyloxy)-naphthalen-2-yl]-ethyl}-carbamic acid tert-butyl ester (172 mg, 0.000368 mol) and 1H-tetrazole (0.255 g, 0.00364 mol, ChemPacific) in tetrahydrofuran (3.00 mL, Acros) was added di-tert-butyl N,N-diethylphosphoramidite (512 µL, 0.00184 mol, Aldrich) and the reaction was stirred at rt for 16 hours. Hydrogen peroxide (250 µL, 0.0024 mol, Aldrich) was added and the reaction was stirred for 1.5 hours. The reaction was then quenched with 10% $NaS_2O_3$ in saturated sodium bicarbonate, extracted with EtOAc, washed with saturated sodium chloride and then dried with $Na_2SO_4$. The drying agent was filtered and the organic layer was concentrated in vacuo. The crude product was taken up in DCM and purified using silica gel chromatography (0-100% ethyl acetate in hexanes). Isolated was the product (Rf=0.52 in 1:1 hexanes/ethyl acetate) in 107.8 mg yield (44%).

Example 263

Phosphoric acid mono-{(R)-2-amino-2-[6-(trans-4-trifluoromethyl-cyclohexyloxy)-naphthalen-2-yl]-propyl} ester To {(R)-2-(Di-tert-butoxy-phosphoryloxy)-1-methyl-1-[6-(trans-4-trifluoromethyl-cyclohexyloxy)-naphthalen-2-yl]-ethyl}-carbamic acid tert-butyl ester (107.8 mg, 0.0001634 mol) was added 12 M of hydrogen chloride in water (1.0 mL, 0.012 mol, Aldrich) and acetic acid (5.0 mL, 0.088 mol, Fisher) and the solution was stirred for 1.5 h at RT. Removal of solvent gave an oil, which was taken up in acetonitrile:$H_2O$ (approx. 1:6) and lyophilized to give the product HCl salt as a white powder (57 mg, 72%). MS: m/z=431.20 [M-NH2]+. 1H NMR (400 MHz, METHANOL-d4) δ ppm: 7.90 (s, 1H), 7.89 (d, J=6.5 Hz, 1H), 7.85 (d, J=8.8 Hz, 1H), 7.57 (dd, J=8.9, 2.1 Hz, 1H), 7.33 (d, J=2.3 Hz, 1H), 7.20 (dd, J=9.0, 2.5 Hz, 1H), 4.44-4.53 (m, 1H), 4.27 (dd, J=11.3, 4.8 Hz, 1H), 4.12 (dd, J=11.3, 5.5 Hz, 1H), 2.31-2.38 (m, 2H), 2.21-2.31 (m, 1H), 2.05-2.12 (m, 2H), 1.85 (s, 3H), 1.47-1.68 (m, 4H).

Example 264

(R)-4-[5-Iodo-6-(trans-4-trifluoromethyl-cyclohexyloxy)-naphthalen-2-yl]-4-methyl-oxazolidin-2-one N-Iodosuccinimide (803 mg, 0.00357 mol, Acros) and zirconium tetrachloride (128 mg, 0.000549 mol, Strem) were added to a solution of (R)-4-methyl-4-[6-(trans-4-trifluoromethyl-cyclohexyloxy)-naphthalen-2-yl]-oxazolidin-2-one (1080 mg, 0.00274 mol) in methylene chloride (40 mL, Acros) and were stirred at room temperature for 30 min. Only starting material visible by HPLC. Note that starting material contained DIAD-H2 impurity. The reaction was filtered and evaporated to dryness. The residue was taken up in methylene chloride, and silica gel was added. The solvent was removed and the residue was purified by silica gel chromatography using 0-100% ethyl acetate in hexanes as eluent. Fractions combined to give the repurified starting material (minus the DIAD-H2 previously seen) in 786 mg (73%) recovery.

N-Iodosuccinimide (588 mg, 0.00261 mol, Acros) and zirconium tetrachloride (98 mg, 0.00042 mol, Strem) was added to a solution of repurified (R)-4-methyl-4-[6-(trans-4-s trifluoromethyl-cyclohexyloxy)-naphthalen-2-yl]-oxazolidin-2-one (786 mg, 0.00200 mol) in methylene chloride (30 mL, Acros) and were stirred at room temperature for 30 min. Silica gel was added and the reaction was evaporated to dryness. The residue was purified by silica gel chromatography using 0-100% ethyl acetate in hexanes as eluent. Cis and trans isomers were fully resolved and isolated was 822 mg (79%) of pure trans product (Rf=0.31 in 1:1 hexanes/ethyl acetate).

Example 265

(R)-4-Methyl-4-[5-trifluoromethyl-6-(trans-4-trifluoromethyl-cyclohexyloxy)-naphthalen-2-yl]-oxazolidin-2-one A solution of (R)-4-[5-iodo-6-(trans-4-trifluoromethyl-cyclohexyloxy)-naphthalen-2-yl]-4-methyl-oxazolidin-2-one (0.822 g, 1.58 mmol), hexamethylphosphoramide (1.39 mL, 7.91 mmol, Aldrich) in N,N-dimethylformamide (7.6 mL, Acros) was degassed by stirring under vacuum and replacing the vacuum with argon (4 times). Note that the starting material was azeotroped 3× toluene prior to use. To this was added copper(I) iodide (512 mg, 2.69 mmol, Aldrich) and methyl fluorosulphonyldifluoroacetate (1040 µL, 7.91 mmol, Aldrich) and the reaction was stirred at 80° C. under an atmosphere of Argon. After stirring for 16 hours, the reaction was evaporated, then diluted with methylene chloride. Silica gel was added and the solvent removed. The material was purified by silica gel chromatography using 0-80% ethyl acetate in hexanes as eluent (Rf=0.34 in 1:1 hexanes/ethyl acetate) to give the product (still impure). The material was taken up in ethyl acetate, washed 3× water, dried with saturated sodium sulfate, filtered and evaporated. The residue was repurified by silica gel chromatography using 0-5% methanol in methylene chloride (Rf=0.38 in 5% methanol in methylene chloride). Isolated was 596 mg (82%) of product.

Example 266

(R)-2-Amino-2-[5-trifluoromethyl-6-(trans-4-trifluoromethylcyclohexyloxy)-naphthalen-2-yl]propan-1-ol (R)-2-Amino-2-[5-trifluoromethyl-6-(trans-4-trifluoromethyl-cyclohexyloxy)-naphthalen-2-yl]-propan-1-ol was synthesized as per (R)-2-Amino-2-[6-(cis-4-trifluoromethyl-cyclohexyloxy)-naphthalen-2-yl]-propan-1-ol (Example 259) in 75% yield, using (R)-4-Methyl-4-[5-trifluoromethyl-6-(trans-4-trifluoromethyl-cyclohexyloxy)-naphthalen-2-yl]-oxazolidin-2-one as starting material. MS: m/z=458.20 [M+Na]+. 1H NMR (400 MHz, CHLOROFORM-d) δ ppm: 8.15 (dd, J=9.4, 1.6 Hz, 1H), 8.09 (d, J=9.3 Hz, 1H), 7.98 (d, J=2.0 Hz, 1H), 7.73 (dd, J=9.3, 2.3 Hz, 1H), 7.52 (d, J=9.0 Hz, 1H), 4.48-4.61 (m, 1H), 3.75 (d, J=11.0 Hz, 1H), 3.67-3.73 (m, 1H), 2.16-2.34 (m, 3H), 2.01-2.13 (m, 2H), 1.45-1.71 (m, 7H).

Example 267

{(R)-2-Hydroxy-1-methyl-1-[5-trifluoromethyl-6-(trans-4-trifluoromethyl-cyclohexyloxy)-naphthalen-2-yl]-ethyl}-carbamic acid tert-butyl ester {(R)-2-Hydroxy-1-methyl-1-[5-trifluoromethyl-6-(trans-4-trifluoromethyl-cyclohexyloxy)-naphthalen-2-yl]-ethyl}-carbamic acid tert-butyl ester was synthesized as per {(R)-2-Hydroxy-1-methyl-1-[6-(trans-4-trifluoromethyl-cyclohexyloxy)-naphthalen-2-yl]-ethyl}-carbamic acid tert-butyl ester (Example 261) in 99% yield, using (R)-2-Amino-2-[5-trifluoromethyl-6-(trans-4-trifluoromethyl-cyclohexyloxy)-naphthalen-2-yl]-propan-1-ol as the starting material.

Example 268

{(R)-2-(Di-tert-butoxy-phosphoryloxy)-1-methyl-1-[5-trifluoromethyl-6-(trans-4-trifluoromethyl-cyclohexyloxy)-naphthalen-2-yl]-ethyl}-carbamic acid tert-butyl ester {(R)-2-(Di-tert-butoxy-phosphoryloxy)-1-methyl-1-[5-trifluoromethyl-6-(trans-4-trifluoromethyl-cyclohexyloxy)-naphthalen-2-yl]-ethyl}-carbamic acid tert-butyl ester was synthesized as per {(R)-2-(Di-tert-butoxy-phosphoryloxy)-1-methyl-1-[6-(trans-4-trifluoromethyl-cyclohexyloxy)-naphthalen-2-yl]-ethyl}-carbamic acid tert-butyl ester (Example 262) in 82% yield, using {(R)-2-Hydroxy-1-methyl-1-[5-trifluoromethyl-6-(trans-4-trifluoromethyl-cyclohexyloxy)-naphthalen-2-yl]-ethyl}-carbamic acid tert-butyl ester as starting material.

Example 269

Phosphoric acid mono-{(R)-2-amino-2-[5-trifluoromethyl-6-(trans-4-trifluoromethyl-cyclohexyloxy)-naphthalen-2-yl]-propyl}ester Phosphoric acid mono-{(R)-2-amino-2-[5-trifluoromethyl-6-(trans-4-trifluoromethyl-cyclohexyloxy)-naphthalen-2-yl]-propyl}ester was synthesized as per Phosphoric acid mono-{(R)-2-amino-2-[6-(trans-4-trifluoromethyl-cyclohexyloxy)-naphthalen-2-yl]-propyl} ester (Example 263) in 89% yield as HCl salt, using {(R)-2-(Di-tert-butoxy-phosphoryloxy)-1-methyl-1-[5-trifluoromethyl-6-(trans-4-trifluoromethyl-cyclohexyloxy)-naphthalen-2-yl]-ethyl}-carbamic acid tert-butyl ester as starting material. MS: m/z=516.30 [M+H]+. 1H NMR (400 MHz, METHANOL-d4) δ ppm: 8.26 (dd, J=9.4, 1.4 Hz, 1H), 8.16 (d, J=9.3 Hz, 1H), 8.02 (d, J=2.3 Hz, 1H), 7.72 (dd, J=9.3, 2.3 Hz, 1H), 7.63 (d, J=9.3 Hz, 1H), 4.55-4.66 (m, 1H), 4.31 (dd, J=11.3, 4.8 Hz, 1H), 4.17 (dd, J=11.2, 5.1 Hz, 1H), 2.20-2.34 (m, 3H), 2.02-2.12 (m, 2H), 1.86 (s, 3H), 1.49-1.72 (m, 4H).

Example 270

(R)-4-Methyl-4-[6-(4-pentyl-cyclohexyloxy)-naphthalen-2-yl]-oxazolidin-2-one

In a 40 mL vial, 4-Pentyl-cyclohexanol (1144.4 mg, 0.0067202 mol) was diluted with tetrahydrofuran (30.0 mL, 0.370 mol, Acros) and subsequently (R)-4-(6-hydroxynaphthalen-2-yl)-4-methyloxazolidin-2-one (1.4924 g, 0.0061350 mol) and triphenylphosphine (2105.5 mg, 0.0080275 mol) were added and the mixture was stirred. Diethyl Azodicarboxylate in toluene (2.6 mL, 0.0086326 mol, Aldrich) was added, and the mixture was then stirred at room temperature for 38 h. The reaction mixture was evaporated to dryness and chromatographed 0-100% EtOAc/Hexanes (adsorbed onto silica gel). Isolated was 0.6142 g (18%) in approx 70% purity, the remainder being reduced DEAD reagent.

Example 271

(R)-2-Amino-2-[6-(4-pentyl-cyclohexyloxy)-naphthalen-2-yl]-propan-1-ol (R)-2-Amino-2-[6-(4-pentyl-cyclohexyloxy)-naphthalen-2-yl]-propan-1-ol was synthesized as per (R)-2-Amino-2-[6-(cis-4-trifluoromethyl-cyclohexyloxy)-naphthalen-2-yl]-propan-1-ol (Example 259) in 35% yield (and 21% recovered starting material) using (R)-4-Methyl-4-[6-(4-pentyl-cyclohexyloxy)-naphthalen-2-yl]-oxazolidin-2-one as starting material. Note that the starting material contained 20% impurity (mixture of reduced DIAD, reduced DEAD).

Example 272

(R)-2-Amino-2-[6-(cis-4-pentyl-cyclohexyloxy)-naphthalen-2-yl]-propan-1-ol and (R)-2-Amino-2-[6-(trans-4-pentyl-cyclohexyloxy)-naphthalen-2-yl]-propan-1-ol Separation of (R)-2-Amino-2-[6-(4-pentyl-cyclohexyloxy)-naphthalen-2-yl]-propan-1-ol (304 mg) was by ChiralPak AD-H (2×15 cm) 20% methanol (0.1% DEA)/CO2, 100 bar 65 mL/min, 220 nm, inj. vol. 1 mL, 20 mg/mL methanol. Analytical method: ChiralPak AD-H (25×0.46 cm) 30% methanol (0.1% DEA)/CO2, 100 bar, 3 mL/min, 220 nm.

Isomer 1 (cis, 30.6 mg, 10%) was characterized by chiral HPLC (RT=3.68 min, 98.76%). MS: m/z=392.30 [M+Na]+. 1H NMR (400 MHz, CHLOROFORM-d) δ ppm: 7.83 (br. s., 1H), 7.74 (d, J=8.8 Hz, 1H), 7.70 (d, J=8.5 Hz, 1H), 7.51 (d, J=8.8 Hz, 1H), 7.18 (dd, J=8.9, 2.4 Hz, 1H), 7.16 (br. s, 1H), 4.66 (br. s., 1H), 3.63-3.80 (m, 2H), 1.93-2.15 (m, 4H), 1.51-1.68 (m, 6H), 1.20-1.50 (m, 10H), 0.90 (t, J=7.0 Hz, 3H).

Isomer 2 (trans, 127 mg, 42%) was characterized by chiral HPLC (RT=4.64 min, 97.73%). MS: m/z=392.30 [M+Na]+. 1H NMR (400 MHz, CHLOROFORM-d) δ ppm: 7.83 (s, 1H), 7.68-7.76 (m, 2H), 7.51 (d, J=10.0 Hz, 1H), 7.11-7.17 (m, 2H), 4.25-4.35 (m, 1H), 3.64-3.79 (m, 2H), 2.17-2.28 (m, 2H), 1.83-1.93 (m, 2H), 1.55 (s, 3H), 1.40-1.52 (m, 2H), 1.19-1.37 (m, 9H), 1.01-1.13 (m, 2H), 0.91 (t, J=7.0 Hz, 3H).

Example 273

2-(trans-4-tert-butyl-cyclohexyloxy)-6-(1-nitroethyl)-1-trifluoromethyl-naphthalene A vial containing a stir bar was charged with 6-bromo-2-(trans-4-tert-butylcyclohexyloxy)-1-(trifluoromethyl)naphthalene (0.435 g, 1.01 mmol), tris(dibenzylideneacetone)dipalladium(0) (16 mg, 0.017 mmol, Strem), 2-(di-t-butylphosphino)-2'-methylbiphenyl (23 mg, 0.074 mmol, Strem), and cesium carbonate (0.401 g, 1.23 mmol, Alfa Aesar). The reaction vessel was capped with a rubber septum, evacuated, and backfilled with argon three times, and 1,2- dimethoxyethane (10.0 mL, Aldrich) and nitroethane (150 µL, 2.1 mmol, Alfa Aesar) were added via syringe under argon. After the mixture was stirred vigorously for 10 min at room temperature, the capped vial was heated at 50° C. After 16 h, the reaction was allowed to cool to ambient temperature. The mixture was quenched with a solution of sat. aqueous NH$_4$Cl and the aqueous phase was extracted with ethyl acetate, washed with water, and the combined organic phases were dried with magnesium sulfate, filtered and evaporated. The residue was taken up in methylene chloride and silica gel was added. The solvent was removed and the residue was purified by flash column chromatography using 0-60% methylene chloride in hexanes. Isolated were 146 mg yield (34% recovery) of starting material (Rf=0.50 in 3:1 hexanes/methylene chloride) and 177 mg yield (41%) of product (Rf=0.39 in 1:1 hexanes/methylene chloride).

Example 274

2-[6-(trans-4-tert-Butyl-cyclohexyloxy)-5-trifluoromethyl-naphthalen-2-yl]-2-nitro-propan-1-ol 2-(trans-4-tert-Butyl-cyclohexyloxy)-6-(1-nitro-ethyl)-1-trifluoromethyl-naphthalene (96 mg, 0.00023 mol) was suspended (partial dissolved) in 2-Methoxy-2-methylpropane (1.25 mL, 0.0105 mol, Fisher). Formaldehyde (253 µL, 0.00340 mol, Aldrich) was added followed by a solution of 2.00 M of Sodium hydroxide in water (23 µL, 0.000046 mol). The mixture was stirred at room temperature overnight then heated at 50° C. for 24 h. The mixture was quenched with water, extracted with methylene chloride, dried over anhydrous magnesium sulfate, filtered, concentrated in under reduced pressure to give the crude material. Chromatography with 0-50% EtOAc in hexanes gave the product (Rf=0.71 in 1:1 hexanes/ethyl acetate) in 74 mg yield (72%).

Example 275

2-[6-(trans-4-tert-Butyl-cyclohexyloxy)-5-trifluoromethyl-naphthalen-2-yl]-propan-1-ol 2-[6-(trans-4-tert-Butyl-cyclohexyloxy)-5-trifluoromethyl-naphthalen-2-yl]-2-nitro-propan-1-ol (74 mg, 0.00016 mol) was dissolved in methanol (5.0 mL) followed by addition of 10% palladium on carbon (19 mg). After evacuating the vessel, the reaction mixture was then allowed to stir at room temperature under an atmosphere of hydrogen (balloon) for 1 hour. The material was diluted with methanol, filtered and evaporated. The material was purified on silica gel, using 0-50% ethyl acetate in hexanes to yield the product (Rf=0.65 in 1:1 hexanes/ethyl acetate) in 19.6 mg yield (29%). MS: m/z=431.37 [M+Na]$^+$. $^1$H NMR (400 MHz, CHLOROFORM-d) δ ppm: 8.18 (dd, J=9.3, 2.0 Hz, 1H), 7.88 (d, J=9.3 Hz, 1H), 7.64 (d, J=1.5 Hz, 1H), 7.44-7.49 (m, 1H), 7.30 (d, J=9.0 Hz, 1H), 4.23-4.34 (m, 1H), 3.80 (d, J=6.8 Hz, 2H), 3.06-3.17 (m, 1H), 2.13-2.23 (m, 2H), 1.82-1.92 (m, 2H), 1.48-1.60 (m, 2H), 1.37 (d, J=7.0 Hz, 3H), 1.03-1.18 (m, 3H), 0.88 (s, 9H).

Example 276

2-Amino-2-[6-(trans-4-tert-butyl-cyclohexyloxy)-5-trifluoromethyl-naphthalen-2-yl]-propan-1-ol 2-[6-(trans-4-tert-Butyl-cyclohexyloxy)-5-trifluoromethyl-naphthalen-2-yl]-nitro-propan-1-ol (57 mg, 0.00012 mol) was dissolved in acetic acid (0.50 mL, Fisher), followed by addition of zinc (76 mg, 0.0012 mol, Aldrich) dust in small portions at room temperature. The reaction mixture was then allowed to stir at room temperature for 1.5 hours. The reaction was diluted with methanol, filtered and evaporated. The white solid was taken up in methylene chloride, washed with 1N NaOH, washed with water, dried with magnesium sulfate, filtered and evaporated. 45 mg of product isolated (85%). MS: m/z=424.57 [M+H]$^+$. $^1$H NMR (400 MHz, CHLOROFORM-d) δ ppm: 8.20 (dd, J=9.3, 1.5 Hz, 1H), 7.90-7.95 (m, 1H), 7.89 (d, J=1.8 Hz, 1H), 7.63 (dd, J=9.2, 2.1 Hz, 1H), 7.31 (d, J=9.0 Hz, 1H), 4.24-4.34 (m, 1H), 3.77 (d, J=10.5 Hz, 1H), 3.68 (d, J=10.5 Hz, 1H), 2.14-2.23 (m, 2H), 1.94-2.13 (m, 3H), 1.81-1.92 (m, 2H), 1.48-1.59 (m, 5H), 1.24-1.38 (m, 1H), 1.03-1.19 (m, 3H), 0.88 (s, 9H).

Example 276

2-Bromo-6-(4-trifluoromethyl-cyclohexyloxy)-naphthalene

4-Trifluoromethyl-cyclohexanol (1170 mg, 0.00697 mol, TCI) and 2-naphthalenol, 6-bromo-(1.30 g, 0.00581 mol, Aldrich) and triphenylphosphine (1.83 g, 0.00697 mol, Aldrich) were dissolved in toluene (36.8 mL, Aldrich) and the mixture was stirred. Then diisopropyl azodicarboxylate (1.37 mL, 0.00697 mol, Acros) was added. After 4 d, the reaction was evaporated to dryness, then taken up in methylene chloride. Silica gel was added and the solvent was removed. The residue was purified on a silica gel column using 0-100% ethyl acetate in hexanes as eluent. Appropriate fractions combined and concentrated to give the product as a 3:1 mixture of cis and trans isomers (minor: Rf=0.65 to and major: Rf=0.52 in 7:1 hexanes/ethyl acetate) in 1.6202 g yield.
The material was repurified using silica gel chromatography (dry load) using 0-5% ethyl acetate in hexanes as eluent but no resolution of cis and trans was seen. 1.548 g isolated (71%).

Example 277

2-(1-Nitro-ethyl)-6-(trans-4-trifluoromethyl-cyclohexyloxy)-naphthalene and 2-(1-Nitro-ethyl)-6-(cis-4-trifluoromethyl-cyclohexyloxy)-naphthalene 2-(1-Nitro-ethyl)-6-(trans-4-trifluoromethyl-cyclohexyloxy)-naphthalene and 2-(1-Nitro-ethyl)-6-(cis-4-trifluoromethyl-cyclohexyloxy)-naphthalene were synthesized as per 2-(trans-4-tert-butyl-cyclohexyloxy)-6-(1-nitro-ethyl)-1-trifluoromethyl-naphthalene (Example 273) in 69% overall yield using 2-bromo-6-(4-trifluoromethyl-cyclohexyloxy)-naphthalene as the starting material. Isolated by silica gel chromatography were the trans product (16%, Rf=0.46 in 7:1 hexanes/ethyl acatate) and the cis product (53%, Rf=0.29 in 7:1 hexanes/ethyl acatate).

Example 278

4-Nitro-4-[6-(trans-4-trifluoromethyl-cyclohexyloxy)-naphthalen-2-yl]-pentanoic acid methyl ester To a mixture of potassium carbonate (78 mg, 0.56 mmol, Fisher), tetrabutylammonium hydrogen sulfate (10. mg, 0.029 mmol, Aldrich) and N,N-dimethylformamide (2.00 mL, Acros) was added 2-(1-nitro-ethyl)-6-(trans-4-trifluoromethyl-cyclohexyloxy)-naphthalene (0.159 g, 0.433 mmol). The mixture was stirred and methyl acrylate (50 µL, 0.56 mmol, Aldrich) was added. The mixture was stirred at room temperature. After 2 h, ethyl acetate was added and the solution was washed with saturated ammonium chloride, then saturated sodium chloride. The organics were dried over $Na_2SO_4$, filtered, concentrated. The residue was taken up in DCM, and silica gel was added. The solvent was removed and the residue was purified by silica gel chromatography (0-25% EtOAc in hexanes). Isolated was 98 mg (50%) of product (Rf=0.19 in 7:1 hexanes/ethyl acetate).

Example 279

4-Nitro-4-[6-(cis-4-trifluoromethyl-cyclohexyloxy)-naphthalen-2-yl]-pentanoic acid methyl ester 4-Nitro-4-[6-(cis-4-trifluoromethyl-cyclohexyloxy)-naphthalen-2-yl]-pentanoic acid methyl ester was synthesized as per 4-nitro-4-[6-(trans-4-trifluoromethyl-cyclohexyloxy)-naphthalen-2-yl]-pentanoic acid methyl ester (Example 205) in 62% yield, using 2-(1-Nitro-ethyl)-6-(cis-4-trifluoromethyl-cyclohexyloxy)-naphthalene as starting material.

Example 280

4-Nitro-4-[6-(trans-4-trifluoromethyl-cyclohexyloxy)-naphthalen-2-yl]-pentanoic acid To a solution of 4-nitro-4-[6-(trans-4-trifluoromethyl-cyclohexyloxy)-naphthalen-2-yl]-pentanoic acid methyl ester (0.098 g, 0.22 mmol) in methanol (1.00 mL, Fisher) and tetrahydrofuran (1.00 mL, Acros) was added 2 M lithium hydroxide in water (1.00 mL, 2.00 mmol). The mixture was stirred at room temperature. After 2 hours, the mixture was concentrated under vacuum. The resulting product was diluted in methylene chloride and washed with 1N HCl. The combined organic phases were dried over $Na_2SO_4$, filtered and concentrated to give the product in 99 mg yield (100%).

Example 281

4-Nitro-4-[6-(cis-4-trifluoromethyl-cyclohexyloxy)-naphthalen-2-yl]-pentanoic acid 4-Nitro-4-[6-(cis-4-trifluoromethyl-cyclohexyloxy)-naphthalen-2-yl]-pentanoic acid was synthesized as per 4-Nitro-4-[6-(trans-4-trifluoromethyl-cyclohexyloxy)-naphthalen-2-yl]-pentanoic acid (Example 280) in 97% yield, using 4-Nitro-4-[6-(cis-4-trifluoromethyl-cyclohexyloxy)-naphthalen-2-yl]-pentanoic acid methyl ester as starting material.

Example 282

4-Amino-4-[6-(trans-4-trifluoromethyl-cyclohexyloxy)-naphthalen-2-yl]-pentanoic acid To a solution of 4-nitro-4-[6-(trans-4-trifluoromethyl-cyclohexyloxy)-naphthalen-2-yl]-pentanoic acid (0.099 g, 0.22 mmol) in acetic acid (2.00 mL, Fisher) at 20° C. was added zinc (0.185 g, 2.83 mmol, Aldrich). The mixture was stirred for 45 minutes at room temperature. The mixture was heated at 50° C. and stirred. After 2.5 h, the mixture was diluted in acetic acid, filtered and concentrated to dryness under reduced pressure. Purification was by preparative HPLC. The fractions were dried to give 61 mg (52%) product as TFA salt. MS: m/z=432.10 [M+Na]+. 1H NMR (400 MHz, CHLOROFORM-d) δ ppm: 7.62-7.74 (m, 3H), 7.36 (dd, J=8.8, 1.8 Hz, 1H), 7.03-7.12 (m, 2H), 4.21-4.32 (m, 1H), 2.20-2.41 (m, 4H), 1.91-2.19 (m, 5H), 1.72 (s, 3H), 1.35-1.51 (m, 4H).

Example 283

4-Amino-4-[6-(cis-4-trifluoromethyl-cyclohexyloxy)-naphthalen-2-yl]-pentanoic acid 4-Amino-4-[6-(cis-4-trifluoromethyl-cyclohexyloxy)-naphthalen-2-yl]-pentanoic acid was synthesized as per 4-amino-4-[6-(trans-4-trifluoromethyl-cyclohexyloxy)-naphthalen-2-yl]-pentanoic acid (Example 282) in 21% yield as TFA salt, using 4-nitro-4-[6-(cis-4-trifluoromethyl-cyclohexyloxy)-naphthalen-2-yl]-pentanoic acid as the starting material. MS: m/z=432.20 [M+Na]+. 1H NMR (400 MHz, CHLOROFORM-d) δ ppm: 7.64-7.75 (m, 3H), 7.35 (dd, J=8.8, 2.0 Hz, 1H), 7.14 (dd, J=8.9, 2.1 Hz, 1H), 7.08 (s, 1H), 4.67 (br. s., 1H), 2.22-2.41 (m, 2H), 1.98-2.20 (m, 5H), 1.63-1.80 (m, 7H), 1.48-1.61 (m, 2H).

Example 284

4-[5-Iodo-6-(trans-4-trifluoromethyl-cyclohexyloxy)-naphthalen-2-yl]-4-nitro-pentanoic acid methyl ester N-Iodosuccinimide (118 mg, 0.000524 mol, Aldrich) and zirconium tetrachloride (24 mg, 0.00010 mol, Aldrich) were added to a solution of 4-nitro-4-[6-(trans-4-trifluoromethyl-cyclohexyloxy)-naphthalen-2-yl]-pentanoic acid methyl ester (160 mg, 0.000353 mol) in methylene chloride (5.0 mL, Acros) and were stirred at room temperature. After 3 h, the reaction was filtered through a PTFE filter. Silica gel was added and the solvent was then evaporated. The residue was purified by silica gel chromatography using 0-50% ethyl acetate in hexanes as eluent to give the product (Rf=0.36 in 3:1 hexanes/ethyl acetate) in 173 mg yield (85%).

Example 285

4-[5-Iodo-6-(cis-4-trifluoromethyl-cyclohexyloxy)-naphthalen-2-yl]-4-nitro-pentanoic acid methyl ester 4-[5-Iodo-6-(cis-4-trifluoromethyl-cyclohexyloxy)-naphthalen-2-yl]-4-nitro-pentanoic acid methyl ester was synthesized as per 4-[5-iodo-6-(trans-4-trifluoromethyl-cyclohexyloxy)-naphthalen-2-yl]-4-nitro-pentanoic acid methyl ester (Example 281) in 51% yield, using 4-nitro-4-[6-(cis-4-trifluoromethyl-cyclohexyloxy)-naphthalen-2-yl]-pentanoic acid as the starting material.

Example 286

4-Nitro-4-[5-trifluoromethyl-6-(4-trifluoromethyl-cyclohexyloxy)-naphthalen-2-yl]-pentanoic acid methyl ester 4-Nitro-4-[5-trifluoromethyl-6-(4-trifluoromethyl-cyclohexyloxy)-naphthalen-2-yl]-pentanoic acid methyl ester was synthesized as per (R)-4-methyl-4-[5-trifluoromethyl-6-(trans-4-trifluoromethyl-cyclohexyloxy)-naphthalen-2-yl]-oxazolidin-2-one (Example 265) in 83% yield using 4-[5-iodo-6-(trans-4-trifluoromethyl-cyclohexyloxy)-naphthalen-2-yl]-4-nitro-pentanoic acid methyl ester as starting material.

Example 287

4-Nitro-4-[5-trifluoromethyl-6-(cis-4-trifluoromethyl-cyclohexyloxy)-naphthalen-2-yl]-pentanoic acid methyl ester 4-Nitro-4-[5-trifluoromethyl-6-(cis-4-trifluoromethyl-cyclohexyloxy)-naphthalen-2-yl]-pentanoic acid methyl ester was synthesized as per (R)-4-methyl-4-[5-trifluoromethyl-6-(trans-4-trifluoromethyl-cyclohexyloxy)-naphthalen-2-yl]-oxazolidin-2-one in (Example 265) 84% yield, using 4-[5-iodo-6-(cis-4-trifluoromethyl-cyclohexyloxy)-naphthalen-2-yl]-4-nitro-pentanoic acid methyl ester as the starting material.

Example 288

4-Nitro-4-[5-trifluoromethyl-6-(trans-4-trifluoromethyl-cyclohexyloxy)-naphthalen-2-yl]-pentanoic acid 4-Nitro-4-[5-trifluoromethyl-6-(trans-4-trifluoromethyl-cyclohexyloxy)-naphthalen-2-yl]-pentanoic acid was synthesized as per 4-nitro-4-[6-(trans-4-trifluoromethylcyclohexyloxy)-naphthalen-2-yl]-pentanoic acid (Example 280) in 93% yield, using 4-nitro-4-[5-trifluoromethyl-6-(trans-4-trifluoromethyl-cyclohexyloxy)-naphthalen-2-yl]-pentanoic acid methyl ester as starting material.

Example 289

4-Nitro-4-[5-trifluoromethyl-6-(cis-4-trifluoromethylcyclohexyloxy)-naphthalen-2-yl]-pentanoic acid 4-Nitro-4-[5-trifluoromethyl-6-(cis-4-trifluoromethyl-cyclohexyloxy)-naphthalen-2-yl]-pentanoic acid was synthesized as per 4-nitro-4-[6-(trans-4-trifluoromethyl-cyclohexyloxy)-naphthalen-2-yl]-pentanoic acid (Example 280) in 93% yield, using 4-nitro-4-[5-trifluoromethyl-6-(cis-4-trifluoromethyl-cyclohexyloxy)-naphthalen-2-yl]-pentanoic acid methyl ester as the starting material.

Example 290

4-Amino-4-[5-trifluoromethyl-6-(trans-4-trifluoromethylcyclohexyloxy)-naphthalen-2-yl]-pentanoic acid 4-Amino-4-[5-trifluoromethyl-6-(trans-4-trifluoromethyl-cyclohexyloxy)-naphthalen-2-yl]-pentanoic acid was synthesized as per 4-amino-4-[6-(trans-4-trifluoromethyl-cyclohexyloxy)-naphthalen-2-yl]-pentanoic acid (Example 282) in 56% yield (as TFA salt), using 4-nitro-4-[5-trifluoromethyl-6-(trans-4-trifluoromethyl-cyclohexyloxy)-naphthalen-2-yl]-pentanoic acid as starting material. MS: m/z=500.20 [M+Na]$^+$. $^1$H NMR (400 MHz, DMSO-d6) δ ppm: 12.23 (br. s., 1H), 8.53 (br. s., 3H), 8.22 (d, J=9.3 Hz, 1H), 8.12 (d, J=8.0 Hz, 1H), 8.05 (d, J=1.5 Hz, 1H), 7.72-7.80 (m, 2H), 4.62-4.73 (m, 1H), 2.35-2.42 (m, 1H), 2.21-2.34 (m, 2H), 2.07-2.20 (m, 3H), 1.88-2.05 (m, 3H), 1.66-1.78 (m, 3H), 1.40-1.60 (m, 4H).

Example 291

4-Amino-4-[5-trifluoromethyl-6-(cis-4-trifluoromethylcyclohexyloxy)-naphthalen-2-yl]-pentanoic acid 4-Amino-4-[5-trifluoromethyl-6-(cis-4-trifluoromethyl-cyclohexyloxy)-naphthalen-2-yl]-pentanoic acid was synthesized as per 4-amino-4-[6-(trans-4-trifluoromethyl-cyclohexyloxy)-naphthalen-2-yl]-pentanoic acid (Example 282) in 46% yield (as TFA salt), using 4-nitro-4-[5-trifluoromethyl-6-(cis-4-trifluoromethyl-cyclohexyloxy)-naphthalen-2-yl]-pentanoic acid as starting material. MS: m/z=500.10 [M+Na]$^+$. $^1$H NMR (400 MHz, to DMSO-d6) δ ppm: 12.23 (br. s., 8.52 (br. s., 3H), 8.23 (d, J=9.3 Hz, 1H), 8.14 (d, J=8.0 Hz, 1H), 8.04 (d, J=1.8 Hz, 1H), 7.77 (dd, J=9.3, 2.0 Hz, 1H), 7.71 (d, J=9.3 Hz, 1H), 5.07-5.13 (br. s., 1H), 2.39-2.59 (m, 2H obscured), 2.21-2.34 (m, 2H), 1.93-2.17 (m, 4H), 1.56-1.78 (m, 9H).

Example 292

Cis-4-hydroxy-N-methoxy-N-methylcyclohexanecarboxamide

Cis-4-hydroxycyclohexanecarboxylic acid (6 g, 0.042 mol) and EDCI (9.6 g, 0.05 mol, 1.2 eq.) were dissolved in DCM (100 mL) at 0° C. and stirred for 10 min. DIPEA (16 mL, 0.126 mol, 3.0 eq.) and N,O-dimethylhydroxylamine hydrochloride (4.44 g, 0.046 mol, 1.1 eq.) were added to the mixture at 0° C. The mixture was warmed to room temperature and stirred for 15 h., water was added and the mixture was extracted with DCM. The organic layer was concentrated and purified by silica gel column chromatography using DCM/CH$_3$OH (10/1) to give product as a colorless oil (3.685 g, 40%). $^1$H NMR (400 MHz, CDCl$_3$) δ: 4.01 (s, 1H), 3.70 (s, 3H), 3.18 (s, 3H), 2.72-2.69 (m, 1H), 1.98-1.85 (m, 4H), 1.62-1.55 (m, 4H).

Example 293

Cis-4-(benzyloxy)-N-methoxy-N-methylcyclohexanecarboxamide

To a mixture of cis-4-hydroxy-N-methoxy-N-methylcyclohexanecarboxamide (3.556 g, 0.0190 mol) and benzyl-2,2,2-trichloroacetimidate (4.0 mL, 0.021 mol, 1.1 eq) in cyclohexane/DCM (20 mL/10 mL) at 0° C. was added trifluoromethanesulfonic acid dropwise with stirring under nitrogen atmosphere over 30 min. There was an immediate precipitate. The mixture was stirred at room temperature for 15 h, filtered, and the filtrate washed with sodium bicarbonate solution and brine. The organic layer was concentrated and purified by silica gel column chromatography using petroleum ether/ethyl acetate (5/1) as eluent to give product as a colorless oil (5.079 g, 77%). $^1$H NMR (400 MHz, CDCl$_3$) δ 7.38-7.23 (m, 5H), 4.50 (s, 2H), 3.71 (s, 3H), 3.70-3.66 (m, 1H), 3.18 (s, 3H), 2.78-2.62 (m, 1H), 2.07-1.89 (m, 4H), 1.59-1.25 (m, 4H).

Example 294

1-(cis-4-(benzyloxy)cyclohexyl)ethanone

Cis-4-(benzyloxy)-N-methoxy-N-methylcyclohexanecarboxamide (1.3 g, 4.7 mmol) was dissolved in THF (10 mL). CH$_3$Li (3.0 M solution in diethoxymethane, 8.0 mL, 14.1 mmol, 3.0 eq.) was added to the solution dropwise at −70° C. The mixture was stirred at −70° C. under nitrogen atmosphere for 1 h. then 1 M HCl solution was added to the mixture until pH=6. The mixture was extracted with ethyl acetate and the organic layer was concentrated and purified by silica gel column chromatography using petroleum ether/ethyl acetate (3/1) as eluent to give product as a slight yellow oil (720 mg, 60%). $^1$H NMR (400 MHz, CDCl$_3$) δ 7.34-7.25 (m, 5H), 4.49

(s, 2H), 3.62-3.60 (m, 1H), 2.40-2.25 (m, 1H), 2.13 (s, 3H), 1.97-1.93 (m, 2H), 1.86-1.80 (m, 2H), 1.67-1.54 (m, 2H), 1.53-1.47 (m, 2H).

Example 295

((cis-4-(1,1-difluoroethyl)cyclohexyloxy)methyl) benzene 1-(cis-4-(benzyloxy)cyclohexyl)ethanone (547 mg, 2.36 mmol) was dissolved in DCM (5 mL). Then DAST (2.3 mL, 18.9 mmol, 8.0 eq.) was added to the mixture at 0° C. Then the mixture was stirred at room temperature for 4 days. water was added to the mixture dropwise. Then saturated sodium carbonate solution was added to the mixture until pH=8. The mixture was extracted with EtOAc and the organic layer was concentrated and purified by silica gel column chromatography using petroleum ether/ethyl acetate (10/1) as eluent to give product (553 mg, 80%) as a slight yellow oil. $^1$H NMR (400 MHz, CDCl$_3$) δ 7.34-7.25 (m, 5H), 4.50 (s, 2H), 3.67-3.66 (m, 1H), 3.08-2.95 (m, 1H), 2.08-2.04 (m, 2H), 1.75-1.65 (m, 2H), 1.61-1.48 (m, 3H), 1.42-1.34 (m, 2H), 1.25-1.19 (m, 2H).

Example 296 cis-4-(1,1-difluoroethyl)cyclohexanol

Compounds ((cis-4-(1,1-difluoroethyl)cyclohexyloxy) methyl)benzene (480 mg, 1.89 mmol) and Pd—C (2.0 g, 0.38 mmol, 0.2 eq.) were dissolved in CH$_3$OH (20 mL). Then the mixture was stirred at 50° C. under 40 atm. of hydrogen atmosphere for 6 h. When the reaction completed by TLC, the mixture was filtrated and the filtrate was concentrated and purified by silica gel column chromatography using petroleum ether/ethyl acetate (10/1) as eluent to give product (140 mg, 45%) as a slight yellow oil. $^1$H NMR (400 MHz, CDCl$_3$) δ 4.07-4.05 (m, 1H), 1.86-1.83 (m, 2H), 1.75-1.72 (m, 2H), 1.63-1.48 (m, 8H).

Example 297 cis-4-(1,1-difluoroethyl)cyclohexyl methanesulfonate cis-4-(1,1-Difluoroethyl)cyclohexanol (430 mg, 2.62 mmol) was dissolved in DCM (10 mL) then methanesulfonic acid anhydride (547 mg, 3.15 mmol, 1.1 eq.) was added to the mixture at 0° C. Triethylamine (0.43 mL, 3.15 mmol, 1.5 eq.) was added to the mixture at 0° C. and the mixture was stirred at room temperature for 3 h. water was added to the mixture and extracted with DCM. The organic layer was concentrated to give product (611 mg, 82%) as a gray solid, which used to next step without purification. $^1$H NMR (400 MHz, CDCl$_3$) δ 5.02-5.01 (m, 1H), 3.02 (s, 3H), 2.19-2.17 (m, 2H), 1.82-1.75 (m, 2H), 1.65-1.50 (m, 8H).

Example 298

(R)-4-(6-(trans-4-(1,1-difluoroethyl)cyclohexyloxy) naphthalen-2-yl)-4-methyloxazolidin-2-one (R)-4-(6-Hydroxynaphthalen-2-yl)-4-methyloxazolidin-2-one (121 mg, 0.5 mmol, 0.9 eq.) and cesium carbonate (407 mg, 1.25 mmol, 2.5 eq.) were dissolved in t-BuOH/2-butanone (10 mL/5 mL). The mixture was stirred at 110° C. for 10 min, then cis-4-(1,1-difluoroethyl)cyclohexyl methanesulfonate (145 mg, 0.6 mmol, 1.1 eq.) was added to the mixture and the mixture was stirred at 110° C. for 15 h. Water was added to the mixture and the mixture was extracted with EtOAc. The organic layer was concentrated and purified by is silica gel column chromatography using petroleum ether/ethyl acetate (1/1) as eluent to give product (203 mg, 58%) as a slight yellow solid. EDI-MS (M+1): 390.1. $^1$H NMR (400 MHz, CDCl$_3$) δ 7.75-7.72 (m, 3H), 7.42 (dd, 1H), 7.16-7.14 (m, 2H), 6.14 (s, 1H), 4.42 (s, 2H), 4.34-4.30 (m, 1H), 2.31-2.29 (m, 2H), 2.04-2.01 (m, 2H), 1.84 (s, 3H), 1.64-1.22 (m, 8H).

Example 299

(R)-2-amino-2-(6-(trans-4-(1,1-difluoroethyl)cyclohexyloxy)naphthalen-2-yl)propan-1-ol (R)-4-(6-(cis-4-(1,1-Difluoroethyl)cyclohexyloxy)naphthalen-2-yl)-4-methyloxazolidin-2-one (32 mg, 0.083 mmol) was dissolved in EtOH (5 mL). Then LION (60 mg, 2.5 mmol, 30.0 eq.) in 1 mL water was added to the mixture. The mixture was heated to 80° C. and stirred for 15 h. LCMS showed starting material was gone. Solvent was removed. DCM was added and filtered. The filtrate was concentrated and purified by silica gel chromatography using DCM/methanol (10/1) to give product (12 mg, 40%) as a slight yellow solid. EDI-MS (M-NH$_2$): 347.0. HPLC: 98.82%. $^1$H NMR (400 MHz, CDCl$_3$) δ 7.82 (s, 1H), 7.72-7.66 (m, 2H), 7.49 (d, 1H), 7.10 (d, 2H), 4.30-4.27 (m, 1H), 3.78-3.68 (AB, 2H), 3.18 (b, 3H), 2.32-2.30 (m, 2H), 2.04-1.99 (m, 2H), 1.63-1.19 (m, 11H).

Example 300

1-(cis-4-(benzyloxy)cyclohexyl)propan-1-one

The preparation of the title compound was performed analogously to 1-(cis-4-(benzyloxy)cyclohexyl)ethanone (Example 294).

480 mg, slight yellow oil, 48%. $^1$H NMR (400 MHz, CDCl$_3$) δ 7.35-7.24 (m, 5H), 4.49 (s, 2H), 3.62-3.60 (m, 1H), 2.49-2.35 (m, 2H), 2.34-2.33 (m, 1H), 1.98-1.93 (m, 2H), 1.90-1.80 (m, 2H), 1.65-1.59 (m, 2H), 1.53-1.45 (m, 2H), 1.05 (t, 3H).

Example 301

((cis-4-(1,1-difluoropropyl)cyclohexyloxy)methyl) benzene

The preparation of the title compound was performed analogously to ((cis-4-(1,1-difluoroethyl)cyclohexyloxy) methyl)benzene (Example 295).

371 mg, slight yellow oil, 70%. $^1$H NMR (400 MHz, CDCl$_3$) δ 7.35-7.25 (m, 5H), 4.50 (s, 2H), 3.67-3.65 (m, 1H), 2.08-2.04 (m, 2H), 1.84-1.78 (m, 3H), 1.64-1.57 (m, 4H), 1.38-1.25 (m, 2H), 1.00 (t, 3H).

Example 302 cis-4-(1,1-difluoropropyl)cyclohexanol

The preparation of the title compound was performed analogously to cis-4-(1,1-difluoroethyl)cyclohexanol (Example 296).

205 mg, slight yellow oil, 38%. $^1$H NMR (400 MHz, CDCl$_3$) δ 4.08-4.05 (m, 1H), 1.89-1.78 (m, 5H), 1.67-1.60 (m, 4H), 1.52-1.45 (m, 2H), 1.01 (t, 3H).

Example 303 cis-4-(1,1-difluoropropyl)cyclohexyl methanesulfonate

The preparation of the title compound was performed analogously to cis-4-(1,1-difluoroethyl)cyclohexyl methanesulfonate (Example 297).

200 mg, gray solid, 85%. $^1$H NMR (400 MHz, CDCl$_3$) δ 5.02-5.01 (m, 1H), 3.02 (s, 3H), 2.19-2.16 (m, 2H), 1.89-1.59 (m, 9H), 1.01 (t, 3H).

Example 304

(R)-4-(6-(trans-4-(1,1-difluoropropyl)cyclohexyloxy)naphthalen-2-yl)-4-methyloxazolidin-2-one The preparation of the title compound was performed analogously to (R)-4-(6-(trans-4-(1,1-difluoroethyl)cyclohexyloxy)naphthalen-2-yl)-4-methyloxazolidin-2-one (Example 298).

70 mg, gray solid, 50%. EDI-MS (M+1): 404.0. $^1$H NMR (400 MHz, CDCl$_3$) δ 8.02 (s, 1H), 7.76-7.72 (m, 2H), 7.434 (dd, 1H), 7.16 (d, 2H), 4.41 (s, 2H), 4.38-4.25 (m, 1H), 2.31-2.29 (m, 2H), 2.04-2.01 (m, 2H), 1.84 (s, 3H), 1.64-1.22 (m, 7H), 1.02 (t, 3H).

Example 305

(R)-2-amino-2-(6-(trans-4-(1,1-difluoropropyl)cyclohexyloxy)naphthalen-2-yl)propan-1-ol The preparation of the title compound was performed analogously to (R)-2-amino-2-(6-(trans-4-(1,1-difluoroethyl)cyclohexyloxy)naphthalen-2-yl)propan-1-ol (Example 299).

4 mg, gray solid, 40%. EDI-MS (M-NH$_2$): 361.0. HPLC: 100.00%. $^1$H NMR (400 MHz, CDCl$_3$) δ 7.82 (s, 1H), 7.74-7.69 (m, 2H), 7.49 (t, 1H), 7.11 (t, 2H), 4.31-4.29 (m, 1H), 3.74-3.66 (AB, 2H), 2.32-2.30 (m, 2H), 2.04-1.79 (m, 9H), 1.48-1.42 (m, 3H), 1.03 (t, 3H).

Example 306

1-(cis-4-(benzyloxy)cyclohexyl)butan-1-one

To a suspension of Mg (0.51 g, 21.6 mmol, 5.0 eq.) in dry THF (15 mL) under N$_2$ was added 1-bromopropane (0.51 g, 2 mL, 5.0 eq.) dropwise and stirred at room temperature until Mg disappeared, then 1-(cis-4-(benzyloxy)cyclohexyl)ethanone (1.2 g, 4.3 mmol, 1.0 eq.) was added to the reaction mixture in an ice bath. The reaction mixture was warmed to r.t and stirred for 3 h., extracted (EtOAc), washed (brine), dried (Na$_2$SO$_4$), filtered and concentrated. The crude was then purified by silica gel chromatography eluting with EtOAc/Petroleum ether (10:1) to give the title compound (0.6 g, 50%) as a pale yellow oil. $^1$H NMR (400 MHz, CDCl$_3$) δ 7.34-7.24 (m, 5H), 4.49 (s, 2H), 3.62-3.60 (m, 1H), 2.44-2.40 (m, 2H), 2.34-2.33 (m, 1H), 1.98-1.80 (m, 4H), 1.64-1.46 (m, 6H), 0.89 (t, 3H).

Example 307

((cis-4-(1,1-difluorobutyl)cyclohexyloxy)methyl)benzene

The preparation of the title compound was performed analogously to ((cis-4-(1,1-difluoroethyl)cyclohexyloxy)methyl)benzene (Example 295).

2.5 g, slight yellow oil, yield: 77%. $^1$H NMR (400 MHz, CDCl$_3$) δ 7.35-7.25 (m, 5H), 4.50 (s, 2H), 3.67-3.65 (m, 1H), 3.02-3.00 (m, 1H), 2.08-2.04 (m, 2H), 1.79-1.05 (m, 10H), 0.89 (t, 3H).

Example 308 cis-4-(1,1-difluorobutyl)cyclohexanol

The preparation of the title compound was performed analogously to cis-4-(1,1-difluoroethyl)cyclohexanol (Example 296).

1.3 g, slight yellow oil, yield: 43%. $^1$H NMR (400 MHz, CDCl$_3$) δ 4.07-4.06 (m, 1H), 1.87-1.71 (m, 5H), 1.67-1.48 (m, 8H), 0.95 (t, 3H).

Example 309 cis-4-(1,1-difluorobutyl)cyclohexyl methanesulfonate

The preparation of the title compound was performed analogously to cis-4-(1,1-difluoroethyl)cyclohexyl methanesulfonate (Example 297).

1.4 g, gray solid, yield: 87%. $^1$H NMR (400 MHz, CDCl$_3$) δ 5.02-5.00 (m, 1H), 3.15 (s, 3H), 2.18-2.16 (m, 2H), 1.82-1.71 (m, 5H), 1.64-1.48 (m, 6H), 0.96 (t, 3H).

Example 310

(R)-4-(6-(trans-4-(1,1-difluorobutyl)cyclohexyloxy)naphthalen-2-yl)-4-methyloxazolidin-2-one The preparation of the title compound was performed analogously to (R)-4-(6-(trans-4-(1,1-difluoroethyl)cyclohexyloxy)naphthalen-2-yl)-4-methyloxazolidin-2-one (Example 298).

700 mg, gray solid, yield: 58%. EDI-MS (M+1): 417.1. $^1$H NMR (400 MHz, CD$_3$OD) δ 7.78-7.73 (m, 3H), 7.42 (dd, 1H), 7.22-7.09 (m, 2H), 4.68-4.63 (m, 1H), 4.44-4.36 (AB, 2H), 2.22-2.18 (m, 2H), 1.88-1.67 (m, 6H), 1.43-1.34 (m, 8H), 0.98 (t, 3H).

Example 311

(R)-2-amino-2-(6-(trans-4-(1,1-difluorobutyl)cyclohexyloxy)naphthalen-2-yl)propan-1-ol The preparation of the title compound was performed analogously to (R)-2-amino-2-(6-(trans-4-(1,1-difluoroethyl)cyclohexyloxy)naphthalen-2-yl)propan-1-ol (Example 299).

12 mg, gray solid, 42%. EDI-MS (M-NH$_2$): 375.0. HPLC: 98.84%. $^1$H NMR (400 MHz, CD$_3$OD) δ 7.73-7.67 (m, 3H), 7.42 (dd, 1H), 7.15 (s, 1H), 7.03 (dd, 1H), 4.30-4.28 m (m, 1H), 3.72-3.64 (AB, 2H), 2.22-2.18 (m, 2H), 1.88-1.67 (m, 6H), 1.43-1.34 (m, 8H), 0.88 (t, 3H).

Example 312 trans-4-hydroxy-N-methoxy-N-methylcyclohexanecarboxamide

The preparation of the title compound was performed analogously to cis-4-hydroxy-N-methoxy-N-methylcyclohexanecarboxamide (Example 292).

7.2 g, colorless oil, yield: 56%. ¹H NMR (400 MHz, CDCl₃) δ: 3.71 (s, 3H), 3.59-3.67 (m, 1H), 3.18 (s, 3H), 2.63-2.64 (m, 1H), 2.04-2.07 (m, 2H), 1.82-1.85 (m, 2H), 1.53-1.62 (m, 2H), 1.26-1.35 (m, 2H).

Example 313 trans-4-(benzyloxy)-N-methoxy-N-methylcyclohexanecarboxamide

The preparation of the title compound was performed analogously to cis-4-(benzyloxy)-N-methoxy-N-methylcyclohexanecarboxamide (Example 293).

3 g, pale yellow oil, yield: 72%. EDI-MS (M+1): 278.2. ¹H NMR (400 MHz, CDCl₃) δ: 7.28-7.35 (m, 5H), 4.57 (s, 2H), 3.70 (s, 3H), 3.34-3.41 (m, 1H), 3.18 (s, 3H), 2.64-2.69 (m, 1H), 2.16-2.20 (m, 2H), 1.84-1.87 (m, 2H), 1.49-1.56 (m, 2H), 1.29-1.38 (m, 2H).

Example 314

1-(trans-4-(benzyloxy)cyclohexyl)ethanone

The preparation of the title compound was performed analogously to 1-(cis-4-(benzyloxy)cyclohexyl)ethanone (Example 294).

1.9 g, slight yellow oil, yield: 76%. EDI-MS (M+1): 233.0. NMR (400 MHz, CDCl₃) δ: 7.27-7.35 (m, 5H), 4.56 (s, 2H), 3.30-3.36 (m, 1H), 2.31-2.36 (m, 1H), 2.14-2.18 (m, 5H), 1.96-1.98 (m, 2H), 1.33-1.39 (m, 4H).

Example 315

((trans-4-(1,1-difluoroethyl)cyclohexyloxy)methyl)benzene

The preparation of the title compound was performed analogously to ((cis-4-(1,1-difluoroethyl)cyclohexyloxy)methyl)benzene (Example 295).

1.4 g, slight yellow oil, yield: 85%. ¹H NMR (400 MHz, CDCl₃) δ: 7.27-7.35 (m, 5H), 4.57 (s, 2H), 3.27-3.34 (m, 1H), 2.17-2.20 (m, 2H), 1.91-1.94 (m, 2H), 1.70-1.77 (m, 1H), 1.58-1.48 (m, 3H), 1.20-1.32 (m, 4H).

Example 316 trans-4-(1,1-difluoroethyl)cyclohexanol

The preparation of the title compound was performed analogously to cis-4-(1,1-difluoroethyl)cyclohexanol (Example 296).

0.5 g, slight yellow oil, yield: 55%. ¹H NMR (400 MHz, CDCl₃) δ: 3.53-3.61 (m, 1H), 2.04-2.06 (m, 2H), 1.90-1.92 (m, 2H), 1.62-1.79 (m, 1H), 1.58-1.49 (m, 3H), 1.24-1.29 (m, 4H).

Example 317 trans-4-(1,1-difluoroethyl)cyclohexyl methanesulfonate

The preparation of the title compound was performed analogously to cis-4-(1,1-difluoroethyl)cyclohexyl methanesulfonate (Example 297).

162 mg, slight yellow oil, yield: 91%. ¹H NMR (400 MHz, CDCl₃) δ: 4.56-4.62 (m, 1H), 3.02 (s, 3H), 2.25-2.27 (m, 2H), 1.97-2.00 (m, 2H), 1.66-1.80 (m, 1H), 1.60 (s, 1H), 1.55 (s, 1H), 1.50 (s, 1H), 1.30-1.40 (m, 4H).

Example 318

(R)-4-(6-(cis-4-(1,1-difluoroethyl)cyclohexyloxy)naphthalen-2-yl)-4-methyloxazolidin-2-one The preparation of the title compound was performed analogously to (R)-4-(6-(trans-4-(1,1-difluoroethyl)cyclohexyloxy)naphthalen-2-yl)-4-methyloxazolidin-2-one (Example 298).

67 mg, pale yellow solid, yield: 42%. EDI-MS (M+1): 390.1. ¹H NMR (400 MHz, CDCl₃) δ: 7.76 (d, 3H), 7.42-7.45 (m, 1H), 7.16-7.22 (m, 1H), 6.99 (d, 1H), 5.25 (s, 1H), 4.72-4.75 (m, 1H), 4.40-4.41 (m, 2H), 2.21-2.25 (m, 2H), 1.98-2.20 (m, 1H), 1.86 (s, 3H), 1.70-1.73 (d, 2H), 1.53-1.63 (m, 3H), 1.21-1.31 (m, 4H).

Example 319

(R)-2-amino-2-(6-(cis-4-(1,1-difluoroethyl)cyclohexyloxy)naphthalen-2-yl)propan-1-ol The preparation of the title compound was performed analogously to (R)-2-amino-2-(6-(trans-4-(1,1-difluoroethyl)cyclohexyloxy)naphthalen-2-yl)propan-1-ol (Example 299).

60 mg, pale yellow solid, yield: 80%. EDI-MS (M-NH₂): 347.0. HPLC: 93.80%. ¹H NMR (400 MHz, CDCl₃) δ: 7.85 (s, 1H), 7.65-7.73 (m, 2H), 7.49-7.51 (m, 1H), 7.10-7.16 (m, 2H), 4.69-4.70 (m, 1H), 3.70-3.84 (AB, 2H), 2.20-2.23 (m, 2H), 1.81-1.87 (m, 1H), 1.53-1.71 (m, 9H), 1.25 (s, 3H).

Example 320

1-(trans-4-(benzyloxy)cyclohexyl)propan-1-one

The preparation of the title compound was performed analogously to 1-(cis-4-(benzyloxy)cyclohexyl)ethanone (Example 294).

1.2 g, slight yellow oil, yield: 56%. EDI-MS (M+1): 247.0. ¹H NMR (400 MHz, CDCl₃) δ: 7.27-7.34 (m, 5H), 4.56 (s, 2H), 3.30-3.36 (m, 1H), 2.44-2.49 (m, 2H), 2.32-2.38 (m, 1H), 2.15-2.17 (m, 2H), 1.91-1.94 (m, 2H), 1.28-1.44 (m, 4H), 1.03 (t, 3H).

Example 321

((trans-4-(1,1-difluoropropyl)cyclohexyloxy)methyl)benzene

The preparation of the title compound was performed analogously to ((cis-4-(1,1-difluoroethyl)cyclohexyloxy)methyl)benzene (Example 295).

0.84 g, yellow oil, yield: 64%. ¹H NMR (400 MHz, CDCl₃) δ: 7.27-7.35 (m, 5H), 4.56 (s, 2H), 3.27-3.33 (m, 1H), 2.17-2.19 (m, 2H), 1.71-1.91 (m, 5H), 1.24-1.30 (m, 4H), 1.00 (t, 3H).

Example 322 trans-4-(1,1-difluoropropyl)cyclohexanol

The preparation of the title compound was performed analogously to cis-4-(1,1-difluoroethyl)cyclohexanol (Example 296).

0.18 g, slight yellow oil, yield: 71%. $^1$H NMR (400 MHz, CDCl$_3$) δ: 3.55-3.61 (m, 1H), 2.05-2.07 (m, 2H), 1.68-1.90 (m, 5H), 1.20-1.35 (m, 4H), 1.01 (t, 3H).

Example 323 trans-4-(1,1-difluoropropyl)cyclohexyl methanesulfonate

The preparation of the title compound was performed analogously to cis-4-(1,1-difluoroethyl)cyclohexyl methanesulfonate (Example 297).

155 mg, slight yellow oil, yield: 90%. $^1$H NMR (400 MHz, CDCl$_3$) δ: 4.56-4.63 (m, 1H), 3.02 (s, 3H), 2.23-2.26 (m, 2H), 1.94-1.98 (m, 2H), 1.75-1.88 (m, 3H), 1.54-1.58 (m, 2H), 1.32-1.42 (m, 2H), 1.01 (t, 3H).

Example 324

(R)-4-(6-(cis-4-(1,1-difluoropropyl)cyclohexyloxy) naphthalen-2-yl)-4-methyloxazolidin-2-one The preparation of the title compound was performed analogously to (R)-4-(6-(trans-4-(1,1-difluoroethyl)cyclohexyloxy)naphthalen-2-yl)-4-methyloxazolidin-2-one (Example 298).

55 mg, pale yellow solid, yield: 29%. EDI-MS (M+1): 404.1. $^1$HNMR (400 MHz, CDCl$_3$) δ: 7.75 (d, 3H), 7.42-7.44 (m, 1H), 7.20-7.23 (m, 1H), 7.15-7.16 (m, 1H), 5.52 (s, 1H), 4.72-4.74 (m, 1H), 4.41-4.43 (m, 2H), 2.21-2.24 (m, 2H), 1.94-2.01 (m, 2H), 1.72-1.82 (m, 5H), 1.25-1.33 (m, 3H), 1.04 (t, 3H), 0.86-0.90 (m, 2H).

Example 325

(R)-2-amino-2-(6-(cis-4-(1,1-difluoropropyl)cyclohexyloxy)naphthalen-2-yl)propan-1-ol The preparation of the title compound was performed analogously to (R)-2-amino-2-(6-(trans-4-(1,1-difluoroethyl)cyclohexyloxy)naphthalen-2-yl)propan-1-ol (Example 299).

40 mg, pale yellow solid, yield: 78% EDI-MS (M-NH$_2$): 361.0. HPLC: 94.88%. $^1$H NMR (400 MHz, CDCl$_3$) δ: 7.88 (s, 1H), 7.67-7.74 (m, 2H), 7.50-7.52 (m, 1H), 7.12-7.18 (m, 2H), 4.70-4.71 (m, 1H), 3.70-3.83 (AB, 2H), 2.20-2.24 (m, 2H), 1.69-1.97 (m, 9H), 1.25 (s, 3H), 1.03 (t, 3H).

Example 326

1-(trans-4-(benzyloxy)cyclohexyl)butan-1-one

The preparation of the title compound was performed analogously to 1-(cis-4-(benzyloxy)cyclohexyl)butan-1-one (Example 294).

600 mg, pale yellow oil, yield: 53%. EDI-MS (M+1): 261.0. $^1$H NMR (400 MHz, CDCl$_3$) δ: 7.27-7.34 (m, 5H), 4.56 (s, 2H), 3.30-3.36 (m, 1H), 2.42 (t, 2H), 2.30-2.36 (m, 1H), 2.15-2.18 (m, 2H), 1.91-1.94 (m, 2H), 1.54-1.63 (m, 2H), 1.31-1.39 (m, 4H), 0.90 (t, 3H).

Example 327

((trans-4-(1,1-difluorobutyl)cyclohexyloxy)methyl) benzene

The preparation of the title compound was performed analogously to ((cis-4-(1,1-difluoroethyl)cyclohexyloxy) methyl)benzene (Example 295).

2.7 g, slight yellow oil, yield: 77%. NMR (400 MHz, CDCl$_3$) δ: 7.27-7.35 (m, 5H), 4.56 (s, 2H), 3.27-3.33 (m, 1H), 2.17-2.19 (m, 2H), 1.84-1.86 (m, 2H), 1.63-1.81 (m, 3H), 1.42-1.55 (m, 2H), 1.20-1.26 (m, 4H), 0.90 (t, 3H).

Example 328 trans-4-(1,1-difluorobutyl)cyclohexanol

The preparation of the title compound was performed analogously to cis-4-(1,1-difluoroethyl)cyclohexanol (Example 296).

0.26 g, slight yellow oil, yield: 58%. $^1$H NMR (400 MHz, CDCl$_3$) δ: 3.56-3.61 (m, 1H), 2.04-2.07 (m, 2H), 1.87-1.90 (m, 2H), 1.70-1.79 (m, 3H), 1.50-1.55 (m, 2H), 1.23-1.31 (m, 4H), 0.96 (t, 3H).

Example 329 trans-4-(1,1-difluorobutyl)cyclohexyl methanesulfonate

The preparation of the title compound was performed analogously to cis-4-(1,1-difluoroethyl)cyclohexyl methanesulfonate (Example 297).

113 mg, slight yellow oil, yield: 90%. $^1$H NMR (400 MHz, CDCl$_3$) δ: 4.56-4.63 (m, 1H), 3.02 (s, 3H), 2.23-2.26 (m, 2H), 1.94-1.98 (m, 2H), 1.64-1.81 (m, 3H), 1.45-1.58 (m, 2H), 1.27-1.42 (m, 4H), 0.96 (t, 3H).

Example 330

(R)-4-(6-(cis-4-(1,1-difluorobutyl)cyclohexyloxy) naphthalen-2-yl)-4-methyloxazolidin-2-one The preparation of the title compound was performed analogously to (R)-4-(6-(trans-4-(1,1-difluoroethyl)cyclohexyloxy)naphthalen-2-yl)-4-methyloxazolidin-2-one (Example 298).

60 mg, pale yellow solid, yield: 35%. EDI-MS (M+1): 418.1. $^1$H NMR (400 MHz, CDCl$_3$) δ: 7.75 (d, 3H), 7.42-7.44 (m, 1H), 7.21-7.24 (m, 1H), 7.15-7.16 (m, 1H), 5.49 (s, 1H), 4.72-4.73 (m, 1H), 4.40-4.41 (m, 2H), 2.21-2.24 (m, 2H), 1.63-1.78 (m, 8H), 1.51-1.57 (m, 6H), 0.98 (t, 3H).

Example 331

(R)-2-amino-2-(6-(cis-4-(1,1-difluorobutyl)cyclohexyloxy)naphthalen-2-yl)propan-1-ol The preparation of the title compound was performed analogously to (R)-2-amino-2-(6-(trans-4-(1,1-difluoroethyl)cyclohexyloxy)naphthalen-2-yl)propan-1-ol (Example 299).

25 mg, pale yellow solid, yield: 70%. EDI-MS (M-NH$_2$): 375.0. HPLC: 93.20%. $^1$H NMR (400 MHz, CDCl$_3$) δ: 7.81 (s, 1H), 7.68-7.75 (m, 2H), 7.48-7.50 (m, 1H), 7.15-7.20 (m, 2H), 4.70-4.71 (m, 1H), 3.66-3.71 (AB, 2H), 2.14-2.24 (m, 4H), 1.52-1.85 (m, 9H), 1.25 (s, 3H), 0.98 (t, 3H).

Example 332

(R)-4-(6-(trans-4-(1,1-difluoroethyl)cyclohexyloxy)-5-iodonaphthalen-2-yl)-4-methyloxazolidin-2-one (R)-4-(6-(trans-4-(1,1-difluoroethyl)cyclohexyloxy) naphthalen-2-yl)-4-methyloxazolidin-2-one (865 mg, 2.22 mmol) and NIS (550 mg, 2.45 mmol, 1.1 eq.) were dissolved in CH₃CN (5 mL). Then CF₃COOH (76 mg, 0.67 mmol, 0.3 eq.) was added to the mixture dropwise at 0° C. The mixture was warmed to 15° C. and stirred for another 1 h. Then the mixture was extracted with EtOAc and the organic layer was concentrated and purified by silica gel chromatography using PE/EA (1/1) as eluent to give the title compound as a slight red solid (1.02 g, 90%). EDI-MS (M+1): 515.8. $^1$H NMR (400 MHz, CDCl₃) δ 8.16 (d, 1H), 7.73 (d, 2H), 7.48 (dd, 1H), 7.18 (d, 1H), 6.49 (s, 1H), 4.45-4.40 (m, 2H), 4.33-4.30 (m, 1H), 2.27-2.25 (m, 2H), 2.03-2.01 (m, 2H), 1.84 (s, 3H), 1.65-1.24 (m, 8H).

Example 333

(R)-4-(6-(trans-4-(1,1-difluoroethyl)cyclohexyloxy)-5-(trifluoromethyl)naphthalen-2-yl)-4-methyloxazolidin-2-one (R)-4-(6-(trans-4-(1,1-difluoroethyl)cyclohexyloxy)-5-iodonaphthalen-2-yl)-4-methyloxazolidin-2-one (1.439 g, 2.8 mmol), CuI (1.33 g, 6.99 mmol, 2.5 eq.), and DIPEA (2.6 mL, 28 mmol, 10.0 eq.) were dissolved in DMF (5 mL) under nitrogen atmosphere. Then FSO₂CF₂CO₂CH₃ (3.5 mL, 28 mmol, 10.0 eq.) was added to the mixture dropwise. The mixture was heated to 80° C. and stirred for 15 h. water was added and the mixture was extracted by EtOAc. The organic layer was concentrated and purified by silica gel chromatography using PE/EA (1/1) to give the title compound. (1.08 g, 85%) as a slight yellow solid. EDI-MS (M+1): 458.0. $^1$H NMR (400 MHz, CDCl₃) δ 8.22 (d, 1H), 7.91 (d, 1H), 7.79 (s, 1H), 7.52 (dd, 1H), 7.31 (d, 1H), 6.31 (s, 1H), 4.46-4.40 (m, 2H), 4.35-4.33 (m, 1H), 2.24-2.22 (m, 2H), 2.05-1.99 (m, 2H), 1.85 (s, 3H), 1.62-1.26 (m, 8H).

Example 334

(R)-2-amino-2-(6-(trans-4-(1,1-difluoroethyl)cyclohexyloxy)-5-(trifluoromethyl)naphthalen-2-yl)propan-1-ol (R)-4-(6-(trans-4-(1,1-difluoroethyl)cyclohexyloxy)-5-(trifluoromethyl)naphthalen-2-yl)-4-methyloxazolidin-2-one (530 mg, 1.16 mmol) was dissolved in EtOH (5 mL). Then LiOH (835 mg, 34.8 mmol, 30.0 eq.) in 2 mL water was added to the mixture. The mixture was heated to 80° C. and stirred for 15 h. Solvent was removed. DCM was added and filtrated. The filtrate was concentrated and purified by silica gel chromatography using DCM/methanol (10/1) to give the title compound (200 mg, 40%) as a slight yellow solid. EDI-MS (M-NH₂): 415.2. HPLC: 99.36%. $^1$H NMR (400 MHz, CD₃OD) δ 8.13 (t, 1H), 8.02 (d, 1H), 7.86 (s, 1H), 7.58 (dd, 1H), 7.48 (d, 1H), 4.45-4.41 (m, 1H), 3.85-3.72 (m, 2H), 2.14-2012 (m, 2H), 1.89-1.86 (m, 2H), 1.74-1.68 (m, 4H), 1.51-1.32 (m, 7H).

Example 335

(R)-4-(6-(trans-4-(1,1-difluoropropyl)cyclohexyloxy)-5-iodonaphthalen-2-yl)-4-methyloxazolidin-2-one The preparation of the title compound was performed analogously to (R)-4-(6-(trans-4-(1,1-difluoroethyl)cyclohexyloxy)-5-iodonaphthalen-2-yl)-4-methyloxazolidin-2-one (Example 332). EDI-MS (M+1): 529.8. $^1$H NMR (400 MHz, CDCl₃) δ 8.17 (d, 1H), 7.76-7.23 (m, 2H), 7.49 (dd, 1H), 7.19 (d, 1H), 6.22 (s, 1H), 4.45-4.39 (m, 2H), 4.36-4.31 (m, 1H), 2.28-2.26 (m, 2H), 2.00-1.96 (m, 2H), 1.86-1.82 (m, 6H), 1.66-1.62 (m, 2H), 1.41-1.36 (m, 2H), 1.03 (t, 3H).

Example 336

(R)-4-(6-(trans-4-(1,1-difluoropropyl)cyclohexyloxy)-5-(trifluoromethyl)naphthalen-2-yl)-4-methyloxazolidin-2-one The preparation of the title compound was performed analogously to (R)-4-(6-(trans-4-(1,1-difluoroethyl)cyclohexyloxy)-5-(trifluoromethyl)naphthalen-2-yl)-4-methyloxazolidin-2-one (Example 333).

Slight yellow solid (430 mg, 60%). EDI-MS (M+1): 472.0. $^1$H NMR (400 MHz, CDCl₃) δ 8.23 (d, 1H), 7.91 (d, 1H), 7.79 (s, 1H), 7.52 (dd, 1H), 7.31 (d, 1H), 6.41 (s, 1H), 4.46-4.40 (m, 2H), 4.36-4.33 (m, 1H), 2.24-2.21 (m, 2H), 2.00-1.96 (m, 2H), 1.86-1.80 (m, 6H), 1.58-1.55 (m, 2H), 1.41-1.36 (m, 2H), 1.02 (t, 3H).

Example 337

(R)-2-amino-2-(6-(trans-4-(1,1-difluoropropyl)cyclohexyloxy)-5-(trifluoromethyl)naphthalen-2-yl)propan-1-ol The preparation of the title compound was performed analogously to (R)-2-amino-2-(6-(trans-4-(1,1-difluoroethyl)cyclohexyloxy)-5-(trifluoromethyl)naphthalen-2-yl)propan-1-ol (Example 334).

Slight yellow solid (240 mg, 54%). EDI-MS (M-NH₂): 429.0. HPLC: 93.73%. $^1$H NMR (400 MHz, CD₃OD) δ 8.31 (d, 1H), 8.20 (d, 8.04 (s, 1H), 7.75 (d, 1H), 7.67 (d, 1H), 4.61-4.64 (m, 1H), 4.03-3.90 (m, 2H), 2.34-2.31 (m, 2H), 2.07-2.04 (m, 2H), 2.02-1.89 (m, 3H), 1.86 (s, 3H), 1.68-1.52 (m, 4H), 1.01 (t, 3H).

Example 338

(R)-4-(6-(cis-4-tert-butylcyclohexyloxy)naphthalen-2-yl)-4-methyloxazolidin-2-one (R)-4-(6-Hydroxy-naphthalen-2-yl)-4-methyl-oxazolidin-2-one (0.0575 g, 0.000236 mol) was dissolved in tetrahydrofuran (3.00 mL, 0.0370 mol) in a capped 40 mL reaction vial equipped with a magnetic stir bar. trans 4-tert-Butyl-cyclohexanol (0.0443 g, 0.000284 mol) was added, followed by triphenylphosphine (0.0992 g, 0.000378 mol) and the mixture was heated to reflux. diisopropyl azodicarboxylate (0.0745 mL, 0.000378 mol) was then added and the reaction mixture was heated at reflux overnight. TLC analysis showed that the reaction was complete. The stir bar was removed and the mixture was concentrated via Genevac. The resulting product was purified by flash chromatography (20-30% EtOAc in methylene chloride) to give 0.0446 g of the title compound (49% yield).

Example 339

(R)-2-amino-2-(6-(cis-4-tert-butylcyclohexyloxy)naphthalen-2-yl)propan-1-ol (R)-4-[6-(cis-4-tert-Butyl-cyclohexyloxy)-naphthalen-2-yl]-4-methyl-oxazolidin-2-one (0.0446 g, 0.000117 mol) was dissolved in ethanol in a capped 40 mL reaction vial equipped with a magnetic stir bar. 4.2 M lithium hydroxide, monohydrate in water (1.00 mL) was added and the mixture was refluxed overnight. TLC analysis showed that the reaction was complete. The solvent was removed via Genevac. The product was diluted in methylene chloride (5 ml) and water was added. The organic phase was then concentrated to dryness via Genevac, and purified by HPLC to give 0.0046 g of the title compound as a TFA salt (11% yield). MS: m/z=339.54 [M-NH$_2$]$^+$ $^1$H NMR (400 MHz, MeOD) Shift 0.91 (s, 9 H), 1.12-1.21 (m, 1 H), 1.54-1.66 (m, 6 H), 1.77-1.79 (m, 3 H), 2.15-2.21 (m, 2 H), 3.82 (d, J=11.55 Hz, 1 H), 3.93 (d, J=11.55 Hz, 1 H), 4.74-4.77 (m, 1 H), 7.23 (dd, J=9.04, 2.51 Hz, 1 H), 7.26 (d, J=2.26 Hz, 1 H), 7.51 (dd, J=8.78, 2.01 Hz, 1 H), 7.81-7.86 (m, 3 H)

Example 340

Further Compounds of Formula (I)

Additional compounds of formula (I) are prepared analogously to those described above. Such compounds include but are not limited to:
(R)-2-amino-2-{6-[trans-4-(1,1-dimethyl-propyl)-cyclohexyloxy]naphthalen-2-yl}-propan-1-ol;
(R)-2-amino-2-(6-(trans-4-tert-butylcyclohexyloxy)-5-methoxynaphthalen-2-yl)propan-1-ol;
(R)-2-amino-2-(6-(trans-4-tert-butylcyclohexyloxy)-5-fluoronaphthalen-2-yl)propan-1-ol;
(R)-2-amino-2-(6-(trans-4-butyl-cyclohexyloxy)-5-trifluoromethylnaphthalen-2-yl)propan-1-ol;
(R)-2-amino-2-(6-(trans-4-butyl-cyclohexyloxy)naphthalen-2-yl)propan-1-ol;
(R)-2-amino-2-(6-(trans-4-trifluoromethylcyclohexyloxy)-5-fluoronaphthalen-2-yl)propan-1-ol;
(R)-2-amino-2-(6-(trans-4-trifluoromethylcyclohexyloxy)-5-trifluoromethylnaphthalen-2-yl)propan-1-ol;
(R)-2-amino-2-(6-((1R,2R,4S)-bicyclo[2.2.1]heptan-2-yloxy)naphthalen-2-yl)propan-1-ol;
(2R)-2-amino-2-(6-(spiro[5.5]undecan-3-yloxy)naphthalen-2-yl)propan-1-ol;
(2R)-2-amino-2-(6-(spiro[5.5]undecan-3-yloxy)-5-(trifluoromethyl)naphthalen-2-yl)propan-1-ol;
(R)-2-amino-2-(6-(bicyclo[2.2.2]oct-2-yloxy)naphthalen-2-yl)propan-1-ol;
(R)-2-amino-2-(6-(bicyclo[2.2.2]oct-1-yloxy)naphthalen-2-yl)propan-1-ol;
(R)-2-amino-2-(6-(decalin-2-yloxy)naphthalen-2-yl)propan-1-ol;
(R)-2-amino-2-(6-(decalin-1-yloxy)naphthalen-2-yl)propan-1-ol;
(R)-2-amino-2-(6-(adamant-2-yloxy)naphthalen-2-yl)propan-1-ol;
(R)-2-amino-2-(6-(adamant-2-yloxy)-5-trifluoromethylnaphthalen-2-yl)propan-1-ol;
(R)-2-amino-2-(6-(adamant-2-yloxy)-5-methoxynaphthalen-2-yl)propan-1-ol; and
(R)-2-amino-2-(6-(adamant-2-yloxy)-5-fluoronaphthalen-2-yl)propan-1-ol.

Example 341

Sphingosine Kinase Assay

To assay a test compound for its properties as a substrate of sphingosine kinase 2 (SK2), an assay using recombinantly expressed SK2 was used. Briefly, HEK293E cells were transiently transfected with plasmids containing DNA encoding a sphingosine kinase 2 (SK2) (canine, mouse, or human). The cells were cultured in Dulbecco's Minimal Essential Medium (DMEM) containing 0.25 mg/mL G418, 10% fetal calf serum (FCS), and 10 mL/L amphotericin/streptomycin for 48 hours, then harvested, washed three times in phosphate buffered saline (PBS) and lysed by incubation in lysis buffer (20 mM Tris pH 7.4, 20% glycerol, 1 mM $\beta$-mercaptoethanol, 1 mM EDTA, 1 mM Na orthovanadate, 40 mM $\beta$-glycerophosphate, 15 mM NaF, 10 mg/mL, leupeptin, 10 mg/mL soybean trypsin inhibitor, 1 mM PMSF, 0.5 mM 4-deoxyperidoxone, 200 mM KCl, 10 mM MgCl$_2$, for about 30 minutes on ice. The lysate was centrifuged at 15,000 rpm for 18 minutes and the cell debris was discarded. The soluble fraction was used in the sphingosine kinase reaction. Examples of SPHK2 concentrations in the resulting lysates were 8.12 µg/µL (in a canine SPHK2 preparation) and 8.47 µg/µL (in a human SPHK2 preparation).

Figure 7:
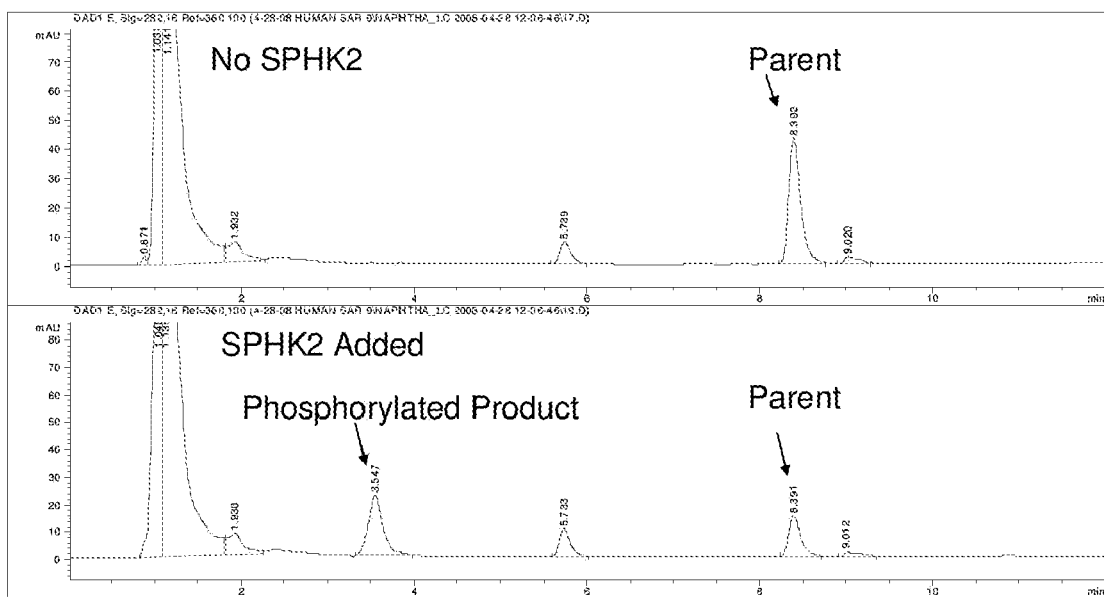
FIGS. 7-11 are graphs depicting the results of various assays on compounds of formula (I).

The SK2 kinase assay was performed in a 200 µL reaction mixture containing 20 µm sphingosine (control) or 20 µM test compound (prepared as a 200 µM stock solution containing 0.1% fatty acid-free bovine serum albumin (BSA)), 38 µL lysate, and 2 µM ATP (freshly prepared). Kinase reactions were incubated at 37° C. for 70 minutes followed by detection of phosphorylated compound (control or test compound) using UV absorbance at 282 nm. To further analyze the test compound from this reaction, test compound kinase reactions were mixed with an equal volume of acidic acetonitrile and shaken for 10 minutes. The protein precipitate was spun down. The supernatant was analyzed on HPLC using a C18 column (FIG. 7). The parent and phosphorylated test compound were quantitated using area under the curve (AUC) calculation. FIG. 7 illustrates HPLC traces of reactions of the compound of Example 21 with and without added SPHK2, which demonstrated that the compound is phosphorylated under these conditions. Test compounds that are phosphorylated in this assay are candidate compounds for use as S1P modulators.

Example 342

Lymphopenia Assay

Measurement of circulating lymphocytes: Compounds were dissolved in 30% HPCD. Mice (C57bl/6 male, 6-10 week-old) were administered 0.5 and 5 mg/kg of a compound via oral gavage. 30% HPCD was included as a negative control.

Blood was collected from the retro-orbital sinus 5 and 24 hours after drug administration under short isoflurane anesthesia. Whole blood samples were subjected to hematology analysis. Peripheral lymphocyte counts were determined using an automated analyzer (HEMAVET™ 3700). Three mice were used to assess the lymphocyte depletion activity of each compound screened.

Compounds of formula (I) induced full lymphopenia at times as short as 3 hours or less to as long as 48 hours or more; for example, 4 to 36 hours, or 5 to 24 hours. In some cases, a compound of formula induced full lymphopenia at 5 hours and partial lymphopenia at 24 hours. The dosage required to induce lymphopenia can be in the range of, e.g., 0.001 mg/kg to 100 mg/kg; or 0.01 mg/kg to 10 mg/kg. The dosage can be 10 mg/kg or less, such as 5 mg/kg or less, 1 mg/kg or less, or 0.1 mg/kg or less

| Example # | Lymphopenia (ED$_{50}$ mg/kg) |
|---|---|
| 6 | 0.75 mg/kg |
| 7 | <0.5 mg/kg |
| 8 | <0.5 mg/kg |
| 14 | >5 mg/kg |
| 17 | 0.07 mg/kg |
| 25 | >5 mg/kg |
| 30 | 0.5-5 mg/kg |
| 47 | >5 mg/kg |
| 49 | 0.4 mg/kg |
| 65 | <0.5 mg/kg |
| 66 | <0.5 mg/kg |
| 73 | <0.5 mg/kg |
| 74 | <0.5 mg/kg |
| 76 | 0.5-5 mg/kg |
| 77 | <0.5 mg/kg |
| 78 | 0.5-5 mg/kg |
| 79 | >5 mg/kg |
| 82 | <0.5 mg/kg |
| 87 | 0.5-5 mg/kg |
| 89 | 0.5-5 mg/kg |
| 91 | 0.5-5 mg/kg |
| 94 | 0.5-5 mg/kg |
| 97 | 0.5-5 mg/kg |
| 100 | >5 mg/kg |
| 103 | >5 mg/kg |
| 105 | >5 mg/kg |
| 112 | 0.5-5 mg/kg |
| 124 | >5 mg/kg |
| 128 | 0.5-5 mg/kg |
| 130 | >5 mg/kg |
| 131 | <0.5 mg/kg |
| 133 | 0.5-5 mg/kg |
| 139 | <0.5 mg/kg |
| 146 | 0.5-5 mg/kg |
| 151 | 0.5-5 mg/kg |
| 153 | <0.5 mg/kg |
| 155 | <0.5 mg/kg |
| 160 | >5 mg/kg |
| 163 | <0.5 mg/kg |
| 167 | <0.5 mg/kg |
| 168 | <0.5 mg/kg |
| 172 | 0.5-5 mg/kg |
| 173 | 0.5-5 mg/kg |
| 174 | >5 mg/kg |
| 175 | 0.5-5 mg/kg |
| 176 | 0.5-5 mg/kg |
| 177 | >5 mg/kg |
| 178 | <0.5 mg/kg |
| 179 | 0.5-5 mg/kg |
| 180 | 0.5-5 mg/kg |
| 181 | >5 mg/kg |
| 182 | 0.5-5 mg/kg |
| 183 | 0.5-5 mg/kg |
| 184 | >5 mg/kg |
| 185 | 0.5-5 mg/kg |
| 186 | 0.5-5 mg/kg |
| 187 | 0.5-5 mg/kg |
| 189 | <0.5 mg/kg |
| 191 | >5 mg/kg |
| 192 | <0.5 mg/kg |
| 194 | <0.5 mg/kg |
| 196 | <0.5 mg/kg |
| 197 | <0.5 mg/kg |
| 198 | 0.5-5 mg/kg |
| 199 | <0.5 mg/kg |
| 200 | <0.5 mg/kg |
| 211 | 0.5-5 mg/kg |
| 215 | <0.5 mg/kg |
| 217 | <0.5 mg/kg |
| 219 | <0.5 mg/kg |
| 221 | >5 mg/kg |
| 223 | >5 mg/kg |
| 225 | >5 mg/kg |
| 227 | 0.5-5 mg/kg |
| 229 | >5 mg/kg |
| 231 | >5 mg/kg |
| 233 | >5 mg/kg |
| 236 | <0.5 mg/kg |
| 237 | <0.5 mg/kg |
| 238 | <0.5 mg/kg |
| 240 | >5 mg/kg |
| 242 | <0.5 mg/kg |
| 245 | <0.5 mg/kg |
| 248 | <0.5 mg/kg |
| 251 | <0.5 mg/kg |
| 259 | 0.5-5 mg/kg |
| 260 | 0.5-5 mg/kg |
| 266 | <0.5 mg/kg |
| 272 | <0.5 mg/kg |
| 275 | >5 mg/kg |
| 276 | <0.5 mg/kg |
| 299 | <0.5 mg/kg |
| 305 | <0.5 mg/kg |
| 311 | <0.5 mg/kg |
| 319 | >5 mg/kg |
| 325 | >5 mg/kg |
| 331 | >5 mg/kg |
| 334 | <0.5 mg/kg |
| 337 | <0.5 mg/kg |

These results demonstrated compounds of the invention can induce lymphopenia.

Example 343

Calcium Mobilization

Compounds that were not specific for the S1P, receptor, can have activity for other S1P receptor subtypes, e.g., $S1P_2$, $S1P_3$, $S1P_4$, or $S1P_5$, and can cause undesirable side effects. Accordingly, compounds were tested to identify those that were specific for $S1P_1$ activity and had little or no activity, or are antagonists of, $S1P_3$ activity. Accordingly, the test compounds were tested in a calcium mobilization assay to determine agonist activity at either the human $S1P_1$ or human $S1P_3$ receptor, and antagonist activity only at the human $S1P_3$ receptor. The procedure was essentially as described (with modifications described below) in Davis et al. (2005) *Journal of Biological Chemistry*, vol. 280, pp. 9833-9841, which is incorporated by reference in its entirety. Calcium mobilization assays were performed in recombinant CHEM cells expressing human $S1P_1$ or $S1P_3$ purchased from Millipore (Billerica, Mass.). To detect free intracellular calcium, $S1P_1$ or $S1P_3$ cells were loaded with FLIPR Calcium 4 dye from Molecular Devices (Sunnyvale, Calif.). Cells were imagined for calcium mobilization using a FLIPR$^{TETRA}$ equipped with a 96-well dispense head.

Figure 8:
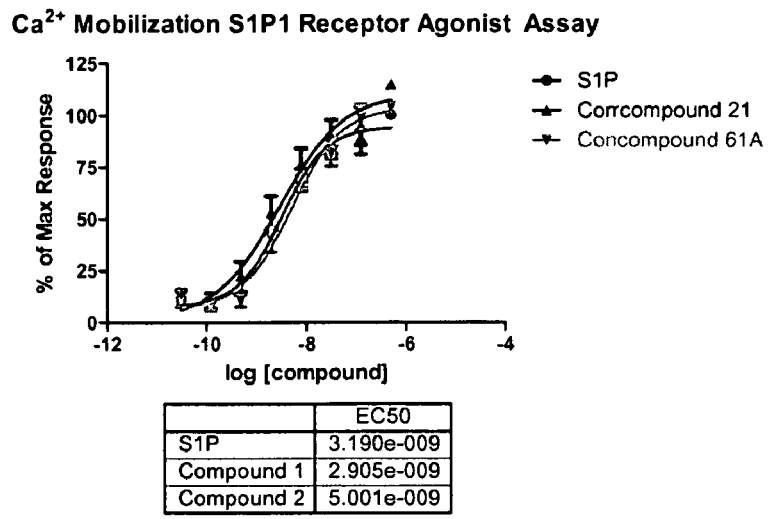
Figure 9:
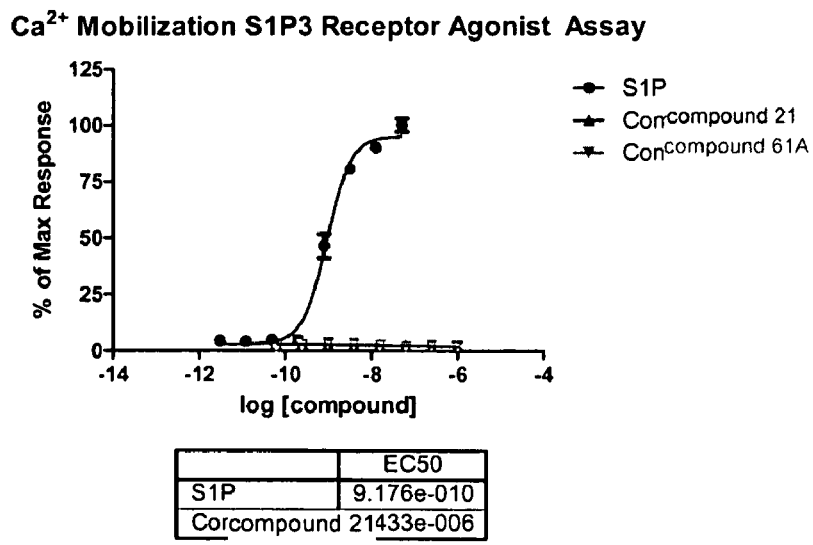
Figure 10:
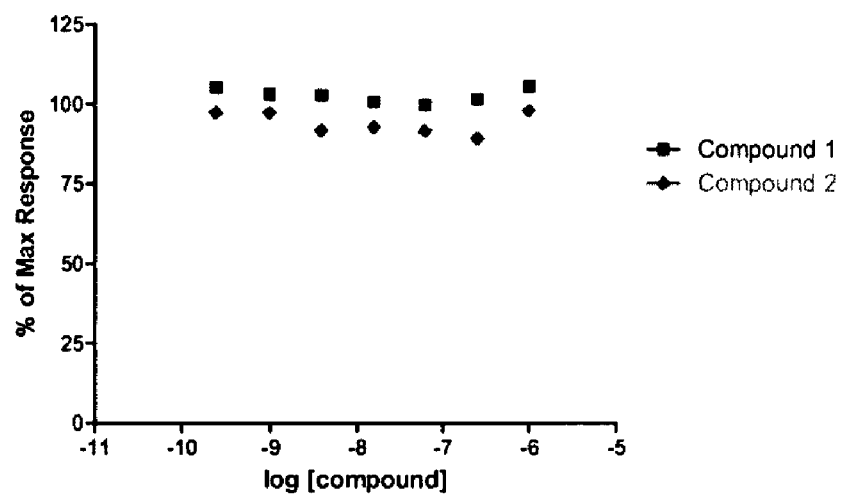
Figure 11:
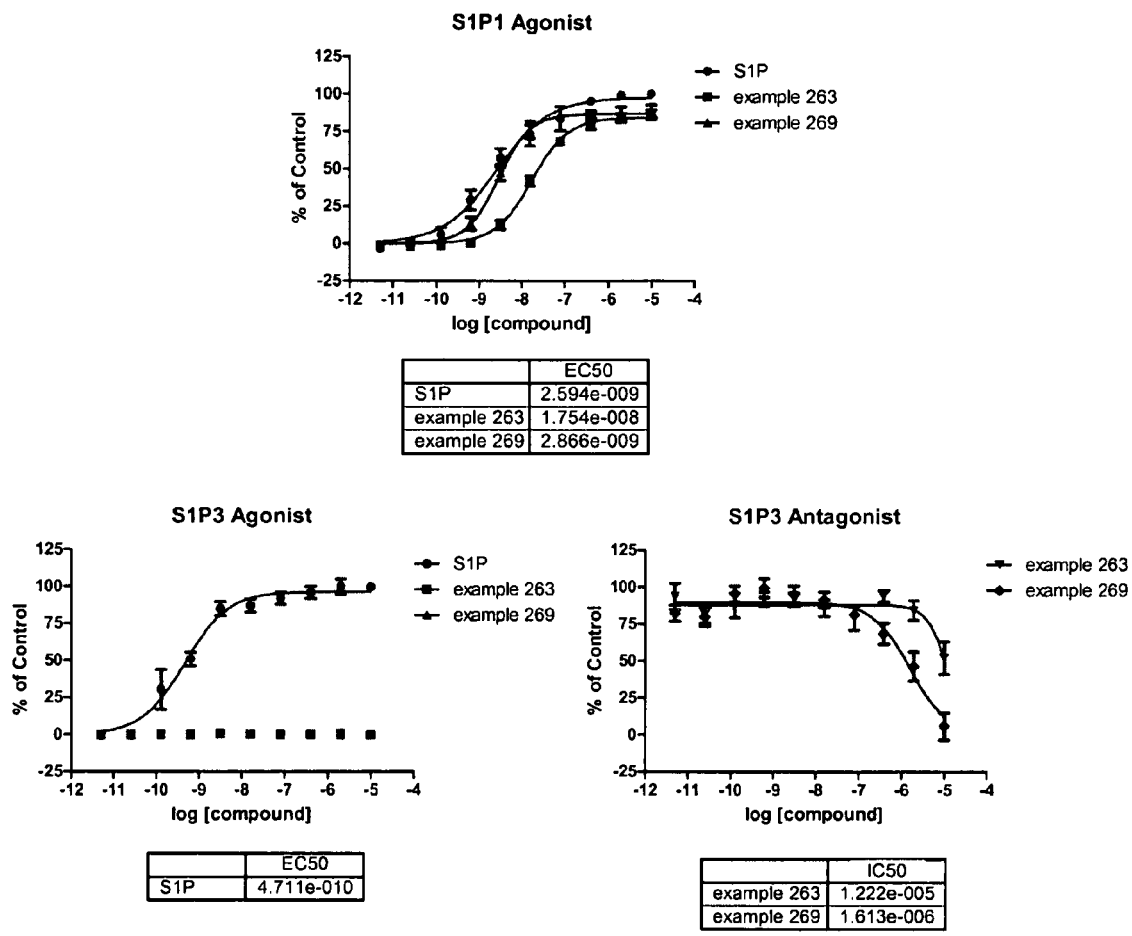

The data of FIG. 8 show that compounds 21 and 61A are agonists of the S1P, receptor, with potencies similar to S1P. The data of FIG. 9 show that compound 21 has weak micromolar partial $S1P_3$ agonist activity, whereas no activity was seen for compound 2. S1P was a full $S1P_3$ agonist in this assay. The data of FIG. 10 show that compounds 21 and 61A do not antagonize the $S1P_3$ receptor. The data of FIG. 11 show that compounds 263 and 269 were S1P, agonists, were not $S1P_3$ agonists, but instead were $S1P_3$ antagonists.

Example 344

In Vivo Blood Lymphocyte Depletion

Compounds useful for treating $S1P_1$-related diseases, such as certain autoimmune diseases, are generally able to sustain lymphopenia, e.g., for at least one day, at least two days, at least three days, or at least one week, or longer. To further characterize the activity of a test compound, a test compound of formula I or the vehicle was administered orally by gavage to rats. Tail blood for hematological monitoring was obtained on day-1 to give the is baseline individual values, and at 2, 6, 24, 48 and 72 hours after drug application.

Example 345

In Vivo Screening Assays

Measurement of circulating lymphocytes: Compounds were dissolved in DMSO and further diluted with deionized water. Mice (C57bl/6 male, 6-10 week-old) were administered 20 µg of a compound (diluted in 200 µL water, 4% DMSO) via intra-peritoneal (IP) injection under short isoflurane anesthesia. 200 µL water, 4% DMSO, and a known S1P agonist were included as negative controls.

Blood was collected from the retro-orbital sinus 18 hours after drug administration under short isoflurane anesthesia. Whole blood samples were subjected to hematology analysis. Peripheral lymphocyte counts were determined using an automated analyzer (HEMAVET™ 3700). Subpopulations of peripheral blood lymphocytes were stained by fluorochrome-conjugated specific antibodies and analyzed using a fluorescent activating cell sorter (FACSCALIBUR™). Two mice were used to assess the lymphocyte depletion activity of each compound screened. This assay indicated that compounds of the invention can suppress the level of circulating lymphocytes.

Example 346

Assessment of Heart Effect

One reported undesirable effect of an S1P agonist can be, e.g., bradycardia. Assays were conducted to determine the effect of test compounds on heart function. The effects of compounds on cardiac function were monitored using the AnonyMOUSE ECG recording system. ECGs were recorded in conscious mice (C57bl/6 male, 6-10 week-old) before and after compound administration. 90 µg of compound further diluted in 200 µL water and 15% DMSO were injected IP. Four mice were used to assess heart rate effect of each compound. Compounds were found to have little or no effect on heart rate at therapeutic levels.

The abbreviations used herein have their conventional meaning within the clinical, chemical, and biological arts. In the case of any inconsistencies, the present disclosure, including any definitions therein will prevail.

The disclosures of each and every patent, patent application, and publication cited herein are expressly incorporated herein by reference in their entirety into this disclosure. Illustrative embodiments of this disclosure are discussed and reference has been made to possible variations within the scope of this disclosure. These and other variations and modifications in the disclosure will be apparent to those skilled in the art without departing from the scope of the disclosure, and it should be understood that this disclosure and the claims shown below are not limited to the illustrative embodiments set forth herein.

What is claimed is:
1. A compound of formula (I):

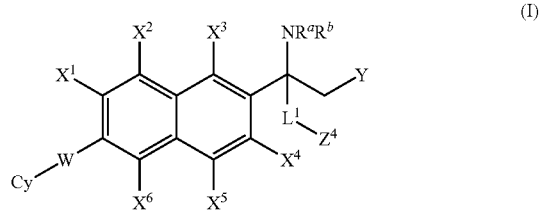

wherein:
$X^1$ is hydrogen, halo, hydroxy, nitro, cyano, alkyl, haloalkyl, cycloalkyl, halocycloalkyl, alkoxy, haloalkoxy, cycloalkoxy, halocycloalkoxy, acyl, aminoacyl, —NR$^f$R$^g$, —N(R$^f$)SO$_2$R$^g$, —SO$_2$R$^f$, —SO$_2$NR$^f$R$^g$, —CO$_2$R$^f$, trialkylamino, aryl, or heteroaryl;
$X^2$ is hydrogen, halo, hydroxy, nitro, cyano, alkyl, haloalkyl, cycloalkyl, halocycloalkyl, alkoxy, haloalkoxy, cycloalkoxy, halocycloalkoxy, acyl, aminoacyl, —NR$^f$R$^g$, —N(R$^f$)SO$_2$R$^g$, —SO$_2$R$^f$, —SO$_2$NR$^f$R$^g$, —CO$_2$R$^f$, trialkylamino, aryl, or heteroaryl;
$X^3$ is hydrogen, halo, hydroxy, nitro, cyano, alkyl, haloalkyl, cycloalkyl, halocycloalkyl, alkoxy, haloalkoxy, cycloalkoxy, halocycloalkoxy, acyl, aminoacyl, —NR$^f$R$^g$, —N(R$^f$)SO$_2$R$^g$, —SO$_2$R$^f$, —SO$_2$NR$^f$R$^g$, —CO$_2$R$^f$, trialkylamino, aryl, or heteroaryl;
$X^4$ is hydrogen, halo, hydroxy, nitro, cyano, alkyl, haloalkyl, cycloalkyl, halocycloalkyl, alkoxy, haloalkoxy, cycloalkoxy, halocycloalkoxy, acyl, aminoacyl, —NR$^f$R$^g$, —N(R$^f$)SO$_2$R$^g$, —SO$_2$R$^f$, —SO$_2$NR$^f$R$^g$, —CO$_2$R$^f$, trialkylamino, aryl, or heteroaryl;
$X^5$ is hydrogen, halo, hydroxy, nitro, cyano, alkyl, haloalkyl, cycloalkyl, halocycloalkyl, alkoxy, haloalkoxy, cycloalkoxy, halocycloalkoxy, acyl, aminoacyl, —NR$^f$R$^g$, —N(R$^f$)SO$_2$R$^g$, —SO$_2$R$^f$, —SO$_2$NR$^f$R$^g$, —CO$_2$R$^f$, trialkylamino, aryl, or heteroaryl;
$X^6$ is hydrogen, halo, hydroxy, nitro, cyano, alkyl, haloalkyl, cycloalkyl, halocycloalkyl, alkoxy, haloalkoxy, cycloalkoxy, halocycloalkoxy, acyl, aminoacyl, —NR$^f$R$^g$, —N(R$^f$)SO$_2$R$^g$, —SO$_2$R$^f$, —SO$_2$NR$^f$R$^g$, —CO$_2$R$^f$, trialkylamino, aryl, or heteroaryl;
Y is —OR$^f$, —(CR$^f$R$^g$)OR$^f$, —(CR$^f$R$^g$)$_2$OR$^f$, —O—P(O)(OR$^f$)OR$^g$, —OC(O)R$^c$, —C(O)OR$^c$, —(CR$^f$R$^g$)—P(O)(OR$^f$)OR$^g$, —(C(OH)R$^f$)—P(O)(OR$^f$)OR$^g$, —S—P(O)(OR$^f$)OR$^g$, tetrazole, —SO$_2$NHR$^f$, —SO$_3$, —CONHR$^f$, —Si(OH)$^2$, or —B(OH)$_2$;
W is —CR$^f$R$^g$—, —NR$^f$—, —O—, —S—, —SO—, or —SO$_2$—;
$L^1$ is —CH$_2$—, —CHF—, or —CF$_2$—;
$Z^4$ is hydrogen, halo, alkyl, haloalkyl, alkenyl, haloalkenyl, alkynyl, or —OR$^f$;
or $Z^4$ is —CH$_2$— bound to the carbon atom to which Y is bound,
or $L^1$, $Z^4$, Y, and the atoms to which they are bound form a 4-7 membered cycloalkyl group or a 4-7 membered heterocyclyl group having 1 or 2 heteroatoms selected from O and N;

R$^a$ is hydrogen, alkyl, haloalkyl, alkenyl, alkynyl, cycloalkyl, cycloalkenyl, aryl, heteroaryl, or heterocyclyl; wherein each of alkyl, cycloalkyl, cycloalkenyl, aryl, heteroaryl and heterocycle are optionally substituted with 1 to 5 substituents independently selected from the group consisting of halo, oxo, —CN, —CHO, —CF$_3$, —OH, —NO$_2$, alkyl, —OCF$_3$ alkoxy cycloalkoxy, cycloalkenoxy, amino, alkylamino, dialkylamino, acylamino, aminoacyl, alkylsulfonyl, alkylaminosulfonyl, and dialkylaminosulfonyl;

R$^b$ is hydrogen, alkyl, haloalkyl, alkenyl, alkynyl, cycloalkyl, cycloalkenyl, aryl, heteroaryl, or heterocyclyl; wherein each of alkyl, cycloalkyl, cycloalkenyl, aryl, heteroaryl and heterocycle are optionally substituted with 1 to 5 substituents independently selected from the group consisting of halo, oxo, —CN, —CHO, —CF$_3$, —OH, —NO$_2$, alkyl, —OCF$_3$, alkoxy, cycloalkoxy, cycloalkenoxy, amino, alkylamino, dialkylamino, acylamino, aminoacyl, alkylsulfonyl, alkylaminosulfonyl, and dialkylaminosulfonyl;

or R$^b$ and Z$^4$ are taken to together to form —C(O)O— or =C(R$^f$)O—;

R$^c$ is alkyl, aryl, trifluoromethyl, methylsulfonyl, trifluoromethylsulfonyl, p-tolylsulfonyl, or a group selected such that —OCOR$^c$ is a leaving group;

each R$^f$, independently, is hydrogen, alkyl, haloalkyl, alkenyl, alkynyl, cycloalkyl, cycloalkenyl, aryl, heteroaryl, or heterocyclyl; wherein each of alkyl, cycloalkyl, cycloalkenyl, aryl, heteroaryl and heterocycle are optionally substituted with 1 to 5 substituents independently selected from the group consisting of halo, oxo, —CN, —CHO, —CF$_3$, —OH, —NO$_2$, alkyl, —OCF$_3$, alkoxy, cycloalkoxy, cycloalkenoxy, amino, alkylamino, dialkylamino, acylamino, aminoacyl, alkylsulfonyl, alkylaminosulfonyl, and dialkylaminosulfonyl;

each R$^g$, independently, is hydrogen, alkyl, haloalkyl, alkenyl, alkynyl, cycloalkyl, cycloalkenyl, aryl, heteroaryl, or heterocyclyl; wherein each of alkyl, cycloalkyl, cycloalkenyl, aryl, heteroaryl and heterocycle are optionally substituted with 1 to 5 substituents independently selected from the group consisting of halo, oxo, —CN, —CHO, —CF$_3$, —OH, —NO$_2$, alkyl, —OCF$_3$, alkoxy, cycloalkoxy, cycloalkenoxy, amino, alkylamino, dialkylamino, acylamino, aminoacyl, alkylsulfonyl, alkylaminosulfonyl, and dialkylaminosulfonyl;

Cy has the formula:

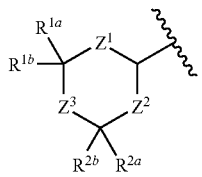

wherein
Z$^1$ is a bond, —[C(R$^d$R$^e$)]$_x$—, —CR$^d$=CR$^e$—, —O—, —NR$^f$—;
Z$^2$ is a bond, —[C(R$^d$R$^e$)]$_y$—, —CR$^d$=CR$^e$—, —O—, —NR$^f$—;
Z$^3$ is a bond, —[C(R$^d$R$^e$)]$_z$—, —CR$^d$=CR$^e$—, —O—, —NR$^f$—;
each of x, y, and z, independently, is 1 to 3;
each R$^d$, independently, is H, halo, hydroxy, alkyl, haloalkyl, alkenyl, alkoxy, cycloalkyl, —C(O)NR$^f$R$^g$, —NR$^f$R$^g$, —NR$^f$C(O)R$^g$, or —SO$_2$NR$^f$R$^g$;

each R$^e$, independently, is H, halo, hydroxy, alkyl, haloalkyl, alkenyl, alkoxy, or cycloalkyl, —C(O)NR$^f$R$^g$, —NR$^f$R$^g$, —NR$^f$C(O)R$^g$, or —SO$_2$NR$^f$R$^g$;

R$^{1a}$ and R$^{1b}$, independently, are hydrogen, halo, hydroxy, nitro, cyano, —NR$^f$R$^g$, alkyl, haloalkyl, cycloalkyl, cycloalkenyl, cycloalkylalkyl, cycloalkenylalkyl, heterocyclylalkyl, arylalkyl, heteroarylalkyl, alkoxy, cycloalkylalkoxy, cycloalkenylalkoxy, heterocyclylalkoxy, arylalkoxy, heteroarylalkoxy, acyl, cycloalkylacyl, cycloalkenylacyl, heterocyclylacyl, arylacyl, heteroarylacyl, thioalkyl, alkenyl, alkynyl, cycloalkenyl, heterocyclyl, aryl, or heteroaryl;

or R$^{1a}$ and R$^{1b}$, when taken together, are C$_2$-C$_5$ alkylene optionally interrupted by 1 or 2 oxygen atoms, or C$_2$-C$_5$ alkenylene optionally interrupted by 1 or 2 oxygen atoms;

R$^{2a}$ and R$^{2b}$, independently, are hydrogen, halo, hydroxy, nitro, cyano, —NR$^f$R$^g$, alkyl, haloalkyl, cycloalkyl, cycloalkenyl, cycloalkylalkyl, cycloalkenylalkyl, heterocyclylalkyl, arylalkyl, heteroarylalkyl, alkoxy, cycloalkylalkoxy, cycloalkenylalkoxy, heterocyclylalkoxy, arylalkoxy, heteroarylalkoxy, acyl, cycloalkylacyl, cycloalkenylacyl, heterocyclylacyl, arylacyl, heteroarylacyl, thioalkyl, alkenyl, alkynyl, cycloalkenyl, heterocyclyl, aryl, or heteroaryl;

or R$^{1a}$ and R$^{2a}$, when taken together, are C$_1$-C$_5$ alkylene optionally terminated-by interrupted by 1 or 2 oxygen atoms, or C$_2$-C$_5$ alkenylene optionally interrupted by 1 or 2 oxygen atoms;

wherein R$^{1a}$, R$^{1b}$, R$^{2a}$, R$^{2b}$ are each, independently, substituted with 0-5 substituents selected from halo, hydroxy, nitro, cyano, —NR$^f$R$^g$, or —CO$_2$R$^f$;

or a pharmaceutically acceptable salt or prodrug thereof.

2. The compound of claim 1, or a pharmaceutically acceptable salt or prodrug thereof, wherein R$^{1a}$ and R$^{2a}$ are both hydrogen.

3. The compound of claim 1, or a pharmaceutically acceptable salt or prodrug thereof, wherein Z$^1$ is —CH$_2$CH$_2$—.

4. The compound of claim 3, or a pharmaceutically acceptable salt or prodrug thereof, wherein Z$^2$ is —CH$_2$—.

5. The compound of claim 4, or a pharmaceutically acceptable salt or prodrug thereof, wherein Z$^3$ is a bond.

6. The compound of claim 2, or a pharmaceutically acceptable salt or prodrug thereof, wherein R$^{1b}$ is fluoro, chloro, bromo, iodo, methyl, difluoromethyl, triflurormethyl, ethyl, 1,1-difluoroethyl, propyl, isopropyl, n-butyl, i-butyl, t-butyl, n-pentyl, isopentyl, 1,1-dimethylpropyl, neopentyl, cyclopentyl, n-hexyl, cyclohexyl, methoxy, trifluoromethoxy, ethoxy, n-propoxy, i-propoxy, n-butoxy, i-butoxy, t-butoxy, n-pentyloxy, i -pentyloxy, 1,1-dimethylpropoxy, neopentyloxy, cyclopentyloxy, n-hexyloxy, or cyclohexyloxy.

7. A compound of formula (II):

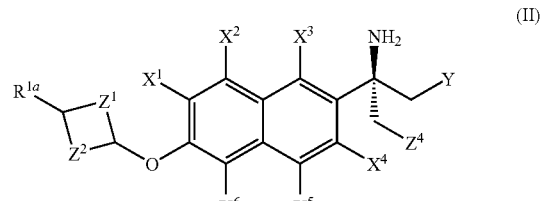

(II)

wherein
X$^1$ is hydrogen, halo, hydroxy, nitro, cyano, alkyl, haloalkyl, cycloalkyl, halocycloalkyl, alkoxy, haloalkoxy, cycloalkoxy, halocycloalkoxy, acyl, aminoacyl, —NR$^f$R$^g$, —N(R$^f$)SO$_2$R$^g$, —SO$_2$R$^f$, —SO$_2$NR$^f$R$^g$, —CO$_2$R$^f$, trialkylamino, aryl, or heteroaryl;

X$^2$ is hydrogen, halo, hydroxy, nitro, cyano, alkyl, haloalkyl, cycloalkyl, halocycloalkyl, alkoxy, haloalkoxy, cycloalkoxy, halocycloalkoxy, acyl, aminoacyl, —NR$^f$R$^g$, —N(R$^f$)SO$_2$R$^g$, —SO$_2$R$^f$, —SO$_2$NR$^f$R$^g$, —CO$_2$R$^f$, trialkylamino, aryl, or heteroaryl;

X$^3$ is hydrogen, halo, hydroxy, nitro, cyano, alkyl, haloalkyl, cycloalkyl, halocycloalkyl, alkoxy, haloalkoxy, cycloalkoxy, halocycloalkoxy, acyl, aminoacyl, —NR$^f$R$^g$, —N(R$^f$)SO$_2$R$^g$, —SO$_2$R$^f$, —SO$_2$NR$^f$R$^g$, —CO$_2$R$^f$, trialkylamino, aryl, or heteroaryl;

X$^4$ is hydrogen, halo, hydroxy, nitro, cyano, alkyl, haloalkyl, cycloalkyl, halocycloalkyl, alkoxy, haloalkoxy, cycloalkoxy, halocycloalkoxy, acyl, aminoacyl, —NR$^f$R$^g$, —N(R$^f$)SO$_2$R$^g$, —SO$_2$R$^f$, —SO$_2$NR$^f$R$^g$, —CO$_2$R$^f$, trialkylamino, aryl, or heteroaryl;

X$^5$ is hydrogen, halo, hydroxy, nitro, cyano, alkyl, haloalkyl, cycloalkyl, halocycloalkyl, alkoxy, haloalkoxy, cycloalkoxy, halocycloalkoxy, acyl, aminoacyl, —NR$^f$R$^g$, —N(R$^f$)SO$_2$R$^g$, —SO$_2$R$^f$, —SO$_2$NR$^f$R$^g$, —CO$_2$R$^f$, trialkylamino, aryl, or heteroaryl;

X$^6$ is hydrogen, halo, hydroxy, nitro, cyano, alkyl, haloalkyl, cycloalkyl, halocycloalkyl, alkoxy, haloalkoxy, cycloalkoxy, halocycloalkoxy, acyl, aminoacyl, —NR$^f$R$^g$, —N(R$^f$)SO$_2$R$^g$, —SO$_2$R$^f$, —SO$_2$NR$^f$R$^g$, —CO$_2$R$^f$, trialkylamino, aryl, or heteroaryl;

Y is —OR$^f$, —(CR$^f$R$^g$)OR$^f$, —(CR$^f$R$^g$)$_2$OR$^f$, —O—P(O)(OR$^f$)OR$^g$, —OC(O)R$^c$, —C(O)OR$^c$, —(CR$^f$R$^g$)—P(O)(OR$^f$)OR$^g$, —(C(OH)R$^f$)—P(O)(OR$^f$)OR$^g$, —S—P(O)(OR$^f$)OR$^g$, tetrazole, —SO$_2$NHR$^f$, —SO$_3$, —CONHR$^f$, —Si(OH)$_2$, or —B(OH)$_2$;

Z$^4$ is hydrogen, halo, alkyl, haloalkyl, alkenyl, haloalkenyl, alkynyl, or —OR$^f$;

or Z$^4$ is —CH$_2$— bound to the carbon atom to which Y is bound;

or Z$^4$, Y, and the atoms to which they are bound form a 4-7 membered cycloalkyl group or a 4-7 membered heterocyclyl group having 1 or 2 heteroatoms selected from O and N;

R$^c$ is alkyl, aryl, trifluoromethyl, methylsulfonyl, trifluoromethylsulfonyl, p-tolylsulfonyl, or a group selected such that —OCOR$^c$ is a leaving group;

each R$^f$, independently, is hydrogen, alkyl, haloalkyl, alkenyl, alkynyl, cycloalkyl, cycloalkenyl, aryl, heteroaryl, or heterocyclyl; wherein each of alkyl, cycloalkyl, cycloalkenyl, aryl, heteroaryl and heterocycle are optionally substituted with 1 to 5 substituents independently selected from the group consisting of halo, oxo, —CN, —CHO, —CF$_3$, —OH, —NO$_2$, alkyl, —OCF$_3$, alkoxy, cycloalkoxy, cycloalkenoxy, amino, alkylamino, dialkylamino, acylamino, aminoacyl, alkylsulfonyl, alkylaminosulfonyl, and dialkylaminosulfonyl;

each R$^g$, independently, is hydrogen, alkyl, haloalkyl, alkenyl, alkynyl, cycloalkyl, cycloalkenyl, aryl, heteroaryl, or heterocyclyl; wherein each of alkyl, cycloalkyl, cycloalkenyl, aryl, heteroaryl and heterocycle are optionally substituted with 1 to 5 substituents independently selected from the group consisting of halo, oxo, —CN, —CHO, —CF$_3$, —OH, —NO$_2$, alkyl, —OCF$_3$, alkoxy, cycloalkoxy, cycloalkenoxy, amino, alkylamino, dialkylamino, acylamino, aminoacyl, alkylsulfonyl, alkylaminosulfonyl, and dialkylaminosulfonyl;

R$^{1a}$ is hydrogen, halo, hydroxy, nitro, cyano, —NR$^f$R$^g$, alkyl, haloalkyl, cycloalkyl, cycloalkenyl, cycloalkylalkyl, cycloalkenylalkyl, heterocyclylalkyl, arylalkyl, heteroarylalkyl, alkoxy, cycloalkylalkoxy, cycloalkenylalkoxy, heterocyclylalkoxy, arylalkoxy, heteroarylalkoxy, acyl, cycloalkylacyl, cycloalkenylacyl, heterocyclylacyl, arylacyl, heteroarylacyl, thioalkyl, alkenyl, alkynyl, cycloalkenyl, heterocyclyl, aryl, or heteroaryl;

Z$^1$ is a bond, —[C(R$^d$R$^e$)]$_x$—, or —CR$^d$=CR$^e$—;
Z$^2$ is a bond, —[C(R$^d$R$^e$)]$_y$—, or —CR$^d$=CR$^e$—;
provided that Z$^1$ and Z$^2$ are not both simultaneously a bond;
each of x and y independently, is 1 to 3;
each R$^d$, independently, is hydrogen, halo, hydroxy, alkyl, alkenyl, alkoxy, or cycloalkyl;
each R$^e$, independently, is hydrogen, halo, hydroxy, alkyl, alkenyl, alkoxy, or cycloalkyl;
or a pharmaceutically acceptable salt or prodrug thereof.

8. The compound of claim 7, or a pharmaceutically acceptable salt or prodrug thereof, wherein Y is —OR$^f$.

9. The compound of claim 8, or a pharmaceutically acceptable salt or prodrug thereof, wherein Y is —OH or —O—P(O)(OR$^f$)OR$^g$.

10. The compound of claim 9, or a pharmaceutically acceptable salt or prodrug thereof, wherein X$^6$ is H, halo, alkyl, cycloalkyl, or haloalkyl.

11. The compound of claim 10, or a pharmaceutically acceptable salt or prodrug thereof, wherein Z$^1$ is —CH$_2$CH$_2$—.

12. The compound of claim 11, or a pharmaceutically acceptable salt or prodrug thereof, wherein Z$^2$ is —CH$_2$CH$_2$—.

13. The compound of claim 12, or a pharmaceutically acceptable salt or prodrug thereof, wherein R$^{1a}$ is hydrogen, halo, hydroxy, alkyl, haloalkyl, cycloalkyl, cycloalkylalkyl, arylalkyl, alkoxy, cycloalkylalkoxy, arylalkoxy, or aryl.

14. The compound of claim 7, or a pharmaceutically acceptable salt or prodrug thereof, wherein Y is —OH or —OP(O)(OH)$_2$; Z$^4$ is H or —OH; X$^1$, X$^2$, X$^3$, X$^4$, and X$^5$ are each H; and X$^6$ is H, halo, alkyl, cycloalkyl, or haloalkyl.

15. The compound of claim 7, or a pharmaceutically acceptable salt or prodrug thereof, wherein Z$^1$ is —(CH$_2$)$_x$— and Z$^2$ is —(CH$_2$)$_y$—.

16. The compound of claim 15, or a pharmaceutically acceptable salt or prodrug thereof, wherein R$^{1a}$ is alkyl, haloalkyl, cycloalkyl, aryl, or arylalkoxy.

17. The compound of claim 7, or a pharmaceutically acceptable salt or prodrug thereof, having the formula:

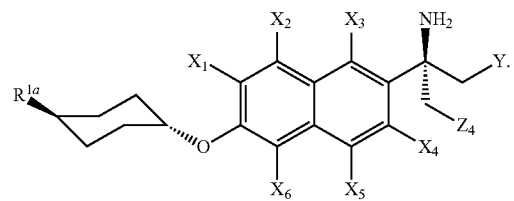

18. A compound selected from the group consisting of: (R)-2-amino-2-(6-(cis-4-butylcyclohexyloxy)naphthalen-2-yl)propan-1-ol; (R)-2-amino-2-(6-(4-butylcyclohexyloxy)naphthalen-2-yl)propan-1-ol; (R)-2-amino-2-(6-(trans-4-butylcyclohexyloxy)naphthalen-2-yl)propan-1-ol; 2-amino-2-(6-(cis-4-butylcyclohexyloxy)naphthalen-2-yl)propane-1,3- diol; (R)-2-amino-2-(6-(cis-4-butylcyclohexyloxy)-5-(trifluoromethyl)naphthalen-2-yl)propan-1-ol; (R)-2-amino-2-(6-(cis-4-butylcyclohexyloxy)-5-(trifluoromethyl) naphthalen-2-yl)propan-1-phosphoric acid; (R)-2-amino-2-(6-(cis-4-butylcyclohexyloxy)naphthalen-2-yl)propyl dihydrogen phosphate; (R)-2-amino-2-(6-(trans-4-butylcyclohexyloxy)naphthalen-2-yl)propyl dihydrogen phosphate; (R)-2-amino-2-(6-(trans-4-tert-butylcyclohexyloxy)naphthalen-2-yl)propan-1-ol; (R)-2-amino-2-(6-(trans-4-tert-butylcyclohexyloxy)naphthalen-2-yl)propyl dihydrogen phosphate; (R)-2-amino-2-(6-(cis-4-(4-(pentan-3-yloxy)phenyl) cyclohexyloxy)naphthalen-2-yl)propan-1-ol; (R)-2-amino -2-(6-(cis-4-(4-isopropoxyphenyl)cyclohexyloxy) naphthalen-2-yl)propan-1-ol; (R)-2-amino-2-(6-(cis-4-(4-methoxyphenyl)cyclohexyloxy)naphthalen-2-yl)propan-1-ol; (R)-2-amino-2-(6-(cis-4-phenylcyclohexyloxy) naphthalen-2-yl)propan-1-ol; (R)-2-amino-2-(6-(cis-4-phenylcyclohexyloxy)-5-(trifluoromethy)naphthalen-2-yl) propan-1-ol; (R)-2-amino-2-{6-[trans -4-(1,1-dimethyl-propyl)-cyclohexyloxy]-5-trifluoromethyl-naphthalen-2-yl}-propan-1-ol; (R)-2-amino-2-(6-(4-pentylcyclohexyloxy) naphthalen-2-yl)propan-1-ol; (R)-2-amino-2-(6-(4-propylcyclohexyloxy)naphthalen-2-yl)propan-1-ol; (R)-2-amino-2-(6-(cis-4-methylcyclohexyloxy)naphthalen-2-yl) propan-1-ol; (R)-2-amino-2-(6-(cis-4-ethylcyclohexyloxy) naphthalen-2-yl)propan-1-ol; (R)-2-amino-2-(6-(4-(trifluoromethyl)cyclohexyloxy)naphthalen-2-yl)propan-1-ol; (R)-2-amino-2-(6-(4,4-dimethylcyclohexyloxy) naphthalen-2-yl)propan-1-ol; (R)-2-amino-2-(6-(trans-4-tert -butylcyclohexyloxy)naphthalen-2-yl)propan-1-ol; (R)-2-amino-2-(6-(trans-4-tert -butylcyclohexyloxy)-5-(trifluoromethypnaphthalen-2-yl)propan-1-ol; 2-amino-2-[6-(cis-4-butylcyclohexyloxy)-5-trifluoromethyl-naphthalen-2-yl]-propane-1,3-diol; 2-amino-2-[6-(cis-4-butylcyclohexyloxy)-5-iodo-naphthalen-2-yl]-propane-1,3-diol; 2-amino-2-[6-(trans-4-tert -butylcyclohexyloxy)-5-trifluoromethyl-naphthalen-2-yl]-propane-1,3-diol; 2-amino-2-[6-(trans -4-tert-butyl-cyclohexyloxy)-naphthalen-2-yl]-propane-1,3-diol; 2-amino-2-[6-(trans-4-tert-butyl -cyclohexyloxy)-5-iodo-naphthalen-2-yl]-propane-1,3-diol; 2-amino-2-(6-trans-[3-(benzyloxymethyl)cyclobutoxy]naphthalen-2-yl) propane-1,3-diol; 2-amino-2-(6-cis-[3-(benzyloxymethyl) cyclobutoxy]naphthalen-2-yl)propane-1,3-diol; 2-amino-2-[6-(3-trans -benzyloxymethylcyclobutoxy)-5-(trifluoromethy)naphthalen-2-yl]propane-1,3-diol; 2-amino-2-[6-(3-cis-benzyloxymethylcyclobutoxy)-5-(trifluoromethy)naphthalen-2-yl]propane-1,3-diol; (R)-2-amino-2-[6-(3-trans-benzyloxymethylcyclobutoxy) naphthalen-2-yl]propan-1-ol; (R)-2-amino-2-[6-(3-cis-benzyloxymethylcyclobutoxy)naphthalen-2-yl]propan-1-ol; (R)-2-amino-2-[6-(4-trans-tert-pentylcyclohexyloxy)naphthalen-2-yl]propan-1-ol; (R)-2-amino-2-[6-(4-cis-tert -pentylcyclohexyloxy)naphthalen-2-yl]propan-1-ol; (R)-2-amino-2-[6-(3-cis -benzyloxymethylcyclobutoxy)-5-trifluoromethylnaphthalen-2-yl]propan-1-ol; 2-amino-2-[6-(3-cis-(benzyloxymethyl)cyclobutoxy)naphthalen-2-yl]-3-hydroxypropyl dihydrogen phosphate; (R)-2-amino-2-{6-[trans-4-(1,1-dimethyl-propyl)-cyclohexyloxy]naphthalen-2-yl}-propan-1-ol; (R)-2-amino-2-(6-(trans-4-tert-butylcyclohexyloxy)-5-methoxynaphthalen-2-yl)propan-1-ol; (R)-2-amino-2-(6-(trans-4-butyl-cyclohexyloxy)-5-trifluoromethylnaphthalen-2-yl)propan-1-ol; (R)-2-amino-2-(6-(trans-4-butyl-cyclohexyloxy)naphthalen-2-yl)propan-1-ol; (R)-2-amino-2-(6-(trans-4-trifluoromethylcyclohexyloxy)-5-fluoronaphthalen-2-yl) propan-1-ol; (R)-2-Amino-2-[6-(decahydro-naphthalen-2-yloxy)-naphthalen-2-yl]-propan-1-ol; (R)-2-Amino-2-[6-(bicyclohexyl-4-yloxy)-naphthalen-2-yl]-propan-1-ol; (R)-2-Amino-2-[6-(4-isopropyl -cyclohexyloxy)-naphthalen-2-yl]-propan-1-ol; (R)-2-Amino-2-[6-(4-cyclopentyl -cyclohexyloxy)-naphthalen-2-yl]-propan-1-ol; (R)-2-Amino-2-[6-(4-sec-butyl-cyclohexyloxy) -naphthalen-2-yl]-propan-1-ol; (R)-2-Amino-2-[6-(cis-4cyclopentyl-cyclohexyloxy)-5-trifluoromethyl-naphthalen-2-yl]-propan-1-ol; (R)-2-Amino-2-[6-(trans-4-cyclopentyl -cyclohexyloxy)-5-trifluoromethyl-naphthalen-2-yl]-propan-1-ol; Phosphoric acid mono-{(R)-2-amino-2-[6-(4-cyclopentyl-cyclohexyloxy)-5-trifluoromethyl-naphthalen-2-yl]-propyl} ester; 2-Amino-2-[5-trifluoromethyl-6-(4-trifluoromethyl-cyclohexyloxy)-naphthalen-2-yl]-propane-1,3-diol; (R)-2-[6-(4-tert-butyl-cyclohexyloxy)-naphthalen-2-yl]-2-methylamino-propan-1-ol; phosphoric acid mono-{(R)-2-amino-2-{6-[4-(1,1-dimethylpropyl)-cyclohexyloxy)-5-trifluoromethyl-naphthalen-2-yl]-propyl}Ester; phosphoric acid mono-{(R)-2-amino-2-[6-(4-tert -butyl-cyclohexyloxy)-5-trifluoromethyl-naphthalen-2-yl]-propyl}Ester; (S)-2-amino-2-[6-(4-trans-tert-butyl-cyclohexyloxy)-5-trifluoromethyl-naphthalen-2-yl]-propan-1-ol; (S)-4-[6-(4-cis -tert-butyl-cyclohexyloxy)-naphthalen-2-yl]-4-methyl-oxazolidin-2-one; (S)-4-[6-(4-cis-tert -butyl-cyclohexyloxy)-5-trifluoromethyl-naphthalen-2-yl]-4-methyl-oxazolidin-2-one; (S)-2-amino-2-[6-(4-cis-tert-butyl-cyclohexyloxy)-5-trifluoromethyl-naphthalen-2-yl]-propan-1-ol; (R)-4-(6-hydroxy-5-(trifluoromethyDnaphthalen-2-yl)-4-methyloxazolidin-2-one; (R)-4-(6-(trans-4-tert-butylcyclohexyloxy)-5-(trifluoromethyl)naphthalen-2-yl)-4-methyloxazolidin-2-one; (R)-2-amino-2-(6-((4-tert-butylcyclohexyl)methyl) naphthalen-2-yl)propan-1-ol; 3-(6-(trans -4-tert-Butylcyclohexyloxy)naphthalen-2-yl)oxetan-3-amine; 3-(6-(trans-4-tert -butylcyclohexyloxy)-5-(trifluoromethyl) naphthalen-2-yl)oxetan-3-amine; (R)-2-Amino-2-(6-(cis-4-cyclohexylcyclohexyloxy)-5-(trifluoromethyl)naphthalen-2-yl)propan-1-ol; (R)-2-Amino-2-(6-(trans-4-cyclohexylcyclohexyloxy)-5-(trifluoromethyl)naphthalen-2-yl)propan-1-ol; (R)-2-amino-2-(6-(trans-4-cyclohexylcyclohexyloxy)-5-(trifluoromethyl)naphthalen-2-yl)propyl dihydrogen phosphate; (R)-2-Amino-2-(6-(cis-4-isopropylcyclohexyloxy)-5-(trifluoromethyl)naphthalen-2-yl)propan-1-ol; (R)-2-Amino-2-(6-(trans-4-isopropylcyclohexyloxy)-5-(frifluoromethyl)naphthalen-2-yl)propan-1-ol; (R)-2-Amino-2-(6-(trans-4-(1,1-difluoroethyl)cyclohexyloxy)-5-(trifluoromethyl) naphthalen-2-yl)propyl dihydrogen phosphate; 4-amino-4-(6-(trans-4-tert -butylcyclohexyloxy)-5-(trifluoromethyl) naphthalen-2-yl)pentanoic acid; (R)-2-amino-2-(6-(trans-4-tert-butylcyclohexyloxy)-5-cyclopropylnaphthalen-2-yl) propan-1-ol; (R)-2-amino-2-(6-(trans-4-tert-butylcyclohexyloxy)-5-methylnaphthalen-2-yl)propan-1-ol; (R)-2-amino-2-(6-(trans-4-tert-butylcyclohexyloxy)-5-vinylnaphthalen-2-yl)propan-1-ol; (R)-2-amino-2-(6-(trans-4-tert-butylcyclohexyloxy)-5-(4-(trifluoromethoxy)phenyl) naphthalen-2- yl)propan-1-ol; (R)-2-amino-2-(6-(trans-4-tert-butylcyclohexyloxy)-5-(4-(methylsulfonyl) phenyl) naphthalen-2-yl) propan-1-ol; (R)-2-amino-2-(6-(trans-4-tert-butylcyclohexyloxy)-5-(pyrimidin-5-yl)naphthalen -2-yl)propan-1-ol; (R)-2-amino-2-(6-(trans-4-tert-butylcyclohexyloxy)-5-(4-ethoxyphenyl)naphthalen-2-yl)propan-1-ol; (R)-2-amino-2-(6-(trans-4-tert-butylcyclohexyloxy) -5- phenylnaphthalen-2-yl)propan-1-ol; (R)-2-amino-2-(6-(trans-4- tert-butylcyclohexyloxy)-5-(3-chlorophenyl)naphthalen-2-yl)propan-1-ol; (R)-2-amino-2-(6-(trans-4-tert-butylcyclohexyloxy) -5-(4-chlorophenyl)naphthalen-2-yl)propan-1-ol; (R)-2-amino-2-(6-(trans-4-tert -butylcyclohexyloxy)-5-chloronaphthalen-2-yl)propan-1-ol; (R)-2-amino-2-(5-bromo-6-(trans-4-tert-butylcyclohexyloxy)naphthalen-2-yl)propan-1-ol; (R)-2-amino-2-(6-(trans-4-tert -butylcyclohexyloxy)-5,7,8-trichloronaphthalen-2-yl)propan-1-ol; (R)-2-amino-2-(6-(trans-4-tert -butylcyclohexyloxy)-5-fluoronaphthalen-2-yl)propan-1ol; 2-amino-2-(6-trans-4-tert -butylcyclohexyloxy)-5-(trifluoromethypnaphthalen-2-yl)-3-hydroxypropyl dihydrogen phosphate Enantiomer 1; 2-amino-2-(6-trans-4-tert-butylcyclohexyloxy)-5-(trifluoromethyl)naphthalen-2-yl)-3-hydroxypropyl dihydrogen phosphate Enantiomer 2; (R)-4-Methyl-4-[6-(4-trifluoromethyl-cyclohexyloxy)-naphthalen-2-yl]-oxazolidin-2-one; (R)-4-Methyl-4-[6-(cis-4-trifluoromethyl-cyclohexyloxy)-naphthalen-2-yl]-oxazolidin-2-one; (R)-4-Methyl-4-[6-(trans-4-trifluoromethyl-cyclohexyloxy)-naphthalen-2-yl]-oxazolidin-2-one; (R)-2-Amino-2-[6-(cis-4-trifluoromethyl-cyclohexyloxy)-naphthalen-2-yl]-propan-1-ol; (R)-2-Amino -2[6-(trans-4-trifluoromethyl-cyclohexyloxy)-naphthalen-2-yl]-propan-1-ol; Phosphoric acid mono-{(R)-2-amino-2[6-(trans-4-trifluoromethyl-cyclohexyloxy)- naphthalen-2-yl]-propyl}Ester; (R)-2-Amino-2-[5-trifluoromethyl-6-(trans-4-trifluoromethyl-cyclohexyloxy) -naphthalen-2-yl]-propan-1-ol; Phosphoric acid mono-{(R)-2-amino-2-[5-trifluoromethyl-6-(trans-4-trifluoromethyl-cyclohexyloxy)-naphthalen-2-yl]-propyl}Ester; (R)-2-Amino-2-[6-(4-pentyl-cyclohexyloxy)-naphthalen-2-yl]-propan-1-ol; (R)-2-Amino-2-[6-(cis-4-pentyl -cyclohexyloxy)-naphthalen-2-yl]-propan-1-ol; (R)-2-Amino-2-[6-(trans-4-pentyl -cyclohexyloxy)-naphthalen-2-yl]-propan-1-ol; 2-[6-(trans-4-tert-Butyl-cyclohexyloxy)-5-trifluoromethyl-naphthalen-2-yl]-propan-1-ol; 2-Amino-2-[6-(trans-4-tert-butyl-cyclohexyloxy) -5-trifluoromethyl-naphthalen-2-yl]-propan-1-ol; 4-Amino-4-[6-(trans-4-trifluoromethyl -cyclohexyloxy)-naphthalen-2-yl]-pentanoic acid; 4-Amino-4-[6-(cis-4-trifluoromethyl -cyclohexyloxy)-naphthalen-2-yl]-pentanoic acid; 4-Amino-4-[5-trifluoromethyl-6-(trans-4-trifluoromethyl-cyclohexyloxy)-naphthalen-2-yl]-pentanoic acid; 4-Amino-4[5-trifluoromethyl -6-(cis-4-trifluoromethyl-cyclohexyloxy)-naphthalen-2-yl]-pentanoic acid; (R)-2-amino-2-(6-(trans-4-(1,1-difluoroethyl)cyclohexyloxy)naphthalen-2-yl)propan-1-ol; (R)-2-amino-2-(6-(trans -4-(1,1-difluoropropyl)cyclohexyloxy)naphthalen-2-yl)propan-1-ol; (R)-2-amino-2-(6-(trans-4-(1,1-difluorobutyl)cyclohexyloxy)naphthalen-2-yl)propan-1-ol; (R)-2-amino-2-(6-(cis-4-(1,1-difluoroethyl)cyclohexyloxy) naphthalen-2-yl)propan-1-ol; (R)-2-amino-2-(6-(cis-4-(1,1-difluoropropyl)cyclohexyloxy)naphthalen-2-yl)propan-1-ol; (R)-2-amino-2-(6-(cis-4-(1,1-difluorobutyl)cyclohexyloxy) naphthalen-2-yl)propan-1-ol; (R)-2-amino-2-(6-(trans-4-(1,1-difluoroethyl)cyclohexyloxy)-5-(trifluoromethyl)naphthalen-2-yl)propan-1-ol; (R)-2-amino-2-(6-(trans-4-(1,1-difluoropropyl)cyclohexyloxy)-5-(trifluoromethyl) naphthalen-2-yl)propan-1-ol; (R)-2-amino-2-(6-(cis-4-tert-butylcyclohexyloxy)naphthalen-2-yl)propan-1-ol;

or a pharmaceutically acceptable salt or prodrug thereof.

19. A pharmaceutical composition comprising a pharmaceutically acceptable carrier and a compound of formula (I):

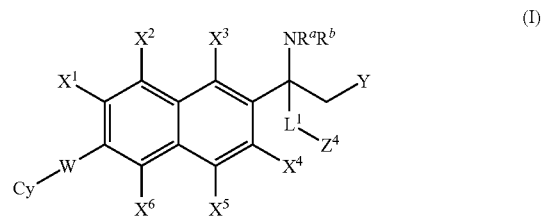

wherein:

$X^1$ is hydrogen, halo, hydroxy, nitro, cyano, alkyl, haloalkyl, cycloalkyl, halocycloalkyl, alkoxy, haloalkoxy, cycloalkoxy, halocycloalkoxy, acyl, aminoacyl, —NR$^f$R$^g$, —N(R$^f$)SO$_2$R$^g$, —SO$_2$R$^f$, —SO$_2$NR$^f$R$^g$, —CO$_2$R$^f$, trialkylamino, aryl, or heteroaryl;

$X^2$ is hydrogen, halo, hydroxy, nitro, cyano, alkyl, haloalkyl, cycloalkyl, halocycloalkyl, alkoxy, haloalkoxy, cycloalkoxy, halocycloalkoxy, acyl, aminoacyl, —NR$^f$R$^g$, —N(R$^f$)SO$_2$R$^g$, —SO$_2$R$^f$, —SO$_2$NR$^f$R$^g$, —CO$_2$R$^f$, trialkylamino, aryl, or heteroaryl;

$X^3$ is hydrogen, halo, hydroxy, nitro, cyano, alkyl, haloalkyl, cycloalkyl, halocycloalkyl, alkoxy, haloalkoxy, cycloalkoxy, halocycloalkoxy, acyl, aminoacyl, —NR$^f$R$^g$, —N(R$^f$)SO$_2$R$^g$, —SO$_2$R$^f$, —SO$_2$NR$^f$R$^g$, —CO$_2$R$^f$, trialkylamino, aryl, or heteroaryl;

$X^4$ is hydrogen, halo, hydroxy, nitro, cyano, alkyl, haloalkyl, cycloalkyl, halocycloalkyl, alkoxy, haloalkoxy, cycloalkoxy, halocycloalkoxy, acyl, aminoacyl, —NR$^f$R$^g$, —N(R$^f$)SO$_2$R$^g$, —SO$_2$R$^f$, —SO$_2$NR$^f$R$^g$, —CO$_2$R$^f$, trialkylamino, aryl, or heteroaryl;

$X^5$ is hydrogen, halo, hydroxy, nitro, cyano, alkyl, haloalkyl, cycloalkyl, halocycloalkyl, alkoxy, haloalkoxy, cycloalkoxy, halocycloalkoxy, acyl, aminoacyl, —NR$^f$R$^g$, —N(R$^f$)SO$_2$R$^g$, —SO$_2$R$^f$, —SO$_2$NR$^f$R$^g$, —CO$_2$R$^f$, trialkylamino, aryl, or heteroaryl;

$X^6$ is hydrogen, halo, hydroxy, nitro, cyano, alkyl, haloalkyl, cycloalkyl, halocycloalkyl, alkoxy, haloalkoxy, cycloalkoxy, halocycloalkoxy, acyl, aminoacyl, —NR$^f$R$^g$, —N(R$^f$)SO$_2$R$^g$, —SO$_2$R$^f$, —SO$_2$NR$^f$R$^g$, —CO$_2$R$^f$, trialkylamino, aryl, or heteroaryl;

Y is —OR$^f$, —(CR$^f$R$^g$)OR$^f$, —(CR$^f$R$^g$)$_2$OR$^f$, —O—P(O)(OR$^f$)OR$^g$, —OC(O)R$^c$, —C(O)OR$^c$, —(CR$^f$R$^g$)—P(O)(OR$^f$)OR$^g$, —(C(OH)R$^f$)—P(O)(OR$^f$)OR$^g$, —S—P(O)(OR$^f$)OR$^g$, tetrazole, —SO$_2$NHR$^f$, —SO$_3$, —CONHR$^f$, —Si(OH)$_2$, or —B(OH)$_2$;

W is —CR$^f$R$^g$—, —NR$^f$—, —O—, —S—, —SO—, or —SO$_2$—;

$L^1$ is —CH$_2$—, —CHF—, or —CF$_2$—;

$Z^4$ is hydrogen, halo, alkyl, haloalkyl, alkenyl, haloalkenyl, alkynyl, or —OR$^f$;

or $Z^4$ is —CH$_2$— bound to the carbon atom to which Y is bound;

or $L^1$, $Z^4$, Y, and the atoms to which they are bound form a 4-7 membered cycloalkyl group or a 4-7 membered heterocyclyl group having 1 or 2 heteroatoms selected from O and N;

$R^a$ is hydrogen, alkyl, haloalkyl, alkenyl, alkynyl, cycloalkyl, cycloalkenyl, aryl, heteroaryl, or heterocyclyl; wherein each of alkyl, cycloalkyl, cycloalkenyl, aryl, heteroaryl and heterocycle are optionally substituted with 1 to 5 substituents independently selected from the group consisting of halo, oxo, —CN, —CHO, —CF$_3$, —OH, —NO$_2$, alkyl, —OCF$_3$, alkoxy, cycloalkoxy, cycloalkenoxy, amino, alkylamino, dialkylamino, acylamino, aminoacyl, alkylsulfonyl, alkylaminosulfonyl, and dialkylaminosulfonyl;

$R^b$ is hydrogen, alkyl, haloalkyl, alkenyl, alkynyl, cycloalkyl, cycloalkenyl, aryl, heteroaryl, or heterocyclyl; wherein each of alkyl, cycloalkyl, cycloalkenyl, aryl, heteroaryl and heterocycle are optionally substituted with 1 to 5 substituents independently selected from the group consisting of halo, oxo, —CN, —CHO, —CF$_3$, —OH, —NO$_2$, alkyl, —OCF$_3$, alkoxy, cycloalkoxy, cycloalkenoxy, amino, alkylamino, dialkylamino, acylamino, aminoacyl, alkylsulfonyl, alkylaminosulfonyl, and dialkylaminosulfonyl;

or $R^b$ and $Z^4$ are taken to together to form —C(O)O— or =C(R$^f$)O—;

$R^c$ is alkyl, aryl, trifluoromethyl, methylsulfonyl, trifluoromethylsulfonyl, p-tolylsulfonyl, or a group selected such that —OCOR$^c$ is a leaving group;

each R$^f$, independently, is hydrogen, alkyl, haloalkyl, alkenyl, alkynyl, cycloalkyl, cycloalkenyl, aryl, heteroaryl, or heterocyclyl; wherein each of alkyl, cycloalkyl, cycloalkenyl, aryl, heteroaryl and heterocycle are optionally substituted with 1 to 5 substituents independently selected from the group consisting of halo, oxo, —CN, —CHO, —CF$_3$, —OH, —NO$_2$, alkyl, —OCF$_3$, alkoxy, cycloalkoxy, cycloalkenoxy, amino, alkylamino, dialkylamino, acylamino, aminoacyl, alkylsulfonyl, alkylaminosulfonyl, and dialkylaminosulfonyl;

each R$^g$, independently, is hydrogen, alkyl, haloalkyl, alkenyl, alkynyl, cycloalkyl, cycloalkenyl, aryl, heteroaryl, or heterocyclyl; wherein each of alkyl, cycloalkyl, cycloalkenyl, aryl, heteroaryl and heterocycle are optionally substituted with 1 to 5 substituents independently selected from the group consisting of halo, oxo, —CN, —CHO, —CF$_3$, —OH, —NO$_2$, alkyl, —OCF$_3$, alkoxy, cycloalkoxy, cycloalkenoxy, amino, alkylamino, dialkylamino, acylamino, aminoacyl, alkylsulfonyl, alkylaminosulfonyl, and dialkylaminosulfonyl;

Cy has the formula:

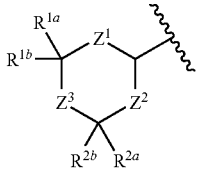

wherein $Z^1$ is a bond, —[C(R$^d$R$^e$)]$_x$—, —CR$^d$=CR$^e$—, —O—, —NR$^f$—;

$Z^2$ is a bond, —[C(R$^d$R$^e$)]$_y$—, —CR$^d$=CR$^e$—, —O—, —NR$^f$—;

$Z^3$ is a bond, —[C(R$^d$R$^e$)]$_z$—, —CR$^d$=CR$^e$—, —O—, —NR$^f$—;

each of x, y, and z, independently, is 1 to 3;

each R$^d$, independently, is H, halo, hydroxy, alkyl, haloalkyl, alkenyl, alkoxy, cycloalkyl, —C(O)NR$^f$R$^g$, —NR$^f$R$^g$, —NR$^f$C(O)R$^g$, or —SO$_2$NR$^f$R$^g$;

each R$^e$, independently, is H, halo, hydroxy, alkyl, haloalkyl, alkenyl, alkoxy, or cycloalkyl, —C(O)NR$^f$R$^g$, —NR$^f$R$^g$, —NR$^f$C(O)R$^g$, or —SO$_2$NR$^f$R$^g$;

$R^{1a}$ and $R^{1b}$, independently, are hydrogen, halo, hydroxy, nitro, cyano, —NR$^f$R$^g$, alkyl, haloalkyl, cycloalkyl, cycloalkenyl, cycloalkylalkyl, cycloalkenylalkyl, heterocyclylalkyl, arylalkyl, heteroarylalkyl, alkoxy, cycloalkylalkoxy, cycloalkenylalkoxy, heterocyclylalkoxy, arylalkoxy, heteroarylalkoxy, acyl, cycloalkylacyl, cycloalkenylacyl, heterocyclylacyl, arylacyl, heteroarylacyl, thioalkyl, alkenyl, alkynyl, cycloalkenyl, heterocyclyl, aryl, or heteroaryl;

or $R^{1a}$ and $R^{1b}$ when taken to ether are C$_2$-C$_5$ alkylene optionally interrupted by 1 or 2 oxygen atoms, or C$_2$-C$_5$ alkenylene optionally interrupted by 1 or 2 oxygen atoms;

$R^{2a}$ and $R^{2b}$, independently, are hydrogen, halo, hydroxy, nitro, cyano, —NR$^f$R$^g$, alkyl, haloalkyl, cycloalkyl, cycloalkenyl, cycloalkylalkyl, cycloalkenylalkyl, heterocyclylalkyl, arylalkyl, heteroarylalkyl, alkoxy, cycloalkylalkoxy, cycloalkenylalkoxy, heterocyclylalkoxy, arylalkoxy, heteroarylalkoxy, acyl, cycloalkylacyl, cycloalkenylacyl, heterocyclylacyl, arylacyl, heteroarylacyl, thioalkyl, alkenyl, alkynyl, cycloalkenyl, heterocyclyl, aryl, or heteroaryl;

or $R^{1a}$ and $R^{2a}$, when taken together, are C$_1$-C$_5$ alkylene optionally interrupted by 1 or 2 oxygen atoms, or C$_2$-C$_5$ alkenylene optionally interrupted by 1 or 2 oxygen atoms;

wherein $R^{1a}$, $R^{1b}$, $R^{2a}$, $R^{2b}$ are each, independently, substituted with 0-5 substituents selected from halo, hydroxy, nitro, cyano, —NR$^f$R$^g$, or —CO$_2$R$^f$;

or a pharmaceutically acceptable salt or prodrug thereof.

* * * * *